United States Patent
Apuya

(10) Patent No.: US 9,828,608 B2
(45) Date of Patent: Nov. 28, 2017

(54) TRANSGENIC PLANTS HAVING ALTERED BIOMASS COMPOSITION

(71) Applicant: Ceres, Inc., Thousand Oaks, CA (US)

(72) Inventor: Nestor Apuya, Culver City, CA (US)

(73) Assignee: Ceres, Inc., Thousand Oaks, CA (US)

( * ) Notice: Subject to any disclaimer, the term of this patent is extended or adjusted under 35 U.S.C. 154(b) by 399 days.

(21) Appl. No.: 13/828,225

(22) Filed: Mar. 14, 2013

(65) Prior Publication Data

US 2013/0191943 A1 Jul. 25, 2013

Related U.S. Application Data

(63) Continuation-in-part of application No. PCT/US2011/057709, filed on Oct. 25, 2011.

(60) Provisional application No. 61/407,280, filed on Oct. 27, 2010.

(51) Int. Cl.
C12N 15/82 (2006.01)
C07K 14/415 (2006.01)

(52) U.S. Cl.
CPC ........ *C12N 15/8261* (2013.01); *C07K 14/415* (2013.01); *Y02E 50/17* (2013.01)

(58) Field of Classification Search
None
See application file for complete search history.

(56) References Cited

U.S. PATENT DOCUMENTS

| | | | |
|---|---|---|---|
| 4,987,071 A | 1/1991 | Cech et al. | |
| 5,034,323 A | 7/1991 | Jorgensen et al. | |
| 5,204,253 A | 4/1993 | Sanford et al. | |
| 5,231,020 A | 7/1993 | Jorgensen et al. | |
| 5,254,678 A | 10/1993 | Haseloff et al. | |
| 5,538,880 A | 7/1996 | Lundquist et al. | |
| 5,766,847 A | 6/1998 | Jackle et al. | |
| 5,878,215 A | 3/1999 | Kling et al. | |
| 6,013,863 A | 1/2000 | Lundquist et al. | |
| 6,326,527 B1 | 12/2001 | Kirihara et al. | |
| 6,329,571 B1 | 12/2001 | Hiei | |
| 6,423,885 B1 | 7/2002 | Waterhouse et al. | |
| PP13,008 P2 | 9/2002 | Walsh | |
| 6,452,067 B1 | 9/2002 | Bedbrook et al. | |
| 6,573,099 B2 | 6/2003 | Graham | |
| PP14,743 P2 | 5/2004 | Speichert et al. | |
| 6,753,139 B1 | 6/2004 | Baulcombe et al. | |
| 6,777,588 B2 | 8/2004 | Waterhouse et al. | |
| PP15,193 P2 | 9/2004 | Smith et al. | |
| 6,906,244 B2 | 6/2005 | Fischer et al. | |
| PP16,176 P3 | 1/2006 | Cosner et al. | |
| 7,112,429 B2 | 9/2006 | Ding | |
| 7,214,789 B2 | 5/2007 | Pennell | |
| PP18,161 P2 | 10/2007 | Probst | |
| 7,312,376 B2 | 12/2007 | Apuya | |
| 7,378,571 B2 | 5/2008 | Apuya | |
| 7,402,667 B2 | 7/2008 | Cook | |
| 7,429,692 B2 | 9/2008 | Dang | |
| 7,598,367 B2 | 10/2009 | Cook | |
| 2003/0175783 A1 | 9/2003 | Waterhouse et al. | |
| 2003/0175965 A1 | 9/2003 | Lowe et al. | |
| 2003/0180945 A1 | 9/2003 | Wang et al. | |
| 2003/0200564 A1* | 10/2003 | Burrell et al. | 800/284 |
| 2004/0034888 A1 | 2/2004 | Liu et al. | |
| 2004/0172684 A1 | 9/2004 | Kovalic et al. | |
| 2004/0214272 A1 | 10/2004 | La Rosa et al. | |
| 2004/0214330 A1 | 10/2004 | Waterhouse et al. | |
| 2005/0032221 A1 | 2/2005 | Chang et al. | |
| 2006/0015970 A1 | 1/2006 | Pennell et al. | |
| 2006/0021083 A1 | 1/2006 | Cook | |
| 2006/0041952 A1 | 2/2006 | Cook | |
| 2006/0260004 A1 | 11/2006 | Fang | |
| 2006/0265788 A1 | 11/2006 | Rommens | |
| 2007/0006335 A1 | 1/2007 | Cook | |
| 2007/0056058 A1 | 3/2007 | Olivier et al. | |
| 2009/0094717 A1* | 4/2009 | Troukhan | C07K 14/415 800/290 |
| 2011/0185449 A1* | 7/2011 | Dupree et al. | 800/278 |
| 2013/0125263 A1* | 5/2013 | Apuya et al. | 800/290 |

FOREIGN PATENT DOCUMENTS

| | | |
|---|---|---|
| EP | 0 534 858 | 3/1993 |
| WO | WO 97/01952 | 1/1997 |
| WO | WO 98/36083 | 8/1998 |
| WO | WO 98/53083 | 11/1998 |
| WO | WO 99/32619 | 7/1999 |
| WO | WO 02/46449 | 6/2002 |
| WO | WO 03/008540 | 1/2003 |
| WO | WO 2005/098007 | 10/2005 |

(Continued)

OTHER PUBLICATIONS

Guo et al., Proc. Natl. Acad. Sci. USA 101: 9205-9210 (2004).*
UniProt_Q8GWB7_At5g18480_2003.*
Chatterjee et al., Plant Sci 168:501-09 (2005).*
Hill & Preiss, Biochem Biophys Res Commun 244(2):573-77 (1998).*
Rhoads et al., J Biol Chem 273(46):30750-56 (1998).*
Whisstock & Lesk, Q Rev Biophys. 36(3):307-40 (2003).*
Rennie et al., Plant Cell 26:3314-25 (2014).*
Zhang et al., Curr Opin Plant Biol 6:430-40 (2003).*
Guo et al., Proc Natl Acad Sci USA 101:9205-10 (2004).*
USPTO Written Description Training Materials (2008).*
Chi-Ham et al., Nat Biotech 28(1):32-36 (2010).*
Kumar, Prateek, et al., "Predicting the effects of coding non-synonymous variants on protein function using the SIFT algorithm," Nature Publishing Group, vol. 4, No. 8, 2009, pp. 1073-1082.

(Continued)

*Primary Examiner* — Cathy Kingdon Worley
*Assistant Examiner* — Russell Boggs
(74) *Attorney, Agent, or Firm* — Dentons US LLP

(57) ABSTRACT

Methods and materials for modulating biomass composition in plants are disclosed. For example, nucleic acids encoding biomass composition-modulating polypeptides are disclosed as well as methods for using such nucleic acids to transform plant cells. Also disclosed are plants having altered biomass composition and plant products produced from plants having altered biomass composition.

18 Claims, 55 Drawing Sheets

(56) References Cited

FOREIGN PATENT DOCUMENTS

| WO | WO 2006/005023 | 1/2006 |
|----|----------------|--------|
| WO | WO 2006/034479 | 3/2006 |
| WO | WO 2006/036864 | 4/2006 |
| WO | WO 2007/044988 | 4/2007 |
| WO | WO 2007/055826 | 5/2007 |
| WO | WO 2007/120989 | 10/2007 |
| WO | WO 2007/127501 | 11/2007 |
| WO | WO 2008/153927 | 12/2008 |
| WO | WO2009/059176 | 5/2009 |
| WO | WO 2009/099899 | 8/2009 |
| WO | WO 2009/146015 | 12/2009 |
| WO | WO 2010/124953 | 11/2010 |
| WO | WO 2011/044254 | 4/2011 |
| WO | WO 2012/009551 | 1/2012 |
| WO | WO 2012/058223 | 5/2012 |

OTHER PUBLICATIONS

Reva, Boris, et al., "Predicting the functional impact of protein mutations: application to cancer genomics," Nucleic Acids Research, 2011, vol. 39, No. 17, pp. 1-14.
Ng, Pauline C., et al., "Predicting the Effects off Amino Acid Substitutions on Protein Function," Annu. Rev. Genomics Hum. Genet. 2006, pp. 61-80.
Guerois, Raphael, "Predicting Changes in the Stability of Proteins and Protein Complexes: A Study of More Than 1000 Mutations," J. Mol. Biol. (2002) 320, 369-387.
National Center for Biotechnology Information GenBank Accession No. XM_002454034, "The Sorghum bicolor genome and the diversification of grasses," Jul. 13, 2009, 2 pages.
National Center for Biotechnology Information GenBank Accession No. XM_002454032, "The Sorghum bicolor genome and the diversification of grasses," Jul. 13, 2009, 2 pages.
National Center for Biotechnology Information GenBank Accession No. XM_002313331, "The genome of black cottonwood, Populus trichocarpa (Toff. & Gray)," Dec. 31, 2013, 2 pages.
National Center for Biotechnology Information GenBank Accession No. XP_002454079, "The Sorghum bicolor genome and the diversification of grasses," Jul. 13, 2009, 2 pages.
National Center for Biotechnology Information GenBank Accession No. XP_002313367, "The genome of black cottonwood, Populus trichocarpa (Toff. & Gray)," Dec. 31, 2013, 2 pages.
National Center for Biotechnology Information GenBank Accession No. XP_002454077, "The Sorghum bicolor genome and the diversification of grasses," Jul. 13, 2009, 2 pages.
National Center for Biotechnology Information GenBank Accession No. ABK96536, "Analysis of 4,664 high-quality sequence-finished poplar full-length cDNA clones and their utility for the discovery of genes responding to insect feeding," Mar. 24, 2009, 2 pages.
"Heavy metal transport/detoxification protein," UniProtKB-A2Q5G7, Mar. 6, 2007, retrieved on Apr. 11, 2016, http://www.uniprot.org/uniprot/A2Q5G7, 5 pages.
International Search Report and Written Opinion in International Application No. PCT/US2011/057709, dated Jan. 17, 2012, 20 pages.
U.S. Appl. No. 60/505,689, filed Sep. 2003, Cook et al.
U.S. Appl. No. 60/518,075, filed Nov. 2003, Pennell et al.
U.S. Appl. No. 60/544,771, filed Feb. 2004, Cook et al.
U.S. Appl. No. 60/558,869, filed Apr. 2004, Cook et al.
U.S. Appl. No. 60/583,609, filed Jun. 2004, Alexandrov.
U.S. Appl. No. 60/583,691, filed Jun. 2004, Alexandrov et al.
U.S. Appl. No. 60/612,891, filed Sep. 2004, Kwok.
U.S. Appl. No. 60/637,140, filed Dec. 2004, Feldmann.
Aasland et al., "The SANT domain: a putative DNA-binding domain in the SWI-SNF and ADA complexes, the transcriptional co-repressor N-CoR and TFIIIB," Trends Biochem Sci. Mar. 1996;21(3):87-8.
Abler and Scandalios, "Isolation and characterization of a genomic sequence encoding the maize Cat3 catalase gene," Plant Molecular Biology, 1993, 22:1031-1038.
Akashi et al., "Gene Discovery by Ribozyme and siRNA Libraries," Nature Reviews Mol. Cell Biology, May 2005, 6:413-422.
Alonso-Blanco et al., "Arabidopsis Protocols," Methods in Molecular Biology, 1998, 82:137-146.
Baerson et al., "Developmental regulation of an acyl carrier protein gene promoter in vegetative and reproductive tissues," Plant Mol. Biol., 1993, 22(2):255-267.
Bateman et al., "Pfam 3.1: 1313 multiple alignments and profile HMMs match the majority of proteins," Nucl. Acids Res., 1999, 27:260-262.
Bode et al., "Refined 1.2 A crystal structure of the complex formed between subtilisin Carlsberg and the inhibitor eglin c. Molecular structure of eglin and its detailed interaction with subtilisin," EMBO J., 1986, 5(4):813-8.
Braga et al., "Expression of the Cry1Ab Protein in Genetically Modified Sugarcane for the Control of Diatraea saccharalis (Lepidoptera: Crambidae)," Journal of New Seeds, 2003, 5:209-221.
Burr et al., "Gene Mapping with Recombinant Inbreds in Maize," Genetics, 1998, 118: 519-526.
Burr et al., "Mapping Genes with Recombinant Inbreds," The Maize Handbook, 1994, pp. 249-254.
Bustos et al., "Regulation of B-Glucuronidase Expression in Transgenic Tobacco Plants by an A/T-Rich, cis-Acting Sequence Found Upstream of a French Bean B-Phaseolin Gene," The Plant Cell, 1989, 1(9):839-853.
Cerdan et al., "A 146 bp fragment of the tobacco Lhcb1*2 promoter confers very-low-fluence and high-irradiance responses of phytochrome to a minimal CaMV 35S promoter," Plant Mol. Biol., 1997, 33:245-255.
Chen et al., "Functional analysis of regulatory elements in a plant embryo-specific gene," Proc. Natl. Acad. Sci. USA, 1986, 83:8560-8564.
Chenna et al., "Multiple sequence alignment with the Clustal series of programs," Nucleic Acids Res., 2003, 31(13):3497-500.
Christian, et al., "Targeting DNA Double-Strand Breaks with TAL Effector Nucleases," Genetics, Oct. 2010, 186: 757-761.
Conceicao, "A cotyledon regulatory region is responsible for the different spatial expression patterns of Arabidopsis 2S albumin genes," The Plant Journal, 1994, 5:493-505.
Conkling et al., "Isolation of Transcriptionally Regulated Root-Specific Genes from Tobacco," Plant Physiol., 1990, 93:1203-1211.
Dai et al., "RF2b, a rice bZIP transcription activator, interacts with RF2a and is involved in symptom development of rice tungro disease," Proc. Natl. Acad. Sci. USA, 2004, 101(2):687-692.
de Feyter and Gaudron, "Expressing Ribozymes in Plants," Methods in Molecular Biology, 74(43).
Deshpande MV, "Ethanol production from cellulose by coupled saccharification/fermentation using Saccharomyces cerevisiae and cellulose complex from Sclerotium rolfsii UV-8 mutant," Appl. Biochem. Biotechnol., Sep. 1992, 36:227.
Dieffenbach and Dveksler, eds., "PCR Primer: A Laboratory Manual," Cold Spring Harbor Laboratory Press, 1995.
Do et al., "ProbCons: Probabilistic consistency-based multiple sequence alignment," Genome Res., 2005, 15(2):330-40.
Durbin et al., Biological Sequence Analysis: Probabilistic Models of Proteins and Nucleic Acids, Cambridge University Press, Cambridge, UK (1998).
Fejes et al., "A 268 bp upstream sequence mediates the circadian clock-regulated transcription of the wheat Cab-1 gene in transgenic plants," Plant Mol. Biol., 1990, 15:921-932.
Fromm et al., An Octopine Synthase Enhancer Element Directs Tissue-Specific Expression and Binds ASF-1, a Factor from Tobacco Nuclear Extracts, The Plant Cell, 1989, 1:977-984.
Gardiner et al., "Development of a Core RFLP Map in Maize Using an Immortalized F2 Population," Genetics Society of America, 1993, 134: 917-930.
GenBank Accession No. AF096096 GI: AF096096, "Arabidopsis thaliana fertilization-independent seed 2 protein (FIS2) mRNA, complete cds," dated Jan. 1999, 2 pages.

(56) References Cited

OTHER PUBLICATIONS

GenBank Accession No. AF129516 GI: AF129516, "Arabidopsis thaliana fertilization-independent endosperm protein (FIE) mRNA, complete cds," dated Apr. 1999, 2 pages.
GenBank Accession No. L05934 GI: L05934, "*Zea mays* catalase (Cat3) gene, complete cds," Oct. 1993, 3 pages.
GenBank Accession No. U93215, dated Feb. 2002, 42 pages.
Green et al., "Binding site requirements for pea nuclear protein factor GT-1 correlate with sequences required for light-dependent transcriptional activation of the rbcS-3A gene," The EMBO J., 1988, 7:4035-4044.
Hong et al., "Promoter sequences from two different Brassica napus tapetal oleosin-like genes direct tapetal expression of B-glucuronidase in transgenic Brassica plants," Plant Mol. Biol., 1997, 34(3):549-555.
Hyrup et al., "Peptide Nucleic Acids (PNA): Synthesis, Properties and Potential Applications," Bioorganic & Medicinal Chemistry, 1996, 4(1):5-23.
Jordano et al., "A Sunflower Helianthinin Gene Upstream Sequence Ensemble Contains an Enhancer and Sites of Nuclear Protein Interaction," The Plant Cell, 1989, 1:855-866.
Kasuga et al., "Improving plant drought, salt, and freezing tolerance by gene transfer of a single stress-inducible transcription factor," Nature Biotechnology, 1999, 17: 287-291.
Keller and Baumgartner, "Vascular-Specific Expression of the Bean GRP 1.8 Gene is Negatively Regulated," The Plant Cell, 1991, 3(10):1051-1061.
Lam et al., "Site-specific mutations alter in vitro factor binding and change promoter expression pattern in transgenic plants," Proc. Natl. Acad. Sci. USA, 1989, 86:7890-7894.
Li et al., "Small dsRNAs induce transcriptional activation in human cells," Proc Natl Acad Sci USA, 2006, 103(46):17337-42.
Lloyd et al., "Targeted mutagenesis using zinc-finger nucleases in Arabidopsis," Proc. Natl. Acad. Sci. USA, Feb. 2005, 102:2232-2237.
Luan et al., A Rice cab Gene Promoter Contains Separate cis-Acting Elements That Regulate Expression in Dicot and Monocot Plants, The Plant Cell, Aug. 1992, 4:971-981.
Lubberstedt et al., "Promoters from Genes for Plastid Proteins Possess Regions with Different Sensitivities toward Red and Blue Light," Plant Physiol., 1994, 104:997-1006.
Matsuoka et al., "Tissue-specific light-regulated expression directed by the promoter of a C4 gene, maize pyruvate, orthophosphate dikinase, in a C3 plant, rice," Proc. Natl. Acad. Sci. USA, Oct. 1993, 90:9586-9590.
Matzke and Birchler, "RNAi-Mediated Pathways in the Nucleus," Nature Reviews Genetics, Jan. 2005, 6:24-35.
McCallum et al., "Targeted screening for induced mutations," Nature Biotechnology, Apr. 2000, 18: 455-457.
Medberry et al., "The Commelina Yellow Mottle Virus Promoter is a Strong Promoter in Vascular and Reproductive Tissues," The Plant Cell, Feb. 1992, 4(2):185-192.
Meier et al., "Elicitor-Inducible and Constitutive in Vivo DNA Footprints Indicate Novel cis-Acting Elements in the Promoter of a Parsley Gene Encoding Pathogenesis-Related Protein 1," The Plant Cell, Mar. 1991, 3:309-316.
Mittal, "Improving the Efficiency of RNA Interference in Mammals," Nature Reviews Genetics, May 2004, 5:355-365.
Moore and Haber, "Cell cycle and genetic requirements of two pathways of nonhomologous end-joining repair of double-strand breaks in *Saccharomyces cerevisiae*," Mol Cell Biol., May 1996, 16(5):2164-73.
Nature.Com, "Nature Reviews RNA interference collection," Oct. 2005, [retrieved on Apr. 12, 2012]. Retrieved from Internet: URL http://www.nature.com/focus/rnai/index.html. 2 pages.
Perriman et al., "Effective ribozyme delivery in plant cells," Proc. Natl. Acad. Sci. USA, Jun. 1995, 92(13):6175-6179.
Perrin et al., "Xyloglucan fucosyltransferase, an enzyme involved in plant cell wall biosynthesis," Science, Jun. 1999, 284:1976-1979.
Rawlings et al., "Evolutionary families of peptidase inhibitors," Biochem J., Mar. 2004, 378(Pt.3):705-16.
Refseth et al., "Hybridization capture of microsatellites directly from genomic DNA," Electrophoresis, 1997, 18: 1519.
Richards et al., "Construction of a GFP-BAR plasmid and its use for switchgrass transformation," Plant Cell. Rep., 2001, 20:48-54.
Riggs et al., "Cotyledon Nuclear Proteins Bind to DNA Fragments Harboring Regulatory Elements of Phytohemagglutinin Genes," The Plant Cell, Jun. 1989, 1(6):609-621.
Rivera et al., "Genomic evidence for two functionally distinct gene classes," Proc. Natl. Acad. Sci. USA, May 1998, 95:6239-6244.
Rosenzweig et al., "Crystal structure of the Atx1 metallochaperone protein at 1.02 A resolution," Structure Fold Des., Jun. 1999, 7:605-617.
Roudier et al., "COBRA, an Arabidopsis Extracellular Clycosyl-Phosphatidyl Inositol-Anchored Protein, Specifically Controls Highly Anisotropic Expansion through Its Involvement in Cellulose Microfibril Orientation," The Plant Cell, Jun. 2005, 17(6):1749-63.
Schroder et al., "Biochemical and molecular characterization of xyloglucan endotransglycosylase from ripe kiwifruit," Planta, Feb. 1998, 204:242-251.
Schultz et al., "The classical arabinogalactan protein gene family of Arabidopsis," Plant Cell, Sep. 2000, 12:1751-68.
Sheridan et al., "The marl Gene: Controlling the Commitment to the Meiotic Pathway in Maize," Genetics, 1996, 142:1009-1020.
Shibuya et al., "RNA-directed DNA methylation induces transcriptional activation in plants," Proc Natl Acad Sci USA, Feb. 2009,106(5):1660-1665.
Slocombe et al., "Temporal and Tissue-Specific Regulation of a Brassica napus Stearoyl-Acyl Carrier Protein Desaturase Gene," Plant Physiol., 1994, 104(4):167-176.
Somleva et al., "Agrobacterium-Mediated Genetic Transformation of Switchgrass," Crop Sci., 2002, 42:2080-2087.
Sonnhammer et al., "Pfam: A Comprehensive Database of Protein Domain Families Based on Seed Alignments," Proteins, 1997, 28:405-420.
Sonnhammer et al., "Pfam: multiple sequence alignments and HMM-profiles of protein domains," Nucl. Acids Res., 1998, 26:320-322.
Stemple, "TILLING—a high-throughput harvest for functional genomics," Nat Rev Genet, Feb. 2004, 5(2):145-50.
Summerton and Weller, "Morpholino Antisense Oligomers: Design, Preparation, and Properties," Antisense Nucleic Acid Drug Dev., 1997, 7:187-195.
Thomas D. Brock in Biotechnology: A Textbook of Industrial Microbiology, Second Edition (1989) Sinauer Associates, Inc., Sunderland, Mass. **Too Voluminous to Provide.
Tovkach et al., "A toolbox and procedural notes for characterizing novel zinc finger nucleases for genome editing in plant cells," The Plant Journal, 2009, 57:747-757.
Townsend et al., "High-frequency modification of plant genes using engineered zinc-finger nucleases," Nature, May 2009, 459:442-445.
Truernit et al., "The promoter of the Arabidopsis thaliana SUC2 sucrose-H+ symporter gene directs expression of B-glucuronidase to the phloem: Evidence for phloem loading and unloading by SUC2," Planta, 1995, 196:564-570.
Urao et al, "Molecular cloning and characterization of a gene that encodes a MYC-related protein in Arabidopsis," Plant Mol. Biol., 1996, 32:571-57.
Weigel et al., "Activation Tagging in Arabidopsis," Plant Physiology, Apr. 2000, 122:1003-1013.
Yamamoto et al., "The Promoter of a Pine Photosynthetic Gene Allows Expression of a B-Glucuronidase Reporter Gene in Transgenic Rice Plants in a Light-Independent but Tissue-Specific Manner," Plant Cell Physiol., 1994, 35:773-778.
Yan et al., "New Construct Approaches for Efficient Gene Silencing in Plants," Plant Physiol., Aug. 2006, 141:1508-1518.
Zhang et al., "From Laboratory to Field. Using Infoimation from Arabidopsis to Engineer Salt, Cold, and Drought Tolerance in Crops," Plant Physiol., Jun. 2004, 135:612-621.

(56) References Cited

OTHER PUBLICATIONS

Zheng et al., "SPK1 is an Essential S-Phase-Specific Gene of *Saccharomyces cerevisiae* That Encodes a Nuclear Serine/Threonine/Tyrosine Kinase," Mol. Cell Biol., Sep. 1993, 13:5829-5842.

* cited by examiner

Figure 1

| | | | | | |
|---|---|---|---|---|---|
| SEQ_ID_NO_483 | MTKQKI VI RV | NLASEKTRSK | AMALVARADG | VSSMGVTGDG | 40 |
| SEQ_ID_NO_485 | M KQKI VI RL | SVASDKCRSK | AMVL AA KADG | VSK MGI TGDG | 39 |
| SEQ_ID_NO_486 | MTKQKI VI KV | SMPCEKSRSRK | AMALVARASG | VNSMEVTGDG | 40 |
| SEQ_ID_NO_488 | MAKQKI VI KV | PMASDKSRSK | AMALVA A AGG | VNSVA I AGDG | 40 |
| SEQ_ID_NO_490 | M KQI VI KV | TVNGPKSRSK | SLQ I AVGFSG | VESAGL GG QD | 39 |
| SEQ_ID_NO_492 | M KQ T MVVKV | TMSDEKSRSK | ALKV VVGFSG | VESASL KGDD | 39 |
| SEQ_ID_NO_493 | M KQI VMRV | HMRCQKCRTK | ALEVVAGANG | VNFVGL EGDE | 39 |

| | | | | | |
|---|---|---|---|---|---|
| SEQ_ID_NO_483 | RDQLEVVGDG | VDTVGL VQCL | RKKI GHAEI L | KVEEVKPAEK | 80 |
| SEQ_ID_NO_485 | KDQLEVEGDG | I DTVCL VNCL | RKKI GR ADI V | KVE VKPEEK | 79 |
| SEQ_ID_NO_486 | KDRLQVVGDG | VDPVCL V ACL | RRKI GYAEI V | QVEEVKD    K | 78 |
| SEQ_ID_NO_488 | KDQVVVVGEG | VDSI KL T T I L | RKKMG DAQL V | EVAED        | 76 |
| SEQ_ID_NO_490 | KSQI EVVGDG | VDAVE L TNRL | RKSVGYAEI V | SVAAVG       | 76 |
| SEQ_ID_NO_492 | KSQI EV T GDG | VDAVQ L TSRL | RKSV GHAEL V | SVSAVG       | 77 |
| SEQ_ID_NO_493 | KDKI VV T GDG | VDAVT L T KCL | RKKVGQT EI V | SLGEVKA      | 76 |

| | | | | | |
|---|---|---|---|---|---|
| SEQ_ID_NO_483 | KPEEKKPEPL |  PDWWWYH    |             |  NYYYHYH P L      | 104 |
| SEQ_ID_NO_485 | KPEEKKPEV  | PL PYGMCYP L |             |  NYYQYH P L       | 105 |
| SEQ_ID_NO_486 | KPEEKKQEPP |  KPVPCYYP L  |             |  APPCI YY PPA TVV L | 108 |
| SEQ_ID_NO_488 | KKEEKKPDPV | AE AAAYN     |             |  QYYYHY PPPX AVV Y DP | 111 |
| SEQ_ID_NO_490 | KKEEKPE AM | VQPVLWSMYG   | GGVP QTY  H | PT H             | 110 |
| SEQ_ID_NO_492 | KKEE AKEPPA | AYVWPYN     |             |  QPLMY QE         | 104 |
| SEQ_ID_NO_493 |            |             |             | P                | 76 |

| | | | | |
|---|---|---|---|---|
| SEQ_ID_NO_483 |            |  PPPC  M   | 109 |
| SEQ_ID_NO_485 |            |        H   | 107 |
| SEQ_ID_NO_486 | CSDEPSPCSI  M |        | 119 |
| SEQ_ID_NO_488 | YPRPGNTCSI  M |        | 122 |
| SEQ_ID_NO_490 | NYYQDPSCSI  M |        | 121 |
| SEQ_ID_NO_492 | YAHQDPCSI  M |         | 115 |
| SEQ_ID_NO_493 |            |  S         | 77 |

Figure 2A

| SEQ_ID_NO_562 | MAAKKVVLKI | DLHDNKDKQR | VLKAVSTLHG | IDSISVDMKD | 40 |
|---|---|---|---|---|---|
| SEQ_ID_NO_564 | MLVQKVVLKL | DLHDNKDKQK | VLKAVSTLHG | IDSISVDMKD | 39 |
| SEQ_ID_NO_565 | MAAKKLVLKL | DLHDDKDKQK | VLKAVSTLHG | IDSISVDMKD | 40 |
| SEQ_ID_NO_567 | M--KKVVLKL | DVHDDRHKAK | ALKAVSGLHG | IDQLGVDIKD | 38 |
| SEQ_ID_NO_568 | MAMKKLVLKL | DLHDDKDKQK | AIKAVTVSTLHG | IDMSMDMKG | 40 |
| SEQ_ID_NO_570 | M--KKFVLKL | DLHDDKDKQK | ALKTVSTLSG | IDAIAMDMKE | 38 |
| SEQ_ID_NO_572 | M--KKTVLKV | DLHDNKDKQK | AMKAVSTLQG | LDSIAMDMKD | 38 |
| SEQ_ID_NO_573 | M--KKAVLKL | DLHDEKAKTK | AMKKVSSLSG | VDSISMDMKD | 38 |
| SEQ_ID_NO_574 | M--KKI LKL | EYFDEKIKQK | AMKKVSGLEG | VESISIDSKD | 38 |
| SEQ_ID_NO_575 | M--KKVLKL | DPRDDKIKQK | AMRTVSGLSG | VDSVAMDMKE | 38 |
| SEQ_ID_NO_576 | M--KKIVLKL | DLHDDRAKQK | ALKTVSTLPG | LDSIAMDMKE | 38 |

| SEQ_ID_NO_562 | SKLTVIGLAD | PVDVVAKLRK | VG-AAHLSV | GPAKEEKKDE | 79 |
|---|---|---|---|---|---|
| SEQ_ID_NO_564 | SKLTVVGLVD | PVDVVAKLRK | VG-AAILSV | GPAKEEKKDG | 78 |
| SEQ_ID_NO_565 | SNLTVVGLAD | PVDVVARLRK | VA-AAEIVSV | GPAKEDKKEG | 79 |
| SEQ_ID_NO_567 | QKLTVVGTVD | PVANVGKLRK | LFPAVQLSV | GPGKEEKKDD | 78 |
| SEQ_ID_NO_568 | QKLTVVGDVD | PVDVVGKLRK | GMPSASLLSV | GPAKEEKKEE | 80 |
| SEQ_ID_NO_570 | KKLTVIGTVD | PVTVVSKLRK | YWKADIVAV | GPVKEPEKKE | 77 |
| SEQ_ID_NO_572 | MKMTVIGATD | PIDVVGKLRK | CWLHTDIVSI | GPAKEPKKED | 77 |
| SEQ_ID_NO_573 | KKLTVIGDVD | PVDIVSKLRK | LCLNTEI ITV | GPAKEPEKKK | 77 |
| SEQ_ID_NO_574 | KKLTVITGNID | PVSLVSKLRK | LCLHTDIVSV | GPAKEPEKKA | 77 |
| SEQ_ID_NO_575 | KKLTVTGDVD | PVHVVSKLRK | LCLHTDIVSV | GPAKEPEKKA | 77 |
| SEQ_ID_NO_576 | KKLTVIGTVD | PVNVVSKLRK | YWPMTDIVLV | GPAKEPEKEK | 78 |

| SEQ_ID_NO | Seq1 | Seq2 | Seq3 | # |
|---|---|---|---|---|
| SEQ_ID_NO_562 | GQYPL-Y | HYVVHSAEED | PNSCVI C | 135 |
| SEQ_ID_NO_564 | QYHPHPY | QYVVHSAEED | PNSCVI C | 141 |
| SEQ_ID_NO_565 | QYHPHPP | QYAVHSAEED | PNSCA C | 137 |
| SEQ_ID_NO_567 | GYPPPLP | RYVVHSAEED | PNSCVI C | 147 |
| SEQ_ID_NO_568 | SYSLYLP | QYVVHSAEED | PNSCVI C | 137 |
| SEQ_ID_NO_570 | AYNPYMT | NYYAPSMEEN | PNACVI C | 151 |
| SEQ_ID_NO_572 | AYNPG-MT | HYYVQSAEEN | PNACVI L | 130 |
| SEQ_ID_NO_573 | AYNPHMT | YYHVRSVEDD | PNACVI C | 132 |
| SEQ_ID_NO_574 | AYNPHVPA | YYHHRSVEED | PNSCVI S | 159 |
| SEQ_ID_NO_575 | HYQPPLMT | YYYVKSAEED | PNACVI C | 131 |
| SEQ_ID_NO_576 | AYNPHLT | YYYAQSTEEN | PNACVI C | 177 |

| | | | | | |
|---|---|---|---|---|---|
| SEQ_ID_NO_246 | - - - - - - - - - | - - - - - - - - - | S D K E Q L S E | - - - - - - - - - | 124 |
| SEQ_ID_NO_248 | - - - - - - - - - | - - - - - - - - - | S E K E Q P S E | - - - - - - - - - | 124 |
| SEQ_ID_NO_250 | - - - - - - - - - | - - - - - - - - - | S D K E H Q S E | - I T | 126 |
| SEQ_ID_NO_251 | - - - - - - - - - | - - - - - - - - - | S E N D R R S G | - M T | 127 |
| SEQ_ID_NO_252 | L F D P K Q N L K L | - - - - - - - - - | E S K T N K K G | - S P | 173 |
| SEQ_ID_NO_254 | - - - - - - - - - | K Q L L H K L Q T K | N N N N A S D R | - S T N Q Y G N E | 172 |
| SEQ_ID_NO_256 | - - - - - - - - - | K S E E | S I T N E E E E | G Q S V A E D R C V S Q | 141 |

| | | | | | |
|---|---|---|---|---|---|
| SEQ_ID_NO_246 | S P E P K L L | - G - | G A P M P I R | A V A A V P P L P P | P F | 151 |
| SEQ_ID_NO_248 | S P E P K L L | - G - | G P M P I R | A V P V V P P L P P | P G | 150 |
| SEQ_ID_NO_250 | R R S P S C L | W - | P P M P I R | A V A A V P P L P P | P F | 152 |
| SEQ_ID_NO_251 | S P A S I R L L | - G - | G A E E S S | S R A V - - A P P | P Y | 150 |
| SEQ_ID_NO_252 | D A F Q A G I G R T | A A - | R T F M P F K | A C S G L S S V P | | 198 |
| SEQ_ID_NO_254 | D P F Q T C S N R N | G G | R A F M P F S | R Y S S S S S | V T T V G L A A S | 212 |
| SEQ_ID_NO_256 | N P F Q T C N Y P N | Q G | G V E M P F N | R P P - - P P P P | P | 168 |

| | | | | | |
|---|---|---|---|---|---|
| SEQ_ID_NO_246 | - - - - - - - - | - G - | S G L S L V | P P A A K P P I P P | M - - | 180 |
| SEQ_ID_NO_248 | - - - - - - - - | - G - | T A R L | P P A A K T S V S P | S A S | 183 |
| SEQ_ID_NO_250 | - - - - - - - - | - G - | P G L S L L | S P A S K A P I S P | P A V - | 181 |
| SEQ_ID_NO_251 | E R R E D S S A | - G - | T C L S L V | P P A S H R S P P P | V - A T S | 184 |
| SEQ_ID_NO_252 | E R R E E V L R | - V - | P A M P L L | T P G I K S L K E E | A - A A A T A | 228 |
| SEQ_ID_NO_254 | S K E E K L P - | - V - | P S L S L S | T P S V K E G C G S | S N S T G S - | 240 |
| SEQ_ID_NO_256 | K E E K E E S V I | - R - | N R L S L L | T P T S E M M D Y | R G S | 188 |

| | | | | | | |
|---|---|---|---|---|---|---|
| SEQ_ID_NO_246 | - D L | G R F C A T M P - | P | S G A N L H S | Q A L Q Q Q A R | 209 |
| SEQ_ID_NO_248 | D E H R Q N A A | A R L S A T M S I - | P | S G L N L H T | Q T Q Q Q Q L A R | 219 |
| SEQ_ID_NO_250 | - D | N A S | G R F C P T M P - | P | S G S G V T L H S | Q A Q Q Q A S R | 212 |
| SEQ_ID_NO_251 | A G D D H R | V V A | S S F A T A V P S P | V P - | A A L S L Q A | Q A Q Q Q Q A R | 223 |
| SEQ_ID_NO_252 | - R F | S S C | S R S V S T I S | - G | P N - | S D S N L R N | Q Q Q S Q Q T A R | 260 |
| SEQ_ID_NO_254 | - R | S S S | N R A V S S I S P | - T - | A Q P G L R A | T S L Q Q T A R | 269 |
| SEQ_ID_NO_256 | - Q | S H - | H H H Q F N K - P | S | - | Q S H H T Q K K | 209 |

Figure 3C

| SEQ_ID_NO_246 | KARRCWSPEL | HRLFVAALHQ | LGGPQVATPK | QIREVMKVDG | 249 |
| --- | --- | --- | --- | --- | --- |
| SEQ_ID_NO_248 | KTRRCWSPEL | HRQFVAALHQ | LGGPQVATPK | QIREVMQVDG | 259 |
| SEQ_ID_NO_250 | KARRCWSPEL | HRQFVAALHQ | LGGPQVATPK | QIREVMQVDG | 252 |
| SEQ_ID_NO_251 | KISRRCWSPEL | HRQFVAALQQ | LGGPQVATPK | QIREVMKVDG | 263 |
| SEQ_ID_NO_252 | KQRRCWSPEL | HRRFVNALQQ | LGGSQAATPK | QIRELMQVDG | 300 |
| SEQ_ID_NO_254 | KQRRCWSPEL | HRRFVNALQK | LGGSQAATPK | QIRELMQVDG | 309 |
| SEQ_ID_NO_256 | EQRRRMSQEL | HRKFVDALHR | LGGPQVATPK | QIRDLMKVDG | 249 |

| SEQ_ID_NO_246 | LTNDEVKSHL | QKYRLHNRRS | -PGV-VAPVS | QSVMLAGGLW | 287 |
| --- | --- | --- | --- | --- | --- |
| SEQ_ID_NO_248 | LTNDEVKSHL | QKYRLHNRRS | -PGM--APVS | QSIVLVGGLW | 296 |
| SEQ_ID_NO_250 | LTNDEVKSHL | QKYRLHNRKS | -PGV--APVS | QPIMLVGGLW | 289 |
| SEQ_ID_NO_251 | LTNDEVKSHL | QKYRLHTRRV | -PGT--ASAS | HSIVLVGDLW | 300 |
| SEQ_ID_NO_252 | LTNDEVKSHL | QKYRLHTRRV | TPATAAAPAN | QSVVVLGGLW | 340 |
| SEQ_ID_NO_254 | LTNDEVKSHL | QKYRLHTRRV | -PAF--ASSN | QPVVVLGGLW | 345 |
| SEQ_ID_NO_256 | LTNDEVKSHL | QKYRMHTRKH | -PLH--PTKT | LSSSDQPGVL | 286 |

| SEQ_ID_NO_246 | APPHQ----- | EQSSSQSGSP | QGPLQFSGSG | VAL---ATVGG | 319 |
| --- | --- | --- | --- | --- | --- |
| SEQ_ID_NO_248 | SSQEQ----- | SSSQSQSGSP | QGPLQFSGSG | MAVSA-ATVGG | 331 |
| SEQ_ID_NO_250 | APQEQ----- | SSSQSQSGSP | QGPLQFSGSG | VAI-ST-ATVGG | 320 |
| SEQ_ID_NO_251 | ASQEL----- | -VSCSQSGSP | QGPLQLSGSG | VAVS---AAIAG | 332 |
| SEQ_ID_NO_252 | MTQDQYGDSS | KATSSGSGSP | QGPLQLAMNT | G-GT-STTGG | 378 |
| SEQ_ID_NO_254 | MSQDQYNDSS | KVSSSGGSGSP | QGPLHLAAGS | RGGT-SPIEG | 384 |
| SEQ_ID_NO_256 | ERESQL---S | LLSLSRSDSP | QSPLVARGLF | ---SSNVG | 317 |

| SEQ_ID_NO_246 | DSSL------ | SDEDDKSL-EG | YSRK------ | ---YV | 338 |
| --- | --- | --- | --- | --- | --- |
| SEQ_ID_NO_248 | DSSL------ | SDEDDKSLDEG | YSRK------ | ------ | 349 |
| SEQ_ID_NO_250 | DSSL-G---- | SDEDDKSLEG | YSRK------ | ------ | 341 |
| SEQ_ID_NO_251 | DSC------- | EDDDKSL-EG | VRK------- | ---CV | 348 |
| SEQ_ID_NO_252 | DSM------- | DDEDARSL-EIS | YSVKSHSFRS | G--KDDV | 406 |
| SEQ_ID_NO_254 | DSL-E----- | DDEDARSL-E | YSVKSHMNKP | G--KVDV | 412 |
| SEQ_ID_NO_256 | HSSEEDEEEE | DEEEEKSDG | RSSCRNDETK | KKRQVLDLEL | 356 |

Figure 4

Column position indicators (top): 33, 33, 32, 36, 28, 34, 31, 38 (left block); 72, 72, 71, 75, 67, 73, 69, 76 (right block)

Left alignment block:

| SEQ_ID_NO | | | | | |
|---|---|---|---|---|---|
| SEQ_ID_NO_111 | MAR--TTP-F | GL------ | -AVAAA | LVFAVAMPAL | AAAQAPAPA |
| SEQ_ID_NO_113 | MAR--TPL-L | GL------ | AI-AAA | LVFAVAMPAV | ADAQAPAPA |
| SEQ_ID_NO_115 | MAR--TL-F  | GF------ | VV-AAA | LVLAVEMPAL | AAAQAPAPA |
| SEQ_ID_NO_117 | MAVARAP--L | GAVA---- | MAVAA  | LVFAILMPAA | AAAQAPAPA |
| SEQ_ID_NO_118 | MAR--PL-F  | AA------ | LVVA-  | LSFAIA-F-- | AAAQAPAPS |
| SEQ_ID_NO_120 | MAS--RNSVT | GF------ | -ALFS  | FVFAVILSLA | GAQSLAPAPA |
| SEQ_ID_NO_122 | MAA--LP-K  | VL------ | VAVLV  | LAL-ATVPSL | -VQAQAPAPS |
| SEQ_ID_NO_124 | MAVI-CASFK | AFTAV--- | -LAVVS | LTLAVVSPSV | EAQSPAPAPA |

Right alignment block:

| SEQ_ID_NO | | | | |
|---|---|---|---|---|
| SEQ_ID_NO_111 | PTSDGTSIDQ | GIAYLLMIVA | LVLTYLIHPL | DASSPYKLF |
| SEQ_ID_NO_113 | PTSDGTSIDQ | GIAYLLMIVA | LVLTYLIHPL | DASSPYRLF |
| SEQ_ID_NO_115 | PTSDASSVDQ | GVAYELMILA | LVLTYLIHPL | DASSPYKLF |
| SEQ_ID_NO_117 | PTSDGTSIDL | GIAYLLMLVA | LVLTYLIHPL | DASSPYKLF |
| SEQ_ID_NO_118 | PTSDGTSVDQ | GIAYLLMIVA | LVLTYLIHPL | DASSAYKLF |
| SEQ_ID_NO_120 | PTSDGTSIDQ | GIAYLLMVVA | LVLTYLIHPL | DASSYSF-F |
| SEQ_ID_NO_122 | PTSDGTSIDQ | GIAYLLMLVA | LVLTYLIHPL | DASFPYKLF |
| SEQ_ID_NO_124 | PTSDGTSIDQ | GIAYLLMLVA | LVLTYLIHPL | DASSYTFFF |

Figure 5A

| SEQ_ID_NO | | | | | | | Count |
|---|---|---|---|---|---|---|---|
| SEQ_ID_NO_348 | MACSTMA- | F------ | LAV--- | EVA--- | A----- | LPAAA- | AL--- | 26 |
| SEQ_ID_NO_350 | MACSFLF- | L------ | -AFL-- | TAA--- | A----- | LSAAE- | AAT-- | 27 |
| SEQ_ID_NO_351 | MAMARCSL | L------ | PLAA-- | VL-SS- | -A---- | PPRAAAY | AAM-- | 33 |
| SEQ_ID_NO_353 | MAGRFLLI | A------ | VLLAS- | LAL--- | ASLSL- | SA---- | GAA-- | 24 |
| SEQ_ID_NO_355 | MACSYLG- | PC----- | ELLICSL | VSV--- | AA---- | ------ | G---- | 23 |
| SEQ_ID_NO_357 | MTKLPSL- | F------ | LV-LTL- | FSL--- | S----- | ------ | G---- | 20 |
| SEQ_ID_NO_359 | MEGGHMG- | W------ | FLFCCC- | VLG--- | -C---- | ------ | G---- | 24 |
| SEQ_ID_NO_360 | MVDSCLL- | L------ | LLCS-- | VLG--- | HSS--- | ------ | G---- | 20 |
| SEQ_ID_NO_361 | MGFITRFL | L------ | VFMSL- | FTS--- | S----- | ------ | G---- | 20 |
| SEQ_ID_NO_362 | MVNLYVN- | L------ | FVMCS- | VV---- | H----- | ------ | GL--- | 20 |
| SEQ_ID_NO_363 | LV------ | ------- | ------ | ------ | ------ | ------ | ---- | 4 |
| SEQ_ID_NO_364 | MALAVAL- | V------ | ALV--- | FI---- | SI---- | LASAV- | GSS-- | 28 |

| SEQ_ID_NO | | | | | | | Count |
|---|---|---|---|---|---|---|---|
| SEQ_ID_NO_348 | -------- | GGPLP-- | PAGTPLS | FREGYTQLFG | DSNLALHGDG | 58 |
| SEQ_ID_NO_350 | A------- | KLVSP-- | SEKPSLS | FGEGYTQLFG | DSNLALHGGG | 60 |
| SEQ_ID_NO_351 | V------- | DSLLP-- | ASATALS | FEEGYTQLFG | DSNLMLHGDG | 66 |
| SEQ_ID_NO_353 | D------- | EVMVP-- | RPAAALT | FGEGYTQLFG | DSNLRLHGDG | 57 |
| SEQ_ID_NO_355 | -------- | SQ----- | IQRTSLPII | FDEGYTQLFG | DDNLVMYRDG | 55 |
| SEQ_ID_NO_357 | -------- | FG----- | KRIPILS | FDEGYSQLFG | DHNLAIHRDG | 49 |
| SEQ_ID_NO_359 | -------- | SP----- | RRNLPIIA | FEDGYTPLFG | DANLALLKDG | 54 |
| SEQ_ID_NO_360 | -------- | SS----- | KELPIIS | FDEGYSPLFG | DQNLIVHRDG | 49 |
| SEQ_ID_NO_361 | -------- | FA----- | LQKLPLI | FDEGYTQLFG | DSNLMIHRDG | 50 |
| SEQ_ID_NO_362 | -------- | SS----- | RNLPIVS | FEEGYSQLFG | DSNLMVQDG | 49 |
| SEQ_ID_NO_363 | -------- | FS----- | ENLETSS | FNEGYSQLFG | HDNLMVQDG | 33 |
| SEQ_ID_NO_364 | RPRLAGKRVT | ------- | ENFASLR | FEEGYTSLFG | EDNVKAEDG | 65 |

| SEQ_ID_NO | | | | | |
|---|---|---|---|---|---|
| SEQ_ID_NO_348 | KVDYKYAPYV | AEFADLALRG | CAVG-GR--- | ACEEPG---- | 250 |
| SEQ_ID_NO_350 | KVDYKYAPYV | AEFADLALRG | CAVG-PASAS | ACATPG---- | 255 |
| SEQ_ID_NO_351 | KVNYKYAPYV | AEFTDLLLHG | CPAGSPP--- | PCEGAA---- | 259 |
| SEQ_ID_NO_353 | KVDYKYAPYV | AEFTDLELRG | CDQ--PAL-- | ACEPEG---- | 248 |
| SEQ_ID_NO_355 | RVNYKYAPYV | AEFSDLVLHG | CAVD-PVEQF | PRCDNTE--- | 251 |
| SEQ_ID_NO_357 | RVNYKYAPYV | AEFSDLILHG | CAVD-PIEFS | SKKCDTTS-- | 246 |
| SEQ_ID_NO_359 | RVNYKYAPYV | AEFSNLVLHG | CAVD-PIEHV | AKCESAQ--- | 250 |
| SEQ_ID_NO_360 | GVNYKYAPYV | SQFTDLILHG | CAVD-PIEKS | PKCDNGPT-- | 246 |
| SEQ_ID_NO_361 | KVNYKYAPYI | AEFSDFVLHG | CAVD-PTEKF | PSCKDEAV-- | 247 |
| SEQ_ID_NO_362 | KVNYKYAPYV | AKFSDFVLHG | CGVD-PIEMS | TSCDTAP--- | 245 |
| SEQ_ID_NO_363 | RVNYKYSPFV | VSLSNLVLEG | CAVD-PLEQF | PKCDIVL--- | 229 |
| SEQ_ID_NO_364 | | | | HTVSCPADT- | 263 |

| SEQ_ID_NO | | | | | |
|---|---|---|---|---|---|
| SEQ_ID_NO_348 | G-------- | TAAPAMSPAQ | RSAMEAFRAQ | HMTYGYCYDR | 282 |
| SEQ_ID_NO_350 | SASDDDDAYG | RAADAISPAR | RSAMEAFRAR | YMTYGYCYDR | 295 |
| SEQ_ID_NO_351 | A-------- | -SATMPPGRQ | RSAMERFRAR | HMTYGYCYDR | 288 |
| SEQ_ID_NO_353 | S-------- | GSAMPSRQ-- | RAAMERVRAR | HMTYGYCYDR | 276 |
| SEQ_ID_NO_355 | SQ------- | AIPTGVTPVQ | RTKMESFRAK | FMTYSYCYDR | 284 |
| SEQ_ID_NO_357 | SL------- | ELSATITPSQ | RSKMDSFRRK | HMTYSYCYDQ | 279 |
| SEQ_ID_NO_359 | SE------- | KVPSGVTPVQ | ITKMRNFRLK | HMAYSYCYDR | 283 |
| SEQ_ID_NO_360 | Q-------- | SIPTGIMPEQ | RSKMEKFRKT | HMTYSYCYDT | 279 |
| SEQ_ID_NO_361 | KA------- | RLASEITESQ | RNKMELFRQK | HMTYSYCYDH | 280 |
| SEQ_ID_NO_362 | NL------- | SVPTGTTKES | RTKMQNLRKK | YMQYSYCYDT | 278 |
| SEQ_ID_NO_363 | K-------- | SIPTRISPDQ | RRKMERFRNK | YLQYSYCYDR | 262 |
| SEQ_ID_NO_364 | D-------- | SQFSELSEDQ | KALMEWFRSK | YISYSYCDDD | 299 |

Figure 5E

| SEQ ID | | | | | | |
|---|---|---|---|---|---|---|
| SEQ_ID_NO_348 | LRYPAPLPEC | SVGPEAAAFL | PSGDALRAAL | RL---- | RRGR | 316 |
| SEQ_ID_NO_350 | LRYPAPLPEC | SVGAEAAAFL | PSGDARA-AL | H----- | RHGR | 329 |
| SEQ_ID_NO_351 | VRYHAPLPEC | SVGAEAEAFL | PSGEARS-TD | RRGG-- | RHGK | 325 |
| SEQ_ID_NO_353 | ARYQAPLPEC | RVGAEAAMYL | PSGEARSLSD | RRL--- | RHGK | 311 |
| SEQ_ID_NO_355 | VRYRAPPSEC | VI-NTKEADRL | KSYDPVTFGG | GRR--- | HHGK | 321 |
| SEQ_ID_NO_357 | TRYKVPPSEC | VI-NPREAERL | KRFDPVTFGG | -RR--- | HHGK | 315 |
| SEQ_ID_NO_359 | VRYKVPPPEC | VI-NHQEAERL | RKFDPVTFGN | GQRL-- | HRGK | 320 |
| SEQ_ID_NO_360 | MRYKVVLSEC | VVNAQEAERL | RVYDPVTFGG | RRHH-- | HHGK | 317 |
| SEQ_ID_NO_361 | TRYQVPPSEC | VVNPAEAKRL | RGFDPVTFGG | IPH--- | GHRR | 317 |
| SEQ_ID_NO_362 | TRYNVPPSEC | VIDPLESERL | RGFDPMTFGG | SHR--- | GHGK | 315 |
| SEQ_ID_NO_363 | VRYPTTPADC | VIDPKEANRL | ATAHV-RFGH | VPRL-- | HQNK | 299 |
| SEQ_ID_NO_364 | | PPRDP-HKKI | | HQRHRKK | NRK | 337 |

| SEQ ID | | | | | |
|---|---|---|---|---|---|
| SEQ_ID_NO_348 | RH-QT-- | RG------ | G-- | AV | DS | 328 |
| SEQ_ID_NO_350 | RN-RM-- | RR------ | G-- | AV | DS | 341 |
| SEQ_ID_NO_351 | RH-RRL- | AG------ | GG- | AL | DS | 338 |
| SEQ_ID_NO_353 | RH-RRL- | AG------ | A-- | SL | DS | 323 |
| SEQ_ID_NO_355 | RH-HHSSH | V------- | A-- | SI | VL | 336 |
| SEQ_ID_NO_357 | RH-HRSRASR | E------- | S-- | TI | AD | 330 |
| SEQ_ID_NO_359 | RHXHSSKGSQ | E------- | E-- | SF | TAS | 338 |
| SEQ_ID_NO_360 | RH-QRNRSSQ | R------- | G-- | TT | AT | 332 |
| SEQ_ID_NO_361 | GK-HRSRSRL | G------- | A-- | SI | TE | 332 |
| SEQ_ID_NO_362 | RH-HNRRSYR | E------- | H-- | SV | IN | 330 |
| SEQ_ID_NO_363 | RH-HQRQSRR | D------- | E-- | AK | TS | 314 |
| SEQ_ID_NO_364 | SH-RS--SS | GAAAA- | SL | VV | 352 |

| SEQ_ID_NO | | | | | |
|---|---|---|---|---|---|
| SEQ_ID_NO_774 | LVSNRGFEAG | GPNTPSNIDP | WL<u>I</u>GNESSI | FVETDRTSCF | 112 |
| SEQ_ID_NO_775 | LVSNRGFEAG | GPHTPSNIDP | WSIIGDDSSI | FVATDRTSCF | 114 |
| SEQ_ID_NO_776 | LVSNRGFEAG | G<u>L</u>HTPSNIDP | WSIIGDDSSI | FVATDRTSCF | 112 |
| SEQ_ID_NO_777 | LVSNRGFEAG | GPNTPSNIDP | WAIIGNESSL | LVSTDRSSCF | 111 |
| SEQ_ID_NO_778 | LVSNRGFEAG | GPNTPSNIDP | WAIIGNESFL | LVSTDRSSCF | 111 |
| SEQ_ID_NO_780 | LVSNRGFEAG | GPNTPSNIDP | WAII<u>N</u>GNESFL | <u>N</u>VETDRTSCF | 113 |
| SEQ_ID_NO_781 | LVSNRGFEAG | GPNTPSNIDP | WSIIGNESFL | LVSTDRSSCF | 111 |
| SEQ_ID_NO_782 | LVSNRGFEAG | GPNVPSNIDP | WSIIGNESSL | LVSTDRSSCF | 111 |
| SEQ_ID_NO_783 | LVSNRGFEAG | GQNTPSNIDP | WSIIGSESSL | LVSTDRSSCF | 103 |
| SEQ_ID_NO_785 | LVSNRGFE<u>G</u>G | GQNVPSNI<u>AP</u> | WSIIGDQSSL | <u>T</u>VSTDRSSCF | 111 |
| SEQ_ID_NO_786 | LV<u>N</u>NRGFEAG | GPNVPSNI<u>MP</u> | WSIIGDESK<u>V</u> | <u>Y</u>VATDRSSCF | 112 |
| SEQ_ID_NO_788 | LVSNRGFEAG | GPNTPSNIDP | WSIVGD<u>H</u>SSI | YVATDRSSCF | 118 |
| SEQ_ID_NO_789 | LVSNRGFEAG | GP<u>I</u>TPSNIDP | WAVIGNESYV | VVATDRSS<u>PF</u> | 111 |

| SEQ_ID_NO | | | | | |
|---|---|---|---|---|---|
| SEQ_ID_NO_774 | SRNIVALRME | VIC------ | ----NNI-- | --CPAGGVGI | YNPGFWGMNI | 145 |
| SEQ_ID_NO_775 | SRN<u>T</u>VALRME | VLC------ | ----DNI-- | --CPAGGVGI | YNPGFWGMNI | 147 |
| SEQ_ID_NO_776 | SRNIALRME | VLC------ | ----DD--- | --CPA<u>S</u>GVGI | YNPGFWGMNI | 145 |
| SEQ_ID_NO_777 | DRNKVALRME | VLC------ | ----DTQGA | NSCPAGGVGI | YNPGFWGMNI | 149 |
| SEQ_ID_NO_778 | DRNKVALRLE | V<u>S</u>C------ | ----DTQGA | NICPA<u>D</u>GVGI | YNPGFWGMNI | 149 |
| SEQ_ID_NO_780 | DRNKVALRME | VLC------ | ----DSE<u>G</u>D | NSCPAGGVGI | YNPGFWGMNI | 151 |
| SEQ_ID_NO_781 | DRNKVALRIE | VLC------ | ----DTQGA | NSCPDGGVGI | YNPGFWGMNI | 149 |
| SEQ_ID_NO_782 | ERNKVALRME | VLC------ | ----DSQGA | SSCPAGGVGI | YNPGFWGMNI | 149 |
| SEQ_ID_NO_783 | ERNKVALR<u>MH</u> | VLC------ | ----DSEGS | NICPAGGVGI | YNPGFWGMNI | 141 |
| SEQ_ID_NO_785 | DRNKIAVQVQ | VLC------ | ----D<u>HTGA</u> | NICPDGGVGI | YNPGFWGMNI | 149 |
| SEQ_ID_NO_786 | ERNKIALRMD | VLC------ | ----DSKG- | -<u>I</u>CPSGGVGV | YNPGFWGMNI | 150 |
| SEQ_ID_NO_788 | DRNKVALRMD | VLC------ | ----DSKG- | -<u>I</u>CPSGGVGV | YNPGYWGMNI | 153 |
| SEQ_ID_NO_789 | ERNKVALRVE | VLCGNDSNST | ----NT-- | --CPAGGVGV | YNPGYWGMNV | 151 |

| SEQ ID NO | | | | | Pos |
|---|---|---|---|---|---|
| SEQ_ID_NO_774 | LQLSEDLGAA | PIWFNSGLS | YNDEVDTAAI | APFVKDVLDS | 343 |
| SEQ_ID_NO_775 | LQLSEDLGAA | PIWFNNNGIS | HNDEVDTAAI | APFVKDVLDS | 345 |
| SEQ_ID_NO_776 | LQLSEDLGAA | PIWFNNNGIS | HNDEVSTAAI | APFVKDVLDS | 343 |
| SEQ_ID_NO_777 | LQLSEDLGSL | PIWFNNNGIS | HNDQVDTSSV | LPFVQEALDG | 349 |
| SEQ_ID_NO_778 | LQLSEDLGSL | PIWFNNNGIS | HNDQVDTSAV | LPFLVQEALDG | 349 |
| SEQ_ID_NO_780 | LQLSEDLGSL | PIWFNNNGIS | HNDQVDTSSV | LPFVQEALDG | 351 |
| SEQ_ID_NO_781 | LQLSEDLGTL | PIWFNNNGIS | HNDQVDTSSV | LPFVQEALDG | 349 |
| SEQ_ID_NO_782 | LQLAEDLGTR | PIWFNNNGIS | HNDQVDTSNI | LPFVQEALDG | 349 |
| SEQ_ID_NO_783 | LQLAEDLGAR | PVWFNNNGVS | HRDEVDTTTV | LPFVQEALDG | 341 |
| SEQ_ID_NO_785 | LQLAEDLDSL | PIWFNNNGIS | HNDEVETASI | SPFVQEDLDG | 347 |
| SEQ_ID_NO_786 | LQMAEDIGAA | PIWFNNNGIS | HNDEVDTASI | MPFVQEALDG | 348 |
| SEQ_ID_NO_788 | LQLAEDIGAL | PVWFNNNGIS | HNDEVDTTSI | GPFVQEVLDS | 353 |
| SEQ_ID_NO_789 | | | | | 351 |

| SEQ ID NO | | | | | Pos |
|---|---|---|---|---|---|
| SEQ_ID_NO_774 | LEFARGSANS | SWGSVRAAMG | HPEPFPVKYA | AIGNEDCGKK | 383 |
| SEQ_ID_NO_775 | LEFARGNADS | TWGSVRAAMG | HPEPFPVKYV | AIGNEDCGKK | 385 |
| SEQ_ID_NO_776 | LEFARGSANS | TWGSVRAAMG | HPEPFPVKYV | AIGNEDCGKK | 383 |
| SEQ_ID_NO_777 | LEFARGSPNS | TWGSLRAAMG | HPEPFDLRYV | AIGNEDCGKK | 389 |
| SEQ_ID_NO_778 | LEFARGSPNS | TWGSLRAAMG | HPEPFDLRYV | AIGNEDCGKK | 389 |
| SEQ_ID_NO_780 | LEFARGSPNS | TWGSLRAAMG | HPEPFDLRYV | AIGNEDCGKK | 391 |
| SEQ_ID_NO_781 | LEFARGDPTS | TWGSIRAAMG | HPEPFDLRYV | AVGNEDCGKK | 389 |
| SEQ_ID_NO_782 | LEFARGSPNS | TWGSIRAAMG | HPEPFDLRYV | AIGNEDCGKK | 389 |
| SEQ_ID_NO_783 | LEFARGSPNS | KWGSLRAAMG | HPEPFDLRYV | AIGNEDCGKK | 381 |
| SEQ_ID_NO_785 | LEFATGSPDS | TWGCLRAAMG | HPEPFDLKYV | AVGNEDCWKK | 387 |
| SEQ_ID_NO_786 | LEFARGDPTS | KWGSIRAKMG | HPEPFDLRYV | AIGNEDCGKT | 388 |
| SEQ_ID_NO_788 | LEFARGDANS | TWGSVRAKMG | RQEPFELKYV | AVGNEDCGKT | 393 |
| SEQ_ID_NO_789 | LEFARGASNS | TWGSVRITAMG | HEDPFNLKYI | AVGNEDCWKK | 391 |

Figure 6F

| SEQ_ID_NO | | | | | |
|---|---|---|---|---|---|
| SEQ_ID_NO_774 | FYNGNYLKFY | NAIREAYPDI | QLISNCDGSS | GPLDHPADLY | 423 |
| SEQ_ID_NO_775 | FYRGNYLKFY | NAIREAYPDI | QMISNCDASS | SPLDHPADLY | 425 |
| SEQ_ID_NO_776 | YYLGNYLKFY | NAIRESYPDI | QMISNCDGSS | KPLDHPADLY | 423 |
| SEQ_ID_NO_777 | NYRGNYLKFY | SAIRNAYPDI | KMISNCDGSS | RQLDHPADMY | 429 |
| SEQ_ID_NO_778 | NYRGNYLKFF | SAIRNAYPDI | KMISNCDGSS | RQLDHPADMY | 429 |
| SEQ_ID_NO_780 | NYRGNYLKFY | SAIKSAYPDI | QIISNCDGSS | RPLDHPADLY | 431 |
| SEQ_ID_NO_781 | NYRGNYLKFY | SAIRNAYPDI | KMISNCDGSS | RQLDHPADMY | 429 |
| SEQ_ID_NO_782 | NYRGNYLKFY | SAIKHAYPDI | KIISNCDGSS | RKLDHPADYY | 429 |
| SEQ_ID_NO_783 | NYRGNYLKFY | SAIKRAYPDI | QIISNCDGSS | HPLDHPADLY | 421 |
| SEQ_ID_NO_785 | QYRGNYLKFY | TAIKDKYPDI | KIISNCDGSS | HSLDHPADYY | 427 |
| SEQ_ID_NO_786 | YYRGNYIVFY | DAIKKAYPDI | KIISNCDGST | RPLDHPADLY | 428 |
| SEQ_ID_NO_788 | YYRGNYMRFY | DAIKRVYPDI | KLITNCDASS | HPLDHPADYY | 433 |
| SEQ_ID_NO_789 | NYRGNYMRFY | DAIKRVYPDI | KLITNCDASS | RKLNHPADYY | 431 |

| SEQ_ID_NO | | | | | |
|---|---|---|---|---|---|
| SEQ_ID_NO_774 | DFHVYADAKT | LFSMKNTFDK | TSRSGPKAFV | SEYAVWKITDA | 463 |
| SEQ_ID_NO_775 | DFHVYTDSKT | LFSMKNTFDR | SSRNGPKAFV | SEYAVWRSDA | 465 |
| SEQ_ID_NO_776 | DFHVYTDSKT | LFNMKGTFDK | TSRTGPKAFV | SEYAVWRTDA | 463 |
| SEQ_ID_NO_777 | DFHVYTSASN | LFSMANHFDH | TSRNGPKAFV | SEYAVTGKDA | 469 |
| SEQ_ID_NO_778 | DYHVYTNAND | LFSMANHFDH | TSRNGPKAFV | SEYAVTGKDA | 469 |
| SEQ_ID_NO_780 | DFHIYTSASN | MFYRANTFDH | TSRNGPKAFV | SEYAVTGKDA | 471 |
| SEQ_ID_NO_781 | DFHVYTDAKN | LFSMANHFDH | TSRSGPKAFV | SEYAVTGKDA | 469 |
| SEQ_ID_NO_782 | DFHVYTSASN | MFSMAHQFDR | TPRKGPKAFV | SEYAVTGKDA | 469 |
| SEQ_ID_NO_783 | DFHIYTSASS | LFSMTHQFDH | TSRSGPKAFV | SEYAVTGNDA | 461 |
| SEQ_ID_NO_785 | DFHVYTSASH | VFSNARHFDS | APRRGPKAFV | SEYAVTGKDA | 467 |
| SEQ_ID_NO_786 | DFHIYSSASS | LFSMYHQFDR | TSRKGPKAFV | SEYAVTGKDA | 468 |
| SEQ_ID_NO_788 | DFHIYTSASN | LYSMAHQFDR | TSRDAPKAFV | SEYAVTGKDA | 473 |
| SEQ_ID_NO_789 | DFHIYTSATN | | | | 471 |

Figure 6G

| SEQ_ID_NO | | | | | |
|---|---|---|---|---|---|
| SEQ_ID_NO_774 | GRGTLLASLA | EAAFLTGLEK | NSDVVEMACH | APLFVNDDE | 503 |
| SEQ_ID_NO_775 | GRGSLLASLA | EAAFLTGLEK | NSDVVQMASY | APLFVNNN-D | 504 |
| SEQ_ID_NO_776 | GRGSLLGSLA | EAAFLTGLEK | NSDV VHMASY | APLFVNDN-D | 502 |
| SEQ_ID_NO_777 | GRGSLLAALA | EAGFLIGLEK | NSDIVEMASY | APLFVNTH-D | 508 |
| SEQ_ID_NO_778 | GRGSLLAALA | EAGFLIGLEK | NSDIVEMASY | APLFVNTH-D | 508 |
| SEQ_ID_NO_780 | GTGSLLAALA | EAGFLIGLEK | NSDIVQMASY | APLFVNTH-D | 510 |
| SEQ_ID_NO_781 | GRGSLLAALG | EAGFLIGLEK | NSDIVESGHL | RPPL-RQ-H | 507 |
| SEQ_ID_NO_782 | GTGSLLAALA | EAGFLIGLEK | NSDVVEMASY | APLFVNAN-N | 508 |
| SEQ_ID_NO_783 | GTGGSLLAALG | EAGFLIGLEK | NSDIVEMASY | APLFVNDN-D | 500 |
| SEQ_ID_NO_785 | GTGSLLASLA | EAAFLIGLEK | NSEAIEMASY | APLFVNDN-D | 506 |
| SEQ_ID_NO_786 | GKGSLLAALA | EAAFLIGVEK | NSDIVEMASY | APLFVNDN-D | 507 |
| SEQ_ID_NO_788 | GTGSLLAALA | EAAFLIGLEK | NSDVVEMASY | APLFVNTN-D | 512 |
| SEQ_ID_NO_789 | GSGTLLAALA | EAAFLIGVEK | NSDVVEMASY | APLFVNSN-D | 510 |

| SEQ_ID_NO | | | | | |
|---|---|---|---|---|---|
| SEQ_ID_NO_774 | KKWNPDVVF | NTVQHYGTPS | YWMQVLFRES | SGAIVHPTTI | 543 |
| SEQ_ID_NO_775 | QTWNPDAIVF | NSVQQYGTPS | YWMQTLFGES | SGAMFHPVTI | 544 |
| SEQ_ID_NO_776 | QTWNPDAIVF | NSVQQYGTPS | YWMQKFFRES | SGAMTHPITI | 542 |
| SEQ_ID_NO_777 | RRWNPDAIVF | DSSQLYGTPS | YWQCLFNES | SGATLYNSTL | 548 |
| SEQ_ID_NO_778 | RRWNPDAIVF | DSSQLYGTPS | YWQCLFSES | SGATLYNSTL | 548 |
| SEQ_ID_NO_780 | RRWNPDAIVF | NSFQLYGTPS | YWQLFFNES | SGATLLSTSL | 550 |
| SEQ_ID_NO_781 | RRWNPDAIVF | DSSQLYGTPS | YWQCLFSES | SGATIFNATL | 547 |
| SEQ_ID_NO_782 | RRWNPDAIVF | NSSQLYGTPS | YWQCFFSES | SGATLFNATL | 548 |
| SEQ_ID_NO_783 | KRWSPDAIVF | TSSQMYGTPS | YWQHFKFFES | NGATLLSSSL | 540 |
| SEQ_ID_NO_785 | RRWNPDAIVF | NSSHLYGTPS | YWQRFAES | SGATLLDAKL | 546 |
| SEQ_ID_NO_786 | RRWNPDAIVF | NSSHLYGTPS | YWMQHFFSNS | SGATLLSSSL | 547 |
| SEQ_ID_NO_788 | RTWSPDAIVF | NSSFVYGTPS | YWMQHFFSNS | SGATLTSTL | 552 |
| SEQ_ID_NO_789 | RTWSPDAIVF | NSSFVYGTPS | YWMQHFFSNS | SGATLLNSTL | 550 |

Figure 6H

| SEQ ID | | | | | | Pos |
|---|---|---|---|---|---|---|
| SEQ_ID_NO_774 | SSSSSGN | SSL | AASAI TWQDS | D-NSSFLRVK | IINFESVAVQ | 582 |
| SEQ_ID_NO_775 | TSSYS- | GSL | AASAI TWQDS | EL--NSFLRVK | IINFGSDPVS | 580 |
| SEQ_ID_NO_776 | SSYS- | GSL | AASAI TWQNS | GL--NNFLRVK | IVNFGSDTVS | 578 |
| SEQ_ID_NO_777 | QMNSS- | TSL | LASAI SWQNS | ENENTYLRIK | VVNLGTYIYT | 586 |
| SEQ_ID_NO_778 | QMNSS- | NSL | LASAI SWQNS | ENENTYLRIK | VVNLGTTAVN | 586 |
| SEQ_ID_NO_780 | QAPS- | TPL | VASAI TFQNS | VDKKNYIRIK | VVNLGTDTVN | 588 |
| SEQ_ID_NO_781 | QMNSS- | TSL | LASAI SWQNS | ENENTYLRIK | IVNFGTTAVN | 585 |
| SEQ_ID_NO_782 | QTNLS- | SSL | LASAI SWKNS | ENGNSYLRIK | IVNFGSNIVN | 586 |
| SEQ_ID_NO_783 | QTESS- | TSL | LASAI TWTNS | EDQKTYLRIK | LVNFGNRHVS | 578 |
| SEQ_ID_NO_785 | QTNSL- | SSL | VASAI TWRNS | LDNNDYLRIK | VVNFGTTAVI | 583 |
| SEQ_ID_NO_786 | QANPS- | NSL | LASAI SWKNN | GL--KDYIRIK | AMNFGANSEN | 585 |
| SEQ_ID_NO_788 | KGNLS- | ITSL | LASAI TWKSS | QDNKTYIKLK | VVNFRNVSVS | 587 |
| SEQ_ID_NO_789 | TNNSS- | SSL | LASAI TWKSS | QDNKTYIKLK | VVNFRNVSVS | 588 |

| SEQ ID | | | | | | Pos |
|---|---|---|---|---|---|---|
| SEQ_ID_NO_774 | ITISTITGLQA | SL-ID- | VLRST | ATVLTSSNVM | DENSFSNQDK | 620 |
| SEQ_ID_NO_775 | LTI-SATGLQA | R-VN- | ALGST | ATVLTSSNVM | DENSFSNPNK | 618 |
| SEQ_ID_NO_776 | LTI-SVSGLQA | SL-N- | ALGSN | ATVLTSSNVK | DENSFSNPTK | 616 |
| SEQ_ID_NO_777 | LKVFVDGLEP | NSVS- | LSGST | KTVLTSNNQM | DENSFNEPKK | 625 |
| SEQ_ID_NO_778 | LQVFVDGLEP | NSIS- | LSGST | KTVLTSANVM | DENSFNDPTK | 625 |
| SEQ_ID_NO_780 | LKISLDGLEP | NSLQ- | LSGST | KTVLTSNNQM | DENSFSQPKK | 627 |
| SEQ_ID_NO_781 | LKVFVDGLEP | NSIN- | LSGST | KTVLTSNNQM | DENSFNEPKK | 624 |
| SEQ_ID_NO_782 | LKIVMDGLEP | NSVS- | LSEST | KTVLTSTNLM | DENSFDEPKK | 625 |
| SEQ_ID_NO_783 | LRIRMDGLDP | -EQ- | MSGST | MTELTSNNVM | DENSFTDPNK | 617 |
| SEQ_ID_NO_785 | LKVSVDGLGL | -Q- | LSGST | KNVLTSNNVM | DENSFREPNK | 621 |
| SEQ_ID_NO_786 | TKISLTGLGQ | NSLET | LFGAV | KTVLTSNNVM | DENSFSQPEK | 625 |
| SEQ_ID_NO_788 | MQVLVTGLDP | NVMR- | VSGSK | KTVLTSNNVM | DENSFSQPEK | 626 |
| SEQ_ID_NO_789 | LKISVDGLQT | NSLQ- | LSGAT | KTVLTSNNVM | DENSFKEPTK | 627 |

Figure 6 I

| SEQ_ID_NO | Sequence | # |
|---|---|---|
| SEQ_ID_NO_774 | VSPVKSQLFD AG-- AHMQV TLAPHSFTSF DLALAPSKL | 656 |
| SEQ_ID_NO_775 | VPVKSQLSN AA-- EQMQV TLAPHSFSSF DLALAQSKL- | 653 |
| SEQ_ID_NO_776 | VVPVTSQLHN AA-- EQMQV TLAAHSFSSF DLALAQSEL- | 651 |
| SEQ_ID_NO_777 | VIPKRSLLES AG-- EEMEV VISPRSFTSI DLLMESSDVI | 662 |
| SEQ_ID_NO_778 | VIPKQSLLES AG-- EEMEV VISPRSFTSI DLLMESSDI- | 662 |
| SEQ_ID_NO_780 | VVPIQSLLQN VE-- KDMNV TVPPRSFTSF DLLKQSSNL- | 663 |
| SEQ_ID_NO_781 | VIPNRLLEK AS-- EEMEV VISPRSFTSI DLLMESSDI- | 661 |
| SEQ_ID_NO_782 | VIPNLGLLEN AGEDGE EEMDV AISPHSFTSI DFLIESSF-- | 664 |
| SEQ_ID_NO_783 | VVPDLSLLEN AG-- EEMDV GLSAHSFTSL DLLVEPSH-L | 653 |
| SEQ_ID_NO_785 | VIPVKTQVEK AD-- KDMNI TIAPYSLTSL DLLTESNN-- | 657 |
| SEQ_ID_NO_786 | VVPHESLLEL VS-- DNMDV VLAPRSLNSI DFLLRKSL-- | 661 |
| SEQ_ID_NO_788 | VAPFRFELKD AE-- EDMTV VLPPHSFSSF DLLKESAKI- | 662 |
| SEQ_ID_NO_789 | VAPFRFELKD VG-- KDLDA ELPAYSFTAF DLLTDSSS-L | 663 |

| SEQ_ID_NO | Sequence | # |
|---|---|---|
| SEQ_ID_NO_774 | VTLAGRV--N KYLISEL | 671 |
| SEQ_ID_NO_775 | ---- LVAEM | 658 |
| SEQ_ID_NO_776 | ---- LVAEM | 656 |
| SEQ_ID_NO_777 | RTTGAD SVSVSSI | 675 |
| SEQ_ID_NO_778 | RTTGAD SVSVSSI | 675 |
| SEQ_ID_NO_780 | KMAGSD SSTWSSI | 676 |
| SEQ_ID_NO_781 | RTTGAD SVSVSSI | 674 |
| SEQ_ID_NO_782 | -TTGAD SSISSS | 677 |
| SEQ_ID_NO_783 | RMPQTD SSARSSI | 665 |
| SEQ_ID_NO_785 | NNVDTIA SVLKSSC | 670 |
| SEQ_ID_NO_786 | RMPISDSS HQKTITTV | 674 |
| SEQ_ID_NO_788 | QTVEITD AGYKSSI | 678 |
| SEQ_ID_NO_789 | | 676 |

| SEQ_ID_NO_416 | GNI PHCCKRT | PAVVDLLPGV | PYNQQIANCC | RGGVISAYGQ | 135 |
|---|---|---|---|---|---|
| SEQ_ID_NO_418 | ANI PHCCKRT | PTVVDLLPGV | PYNQQIANCC | RGGVISAYGQ | 135 |
| SEQ_ID_NO_419 | ANI PHCCKRT | PAVVDLLPGV | PYNQQIANCC | RGGVVSAYGQ | 137 |
| SEQ_ID_NO_420 | ANL PHCCRRT | PAVVDLLPGV | PYNQQIANCC | RGGVLPAYGQ | 135 |
| SEQ_ID_NO_422 | GGI PHCCKHT | PSVVDLLPGV | PYNQQIANCC | RGGVSAYGQ | 136 |
| SEQ_ID_NO_423 | GNI PHCCKKT | PTVVDLLPGV | PYNQQFSNCC | KGGVMAAWGQ | 154 |
| SEQ_ID_NO_424 | GNV PHCCKKT | PTLVDLLPGV | PYNQQFSNCC | KGGVAAWGQ | 139 |
| SEQ_ID_NO_426 | GNI PHCCKKT | PTVVDLLPGV | PYNQQIANCC | KAGVAAWGQ | 133 |
| SEQ_ID_NO_427 | ANI PHCCKKT | PTVVDLLPGV | PYNQQFSNCC | KGGVIGAWGQ | 164 |
| SEQ_ID_NO_429 | GNV PHCCKKT | PTVVDLLPGT | PYNQQFSNCC | KGGVAAWGQ | 134 |
| SEQ_ID_NO_430 | GNV PHCCKKT | PTVVDLLPGV | PYNQQIANCC | KGGVLASWAQ | 165 |
| SEQ_ID_NO_431 | GNI PHCCKNK | PTVVDLLPGT | PYNQQIANCC | KGGVLNSWVQ | 153 |
| SEQ_ID_NO_433 | GNV PHCCKKD | PTVVDLLPGT | PYNQQIANCC | KGGVLASWAQ | 150 |
| SEQ_ID_NO_434 | AGSPHCCKKD | PTVVDLLPGV | PYNQQFTNCC | KGGALASWAQ | 160 |

| SEQ_ID_NO_416 | DPGAVAAFQ | VSVGQAGTTN | RTVKVPKNFT | LLGPGPGYTC | 175 |
|---|---|---|---|---|---|
| SEQ_ID_NO_418 | DPAVAAFQ | VSVGQAGTTN | RTVKVPKNFT | LLGPGPGYTC | 175 |
| SEQ_ID_NO_419 | DPATAVAAFQ | VSVGQAGTTN | RTVKVPKNFT | LLGPGPGYTC | 177 |
| SEQ_ID_NO_420 | APSAAAAAFQ | VSVGQAGTTN | RTVRLPKNFT | LLGPGPGYTC | 175 |
| SEQ_ID_NO_422 | DPAGALSAFQ | VSVGLAGTTN | KTVKLPKNFT | LMGPGPGYTC | 176 |
| SEQ_ID_NO_423 | DPTASVSAFQ | VSVGLAGTSN | KTVKLPKNFT | LLGPLGYTC | 194 |
| SEQ_ID_NO_424 | DPSASVSQFQ | VSVGLAGTSN | KTVKLPKNFT | LLGPGPGYTC | 179 |
| SEQ_ID_NO_426 | DPQAISSFQ | VSVGQAGTTN | KTVKLPKNFT | LFAPGPGYTC | 173 |
| SEQ_ID_NO_427 | DPAGSVVSFQ | VSVGQAGTTN | KTVKLPKNFT | LLGPGPGYTC | 204 |
| SEQ_ID_NO_429 | DPSAAVSQFQ | VSVGQAGTTN | KTVKLPKNFT | LLGPGPGYTC | 174 |
| SEQ_ID_NO_430 | DPSSAVSAFQ | VSAGLAGTTN | KTVKLPKNFT | LLGPGPGYTC | 205 |
| SEQ_ID_NO_431 | DPVNAVSAFQ | VSTGLAGTTN | TTVRLPKNFT | LLGPGPGYTC | 193 |
| SEQ_ID_NO_433 | DPANAASSFQ | VSVGNAGTTN | KTVRVPRNFT | LKAPGPGYTC | 190 |
| SEQ_ID_NO_434 | DPPNSVASFQ | VSVGNSGTTN | KTVKLPKNFT | LKAPGPGYTC | 200 |

| SEQ_ID_NO | | | | | | Pos |
|---|---|---|---|---|---|---|
| SEQ_ID_NO_416 | TCVQG- | -DS | KRP LAVTGKH | THAAL-ATRL | ----- | HRDK 272 |
| SEQ_ID_NO_418 | TCVQG- | -DS | KRL LAVTGKH | EHAHA-AARL | -G--- | HRDK 273 |
| SEQ_ID_NO_419 | TCVQG- | -DS | KRL LAVTGKH | AHTAA-AVRL | -G--- | HRDK 275 |
| SEQ_ID_NO_420 | PCVRSERDG | DS | KRL LAVTGKK | NAHANA-AM | RGNGVAAAM | QHRDK 281 |
| SEQ_ID_NO_422 | DGCI-AG- | NS | KKR ALTPGVN | HD-T- | ----- | PKKD 278 |
| SEQ_ID_NO_423 | SCVKSI- | DS | KE- SHKKGI N | T- | ----- | PKKD 284 |
| SEQ_ID_NO_424 | GCVKSI- | DS | KIT SVKGI N | T- | ----- | PRKD 269 |
| SEQ_ID_NO_426 | HCVKG- | DS | KKI LSMVGVH | T- | ----- | PKKD 263 |
| SEQ_ID_NO_427 | MCI SSI- | DS | KKL LK- AL H | N- | ----- | PKRS 292 |
| SEQ_ID_NO_429 | SCVKA- | DS | KRL TKKGL L | T- | ----- | PKKD 264 |
| SEQ_ID_NO_430 | NCI KSI- | DS | KRL NMVGI H | T- | ----- | PKKD 295 |
| SEQ_ID_NO_431 | GTCVESI- | DS | PVI LPSLLN- | G- | ----- | SPKN 286 |
| SEQ_ID_NO_433 | GSCVSE- | RS | SH- LASAVPL | ----- | ----- | KSTN 283 |
| SEQ_ID_NO_434 | PSCVHSI- | DS | PVI LKLPGPT | N- | ----- | PITN 293 |

| SEQ_ID_NO | | | | | | Pos |
|---|---|---|---|---|---|---|
| SEQ_ID_NO_416 | ----EAPLLQCT | THMCPVRVHW | HVKLNYKEYW | RAKI AI TNFN | 310 |
| SEQ_ID_NO_418 | ----EAPLLQCT | THMCPVRVHW | HVKLNYKEYW | RAKI AI TNFN | 311 |
| SEQ_ID_NO_419 | ----EAPLLQCT | THMCPVRVHW | HVKLNYKEYW | RAKI AI TNFN | 313 |
| SEQ_ID_NO_420 | ----AAPLLQCT | HHMCPVRVHW | HVKLNYKREYW | RAKI TI VNFN | 319 |
| SEQ_ID_NO_422 | ----GAQLLQCT | LLQCT NHMCPI RVHW | HVKLNYKEYW | RAKI AVTNFN | 316 |
| SEQ_ID_NO_423 | ----NTPLLQCT | HHMCPI RVHW | HVKVNYRDYW | RAKVAVTNFN | 322 |
| SEQ_ID_NO_424 | ----NAPLLQCT | HHMCPI RVHW | HVKVNYKDYW | RAKVAI TNFN | 307 |
| SEQ_ID_NO_426 | ----NTPLLQCT | HHMCPI RVHW | HVKLNYKDYW | RAKI AI TNFN | 301 |
| SEQ_ID_NO_427 | ----NEPLLQCT | HHMCPI RVHW | HVKLNYKDYW | RVKI AI TNFN | 330 |
| SEQ_ID_NO_429 | ----NTPLLQCT | HHMCPI RVHW | HVKLNYMDYW | RVKVAI TNFN | 302 |
| SEQ_ID_NO_430 | ----NEPLLQCT | PHMCPI KI HW | HVKLNYKEYW | RVKVAI TNFN | 333 |
| SEQ_ID_NO_431 | ----LAPLI QCT | SHMCPVRI HW | HVKLNYKEYW | RVKVAVTNFN | 324 |
| SEQ_ID_NO_433 | ----APPLLQCT | APPLLQCT RHMCPVRVHW | HVKLNYKDYW | RVKI TI TNFN | 321 |
| SEQ_ID_NO_434 | SLQPPLLQCT | RHMCPVRVHW | HVKLNYKDYW | RVKI TVTNFN | 333 |

Figure 7F

| | 350 | 351 | 353 | 359 | 356 | 362 | 347 | 341 | 370 | 342 | 373 | 364 | 361 | 373 |
|---|---|---|---|---|---|---|---|---|---|---|---|---|---|---|
| SEQ_ID_NO_416 | YRMNYTQWTL | VAQHPNLDNI | TEVFSFDYKP | VVAYGSI NDT |
| SEQ_ID_NO_418 | YHMNYTQWTL | VAQHPNLDNI | TEVFSFDYKP | VVAYGSI NDT |
| SEQ_ID_NO_419 | YHMNYTQWTL | VAQHPNLDNI | TEVFSFDYKP | VVSYGSI NDT |
| SEQ_ID_NO_420 | YRMNYTQ[G]MTL | VAQHPNLDNI | TEVFSF[G]YKP | VVSYGSI NDT |
| SEQ_ID_NO_422 | YRMNYTQWTL | VAQHPNLNNV | TEVFSF[Q]YKP | LLPYGNI NDT |
| SEQ_ID_NO_423 | YRMNYTEWTL | VAQHPNLNNV | TQVFSFDYKP | LVPYESI NDT |
| SEQ_ID_NO_424 | YRMNFSLWTL | AI QHPNLNNL | TQVFSFDYKP | LVPYESI NDT |
| SEQ_ID_NO_426 | YRMNHSLW[S]L | AVQHPNLDNI | TQVFSFDYKP | LLPYGSI NDT |
| SEQ_ID_NO_427 | YRMNHTLWTL | AI QHPNLNNV | TQVFSFNYKP | LVPYGSI NDT |
| SEQ_ID_NO_429 | YRMNYSLWTL | AVQHPNFDNV | TQLFSFDYKP | V[SP]YGSI NDT |
| SEQ_ID_NO_430 | Y[A]LNYSQWNL | VVQHPNFDNL | TQLFSFNYKP | LPYESI NDT |
| SEQ_ID_NO_431 | YRMNYTQWNI | VVQHPNFDNV | TQVFSFNYKP | LTPYG[K]I NDT |
| SEQ_ID_NO_433 | YRMNYT[D]MTL | VAQHPNLDNV | TQVFSFNYKP | LTPY[AG]L NDT |
| SEQ_ID_NO_434 | | | | LTPYGSI NDT |

| | 390 | 391 | 393 | 399 | 396 | 402 | 387 | 381 | 410 | 382 | 413 | 404 | 401 | 413 |
|---|---|---|---|---|---|---|---|---|---|---|---|---|---|---|
| SEQ_ID_NO_416 | AMFYGLKYFN | DHLMQAGPYG | NVQSEVLMRK | DASTFTFRQG |
| SEQ_ID_NO_418 | AFYGLKYFN | DHLMQAGPYG | NVQSEVLMRK | DASTFTFRQG |
| SEQ_ID_NO_419 | AMFYGLKYFN | DHLMQAGPYG | NVQSEVLMRK | DASTFTFRQG |
| SEQ_ID_NO_420 | AMFYGLKYFN | DLMEAGPHG | NVQSEVLMRK | DASTFTF[G]QG |
| SEQ_ID_NO_422 | GMFYGLK[L]YN | D[Q]LMEAGPFG | NVQSEVLMRK | AR[T]FTF[G]KQG |
| SEQ_ID_NO_423 | GMFYGMK[FYN | DLLMEAGPFG | NVQSELLLQK | D[A]TFTFKQG |
| SEQ_ID_NO_424 | GMFYGMKYYN | DLLMEAGPTG | NVQSELLLQK | DKNTFSLKQG |
| SEQ_ID_NO_426 | GMFYGMKYYN | DLLVEAGP[H]G | NVQSELLLQK | DRNTFTFKQG |
| SEQ_ID_NO_427 | GMFYG[T]KFYN | DLLMEAGPTG | NVQSELLLQK | D[K]TFTFKQG |
| SEQ_ID_NO_429 | GMFYGMKYFN | DMLMEAGP[SG] | NVQSEI LLQK | NKDTFTFKQG |
| SEQ_ID_NO_430 | AMLWGVKYYN | DML NEAGP[MG] | NVQSELLFQK | DKDTFTLKQG |
| SEQ_ID_NO_431 | AMLWGLKFYN | D[F]LNEAGP[LG] | NVQSELLFRK | DKDTFTFEKG |
| SEQ_ID_NO_433 | AMFWG[Q]KYYN | DLLMQAGPMG | SVQSELLLRK | DKQTFTFKQG |
| SEQ_ID_NO_434 | | | | |

| | | | | | | |
|---|---|---|---|---|---|---|
| SEQ_ID_NO_2 | ---- | ---- | GLL- | -AAA | LVAAA | -LAL | 20 |
| SEQ_ID_NO_4 | ---- | ---- | -AL- | -AAA | LVAAV | -AAG | 22 |
| SEQ_ID_NO_6 | ---- | ---- | PIT- | LAA- | LVAAA | -A-G | 21 |
| SEQ_ID_NO_7 | RGAPSG | MRSP- | RWP- | -AAL | LVAAA | -AAG | 29 |
| SEQ_ID_NO_8 | ---- | MKSR- | GLW- | FMFL | LILL- | RSP- | 22 |
| SEQ_ID_NO_10 | ---- | MKLP- | LFN- | LFL- | LLLL- | TKAA | 25 |
| SEQ_ID_NO_12 | ---- | MVRL- | KLS- | LWL- | LALV- | QLN- | 23 |
| SEQ_ID_NO_14 | ---- | MTRT- | KTS- | ANLT | QIRYT | AAS- | 22 |
| SEQ_ID_NO_15 | ---- | MFRG- | VLQ- | LMLF | LVI-FSNM | AGSS | 28 |
|  |  | RLV- |  |  |  | VSS |  |

| | | | | | | |
|---|---|---|---|---|---|---|
| SEQ_ID_NO_2 | ---- | ---- | G--- | AGAA | TEEAYVTLLY | GDEFVLGVRV | 45 |
| SEQ_ID_NO_4 | ---- | ---- | V--- | AAAA | TEEAYVTLLY | GDEFVLGVRV | 47 |
| SEQ_ID_NO_6 | ---- | ---- | G--- | AAAA | TEEAYVTLLY | GDEFVLGVRV | 46 |
| SEQ_ID_NO_7 | ---- | ---- | A--- | AAAA | KDEAYVTLLY | GDEFVLGVRV | 55 |
| SEQ_ID_NO_8 | ---- | ---- | P--- | VRAS | GSEAYVTLLY | GDEFLLGVRV | 47 |
| SEQ_ID_NO_10 | ---- | ---- | K--- | AQSS | SKVAYVTLLY | GDEFLLGVRV | 50 |
| SEQ_ID_NO_12 | ---- | ---- | F--- | GSES | SKVAYVTLLY | GDEFLLGVRV | 48 |
| SEQ_ID_NO_14 | ---- | ---- | Q--- | RISQR | TEEAYVTLLY | GDEFLLGVRV | 47 |
| SEQ_ID_NO_15 | RSFLTEGLNP | QAKI | A--- | GQSR | SEHAYATLLY | GDEFLLGVRV | 67 |

| | | | | | | |
|---|---|---|---|---|---|---|
| SEQ_ID_NO_2 | LGKSL | RDTGT | RRDMVVLVSD | GVSEYSRKLL | QEDGW VNRI | 85 |
| SEQ_ID_NO_4 | LGKSL | RDTGT | RRDMVVLVSD | GVSEYSRKLL | QADGW VNRI | 87 |
| SEQ_ID_NO_6 | LGKSI | RDTGT | RRDMVVLVSD | GVSEYSRKLL | EADGW VKRI | 86 |
| SEQ_ID_NO_7 | LGKSI | RDTGT | SRDLVVLVSD | GVSEYSRELL | EADGFI VKH | 95 |
| SEQ_ID_NO_8 | LGKSI | RDTDT | TKDMVVLVSD | GVSDYAKKLL | QADGWM VELJ | 87 |
| SEQ_ID_NO_10 | LGKSI | RDTGS | TKDMVVLVSD | GVSDYAKKLL | KADGWMVEM | 90 |
| SEQ_ID_NO_12 | LGKSI | RDTGS | TKDMVVLVSD | GVSDYSKKLL | KADGWKVEKI | 88 |
| SEQ_ID_NO_14 | LGKSI | RDTGS | TKDMVALVSD | GVSDAGI RLL | LADGW VEKI | 87 |
| SEQ_ID_NO_15 | LGKSI | RDTGV | TKDMVALVSD | GVSDAGI RLL | EADGW VQRI | 107 |

| | | | | | | | |
|---|---|---|---|---|---|---|---|
| SEQ_ID_NO_157 | DS-ED- | | | | | | 177 |
| SEQ_ID_NO_158 | DT-ED- | | | | | | 178 |
| SEQ_ID_NO_160 | DT-ED- | | | | | | 177 |
| SEQ_ID_NO_161 | DT-ED- | | | | | | 177 |
| SEQ_ID_NO_162 | DAAED- | | | | | | 181 |
| SEQ_ID_NO_163 | DA-ED- | | | | | | 177 |
| SEQ_ID_NO_164 | DQ-DQPLPVE | EETRKAGGK | IKLQAEPAAT | EPQQLPTPGR | | | 242 |
| SEQ_ID_NO_165 | TT-IS- | | | | | | 137 |
| SEQ_ID_NO_167 | NT-NS- | | | | | | 74 |
| SEQ_ID_NO_168 | NS-QT- | | | | | | 115 |
| SEQ_ID_NO_170 | -L | | | | | | 69 |

| | | | | | | | |
|---|---|---|---|---|---|---|---|
| SEQ_ID_NO_157 | TE-NGKQ | DDGT | GSDLQGSK | PLCDFSN- | FR | | 204 |
| SEQ_ID_NO_158 | TE-NAKR | DDI-T- | SYDQGSK | PLCDFSN- | FR | | 204 |
| SEQ_ID_NO_160 | TE-TAKK | DDI-T- | SYDQGSK | PLCDFSN- | FR | | 203 |
| SEQ_ID_NO_161 | TQ-NAKQ | DDI-T- | SNDQGSK | PLCDFSN- | FR | | 203 |
| SEQ_ID_NO_162 | TE-NAKQ | EGI-M- | NNVQGSK | PLCDFSN- | FR | | 207 |
| SEQ_ID_NO_163 | AE-PERR | EG-LSLSNVQ | HEQQQGSK | PLCDFSD- | FR | | 211 |
| SEQ_ID_NO_164 | LETSE-EVIS | AS-R- | DQPPQLLP | PLCTKLA- | RR | | 271 |
| SEQ_ID_NO_165 | KE-SLPKATD | DE-- | NKLEKTMK | PICTKLA- | -R | | 161 |
| SEQ_ID_NO_167 | -SLPKATD | AD-V- | VTKNNTLE | PLCTLMG- | -R | | 100 |
| SEQ_ID_NO_168 | -EHPIGEA | SK-I- | TAEESAPAKK | PACDIQGPMA | | | 147 |
| SEQ_ID_NO_170 | -LQ-ELVE | E- | S-TSAKSIF | NACDCEP- | -I | | 92 |

| SEQ_ID_NO_157 | RMFLNLDEII | AMAEELGFEV | VTDEANVSSD | ISKFARLVNT | 454 |
| --- | --- | --- | --- | --- | --- |
| SEQ_ID_NO_158 | RMFLNLDEII | AMAEELGFEV | VIDEANVSSD | ISKFASLVNT | 454 |
| SEQ_ID_NO_160 | RMFLNLDEIV | AMAEELGFEV | VIDEANVSSD | ISKFARLVNT | 453 |
| SEQ_ID_NO_161 | RMFLNLDEII | AMAEELGFEV | VIDEANVSSD | ISKFAALVNT | 453 |
| SEQ_ID_NO_162 | RMFLNLDEII | AMAEELGFEV | VIDEANVSSD | SRFARLVNS | 457 |
| SEQ_ID_NO_163 | RMFLNLEEII | SMAEELGFEV | VIDEANVSSD | INGFAKLVNS | 461 |
| SEQ_ID_NO_164 | RILLNLGDMM | GMAEEIAGFE | ANSELDVGDP | SRVGAEINS | 524 |
| SEQ_ID_NO_165 | RAFVNTGEIA | RAJARQGFKV | VVAEANIG-- | LAKFAQTVNS | 418 |
| SEQ_ID_NO_167 | RAFTNVGEIV | TMAKRLGYRV | VVAEPDF-AD | VSGFAQIINS | 356 |
| SEQ_ID_NO_168 | RKLVNVDEVV | ALAKRIGFEV | VIGDPPFNVD | VADFAREVNA | 406 |
| SEQ_ID_NO_170 | RSFTNIDKIT | RMASSLGYNM | VTMEPNISTS | LGSVAETVNS | 341 |

| SEQ_ID_NO_157 | VDVMMGVHGA | GLTNCVFLPQ | NATLIQIVPW | GGLEWSRTD | 494 |
| --- | --- | --- | --- | --- | --- |
| SEQ_ID_NO_158 | VDVMMGVHGA | GLTNCVFLPQ | NATLIQIVPW | GGLEWSRTD | 494 |
| SEQ_ID_NO_160 | VDVMMGVHGA | GLTNCVFLPQ | NATLIQIVPW | GGLEWSRTD | 493 |
| SEQ_ID_NO_161 | VDVMMGVHGA | GLTNCVFLPQ | NATLIQIVPW | GGLDWSRTD | 493 |
| SEQ_ID_NO_162 | VDVMMGVHGA | GLTNCVFLPQ | NATLIQIVPW | GGLDWSRTD | 497 |
| SEQ_ID_NO_163 | VDVMMGVHGA | GLTNCVFLPQ | HATLIQIVPF | GGLDMSRTD | 501 |
| SEQ_ID_NO_164 | ADVLVGVHGA | GLTNMMSLAP | GATMVQVVPW | GGLQWFARMD | 564 |
| SEQ_ID_NO_165 | CDVVMGVHGA | GLTNMVFLPE | NAVVIQVLPI | GGFEWLAKTD | 458 |
| SEQ_ID_NO_167 | CDVLMGVHGA | GLTNVFLPE | NAVLVQVIPF | GGTEWLSRTIY | 396 |
| SEQ_ID_NO_168 | ADVLMGVHGA | GMTNSLFLPT | GAVFIQVNPF | GKMEHIGEVD | 446 |
| SEQ_ID_NO_170 | CDVLMGIHGA | GLTNMVFLPD | NATVIQIVPL | GSIDELAKQD | 381 |

Figure 9 I

| SEQ_ID_NO | | | | | | |
|---|---|---|---|---|---|---|
| SEQ_ID_NO_157 | FGNPAELMGM | HYKQYSI SVD | ESSLTEQYPR | DHEIFKNPIA | 534 |
| SEQ_ID_NO_158 | FGNPAELMGL | HYKQYSI GVD | ESSLTEQYPR | DHEIFKNPIA | 534 |
| SEQ_ID_NO_160 | FGNPAELMGL | HYKQYSI GVD | ESSLTEQYPR | DHEIFKNPIA | 533 |
| SEQ_ID_NO_161 | FGNPAELMGL | HYKQYSI GVH | ESSLTEQYPS | DHEIFKNPIA | 533 |
| SEQ_ID_NO_162 | FGNPAELMGL | RYKQYSI GVD | ESSLTDQYPR | DHEIFKNPIS | 537 |
| SEQ_ID_NO_163 | FGNPSEMMGL | RYKQYAI TVD | ESSLTDHYPR | DHKIFKDPIS | 541 |
| SEQ_ID_NO_164 | YGDPAEALGL | RYVQYEI GVD | ESSLKDKYPR | GHKIFTDPTS | 604 |
| SEQ_ID_NO_165 | FEKPSEGMNL | RYLEYKI AVE | ESTLVKKYGR | DHEIVRDPSA | 498 |
| SEQ_ID_NO_167 | FEEPAKGMNI | RYLDYKI RLE | ESTLIQQYPA | DHVMLRDPSA | 436 |
| SEQ_ID_NO_168 | FGTPAVDMGL | KYMSYSCGME | ESTLVDTLGR | DHPAVKDPES | 486 |
| SEQ_ID_NO_170 | FEQPAMDMEL | SYLEYKI KAK | ESSLISKYKA | DHLTKDPLS | 421 |

| SEQ_ID_NO | | | | | | |
|---|---|---|---|---|---|---|
| SEQ_ID_NO_157 | FHKGFDFIR | QTFMDKQNVK | LDCKRFRPIL | LEALDNLNP | 573 |
| SEQ_ID_NO_158 | FHKGFDFIR | QTFMDKQNVK | LDCKRFRPIL | LEALDNLNP | 573 |
| SEQ_ID_NO_160 | FHKNGFDFIR | QTFMDKQNVK | LDCKRFRPIL | LEALDNLNP | 572 |
| SEQ_ID_NO_161 | FHKKGFDFIR | QTFMDKQNVK | LDCKRFRPIL | LEALDNLNA | 572 |
| SEQ_ID_NO_162 | FHQRGFEFIR | QTFMDKQNVR | LDCKRFRPVL | LEALDNLNP | 576 |
| SEQ_ID_NO_163 | FHKKGFGFMR | RTFMDKQNVR | LDCKRFRPIL | LEALDNLNQ | 580 |
| SEQ_ID_NO_164 | LHKKGFGFMR | RTLMDGQNIT | DLGRFRACS | - - - - SRR | 637 |
| SEQ_ID_NO_165 | VAKHGWEMFK | SVYLVQQNVS | DINRFKPVL | VKALELL - | 535 |
| SEQ_ID_NO_167 | LMKQGWSAVE | SIYLRQQNVT | LVNRFRPTL | VKALDLLHQ | 475 |
| SEQ_ID_NO_168 | HRSGWNKVA | EFYLGKQDVK | LDQRFEPVL | LKAMAMLRE | 525 |
| SEQ_ID_NO_170 | VHKQGWDAVR | SIYLDKQNVK | LDIKRFRPTL | LKALQLLHQ | 460 |

Figure 10A

| SEQ_ID_NO | | | | | | |
|---|---|---|---|---|---|---|
| SEQ_ID_NO_280 | M-M-MGRP | NQSH | G- | SGGDEER | L-P- | -RGGLET | 27 |
| SEQ_ID_NO_282 | -MGRQ- | SNSY | G- | SGGDEER | L-P- | -RGVLET | 25 |
| SEQ_ID_NO_283 | -MGRP- | SNSH | G- | GGGDEER | L-P- | -RGVLET | 25 |
| SEQ_ID_NO_284 | M- | | | | | | 1 |
| SEQ_ID_NO_285 | MDLK- | SSTR- | R- | | S-P- | P-SEDTDQ | 19 |
| SEQ_ID_NO_286 | MKSI- | TLVA | TE- | SGSGAKK | G-P- | RR-AGYGM | 27 |
| SEQ_ID_NO_288 | MWE- | F- | | | | | 5 |
| SEQ_ID_NO_289 | MD-QN- | SYRR | | S- | S-P- | -RT-T-TGG | 19 |
| SEQ_ID_NO_290 | MNMLI | KRVIA | I- | | N-P- | R-GDDNNN | 21 |
| SEQ_ID_NO_292 | MQQR- | -KAPK | ASAEG | VTEQE | ASP-AAVLPRT | ATA-RDLLEA | 37 |

| SEQ_ID_NO_280 | E- | RA- | PHHA | -AEQ | -LKEARRGG | | 49 |
|---|---|---|---|---|---|---|---|
| SEQ_ID_NO_282 | QQ | RAPGT | PPP | -AEQ | -LKEARRGGS | | 51 |
| SEQ_ID_NO_283 | S- | | P- | -AVQA | KDKEARRGGS | | 45 |
| SEQ_ID_NO_284 | | | | | | | 1 |
| SEQ_ID_NO_285 | Q- | | L- | AQN- | SKMQAKRFGS | FHRQRTLTSE | 34 |
| SEQ_ID_NO_286 | E- | PNPRGPFL | TQNR | QVQ- | L-PARSFES | | 62 |
| SEQ_ID_NO_288 | | | | | | | 5 |
| SEQ_ID_NO_289 | S- | K- | SVNF | SELLQ | MKYLSSGTM | | 39 |
| SEQ_ID_NO_290 | N- | KLSDL | E- | TL- | L- | | 30 |
| SEQ_ID_NO_292 | E- | PJ- | DQCS- | MTPR | KKNKKRQTGA | | 59 |

| SEQ_ID_NO_280 | | | | | | | 49 |
|---|---|---|---|---|---|---|---|
| SEQ_ID_NO_282 | | | | | | | 51 |
| SEQ_ID_NO_283 | | | | | | | 45 |
| SEQ_ID_NO_284 | | | | | | | 1 |
| SEQ_ID_NO_285 | YPFLTHPFXA | SWSRTASAQQ | PBVDSTHVMR | LRRNTDDEQL | | | 34 |
| SEQ_ID_NO_286 | | | | | | | 102 |
| SEQ_ID_NO_288 | | | | | | | 9 |
| SEQ_ID_NO_289 | | | | | | | 39 |
| SEQ_ID_NO_290 | | | | NEDD- | | | 30 |
| SEQ_ID_NO_292 | | | | | | | 59 |

| SEQ ID NO | | | | | | | | | |
|---|---|---|---|---|---|---|---|---|---|
| SEQ_ID_NO_280 | RLLGGLLLEG | FDEKSCRSRY | QFARYHKISP | SIPSPYLIER | 156 |
| SEQ_ID_NO_282 | RLLGGLLVEG | FDEKSCRSRY | QFARYHN-SP | SIPSAYLIER | 157 |
| SEQ_ID_NO_283 | RLLGGLLVEG | FDDKSCRSRY | RFARYHS-SP | SIPSPYLIER | 151 |
| SEQ_ID_NO_284 | KFLGGLLQEG | FDEVSCRSRY | QFARYHKNFT | RIPSSYLLER | 92 |
| SEQ_ID_NO_285 | KLLGGLLADG | FDEASCRSRY | SSFLYRKLSL | HKPSSYLISK | 147 |
| SEQ_ID_NO_286 | KLLGGLLDAG | FNERSCLSRY | QSALYRKELL | HKPSSYLLSK | 226 |
| SEQ_ID_NO_288 | KLHGGLLAAG | FDETSCVSRY | QSVLYRKESQ | HKPSSYLISR | 120 |
| SEQ_ID_NO_289 | KLLGGLLASG | FDEDSCLSRY | QSVHYRKPSP | YKPSSYLISK | 135 |
| SEQ_ID_NO_290 | KLLGGLLADG | FDEKSCLSRY | QSAIFGKGLS | GKPSSYLIER | 140 |
| SEQ_ID_NO_292 | KLLGGLLADG | VDGETCRSRH | ESSAYRRSTP | RRPSPYLVAK | 161 |

| SEQ ID NO | | | | | | | | | |
|---|---|---|---|---|---|---|---|---|---|
| SEQ_ID_NO_280 | LRKQELQKK | CGPGTKAYKE | ASKQLRSGQS | QT---TNTTDCN | 195 |
| SEQ_ID_NO_282 | LRKQEALQKK | CGPGTKAYKE | ASKQLKYGQS | ----INTTDCN | 194 |
| SEQ_ID_NO_283 | LRRQEALQKK | CGPGTKSYKQ | ASKQLKSGQS | MSI-NATDDCN | 191 |
| SEQ_ID_NO_284 | LRSYEDLHKR | CGPGTKSYKQ | AVKLLKSGNK | VF--NMTDCN | 130 |
| SEQ_ID_NO_285 | LRSYEALHKR | CGPNTQSYNR | ALEQLKQLGQH | ----GLTDCN | 184 |
| SEQ_ID_NO_286 | LRNYEALHKR | CGPYTESYNR | TLEKLTGHH | ----MEQSDCN | 263 |
| SEQ_ID_NO_288 | LRNYEALHKR | CGPYTESYKK | ALKQLDOEHI | ----LESTDCN | 157 |
| SEQ_ID_NO_289 | LRKYEARHKQ | CGPYTESYNK | TVKELGSGQF | ----DGDGECK | 172 |
| SEQ_ID_NO_290 | LRRHEELQRR | CGPGSDAYSR | AVQQLSIAGRS | ----SESVDCK | 177 |
| SEQ_ID_NO_292 | | | | ----AVDAECK | 198 |

| SEQ ID NO | | | | | | | | | |
|---|---|---|---|---|---|---|---|---|---|
| SEQ_ID_NO_280 | YLLLTIHAGL | GNRMLEITSA | LLYALLTNRI | LLVDRYKEIG | 235 |
| SEQ_ID_NO_282 | YLYLIIHAGL | GNRMLEITSA | FLYALLTNRI | LLDRYKEIA | 234 |
| SEQ_ID_NO_283 | YLFLILTVHAGL | GNRMLEITSA | FLYALLTNRI | LLDRYKEIA | 231 |
| SEQ_ID_NO_284 | YLFLTVHAGL | GNRMLEIASA | FLYALLTNRI | LLDRYQEIG | 170 |
| SEQ_ID_NO_285 | YIVMSFSGL | GNRILSLASIT | FLYALLTNRV | LLVDQGKDMA | 224 |
| SEQ_ID_NO_286 | YLVMSFSGL | GNRILTLASA | FLYALLTNRV | LLVDPGADMP | 303 |
| SEQ_ID_NO_288 | YLVMSFSGL | GNRILSLASA | FLYALLTNRV | LLVDPGTDMV | 197 |
| SEQ_ID_NO_289 | YVVMSFSGL | GNRILLTLVSA | FLYALLTDRV | LLVDRGKDMD | 212 |
| SEQ_ID_NO_290 | YVVWSFSGL | GNRILAASA | FLYTLLTDRV | LLVDPGVDMT | 217 |
| SEQ_ID_NO_292 | YVVSVCNRGL | GNRILAASA | FLYTLLTDRV | LLVYRGNGMG | 238 |

| | | | | |
|---|---|---|---|---|
| SEQ_ID_NO_280 | RHCEDVSWGL | KIVN- | ---- | ET | KL | 605 |
| SEQ_ID_NO_282 | RHCEDVSWGL | KIVN- | ---- | QT | HL | 604 |
| SEQ_ID_NO_283 | RHCEDVSWGL | KIVD- | ---- | QT | HL | 604 |
| SEQ_ID_NO_284 | RHCEDVSWGL | KVVN- | ---- | QT | QW | 533 |
| SEQ_ID_NO_285 | RHCEDISWGL | KVVD- | ---- | DHD | DL | 578 |
| SEQ_ID_NO_286 | RHCEDMSWGL | KLVD- | BSX | EHG | AL | 661 |
| SEQ_ID_NO_288 | RHCEDMSWGL | KLVD- | ---- | NES | EL | 550 |
| SEQ_ID_NO_289 | RHCEDISWGL | KLVE- | ---- | ---- | -N | 558 |
| SEQ_ID_NO_290 | RHCEDMSWGL | KLVD- | ---- | ---- | -- | 565 |
| SEQ_ID_NO_292 | RRCEDVKMGL | KLVG- | ---- | ---- | PK | 593 |

Figure 11A

| SEQ ID | | | | | | | | | |
|---|---|---|---|---|---|---|---|---|---|
| SEQ_ID_NO_641 | MRSLA | - - - - - | - - - - - | - - - - - | A | VAAM | ACLA | AVARAGNFY | 24 |
| SEQ_ID_NO_643 | MRSTA | - - - - - | - - - - - | V | A | FVAV | ACLA | AVAHGGNFY | 25 |
| SEQ_ID_NO_645 | MRSFA | - - - - - | - - - - - | L | - | VVAW | ELA- | GTAQGGNFY | 28 |
| SEQ_ID_NO_646 | MRTVA | - - - - - | - - - - - | P - | VFLSA | I VAM | ACLV- | AIAHGGNFF | 24 |
| SEQ_ID_NO_647 | MRTVE | - - - - - | - - - - - | L | G | VAM- | ACLV- | AVARGGNFF | 24 |
| SEQ_ID_NO_648 | MRTVA | - - - - - | - - - - - | L | G | I LAM | ACLV- | AVARGGNFY | 24 |
| SEQ_ID_NO_649 | MARMA | - - - - - | - - - - - | V - | S | VLAI L | ASC- | AVAAASFD | 25 |
| SEQ_ID_NO_650 | MASSS | - - - - - | - - - - - | - - - - - | M | VLM- | LSFM | XVVASAGNFN | 23 |
| SEQ_ID_NO_651 | MAPI | CSSSA | VSTAL | - - - - - | - | SV-- | VSFL- | MAASAGNFY | 33 |
| SEQ_ID_NO_652 | MAM- | - - - - - | - - - - - | RF- | - | LVA- | CSLV- | AT ASAGNFY | 22 |
| SEQ_ID_NO_653 | MASLL | - - - - - | - - - - - | F- | A | VLA- | LSSV- | GI AVAGNFN | 23 |
| SEQ_ID_NO_654 | MAPP | PSF-- | SS- | - - - - - | L | LLF- | LSLLS | VSSVFCSNFY | 28 |

| SEQ ID | | | | | |
|---|---|---|---|---|---|
| SEQ_ID_NO_641 | QDTEMTWGGG | RGKVVDGGRG | LDLTLDRTSG | SGFQSKSEYL | 64 |
| SEQ_ID_NO_643 | KDTEMTWGQG | RGKVVDGGRG | LDLTLDRTSG | SGFQSKSEYL | 65 |
| SEQ_ID_NO_645 | QDTEMTWGDG | RGKVVDGGRG | LDLTLDRTSG | SGFQSKSEYL | 68 |
| SEQ_ID_NO_646 | QDAEVSWGQG | RGKI VDGGRG | LDLTLDRSSG | SGFQSKSEYL | 64 |
| SEQ_ID_NO_647 | QDSEMSWGQG | RGKVVDGGRG | LDLTLDKTSG | SGFQSKSEYL | 64 |
| SEQ_ID_NO_648 | QDSEMTWGDG | RGKVVDGGRG | LDLTLDKTSG | SGFQSKI TEYL | 64 |
| SEQ_ID_NO_649 | KEFDI TWGDG | RGKI LNNGQL | LDLTLGLDKT | SGFQSKREYL | 65 |
| SEQ_ID_NO_650 | QDFDI TWGDG | RAKI LNNGQL | TLSLDKASG | SGFQSKNEYL | 63 |
| SEQ_ID_NO_651 | QDFDI TWGDG | RGKI LNNGEL | TLSLDKPSG | SGFQSKNQYL | 73 |
| SEQ_ID_NO_652 | QEFDVTWGGD | RAKNLDNGQL | SLSLDKASG | SGFESTHEYL | 62 |
| SEQ_ID_NO_653 | DDFKI TWGDG | RGRI VDNGQL | SLSLDKASG | SGFQSKNVYL | 63 |
| SEQ_ID_NO_654 | NDFEI TWGND | RAKI LNNGDL | TLSLDRGSG | SGFQSKNVYL | 68 |

| SEQ_ID_NO | | | | | | | |
|---|---|---|---|---|---|---|---|
| SEQ_ID_NO_641 | GRQQCPVGTM | EAAA- | --- | --- | RGWWSQ | QLSDTSYRRM | 253 |
| SEQ_ID_NO_643 | GKQQCPVGTM | AAAT- | -GGR | RGGP | GSWWNQ | QLSDMSYRRM | 262 |
| SEQ_ID_NO_645 | GRQRCPEGTM | EAAAV- | -AGA | -GSGRGWWNQ | | QLSDMSYRRM | 264 |
| SEQ_ID_NO_646 | GAQRCPVGTM | ETVAAPA- | -AGGR | RGGA | GGWWNQ | ELSDMSYRRM | 263 |
| SEQ_ID_NO_647 | GAQRCPAGTM | EASAA- | --- | -GGGS | VWWNQ | ELSGMYRRM | 256 |
| SEQ_ID_NO_648 | GAQRCPAGTM | EASAA- | --- | -GSGS | VWWNQ | ELSGMGYRRM | 257 |
| SEQ_ID_NO_649 | GAQRCPAGTM | DASG- | --- | -TGSS | SWWNQ | ELGDMSYRRM | 257 |
| SEQ_ID_NO_650 | GASSCSSTTP | SSTSI- | --- | -TSGWYSQ | | ELDSTSQERM | 254 |
| SEQ_ID_NO_651 | GSSSCSSTSP | SSTS- | --- | -TNGGWWNQ | | ELDSTSQERM | 264 |
| SEQ_ID_NO_652 | ATTECASNSV | PF-- | --- | -SNGGWWNQ | | ELDSMGQQRM | 250 |
| SEQ_ID_NO_653 | GTSTCSSKKS | PSAS- | --- | PSNAWLNE | | ELDSTRQERM | 254 |
| SEQ_ID_NO_654 | GVSSCSSGGN | V--- | --- | GGRGWLSE | | NLDTTRQQRM | 256 |

| SEQ_ID_NO | | | | | | | |
|---|---|---|---|---|---|---|---|
| SEQ_ID_NO_641 | RWQRKFMIY | NYCTDAKRFP | QGVPAECHL | -R | 283 |
| SEQ_ID_NO_643 | RWQRKFMIY | NYCTDAKRFP | QGVPAECKL | -R | 292 |
| SEQ_ID_NO_645 | RWQRKFMIY | NYCTDAKRFP | QGVPAECKL | -R | 294 |
| SEQ_ID_NO_646 | RWQRKFMIY | NYCTDAKRFP | QGTPAECKL | -R | 293 |
| SEQ_ID_NO_647 | RWQRKFMIY | NYCTDPKRFP | QGVPAECKL | -R | 286 |
| SEQ_ID_NO_648 | RWQRKFMIY | NYCTDPKRVA | QGVPAECKL | -R | 287 |
| SEQ_ID_NO_649 | RWQRKFMIY | NYCTDPKRVA | EGLPAECKIR | | 291 |
| SEQ_ID_NO_650 | KWQKNYMIY | NYCTDTKRFP | QGLPPECTAT | LRSK | 287 |
| SEQ_ID_NO_651 | KWQKNYMIY | NYCADTKRFP | QGLPPECSAT | TLS | 297 |
| SEQ_ID_NO_652 | KWQKNYMIY | NYCSDLKRFS | QGLPPECSI- | TMS | 280 |
| SEQ_ID_NO_653 | RWQKNYMIY | NYCADLKRFP | QGLPPECSF- | VA | 284 |
| SEQ_ID_NO_654 | KWQRNYMIY | NYCTDAKRFP | QGYPPECAT | AP | 287 |

TRANSGENIC PLANTS HAVING ALTERED BIOMASS COMPOSITION

CROSS-REFERENCE TO RELATED APPLICATION

This application is a continuation-in-part of International Application No. PCT/US2011/057709, filed Oct. 25, 2011, which claims the benefit of U.S. Provisional Application No. 61/407,280, filed Oct. 27, 2010. The contents of the foregoing applications are hereby incorporated by reference in their entirety.

STATEMENT AS TO FEDERALLY SPONSORED RESEARCH

This invention was made with government support under USDA Biomass Research and Development Initiative Grant 68-3A75-7-601 and 68-3A75-6-501. The government has certain rights in the invention. The material in the accompanying sequence listing is hereby incorporated by reference into this application.

TECHNICAL FIELD

This document relates to methods and materials involved in modulating biomass composition in plants. For example, this document provides plants having altered sucrose or conversion efficiency, as well as materials and methods for making plants and plant products having altered sucrose or conversion efficiency.

BACKGROUND

Plants store energy from sunlight in the form of chemical bonds that compose plants. The energy stored in plant materials can be converted to forms of energy such as heat, electricity and liquid fuels, depending upon the plant material employed and the process applied to extract energy from it. Other processes can produce chemical intermediates from plant biomass that are useful in a variety of industrial processes, for instance lactic acid, succinic acid, etc.

Plant materials have been used for millennia by humans to generate heat by direct combustion in air. For building and process heating purposes, this heat is typically used to generate steam, which is a more transportable heat source used to heat buildings and public areas using heat exchangers of various design. The production of steam may also be used to drive turbines, which transform heat energy into electrical energy. These processes typically involve a simple, direct combustion process of the plant material alone, or a co-firing process with coal or other energy source.

Fuels such as ethanol can be produced from plant materials by a number of different processes. For example, the sucrose in sugarcane can be extracted from the plant material and directly fermented to ethanol using a microorganism, such as brewer's yeast. Brazil has converted a significant portion of its transportation sector over to ethanol derived from sugarcane, proving this can be done on a very large scale over broad geography. As another example, the starch from corn can be processed using α-amylase and glucoamylase to liberate free glucose that is subsequently fermented to ethanol. The US uses a significant portion of its corn crop to produce ethanol from starch. While these advances are significant, the ability to increase the amount of liquid transportation fuel obtained from plant material is limited and insufficient to achieve federally mandated renewable energy targets because only a small fraction of the solar energy captured and transformed into chemical energy in plants is converted into biofuels in these industrial processes.

Plant material can be used for the production of cellulosic biofuels by biochemical processes employing enzymes and/or microorganisms or by thermochemical processes such as Biomass to Liquids (BtL) technology using high temperature and non-enzymatic catalysts. There are also examples of hybrid thermochemical/biochemical processes. Biochemical processes typically employ physical and chemical pretreatments, enzymes, and microorganisms to deconstruct the lignocellulose matrix of biomass in order to liberate the fermentable from cellulose, hemicellulose, and other cell wall carbohydrates, which are subsequently fermented to ethanol by a microorganism. Currently, many different processing methods are being developed for biofuel production that employ different strategies for pretreatment, enzyme cocktails, and microorganisms. Many of these processes are focused on the production of ethanol, but butanol and other useful molecules (e.g., lactic acid, succinic acid, polyalkanoates, etc.) can also be produced in this type of process. The conversion product molecule produced is usually defined by the microorganisms selected for fermentation.

Thermochemical processes employ very high temperatures in a low oxygen (i.e., $O_2$) environment to completely degrade the organic constituents of biomass to syngas, largely composed of molecular hydrogen ($H_2$) and carbon monoxide (CO) gas. These simple molecules are then reformed into more useful and valuable molecules (fuels or chemical intermediates) utilizing a Fischer-Tropsch process or other methods usually employing a chemical catalyst of some sort. These processes are effective at producing biofuels that are similar to current petrochemical-based hydrocarbon fuels (i.e., gasoline, diesel, jet fuel), although other biofuel molecules can also be produced in these types of processes (i.e., ethanol, butanol, kerosene).

A variant form of thermochemical process uses pyrolysis (i.e., thermal degradation in the complete absence of oxygen) to partially degrade the organic constituents present in plant biomass to a chemically heterogeneous liquid bio-oil. This serves to increase the energy density of the biomass to facilitate transport to centralized processing facilities where the bio-oil is further processed to a desired product slate.

The economic viability of biomass conversion processes is significantly impacted by the composition of the plant material and its conversion efficiency to heat, electricity, biofuels or chemical intermediates under specific processing conditions. For biochemical processes producing biofuels or other chemicals, the recalcitrance of the lignocellulose matrix of the biomass is a major factor in conversion efficiency.

SUMMARY

The present invention relates to methods of altering biomass composition in plants and plants generated thereby. Plants having altered biomass composition are useful for agriculture, forage, horticulture, biomass to energy conversion, paper production, plant product production, and other industries. For example, this document features dedicated energy crops such as *Panicum virgatum* L. (switchgrass), *Miscanthus×gigantus* (miscanthus), *Sorghum* sp., and *Saccharum* sp. (sugar cane) having altered biomass composition.

This document features a method of producing a plant. The method includes growing a plant cell comprising an exogenous nucleic acid. The exogenous nucleic acid includes a regulatory region operably linked to a nucleotide sequence encoding a polypeptide, where the HMM bit score of the amino acid sequence of the polypeptide is greater than about 65, based on the HMM of the amino acid sequences depicted in one of FIGS. 1-12. A plant produced from the plant cell has a difference in biomass composition compared to the corresponding composition of a control plant that does not comprise the nucleic acid. The difference in biomass composition in the plant can be a difference in the sucrose content or conversion efficiency.

This document also features a method of producing a plant that includes growing a plant cell comprising an exogenous nucleic acid. The exogenous nucleic acid comprises a regulatory region operably linked to a nucleotide sequence encoding a polypeptide having 80 percent or greater sequence identity to an amino acid sequence selected from the group consisting of SEQ ID NOs: 2, 4, 6, 7, 8, 10, 12, 14, 15, 17, 18, 19, 20, 21, 22, 24, 26, 28, 29, 30, 32, 34, 36, 37, 39, 41, 43, 45, 47, 49, 50, 52, 53, 55, 57, 59, 61, 63, 65, 66, 68, 70, 71, 72, 73, 75, 77, 78, 79, 81, 82, 84, 86, 88, 90, 92, 94, 96, 97, 99, 100, 101, 102, 104, 105, 107, 109, 111, 113, 115, 117, 118, 120, 122, 124, 126, 128, 130, 132, 133, 135, 136, 138, 139, 141, 143, 145, 147, 148, 149, 151, 152, 153, 155, 157, 158, 160, 161, 162, 163, 164, 165, 167, 168, 170, 171, 172, 173, 175, 177, 179, 181, 182, 184, 185, 187, 189, 190, 192, 194, 196, 197, 199, 201, 202, 204, 205, 207, 208, 210, 211, 213, 215, 216, 218, 220, 221, 222, 223, 225, 226, 228, 230, 232, 234, 236, 238, 240, 242, 244, 246, 248, 250, 251, 252, 254, 256, 258, 260, 261, 262, 264, 266, 268, 270, 272, 274, 275, 276, 278, 280, 282, 283, 284, 285, 286, 288, 289, 290, 292, 294, 295, 296, 297, 298, 299, 300, 302, 303, 305, 306, 308, 309, 310, 311, 312, 314, 316, 317, 318, 320, 321, 323, 325, 326, 327, 328, 329, 331, 333, 335, 336, 337, 338, 339, 340, 342, 344, 346, 348, 350, 351, 353, 355, 357, 359, 360, 361, 362, 363, 364, 365, 366, 368, 370, 372, 373, 374, 375, 376, 377, 379, 380, 381, 383, 384, 386, 388, 390, 392, 393, 394, 396, 398, 400, 402, 404, 406, 407, 408, 410, 412, 413, 414, 416, 418, 419, 420, 422, 423, 424, 426, 427, 429, 430, 431, 433, 434, 436, 437, 439, 441, 442, 444, 446, 448, 449, 450, 451, 452, 454, 456, 458, 459, 460, 462, 463, 465, 466, 468, 470, 472, 473, 474, 476, 478, 479, 480, 481, 483, 485, 486, 488, 490, 492, 493, 495, 497, 498, 500, 501, 503, 504, 506, 508, 509, 510, 512, 514, 515, 516, 517, 519, 521, 522, 523, 525, 527, 529, 531, 533, 534, 535, 537, 539, 541, 543, 545, 547, 549, 551, 552, 554, 556, 557, 559, 562, 564, 565, 567, 568, 570, 572, 573, 574, 575, 576, 578, 580, 582, 584, 586, 588, 589, 590, 592, 594, 596, 598, 599, 601, 602, 603, 605, 607, 608, 609, 611, 613, 615, 617, 619, 621, 622, 624, 625, 627, 629, 630, 632, 634, 636, 638, 641, 643, 645, 646, 647, 648, 649, 650, 651, 652, 653, 654, 656, 658, 660, 662, 664, 666, 668, 670, 672, 674, 676, 677, 679, 680, 682, 684, 686, 687, 688, 689, 690, 691, 692, 694, 695, 697, 699, 701, 702, 704, 706, 708, 710, 712, 713, 715, 716, 718, 720, 721, 723, 724, 726, 727, 729, 730, 732, 733, 735, 736, 737, 739, 740, 742, 744, 746, 747, 748, 749, 750, 751, 753, 755, 757, 758, 760, 761, 763, 764, 765, 766, 767, 768, 769, 771, 772, 774, 775, 776, 777, 778, 780, 781, 782, 783, 785, 786, 788, 789, 791, 793, 795, 796, 798, 799, 800, 801, 802, 803, 805, 807, 808, 810, 811, 812, 813, 814, 815, 816, 817, 818, 819, 820, 821, and 823. A plant produced from the plant cell has a difference in biomass composition as compared to the corresponding composition of a control plant that does not comprise the nucleic acid. The difference in biomass composition in the plant can be a difference in the sucrose content or conversion efficiency.

In another aspect, this document features a method of producing a plant. The method includes growing a plant cell comprising an exogenous nucleic acid, where the exogenous nucleic acid includes a regulatory region operably linked to a nucleotide sequence having 80 percent or greater sequence identity to a nucleotide sequence selected from the group consisting of SEQ ID NO: 1, 3, 5, 9, 11, 13, 16, 23, 25, 27, 31, 33, 35, 38, 40, 42, 44, 46, 48, 51, 54, 56, 58, 60, 62, 64, 67, 69, 74, 76, 80, 83, 85, 87, 89, 91, 93, 95, 98, 103, 106, 108, 110, 112, 114, 116, 119, 121, 123, 125, 127, 129, 131, 134, 137, 140, 142, 144, 146, 150, 154, 156, 159, 166, 169, 174, 176, 178, 180, 183, 186, 188, 191, 193, 195, 198, 200, 203, 206, 209, 212, 214, 217, 219, 224, 227, 229, 231, 233, 235, 237, 239, 241, 243, 245, 247, 249, 253, 255, 257, 259, 263, 265, 267, 269, 271, 273, 277, 279, 281, 287, 291, 293, 301, 304, 307, 313, 315, 319, 322, 324, 330, 332, 334, 341, 343, 345, 347, 349, 352, 354, 356, 358, 367, 369, 371, 378, 382, 385, 387, 389, 391, 395, 397, 399, 401, 403, 405, 409, 411, 415, 417, 421, 425, 428, 432, 435, 438, 440, 443, 445, 447, 453, 455, 457, 461, 464, 467, 469, 471, 475, 477, 482, 484, 487, 489, 491, 494, 496, 499, 502, 505, 507, 511, 513, 518, 520, 524, 526, 528, 530, 532, 536, 538, 540, 542, 544, 546, 548, 550, 553, 555, 558, 560, 561, 563, 566, 569, 571, 577, 579, 581, 583, 585, 587, 591, 593, 595, 597, 600, 604, 606, 610, 612, 614, 616, 618, 620, 623, 626, 628, 631, 633, 635, 637, 639, 640, 642, 644, 655, 657, 659, 661, 663, 665, 667, 669, 671, 673, 675, 678, 681, 683, 685, 693, 696, 698, 700, 703, 705, 707, 709, 711, 714, 717, 719, 722, 725, 728, 731, 734, 738, 741, 743, 745, 752, 754, 756, 759, 762, 770, 773, 779, 784, 787, 790, 792, 794, 797, 804, 806, 809, and 822, or a fragment thereof. A plant produced from the plant cell has a difference in biomass composition as compared to the corresponding composition of a control plant that does not include the nucleic acid. The difference in biomass composition in the plant can be a difference in the sucrose content or conversion efficiency.

This document also features a method of producing a plant that includes growing a plant cell comprising an exogenous nucleic acid. The exogenous nucleic acid is effective for down regulating an endogenous nucleic acid in the plant cell, wherein the endogenous nucleic acid encodes a polypeptide, and wherein the HMM bit score of the amino acid sequence of the polypeptide is greater than about 65, where the HMM is based on the amino acid sequences depicted in one of FIGS. 1-12.

In another aspect, this document features a method of modulating biomass composition in a plant. The method includes introducing into a plant cell an exogenous nucleic acid, the exogenous nucleic acid comprising a regulatory region operably linked to a nucleotide sequence encoding a polypeptide, wherein the HMM bit score of the amino acid sequence of the polypeptide is greater than about 65, where the HMM is based on the amino acid sequences depicted in one of FIGS. 1-12, and wherein a plant produced from the plant cell has a difference in biomass composition as compared to the corresponding composition of a control plant that does not comprise the exogenous nucleic acid. The difference in biomass composition in the plant can be a difference in the sucrose content or conversion efficiency.

A method of modulating biomass composition in a plant also is featured. The method includes introducing into a plant cell an exogenous nucleic acid, the exogenous nucleic acid comprising a regulatory region operably linked to a nucleotide sequence encoding a polypeptide having 80 percent or greater sequence identity to an amino acid sequence selected from the group consisting of SEQ ID NOs: 2, 4, 6, 7, 8, 10, 12, 14, 15, 17, 18, 19, 20, 21, 22, 24, 26, 28, 29, 30, 32, 34, 36, 37, 39, 41, 43, 45, 47, 49, 50, 52, 53, 55, 57, 59, 61, 63, 65, 66, 68, 70, 71, 72, 73, 75, 77, 78, 79, 81, 82, 84, 86, 88, 90, 92, 94, 96, 97, 99, 100, 101, 102, 104, 105, 107, 109, 111, 113, 115, 117, 118, 120, 122, 124, 126, 128, 130, 132, 133, 135, 136, 138, 139, 141, 143, 145, 147, 148, 149, 151, 152, 153, 155, 157, 158, 160, 161, 162, 163, 164, 165, 167, 168, 170, 171, 172, 173, 175, 177, 179, 181, 182, 184, 185, 187, 189, 190, 192, 194, 196, 197, 199, 201, 202, 204, 205, 207, 208, 210, 211, 213, 215, 216, 218, 220, 221, 222, 223, 225, 226, 228, 230, 232, 234, 236, 238, 240, 242, 244, 246, 248, 250, 251, 252, 254, 256, 258, 260, 261, 262, 264, 266, 268, 270, 272, 274, 275, 276, 278, 280, 282, 283, 284, 285, 286, 288, 289, 290, 292, 294, 295, 296, 297, 298, 299, 300, 302, 303, 305, 306, 308, 309, 310, 311, 312, 314, 316, 317, 318, 320, 321, 323, 325, 326, 327, 328, 329, 331, 333, 335, 336, 337, 338, 339, 340, 342, 344, 346, 348, 350, 351, 353, 355, 357, 359, 360, 361, 362, 363, 364, 365, 366, 368, 370, 372, 373, 374, 375, 376, 377, 379, 380, 381, 383, 384, 386, 388, 390, 392, 393, 394, 396, 398, 400, 402, 404, 406, 407, 408, 410, 412, 413, 414, 416, 418, 419, 420, 422, 423, 424, 426, 427, 429, 430, 431, 433, 434, 436, 437, 439, 441, 442, 444, 446, 448, 449, 450, 451, 452, 454, 456, 458, 459, 460, 462, 463, 465, 466, 468, 470, 472, 473, 474, 476, 478, 479, 480, 481, 483, 485, 486, 488, 490, 492, 493, 495, 497, 498, 500, 501, 503, 504, 506, 508, 509, 510, 512, 514, 515, 516, 517, 519, 521, 522, 523, 525, 527, 529, 531, 533, 534, 535, 537, 539, 541, 543, 545, 547, 549, 551, 552, 554, 556, 557, 559, 562, 564, 565, 567, 568, 570, 572, 573, 574, 575, 576, 578, 580, 582, 584, 586, 588, 589, 590, 592, 594, 596, 598, 599, 601, 602, 603, 605, 607, 608, 609, 611, 613, 615, 617, 619, 621, 622, 624, 625, 627, 629, 630, 632, 634, 636, 638, 641, 643, 645, 646, 647, 648, 649, 650, 651, 652, 653, 654, 656, 658, 660, 662, 664, 666, 668, 670, 672, 674, 676, 677, 679, 680, 682, 684, 686, 687, 688, 689, 690, 691, 692, 694, 695, 697, 699, 701, 702, 704, 706, 708, 710, 712, 713, 715, 716, 718, 720, 721, 723, 724, 726, 727, 729, 730, 732, 733, 735, 736, 737, 739, 740, 742, 744, 746, 747, 748, 749, 750, 751, 753, 755, 757, 758, 760, 761, 763, 764, 765, 766, 767, 768, 769, 771, 772, 774, 775, 776, 777, 778, 780, 781, 782, 783, 785, 786, 788, 789, 791, 793, 795, 796, 798, 799, 800, 801, 802, 803, 805, 807, 808, 810, 811, 812, 813, 814, 815, 816, 817, 818, 819, 820, 821, and 823. A plant produced from the plant cell has a difference in biomass composition as compared to the corresponding composition of a control plant that does not include the nucleic acid. The difference in biomass composition in the plant can be a difference in the sucrose content or conversion efficiency.

In the methods described herein, the polypeptide can include a heavy-metal-associated domain having 60 percent or greater sequence identity to residues 6 to 73 of SEQ ID NO: 562. The polypeptide can include a Myb-like DNA-binding domain having 60 percent or greater sequence identity to residues 212 to 263 of SEQ ID NO: 246. The polypeptide can include a DUF1070 domain having 60 percent or greater sequence identity to residues 4-52 of SEQ ID NO: 111. The polypeptide can include a glycosyl hydrolase family 16 domain and a xyloglucan endo-transglycosylase (XET) domain having 60 percent or greater sequence identity to residues 39 to 224 and 246 to 292 of SEQ ID NO: 348, respectively. The polypeptide can include an Alpha-L-AF_C domain having 60 percent or greater sequence identity to residues 454 to 643 of SEQ ID NO: 774 and a CBM_4_9 domain having 60 percent or greater sequence identity to residues 71 to 229 of SEQ ID NO: 774. The polypeptide can include a COBRA domain having 60 percent or greater sequence identity to residues 45 to 209 of SEQ ID NO: 416. The polypeptide can include a glycosyl transferase family 8 domain having 60 percent or greater sequence identity to residues 30 to 253 of SEQ ID NO: 2. The polypeptide can include a DUF563 domain having 60 percent or greater sequence identity to residues 196 to 439 of SEQ ID NO: 157. The polypeptide can include an XG_FTase domain having 60 percent or greater sequence identity to residues 72 to 574 of SEQ ID NO: 280. The polypeptide can include a glycosyl hydrolase family 16 domain having 60 percent or greater sequence identity to residues 23 to 204 of SEQ ID NO: 641 and a XET domain having 60 percent or greater sequence identity to residues 228 to 280 of SEQ ID NO: 641. The polypeptide can include a potato inhibitor I family domain having 60 percent or greater sequence identity to residues 17 to 76 of SEQ ID NO: 26.

In the methods described herein, the polypeptide can be selected from the group consisting of SEQ ID NOs: 2, 4, 6, 7, 8, 10, 12, 14, 15, 17, 18, 19, 20, 21, 22, 24, 26, 28, 29, 30, 32, 34, 36, 37, 39, 41, 43, 45, 47, 49, 50, 52, 53, 55, 57, 59, 61, 63, 65, 66, 68, 70, 71, 72, 73, 75, 77, 78, 79, 81, 82, 84, 86, 88, 90, 92, 94, 96, 97, 99, 100, 101, 102, 104, 105, 107, 109, 111, 113, 115, 117, 118, 120, 122, 124, 126, 128, 130, 132, 133, 135, 136, 138, 139, 141, 143, 145, 147, 148, 149, 151, 152, 153, 155, 157, 158, 160, 161, 162, 163, 164, 165, 167, 168, 170, 171, 172, 173, 175, 177, 179, 181, 182, 184, 185, 187, 189, 190, 192, 194, 196, 197, 199, 201, 202, 204, 205, 207, 208, 210, 211, 213, 215, 216, 218, 220, 221, 222, 223, 225, 226, 228, 230, 232, 234, 236, 238, 240, 242, 244, 246, 248, 250, 251, 252, 254, 256, 258, 260, 261, 262, 264, 266, 268, 270, 272, 274, 275, 276, 278, 280, 282, 283, 284, 285, 286, 288, 289, 290, 292, 294, 295, 296, 297, 298, 299, 300, 302, 303, 305, 306, 308, 309, 310, 311, 312, 314, 316, 317, 318, 320, 321, 323, 325, 326, 327, 328, 329, 331, 333, 335, 336, 337, 338, 339, 340, 342, 344, 346, 348, 350, 351, 353, 355, 357, 359, 360, 361, 362, 363, 364, 365, 366, 368, 370, 372, 373, 374, 375, 376, 377, 379, 380, 381, 383, 384, 386, 388, 390, 392, 393, 394, 396, 398, 400, 402, 404, 406, 407, 408, 410, 412, 413, 414, 416, 418, 419, 420, 422, 423, 424, 426, 427, 429, 430, 431, 433, 434, 436, 437, 439, 441, 442, 444, 446, 448, 449, 450, 451, 452, 454, 456, 458, 459, 460, 462, 463, 465, 466, 468, 470, 472, 473, 474, 476, 478, 479, 480, 481, 483, 485, 486, 488, 490, 492, 493, 495, 497, 498, 500, 501, 503, 504, 506, 508, 509, 510, 512, 514, 515, 516, 517, 519, 521, 522, 523, 525, 527, 529, 531, 533, 534, 535, 537, 539, 541, 543, 545, 547, 549, 551, 552, 554, 556, 557, 559, 562, 564, 565, 567, 568, 570, 572, 573, 574, 575, 576, 578, 580, 582, 584, 586, 588, 589, 590, 592, 594, 596, 598, 599, 601, 602, 603, 605, 607, 608, 609, 611, 613, 615, 617, 619, 621, 622, 624, 625, 627, 629, 630, 632, 634, 636, 638, 641, 643, 645, 646, 647, 648, 649, 650, 651, 652, 653, 654, 656, 658, 660, 662, 664, 666, 668, 670, 672, 674, 676, 677, 679, 680, 682, 684, 686, 687, 688, 689, 690, 691, 692, 694, 695, 697, 699, 701, 702, 704, 706, 708, 710, 712, 713, 715, 716, 718, 720, 721, 723, 724, 726, 727, 729, 730, 732, 733, 735, 736, 737, 739, 740, 742, 744, 746, 747, 748, 749, 750, 751, 753, 755, 757, 758, 760, 761, 763, 764, 765, 766, 767, 768, 769, 771, 772, 774, 775, 776, 777, 778, 780, 781, 782, 783, 785, 786, 788, 789, 791, 793, 795, 796, 798, 799, 800, 801, 802, 803, 805, 807, 808, 810, 811, 812, 813, 814, 815, 816, 817, 818, 819, 820, 821, and 823.

This document also features a method of modulating the biomass composition in a plant. The method includes introducing into a plant cell an exogenous nucleic acid, the exogenous nucleic acid comprising a regulatory region operably linked to a nucleotide sequence having 80 percent or greater sequence identity to a nucleotide sequence selected from the group consisting of SEQ ID NO: 1, 3, 5, 9, 11, 13, 16, 23, 25, 27, 31, 33, 35, 38, 40, 42, 44, 46, 48, 51, 54, 56, 58, 60, 62, 64, 67, 69, 74, 76, 80, 83, 85, 87, 89, 91, 93, 95, 98, 103, 106, 108, 110, 112, 114, 116, 119, 121, 123, 125, 127, 129, 131, 134, 137, 140, 142, 144, 146, 150, 154, 156, 159, 166, 169, 174, 176, 178, 180, 183, 186, 188, 191, 193, 195, 198, 200, 203, 206, 209, 212, 214, 217, 219, 224, 227, 229, 231, 233, 235, 237, 239, 241, 243, 245, 247, 249, 253, 255, 257, 259, 263, 265, 267, 269, 271, 273, 277, 279, 281, 287, 291, 293, 301, 304, 307, 313, 315, 319, 322, 324, 330, 332, 334, 341, 343, 345, 347, 349, 352, 354, 356, 358, 367, 369, 371, 378, 382, 385, 387, 389, 391, 395, 397, 399, 401, 403, 405, 409, 411, 415, 417, 421, 425, 428, 432, 435, 438, 440, 443, 445, 447, 453, 455, 457, 461, 464, 467, 469, 471, 475, 477, 482, 484, 487, 489, 491, 494, 496, 499, 502, 505, 507, 511, 513, 518, 520, 524, 526, 528, 530, 532, 536, 538, 540, 542, 544, 546, 548, 550, 553, 555, 558, 560, 561, 563, 566, 569, 571, 577, 579, 581, 583, 585, 587, 591, 593, 595, 597, 600, 604, 606, 610, 612, 614, 616, 618, 620, 623, 626, 628, 631, 633, 635, 637, 639, 640, 642, 644, 655, 657, 659, 661, 663, 665, 667, 669, 671, 673, 675, 678, 681, 683, 685, 693, 696, 698, 700, 703, 705, 707, 709, 711, 714, 717, 719, 722, 725, 728, 731, 734, 738, 741, 743, 745, 752, 754, 756, 759, 762, 770, 773, 779, 784, 787, 790, 792, 794, 797, 804, 806, 809, and 822, or a fragment thereof. A plant produced from the plant cell has a difference in biomass composition as compared to the corresponding composition of a control plant that does not comprise the nucleic acid. The difference in biomass composition in the plant can be a difference in the sucrose content or conversion efficiency.

In another aspect, this document features a plant cell that includes an exogenous nucleic acid. The exogenous nucleic acid includes a regulatory region operably linked to a nucleotide sequence encoding a polypeptide, wherein the HMM bit score of the amino acid sequence of the polypeptide is greater than about 65, where the HMM is based on the amino acid sequences depicted in one of FIGS. 1-12, and wherein a plant produced from the plant cell has a difference in biomass composition as compared to the corresponding composition of a control plant that does not comprise the nucleic acid. The difference in biomass composition in the plant can be a difference in the sucrose content or conversion efficiency.

This document also features a plant cell that includes an exogenous nucleic acid, where the exogenous nucleic acid includes a regulatory region operably linked to a nucleotide sequence encoding a polypeptide having 80 percent or greater sequence identity to an amino acid sequence selected from the group consisting of SEQ ID NO: 2, 4, 6, 7, 8, 10, 12, 14, 15, 17, 18, 19, 20, 21, 22, 24, 26, 28, 29, 30, 32, 34, 36, 37, 39, 41, 43, 45, 47, 49, 50, 52, 53, 55, 57, 59, 61, 63, 65, 66, 68, 70, 71, 72, 73, 75, 77, 78, 79, 81, 82, 84, 86, 88, 90, 92, 94, 96, 97, 99, 100, 101, 102, 104, 105, 107, 109, 111, 113, 115, 117, 118, 120, 122, 124, 126, 128, 130, 132, 133, 135, 136, 138, 139, 141, 143, 145, 147, 148, 149, 151, 152, 153, 155, 157, 158, 160, 161, 162, 163, 164, 165, 167, 168, 170, 171, 172, 173, 175, 177, 179, 181, 182, 184, 185, 187, 189, 190, 192, 194, 196, 197, 199, 201, 202, 204, 205, 207, 208, 210, 211, 213, 215, 216, 218, 220, 221, 222, 223, 225, 226, 228, 230, 232, 234, 236, 238, 240, 242, 244, 246, 248, 250, 251, 252, 254, 256, 258, 260, 261, 262, 264, 266, 268, 270, 272, 274, 275, 276, 278, 280, 282, 283, 284, 285, 286, 288, 289, 290, 292, 294, 295, 296, 297, 298, 299, 300, 302, 303, 305, 306, 308, 309, 310, 311, 312, 314, 316, 317, 318, 320, 321, 323, 325, 326, 327, 328, 329, 331, 333, 335, 336, 337, 338, 339, 340, 342, 344, 346, 348, 350, 351, 353, 355, 357, 359, 360, 361, 362, 363, 364, 365, 366, 368, 370, 372, 373, 374, 375, 376, 377, 379, 380, 381, 383, 384, 386, 388, 390, 392, 393, 394, 396, 398, 400, 402, 404, 406, 407, 408, 410, 412, 413, 414, 416, 418, 419, 420, 422, 423, 424, 426, 427, 429, 430, 431, 433, 434, 436, 437, 439, 441, 442, 444, 446, 448, 449, 450, 451, 452, 454, 456, 458, 459, 460, 462, 463, 465, 466, 468, 470, 472, 473, 474, 476, 478, 479, 480, 481, 483, 485, 486, 488, 490, 492, 493, 495, 497, 498, 500, 501, 503, 504, 506, 508, 509, 510, 512, 514, 515, 516, 517, 519, 521, 522, 523, 525, 527, 529, 531, 533, 534, 535, 537, 539, 541, 543, 545, 547, 549, 551, 552, 554, 556, 557, 559, 562, 564, 565, 567, 568, 570, 572, 573, 574, 575, 576, 578, 580, 582, 584, 586, 588, 589, 590, 592, 594, 596, 598, 599, 601, 602, 603, 605, 607, 608, 609, 611, 613, 615, 617, 619, 621, 622, 624, 625, 627, 629, 630, 632, 634, 636, 638, 641, 643, 645, 646, 647, 648, 649, 650, 651, 652, 653, 654, 656, 658, 660, 662, 664, 666, 668, 670, 672, 674, 676, 677, 679, 680, 682, 684, 686, 687, 688, 689, 690, 691, 692, 694, 695, 697, 699, 701, 702, 704, 706, 708, 710, 712, 713, 715, 716, 718, 720, 721, 723, 724, 726, 727, 729, 730, 732, 733, 735, 736, 737, 739, 740, 742, 744, 746, 747, 748, 749, 750, 751, 753, 755, 757, 758, 760, 761, 763, 764, 765, 766, 767, 768, 769, 771, 772, 774, 775, 776, 777, 778, 780, 781, 782, 783, 785, 786, 788, 789, 791, 793, 795, 796, 798, 799, 800, 801, 802, 803, 805, 807, 808, 810, 811, 812, 813, 814, 815, 816, 817, 818, 819, 820, 821, and 823, wherein a plant produced from the plant cell has a difference in biomass composition as compared to the corresponding composition of a control plant that does not comprise the nucleic acid. The difference in biomass composition in the plant can be a difference in the sucrose content or conversion efficiency.

In yet another aspect, this document features a plant cell that includes an exogenous nucleic acid. The exogenous nucleic acid includes a regulatory region operably linked to a nucleotide sequence having 80 percent or greater sequence identity to a nucleotide sequence selected from the group consisting of SEQ ID NO: 1, 3, 5, 9, 11, 13, 16, 23, 25, 27, 31, 33, 35, 38, 40, 42, 44, 46, 48, 51, 54, 56, 58, 60, 62, 64, 67, 69, 74, 76, 80, 83, 85, 87, 89, 91, 93, 95, 98, 103, 106, 108, 110, 112, 114, 116, 119, 121, 123, 125, 127, 129, 131, 134, 137, 140, 142, 144, 146, 150, 154, 156, 159, 166, 169, 174, 176, 178, 180, 183, 186, 188, 191, 193, 195, 198, 200, 203, 206, 209, 212, 214, 217, 219, 224, 227, 229, 231, 233, 235, 237, 239, 241, 243, 245, 247, 249, 253, 255, 257, 259, 263, 265, 267, 269, 271, 273, 277, 279, 281, 287, 291, 293, 301, 304, 307, 313, 315, 319, 322, 324, 330, 332, 334, 341, 343, 345, 347, 349, 352, 354, 356, 358, 367, 369, 371, 378, 382, 385, 387, 389, 391, 395, 397, 399, 401, 403, 405, 409, 411, 415, 417, 421, 425, 428, 432, 435, 438, 440, 443, 445, 447, 453, 455, 457, 461, 464, 467, 469, 471, 475, 477, 482, 484, 487, 489, 491, 494, 496, 499, 502, 505, 507, 511, 513, 518, 520, 524, 526, 528, 530, 532, 536, 538, 540, 542, 544, 546, 548, 550, 553, 555, 558, 560, 561, 563, 566, 569, 571, 577, 579, 581, 583, 585, 587, 591, 593, 595, 597, 600, 604, 606, 610, 612, 614, 616, 618, 620, 623, 626, 628, 631, 633, 635, 637, 639, 640, 642, 644, 655, 657, 659, 661, 663, 665, 667, 669, 671, 673, 675, 678, 681, 683, 685, 693, 696, 698, 700, 703, 705, 707, 709, 711, 714, 717, 719, 722, 725, 728, 731, 734, 738, 741, 743, 745, 752, 754, 756, 759, 762, 770, 773, 779, 784, 787, 790, 792, 794, 797, 804, 806, 809, and 822, or a fragment thereof, wherein a plant produced from the plant cell has a difference in biomass composition as compared to the corresponding composition of a control plant that does not comprise the nucleic acid. The difference in biomass composition in the plant can be a difference in the sucrose content or conversion efficiency.

This document also features a transgenic plant comprising any of the plant cells described herein. The plant can be a member of a species selected from the group consisting of *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), and *Pennisetum glaucum* (pearl millet). A transgenic plant can include a polypeptide selected from the group consisting of SEQ ID NO: 2, 4, 6, 7, 8, 10, 12, 14, 15, 17, 18, 19, 20, 21, 22, 24, 26, 28, 29, 30, 32, 34, 36, 37, 39, 41, 43, 45, 47, 49, 50, 52, 53, 55, 57, 59, 61, 63, 65, 66, 68, 70, 71, 72, 73, 75, 77, 78, 79, 81, 82, 84, 86, 88, 90, 92, 94, 96, 97, 99, 100, 101, 102, 104, 105, 107, 109, 111, 113, 115, 117, 118, 120, 122, 124, 126, 128, 130, 132, 133, 135, 136, 138, 139, 141, 143, 145, 147, 148, 149, 151, 152, 153, 155, 157, 158, 160, 161, 162, 163, 164, 165, 167, 168, 170, 171, 172, 173, 175, 177, 179, 181, 182, 184, 185, 187, 189, 190, 192, 194, 196, 197, 199, 201, 202, 204, 205, 207, 208, 210, 211, 213, 215, 216, 218, 220, 221, 222, 223, 225, 226, 228, 230, 232, 234, 236, 238, 240, 242, 244, 246, 248, 250, 251, 252, 254, 256, 258, 260, 261, 262, 264, 266, 268, 270, 272, 274, 275, 276, 278, 280, 282, 283, 284, 285, 286, 288, 289, 290, 292, 294, 295, 296, 297, 298, 299, 300, 302, 303, 305, 306, 308, 309, 310, 311, 312, 314, 316, 317, 318, 320, 321, 323, 325, 326, 327, 328, 329, 331, 333, 335, 336, 337, 338, 339, 340, 342, 344, 346, 348, 350, 351, 353, 355, 357, 359, 360, 361, 362, 363, 364, 365, 366, 368, 370, 372, 373, 374, 375, 376, 377, 379, 380, 381, 383, 384, 386, 388, 390, 392, 393, 394, 396, 398, 400, 402, 404, 406, 407, 408, 410, 412, 413, 414, 416, 418, 419, 420, 422, 423, 424, 426, 427, 429, 430, 431, 433, 434, 436, 437, 439, 441, 442, 444, 446, 448, 449, 450, 451, 452, 454, 456, 458, 459, 460, 462, 463, 465, 466, 468, 470, 472, 473, 474, 476, 478, 479, 480, 481, 483, 485, 486, 488, 490, 492, 493, 495, 497, 498, 500, 501, 503, 504, 506, 508, 509, 510, 512, 514, 515, 516, 517, 519, 521, 522, 523, 525, 527, 529, 531, 533, 534, 535, 537, 539, 541, 543, 545, 547, 549, 551, 552, 554, 556, 557, 559, 562, 564, 565, 567, 568, 570, 572, 573, 574, 575, 576, 578, 580, 582, 584, 586, 588, 589, 590, 592, 594, 596, 598, 599, 601, 602, 603, 605, 607, 608, 609, 611, 613, 615, 617, 619, 621, 622, 624, 625, 627, 629, 630, 632, 634, 636, 638, 641, 643, 645, 646, 647, 648, 649, 650, 651, 652, 653, 654, 656, 658, 660, 662, 664, 666, 668, 670, 672, 674, 676, 677, 679, 680, 682, 684, 686, 687, 688, 689, 690, 691, 692, 694, 695, 697, 699, 701, 702, 704, 706, 708, 710, 712, 713, 715, 716, 718, 720, 721, 723, 724, 726, 727, 729, 730, 732, 733, 735, 736, 737, 739, 740, 742, 744, 746, 747, 748, 749, 750, 751, 753, 755, 757, 758, 760, 761, 763, 764, 765, 766, 767, 768, 769, 771, 772, 774, 775, 776, 777, 778, 780, 781, 782, 783, 785, 786, 788, 789, 791, 793, 795, 796, 798, 799, 800, 801, 802, 803, 805, 807, 808, 810, 811, 812, 813, 814, 815, 816, 817, 818, 819, 820, 821, and 823. A seed product can include embryonic tissue from a transgenic plant described herein.

This document also features an isolated nucleic acid that includes a nucleotide sequence having 85% or greater sequence identity to the nucleotide sequence set forth in SEQ ID NO: 9, 13, 16, 23, 166, 169, 186, 198, 212, 219, 229, 231, 235, 265, 267, 269, 287, 307, 313, 322, 324, 330, 332, 334, 341, 343, 354, 356, 385, 387, 389, 395, 401, 411, 542, 550, 553, 558, 571, 579, 585, 591, 593, 597, 600, 606, 614, 618, 623, 628, 631, 635, or 637.

In another aspect, an isolated nucleic acid is featured that includes a nucleotide sequence encoding a polypeptide having 80% or greater sequence identity to the amino acid sequence set forth in SEQ ID NO: 8, 10, 14, 15, 17, 21, 22, 24, 57, 167, 170, 187, 213, 220, 230, 232, 236, 266, 268, 270, 285, 286, 288, 290, 295, 296, 297, 299, 308, 309, 310, 311, 314, 317, 318, 323, 325, 327, 329, 331, 333, 335, 338, 342, 344, 355, 357, 360, 362, 363, 364, 366, 374, 377, 381, 386, 388, 390, 392, 393, 394, 396, 402, 408, 412, 413, 414, 493, 543, 551, 554, 557, 559, 572, 573, 574, 575, 586, 589, 590, 592, 594, 598, 599, 601, 602, 603, 607, 609, 615, 619, 622, 624, 625, 629, 630, 632, 636, 638, 776, 814, 815, 816, 817, 818, 819, 820, or 821.

This document also features a method of identifying whether a polymorphism is associated with variation in a trait. The method includes determining whether one or more genetic polymorphisms in a population of plants is associated with the locus for a polypeptide selected from the group consisting of the polypeptides depicted in FIGS. 1-12 and functional homologs thereof; and measuring the correlation between variation in the trait in plants of the population and the presence of one or more genetic polymorphisms in plants of the population, thereby identifying whether or not the one or more genetic polymorphisms are associated with variation in the trait. The variation in biomass composition can be a variation in sucrose content or conversion efficiency. The population can be a population of switchgrass plants.

In another aspect, this document features a method of making a plant line. The method includes determining whether one or more genetic polymorphisms in a population of plants is associated with the locus for a polypeptide selected from the group consisting of the polypeptides depicted in FIGS. 1-12 and functional homologs thereof; identifying one or more plants in the population in which the presence of at least one of the genetic polymorphisms is associated with variation in biomass composition; crossing one or more of the identified plants with itself or a different plant to produce seed; crossing at least one progeny plant grown from the seed with itself or a different plant; and repeating the crossing steps for an additional 0-5 generations to make the plant line, wherein at least one of the genetic polymorphisms is present in the plant line. The variation in biomass composition can be a variation in sucrose content or conversion efficiency. The population can be a population of switchgrass plants.

This document also features a method of altering biomass composition in a plant. The method includes modifying an endogenous biomass composition-modulating nucleic acid, the nucleic acid comprising a nucleotide sequence with an open reading frame having 80 percent or greater (e.g., 90 percent or greater, or 95 percent or greater) sequence identity to the nucleotide sequence selected from the group consisting of SEQ ID NO: 1, 3, 5, 9, 11, 13, 16, 23, 25, 27, 31, 33, 35, 38, 40, 42, 44, 46, 48, 51, 54, 56, 58, 60, 62, 64, 67, 69, 74, 76, 80, 83, 85, 87, 89, 91, 93, 95, 98, 103, 106, 108, 110, 112, 114, 116, 119, 121, 123, 125, 127, 129, 131, 134, 137, 140, 142, 144, 146, 150, 154, 156, 159, 166, 169, 174, 176, 178, 180, 183, 186, 188, 191, 193, 195, 198, 200, 203, 206, 209, 212, 214, 217, 219, 224, 227, 229, 231, 233, 235, 237, 239, 241, 243, 245, 247, 249, 253, 255, 257, 259, 263, 265, 267, 269, 271, 273, 277, 279, 281, 287, 291, 293, 301, 304, 307, 313, 315, 319, 322, 324, 330, 332, 334, 341, 343, 345, 347, 349, 352, 354, 356, 358, 367, 369, 371, 378, 382, 385, 387, 389, 391, 395, 397, 399, 401, 403, 405, 409, 411, 415, 417, 421, 425, 428, 432, 435, 438, 440, 443, 445, 447, 453, 455, 457, 461, 464, 467, 469, 471, 475, 477, 482, 484, 487, 489, 491, 494, 496, 499, 502, 505, 507, 511, 513, 518, 520, 524, 526, 528, 530, 532, 536, 538, 540, 542, 544, 546, 548, 550, 553, 555, 558, 560, 561, 563, 566, 569, 571, 577, 579, 581, 583, 585, 587, 591, 593, 595, 597, 600, 604, 606, 610, 612, 614, 616, 618, 620, 623, 626, 628, 631, 633, 635, 637, 639, 640, 642, 644, 655, 657, 659, 661, 663, 665, 667, 669, 671, 673, 675, 678, 681, 683, 685, 693, 696, 698, 700, 703, 705, 707, 709, 711, 714, 717, 719, 722, 725, 728, 731, 734, 738, 741, 743, 745, 752, 754, 756, 759, 762, 770, 773, 779, 784, 787, 790, 792, 794, 797, 804, 806, 809, and 822, wherein the plant has a difference in biomass composition as compared to the corresponding composition of a control plant where the nucleic acid has not been modified. The modification can be effected by introducing a genetic modification in the locus comprising the nucleic acid. The method further can include selecting for plants having altered biomass composition. The endogenous nucleic acid can encode a polypeptide having 80 percent or greater (e.g., 90 percent or greater, or 95 percent or greater) sequence identity to an amino acid sequence selected from the group consisting of SEQ ID NO: 2, 4, 6, 7, 8, 10, 12, 14, 15, 17, 18, 19, 20, 21, 22, 24, 26, 28, 29, 30, 32, 34, 36, 37, 39, 41, 43, 45, 47, 49, 50, 52, 53, 55, 57, 59, 61, 63, 65, 66, 68, 70, 71, 72, 73, 75, 77, 78, 79, 81, 82, 84, 86, 88, 90, 92, 94, 96, 97, 99, 100, 101, 102, 104, 105, 107, 109, 111, 113, 115, 117, 118, 120, 122, 124, 126, 128, 130, 132, 133, 135, 136, 138, 139, 141, 143, 145, 147, 148, 149, 151, 152, 153, 155, 157, 158, 160, 161, 162, 163, 164, 165, 167, 168, 170, 171, 172, 173, 175, 177, 179, 181, 182, 184, 185, 187, 189, 190, 192, 194, 196, 197, 199, 201, 202, 204, 205, 207, 208, 210, 211, 213, 215, 216, 218, 220, 221, 222, 223, 225, 226, 228, 230, 232, 234, 236, 238, 240, 242, 244, 246, 248, 250, 251, 252, 254, 256, 258, 260, 261, 262, 264, 266, 268, 270, 272, 274, 275, 276, 278, 280, 282, 283, 284, 285, 286, 288, 289, 290, 292, 294, 295, 296, 297, 298, 299, 300, 302, 303, 305, 306, 308, 309, 310, 311, 312, 314, 316, 317, 318, 320, 321, 323, 325, 326, 327, 328, 329, 331, 333, 335, 336, 337, 338, 339, 340, 342, 344, 346, 348, 350, 351, 353, 355, 357, 359, 360, 361, 362, 363, 364, 365, 366, 368, 370, 372, 373, 374, 375, 376, 377, 379, 380, 381, 383, 384, 386, 388, 390, 392, 393, 394, 396, 398, 400, 402, 404, 406, 407, 408, 410, 412, 413, 414, 416, 418, 419, 420, 422, 423, 424, 426, 427, 429, 430, 431, 433, 434, 436, 437, 439, 441, 442, 444, 446, 448, 449, 450, 451, 452, 454, 456, 458, 459, 460, 462, 463, 465, 466, 468, 470, 472, 473, 474, 476, 478, 479, 480, 481, 483, 485, 486, 488, 490, 492, 493, 495, 497, 498, 500, 501, 503, 504, 506, 508, 509, 510, 512, 514, 515, 516, 517, 519, 521, 522, 523, 525, 527, 529, 531, 533, 534, 535, 537, 539, 541, 543, 545, 547, 549, 551, 552, 554, 556, 557, 559, 562, 564, 565, 567, 568, 570, 572, 573, 574, 575, 576, 578, 580, 582, 584, 586, 588, 589, 590, 592, 594, 596, 598, 599, 601, 602, 603, 605, 607, 608, 609, 611, 613, 615, 617, 619, 621, 622, 624, 625, 627, 629, 630, 632, 634, 636, 638, 641, 643, 645, 646, 647, 648, 649, 650, 651, 652, 653, 654, 656, 658, 660, 662, 664, 666, 668, 670, 672, 674, 676, 677, 679, 680, 682, 684, 686, 687, 688, 689, 690, 691, 692, 694, 695, 697, 699, 701, 702, 704, 706, 708, 710, 712, 713, 715, 716, 718, 720, 721, 723, 724, 726, 727, 729, 730, 732, 733, 735, 736, 737, 739, 740, 742, 744, 746, 747, 748, 749, 750, 751, 753, 755, 757, 758, 760, 761, 763, 764, 765, 766, 767, 768, 769, 771, 772, 774, 775, 776, 777, 778, 780, 781, 782, 783, 785, 786, 788, 789, 791, 793, 795, 796, 798, 799, 800, 801, 802, 803, 805, 807, 808, 810, 811, 812, 813, 814, 815, 816, 817, 818, 819, 820, 821, and 823.

This document also features a method of producing a plant. The method includes growing a plant cell containing a modified endogenous nucleic acid encoding a polypeptide, wherein the HMM bit score of the amino acid sequence of the polypeptide is greater than about 65, the HMM based on the amino acid sequences depicted in one of FIGS. 1-12, and wherein the plant has a difference in biomass composition as compared to the corresponding composition of a control plant where the nucleic acid has not been modified.

In another aspect, this document features a plant cell containing a modified endogenous nucleic acid encoding a polypeptide, wherein the HMM bit score of the amino acid sequence of the polypeptide is greater than about 65, the HMM based on the amino acid sequences depicted in one of FIGS. 1-12, and wherein a plant produced from the plant cell has a difference in biomass composition as compared to the corresponding composition of a control plant where the nucleic acid has not been modified.

In yet another aspect, this document features a plant cell containing a modified biomass composition-modulating endogenous nucleic acid. The nucleic acid includes a nucleotide sequence with an open reading frame having 80 percent or greater sequence identity to the nucleotide sequence selected from the group consisting of SEQ ID NO: 1, 3, 5, 9, 11, 13, 16, 23, 25, 27, 31, 33, 35, 38, 40, 42, 44, 46, 48, 51, 54, 56, 58, 60, 62, 64, 67, 69, 74, 76, 80, 83, 85, 87, 89, 91, 93, 95, 98, 103, 106, 108, 110, 112, 114, 116, 119, 121, 123, 125, 127, 129, 131, 134, 137, 140, 142, 144, 146, 150, 154, 156, 159, 166, 169, 174, 176, 178, 180, 183, 186, 188, 191, 193, 195, 198, 200, 203, 206, 209, 212, 214, 217, 219, 224, 227, 229, 231, 233, 235, 237, 239, 241, 243, 245, 247, 249, 253, 255, 257, 259, 263, 265, 267, 269, 271, 273, 277, 279, 281, 287, 291, 293, 301, 304, 307, 313, 315, 319, 322, 324, 330, 332, 334, 341, 343, 345, 347, 349, 352, 354, 356, 358, 367, 369, 371, 378, 382, 385, 387, 389, 391, 395, 397, 399, 401, 403, 405, 409, 411, 415, 417, 421, 425, 428, 432, 435, 438, 440, 443, 445, 447, 453, 455, 457, 461, 464, 467, 469, 471, 475, 477, 482, 484, 487, 489, 491, 494, 496, 499, 502, 505, 507, 511, 513, 518, 520, 524, 526, 528, 530, 532, 536, 538, 540, 542, 544, 546, 548, 550, 553, 555, 558, 560, 561, 563, 566, 569, 571, 577, 579, 581, 583, 585, 587, 591, 593, 595, 597, 600, 604, 606, 610, 612, 614, 616, 618, 620, 623, 626, 628, 631, 633, 635, 637, 639, 640, 642, 644, 655, 657, 659, 661, 663, 665, 667, 669, 671, 673, 675, 678, 681, 683, 685, 693, 696, 698, 700, 703, 705, 707, 709, 711, 714, 717, 719, 722, 725, 728, 731, 734, 738, 741, 743, 745, 752, 754, 756, 759, 762, 770, 773, 779, 784, 787, 790, 792, 794, 797, 804, 806, 809, and 822, and wherein a plant produced from the plant cell has a difference in biomass composition as compared to the corresponding composition of a control plant where the nucleic acid has not been modified. The difference in biomass composition in the plant can be a difference in the sucrose content or conversion efficiency.

An endogenous nucleic acid can encode a polypeptide having 80 percent or greater sequence identity to an amino acid sequence selected from the group consisting of SEQ ID NO: 2, 4, 6, 7, 8, 10, 12, 14, 15, 17, 18, 19, 20, 21, 22, 24, 26, 28, 29, 30, 32, 34, 36, 37, 39, 41, 43, 45, 47, 49, 50, 52, 53, 55, 57, 59, 61, 63, 65, 66, 68, 70, 71, 72, 73, 75, 77, 78, 79, 81, 82, 84, 86, 88, 90, 92, 94, 96, 97, 99, 100, 101, 102, 104, 105, 107, 109, 111, 113, 115, 117, 118, 120, 122, 124, 126, 128, 130, 132, 133, 135, 136, 138, 139, 141, 143, 145, 147, 148, 149, 151, 152, 153, 155, 157, 158, 160, 161, 162, 163, 164, 165, 167, 168, 170, 171, 172, 173, 175, 177, 179, 181, 182, 184, 185, 187, 189, 190, 192, 194, 196, 197, 199, 201, 202, 204, 205, 207, 208, 210, 211, 213, 215, 216, 218, 220, 221, 222, 223, 225, 226, 228, 230, 232, 234, 236, 238, 240, 242, 244, 246, 248, 250, 251, 252, 254, 256, 258, 260, 261, 262, 264, 266, 268, 270, 272, 274, 275, 276, 278, 280, 282, 283, 284, 285, 286, 288, 289, 290, 292, 294, 295, 296, 297, 298, 299, 300, 302, 303, 305, 306, 308, 309, 310, 311, 312, 314, 316, 317, 318, 320, 321, 323, 325, 326, 327, 328, 329, 331, 333, 335, 336, 337, 338, 339, 340, 342, 344, 346, 348, 350, 351, 353, 355, 357, 359, 360, 361, 362, 363, 364, 365, 366, 368, 370, 372, 373, 374, 375, 376, 377, 379, 380, 381, 383, 384, 386, 388, 390, 392, 393, 394, 396, 398, 400, 402, 404, 406, 407, 408, 410, 412, 413, 414, 416, 418, 419, 420, 422, 423, 424, 426, 427, 429, 430, 431, 433, 434, 436, 437, 439, 441, 442, 444, 446, 448, 449, 450, 451, 452, 454, 456, 458, 459, 460, 462, 463, 465, 466, 468, 470, 472, 473, 474, 476, 478, 479, 480, 481, 483, 485, 486, 488, 490, 492, 493, 495, 497, 498, 500, 501, 503, 504, 506, 508, 509, 510, 512, 514, 515, 516, 517, 519, 521, 522, 523, 525, 527, 529, 531, 533, 534, 535, 537, 539, 541, 543, 545, 547, 549, 551, 552, 554, 556, 557, 559, 562, 564, 565, 567, 568, 570, 572, 573, 574, 575, 576, 578, 580, 582, 584, 586, 588, 589, 590, 592, 594, 596, 598, 599, 601, 602, 603, 605, 607, 608, 609, 611, 613, 615, 617, 619, 621, 622, 624, 625, 627, 629, 630, 632, 634, 636, 638, 641, 643, 645, 646, 647, 648, 649, 650, 651, 652, 653, 654, 656, 658, 660, 662, 664, 666, 668, 670, 672, 674, 676, 677, 679, 680, 682, 684, 686, 687, 688, 689, 690, 691, 692, 694, 695, 697, 699, 701, 702, 704, 706, 708, 710, 712, 713, 715, 716, 718, 720, 721, 723, 724, 726, 727, 729, 730, 732, 733, 735, 736, 737, 739, 740, 742, 744, 746, 747, 748, 749, 750, 751, 753, 755, 757, 758, 760, 761, 763, 764, 765, 766, 767, 768, 769, 771, 772, 774, 775, 776, 777, 778, 780, 781, 782, 783, 785, 786, 788, 789, 791, 793, 795, 796, 798, 799, 800, 801, 802, 803, 805, 807, 808, 810, 811, 812, 813, 814, 815, 816, 817, 818, 819, 820, 821, and 823, and wherein a plant produced from the plant cell has a difference in biomass composition as compared to the corresponding composition of a control plant where the nucleic acid has not been modified. The difference in biomass composition in the plant can be a difference in the sucrose content or conversion efficiency.

This document also features a plant cell that includes an exogenous nucleic acid, the exogenous nucleic acid encoding a polypeptide having E.C. 3.2.1.55 activity, and wherein a plant produced from the plant cell has a difference in biomass composition as compared to the corresponding level of a control plant that does not comprise said nucleic acid. The difference in biomass composition in the plant can be a difference in the sucrose content or conversion efficiency.

In another aspect, this document features a method of modulating biomass composition of a plant. The method includes introducing into a plant cell an exogenous nucleic acid, the exogenous nucleic acid encoding a polypeptide having E.C. 3.2.1.55 activity.

This document also features a process for making a biofuel. The process includes planting seeds of a sorghum plant described herein, or a sorghum plant produced by a method described herein in one or more fields to obtain at least about 10 acres of the sorghum plants; harvesting sorghum biomass from the one or more fields to obtain harvested sorghum biomass; extracting sorghum stem juice from the harvested sorghum biomass to obtain extracted stem juice comprising sugar; using said sugar of the extracted stem juice in a fermentation reaction to produce a fermentation product comprising a biofuel; and isolating the biofuel from the fermentation product to obtain a composition comprising the biofuel (e.g., ethanol or anhydrous ethanol). The sorghum plants can have an average BRIX value that is greater than about 10 percent at harvest time.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims. The word "comprising" in the claims may be replaced by "consisting essentially of" or with "consisting of," according to standard practice in patent law.

DESCRIPTION OF DRAWINGS

FIG. 1 is an alignment of the amino acid sequence of CeresClone:1767521 (SEQ ID NO: 483) with homologous and/or orthologous amino acid sequences. In all the alignment figures shown herein, a dash in an aligned sequence represents a gap, i.e., a lack of an amino acid at that position. Identical amino acids or conserved amino acid substitutions among aligned sequences are identified by boxes. FIG. 1 and the other alignment figures provided herein were generated using the program MUSCLE version 3.52.

FIGS. 2A-2C are an alignment of the amino acid sequence of CeresClone: 1871180 (SEQ ID NO: 562) with homologous and/or orthologous amino acid sequences.

FIGS. 3A-3C are an alignment of the amino acid sequence of CeresClone: 240112 (SEQ ID NO: 246) with homologous and/or orthologous amino acid sequences.

FIG. 4 are an alignment of the amino acid sequence of CeresClone: 1764605 (SEQ ID NO:111) with homologous and/or orthologous amino acid sequences.

FIGS. 5A-5E are an alignment of the amino acid sequence of CeresClone: 1776501 (SEQ ID NO: 348) with homologous and/or orthologous amino acid sequences.

FIGS. 6A-6I are an alignment of the amino acid sequence of CeresClone: 1789981 (SEQ ID NO: 774) with homologous and/or orthologous amino acid sequences.

Figure 7A:
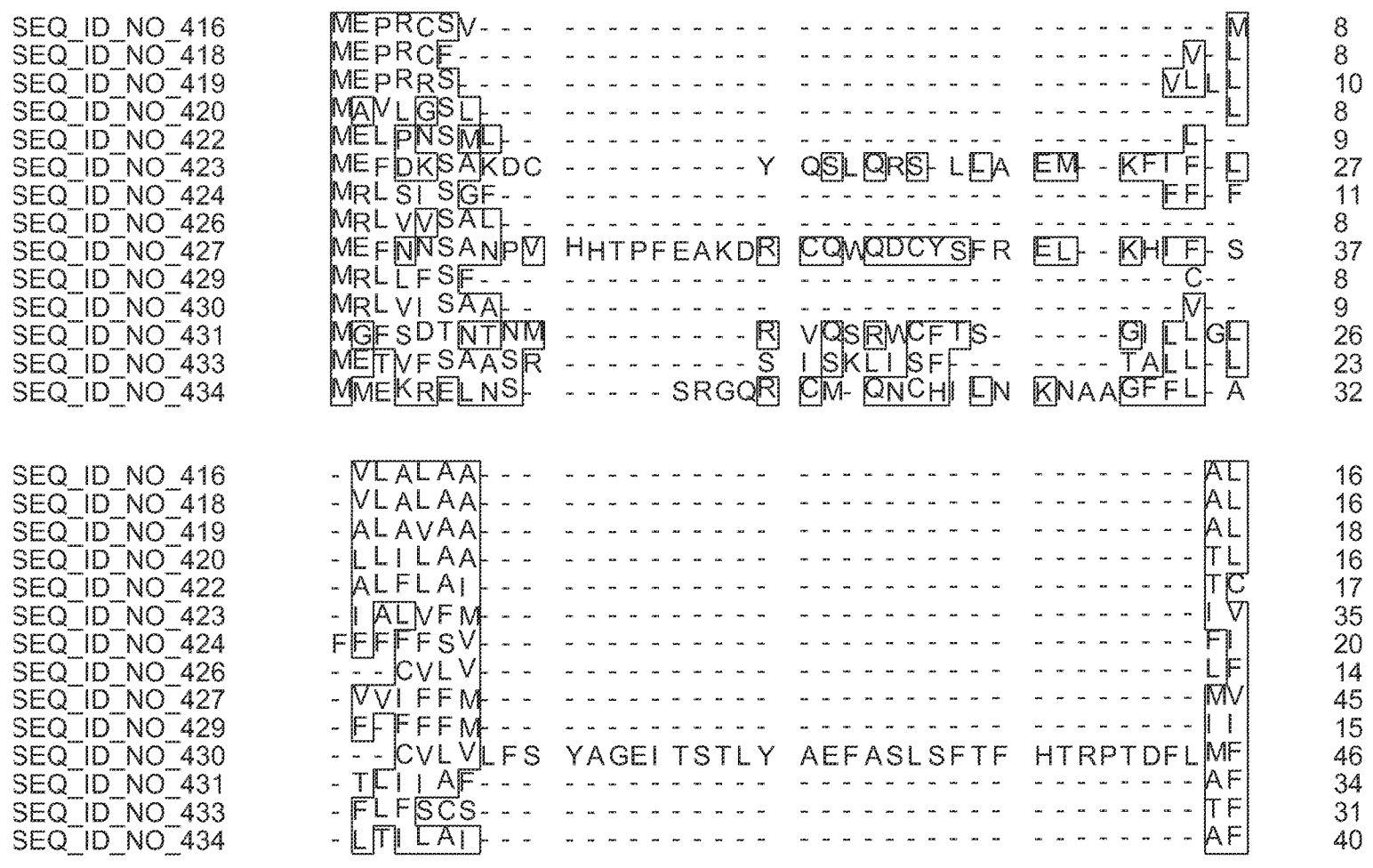
Figure 7B:
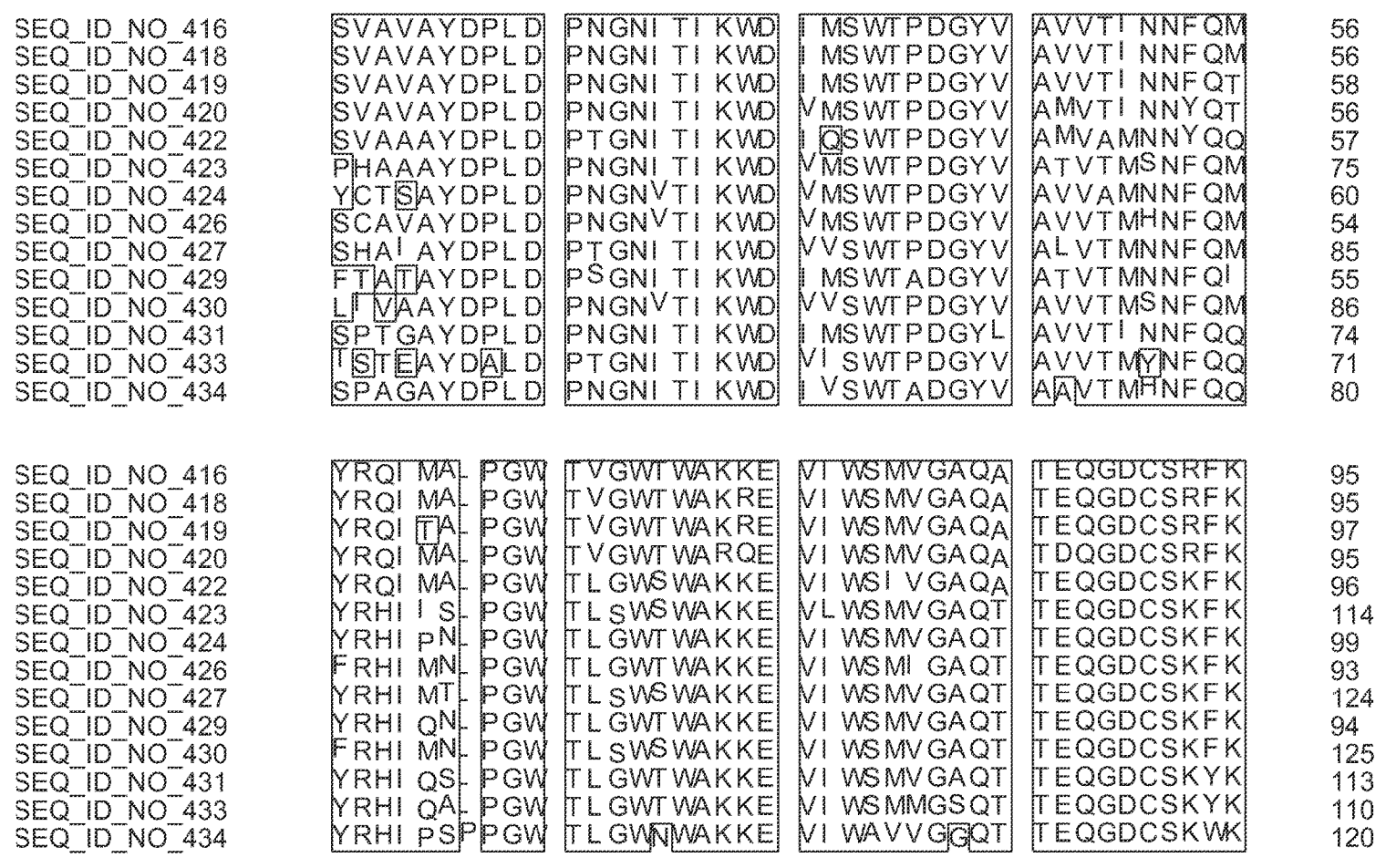
Figure 7D:
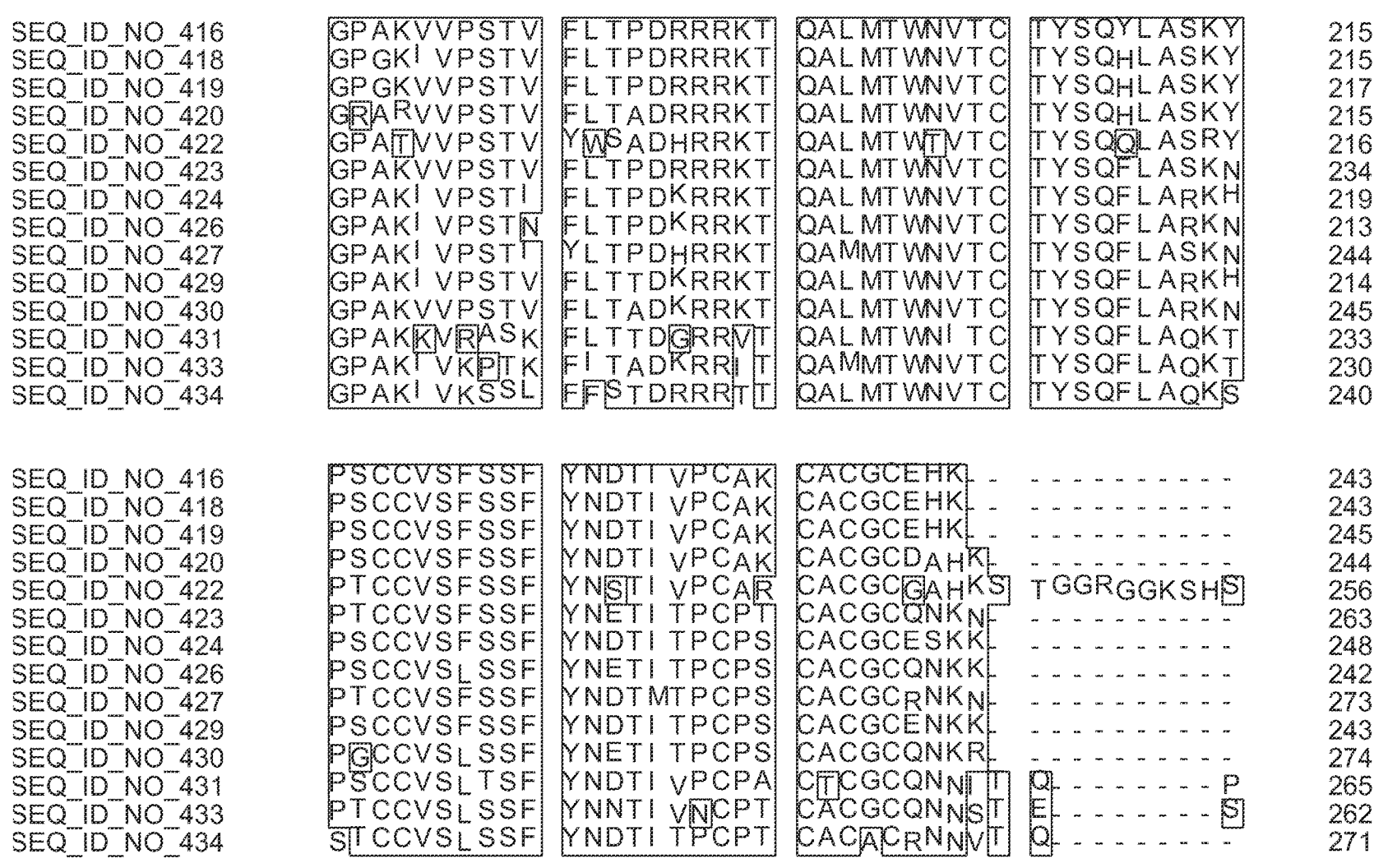
Figure 7G:
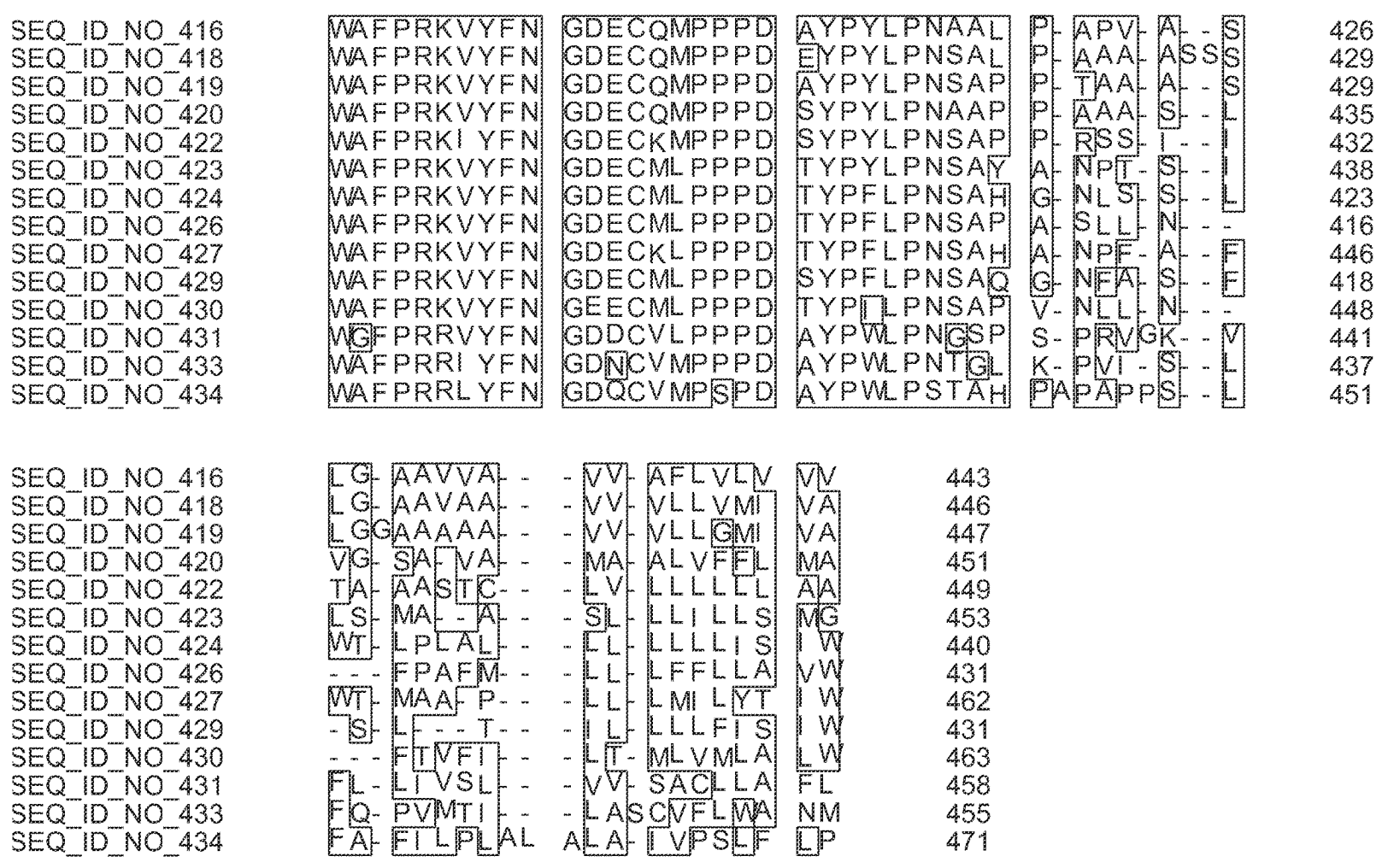

FIGS. 7A-7G are an alignment of the amino acid sequence of CeresClone: 1804732 (SEQ ID NO: 416) with homologous and/or orthologous amino acid sequences.

Figure 8E:
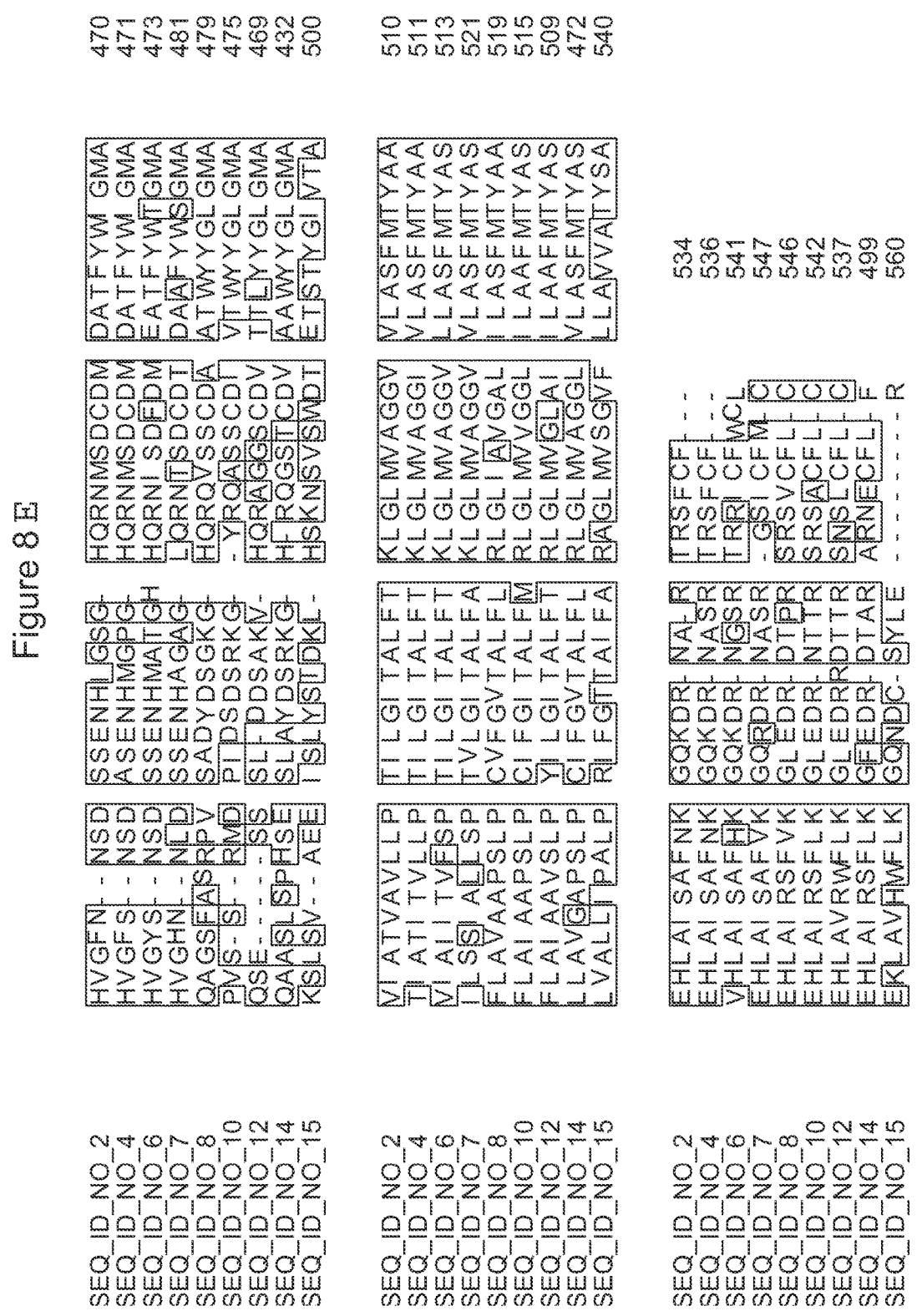

FIGS. 8A-8E are an alignment of the amino acid sequence of CeresClone: 1807011 (SEQ ID NO: 2) with homologous and/or orthologous amino acid sequences.

Figure 9A:
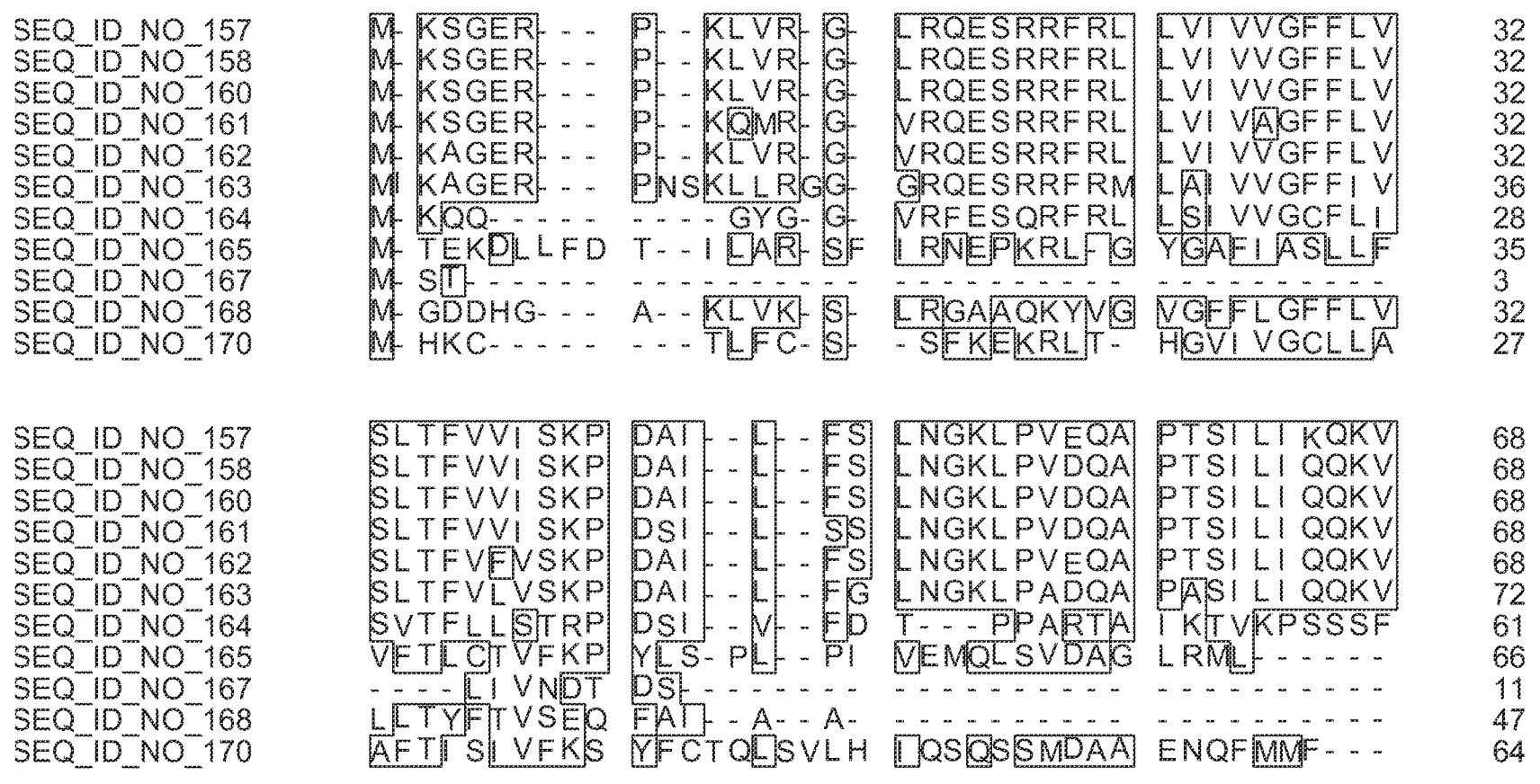
Figure 9E:
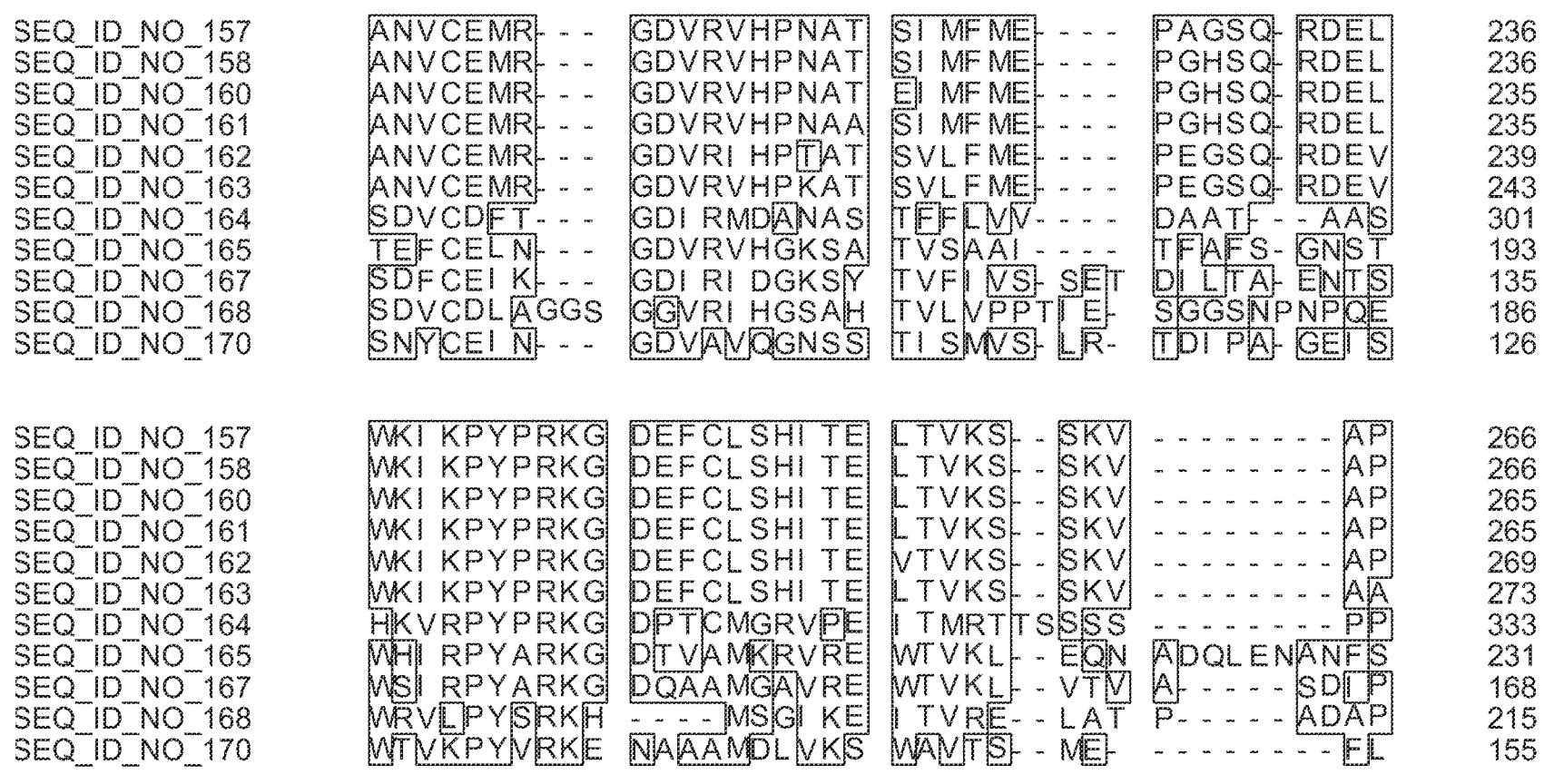
Figure 9F:
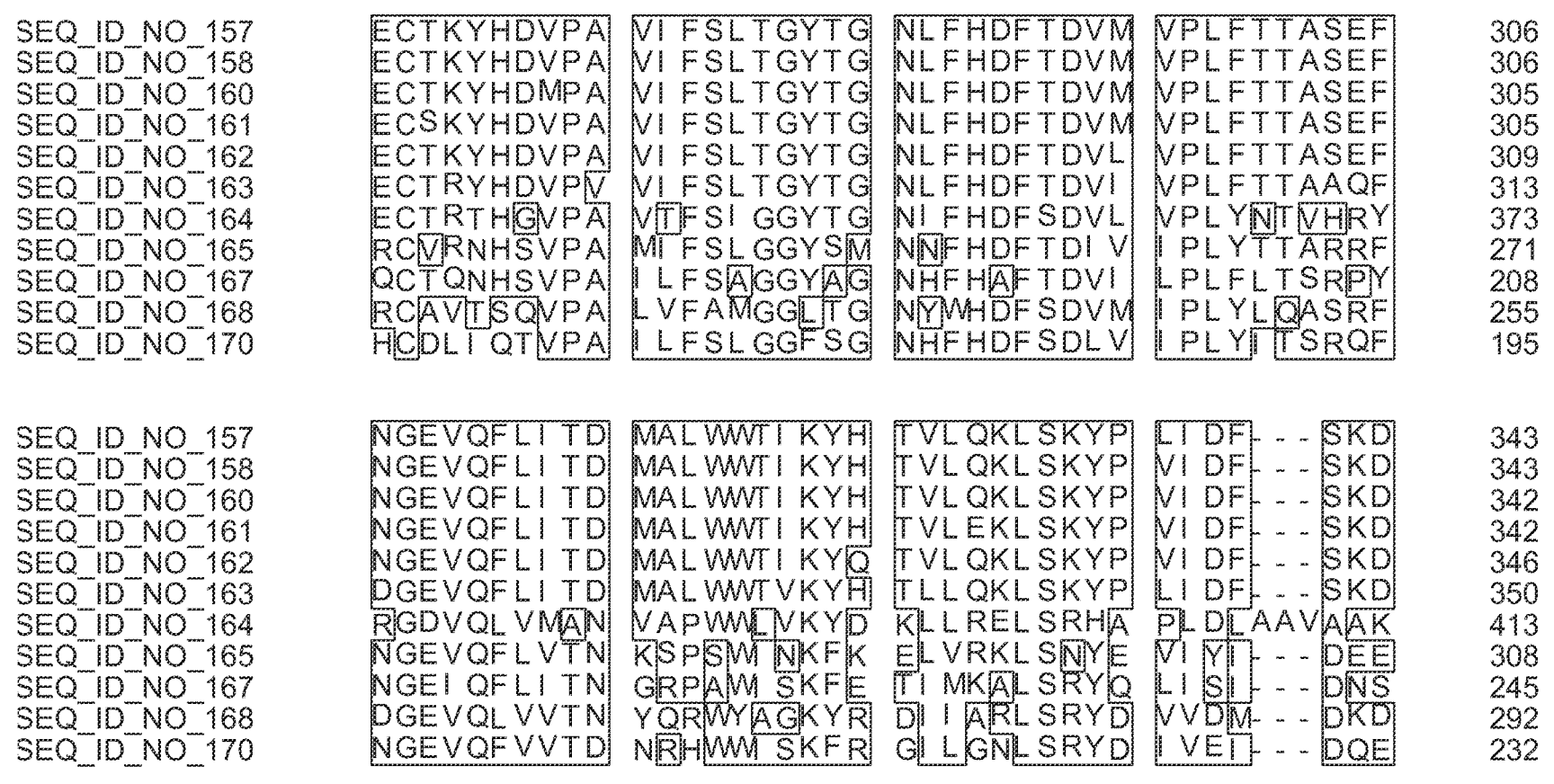
Figure 9G:
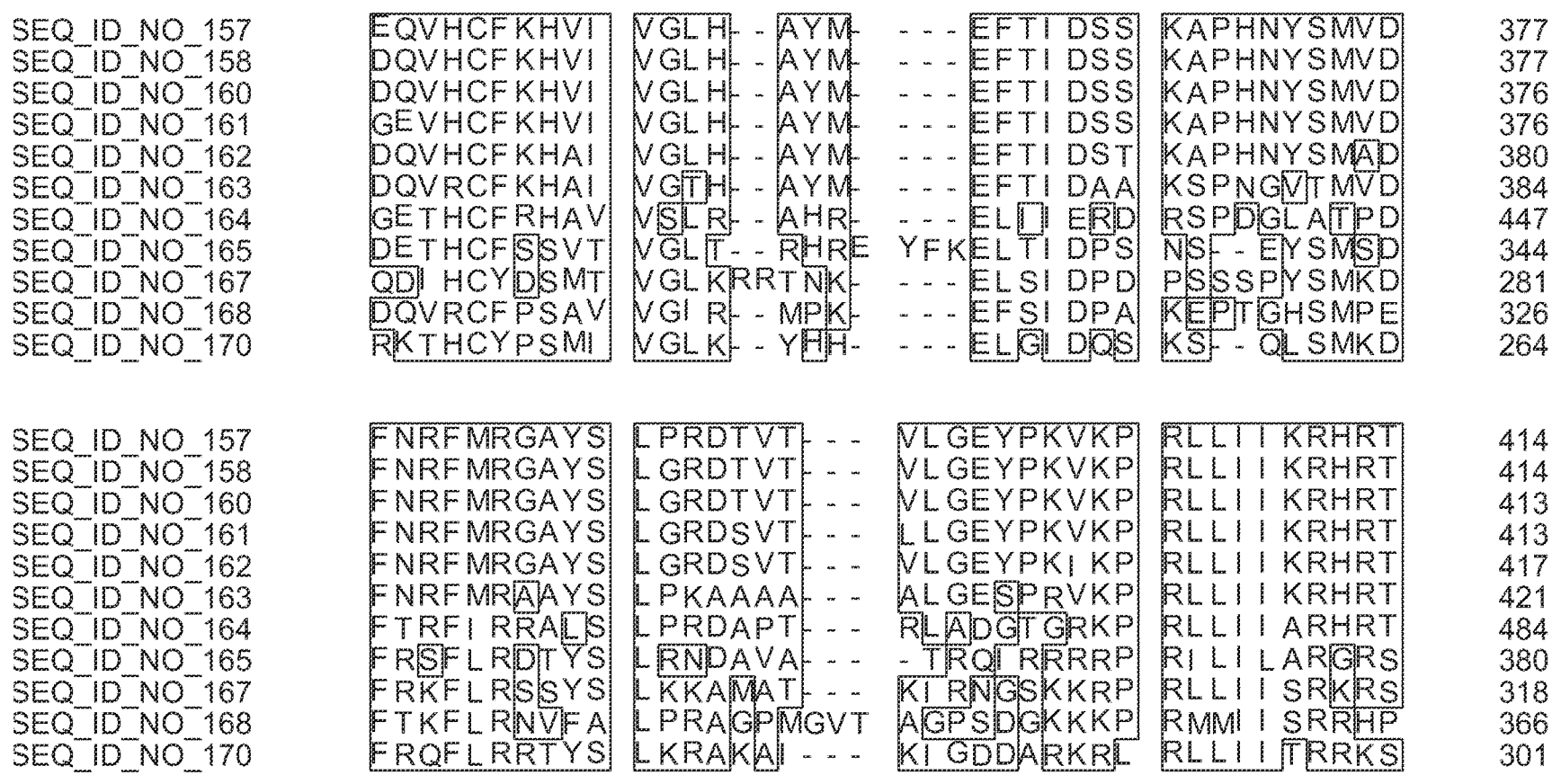

FIGS. 9A-9I are an alignment of the amino acid sequence of CeresClone: 1888614 (SEQ ID NO: 157) with homologous and/or orthologous amino acid sequences.

FIGS. 10A-10G are an alignment of the amino acid sequence of CeresClone: 1900192 (SEQ ID NO:280) with homologous and/or orthologous amino acid sequences.

FIGS. 11A-11D are an alignment of the amino acid sequence of CeresClone: 1955550 (SEQ ID NO: 641) with homologous and/or orthologous amino acid sequences.

DETAILED DESCRIPTION

Figure 9C:
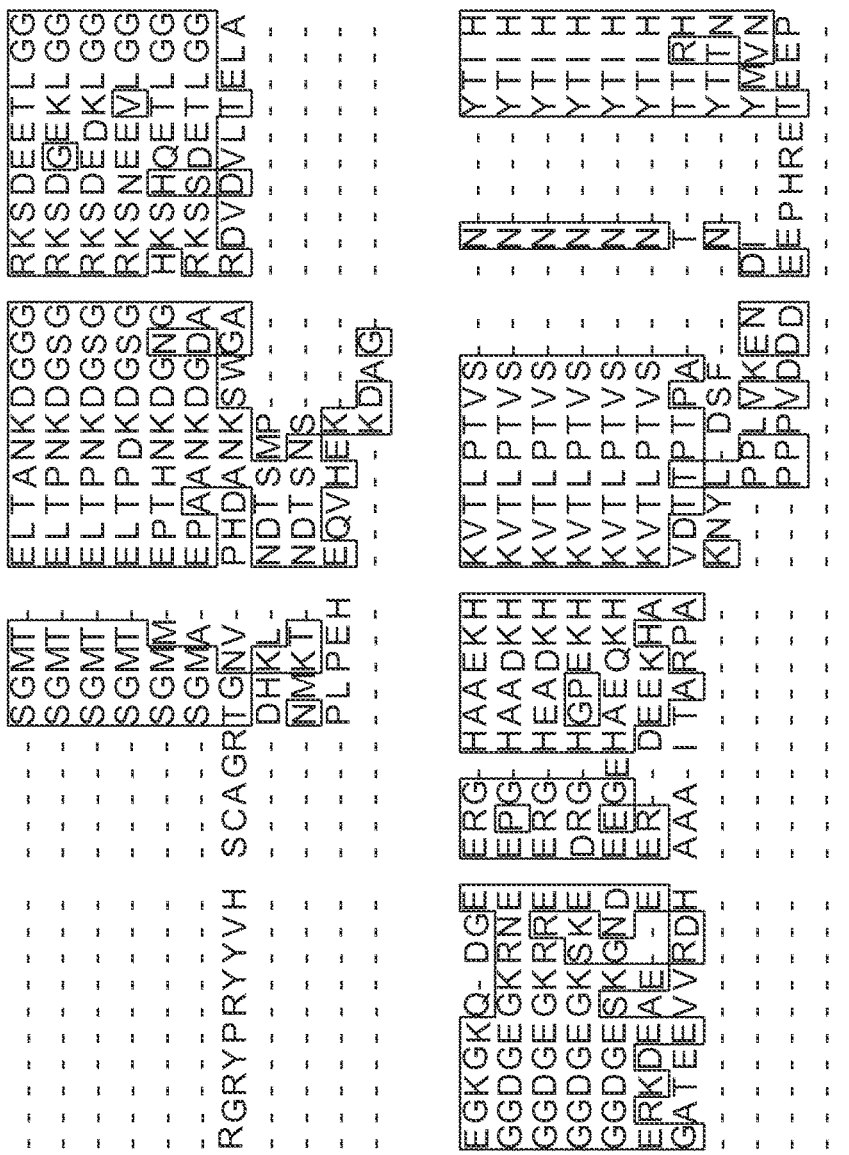

This document features methods and materials related to modulating biomass composition (e.g., sucrose content or conversion efficiency) in plants. For example, this document features methods and materials for increasing or decreasing sucrose content and conversion efficiency in plants. In some embodiments, the plants also may have modulated levels of, for example, lignin, modified root architecture, modified herbicide resistance, or modified carotenoid biosynthesis. The methods can include transforming a plant cell with a nucleic acid encoding a biomass composition-modulating polypeptide, wherein expression of the polypeptide results in modulated biomass composition. Plant cells produced using such methods can be grown to produce plants having an increased or decreased sucrose content and/or conversion efficiency. Such plants may produce more grazable forage. Increased brix levels (an approximate amount of sugar as measured by, for example, a digital refractometer) and/or sucrose content can result in increased palatability as a forage crop. In addition, such plants, and the seeds of such plants, may be used to produce, for example, switchgrass, miscanthus, *Sorghum* sp., and sugar cane plants having increased value as a biofuel feedstock.

I. Definitions

"Accessible Carbohydrate" refers to mono- and oligosaccharides released into the aqueous phase after processing of a biomass feedstock. The amount of accessible carbohydrate in a feedstock is related to the pretreatment and enzymatic saccharification conditions chosen for the saccharification process and to the composition and structure of the initial biomass feedstock.

"Amino acid" refers to one of the twenty biologically occurring amino acids and to synthetic amino acids, including D/L optical isomers.

"Ash" refers to inorganic material that contributes to the dry weight of the feedstock. Ash content in biomass feedstocks can be determined using published, standard methods such as ASTM Standard E1755.

"Biofuels" include, but are not limited to, biodiesel, methanol, ethanol, butanol, linear alkanes ($C_5$-$C_{20}$), branched-chain alkanes ($C_5$-$C_{26}$), mixed alkanes, linear alcohols ($C_1$-$C_{20}$), branched-chain alcohols ($C_1$-$C_{26}$), linear carboxylic acids ($C_2$-$C_{20}$), and branched-chain carboxylic acids ($C_2$-$C_{26}$). In addition, ethers, esters and amides of the aforementioned acids and alcohols, as well as other conjugates of these chemicals may be of interest. Many of these chemicals can be subsequently converted by chemical reactions to other high value, high volume chemicals.

"Biomass" refers to organic matter. Biomass includes plant matter derived from herbaceous and woody energy crops, agricultural food and feed crops, agricultural crop wastes and residues, wood wastes and residues, aquatic plants, and other plant-derived materials. Biomass may also include algae, yard wastes, and include some municipal wastes. Biomass is a heterogeneous and chemically complex renewable resource. Components of biomass include glucan, xylan, fermentable sugars, arabinan, sucrose, lignin, protein, ash, extractives, ferulate, and acetate.

"Cell type-preferential promoter" or "tissue-preferential promoter" refers to a promoter that drives expression preferentially in a target cell type or tissue, respectively, but may also lead to some transcription in other cell types or tissues as well.

"Control plant" refers to a plant that does not contain the exogenous nucleic acid present in a transgenic plant of interest, but otherwise has the same or similar genetic background as such a transgenic plant. A suitable control plant can be a non-transgenic wild type plant, a non-transgenic segregant from a transformation experiment, or a transgenic plant that contains an exogenous nucleic acid other than the exogenous nucleic acid of interest.

"Conversion efficiency" refers to the conversion of biomass feedstock to free sugars, fermentable sugars, syngas, biofuel, ethanol, heat, or energy in a laboratory-, pilot-, or production-scale process. The relevant conversion efficiency parameters are dependent on the type of conversion process employed (biochemical, thermochemical to biofuel, or thermochemical to heat and electricity). NIR spectra of biomass samples are collected and translated by a NIR model (see below) to predict feedstock conversion properties (such as free sugars or accessible carbohydrate), one or more intermediate values that may serve for predicting feedstock conversion properties (such as recalcitrant carbohydrate), or one or more downstream parameters that are influenced by feedstock conversion efficiency (such as biofuel or energy yield). Predictions of conversion properties may be used to calculate the feedstock performance characteristics in one or more processing methods of interest. Such performance characteristics include saccharification efficiency or sugar yield (Glu, Xyl, Ara, Man, Gal), various enzymatic conditions (type, ratio, load) for saccharification, pretreatment conditions, total or net energy yield or energy conversion efficiency, biofuel yield or biofuel conversion efficiency, biopower yield or biopower conversion efficiency, coproduct yield or extraction/conversion efficiency, economic value of the original feedstock, NOX emissions, protein coproducts, or sustainability indicators.

"Domains" are groups of substantially contiguous amino acids in a polypeptide that can be used to characterize protein families and/or parts of proteins. Such domains have a "fingerprint" or "signature" that can comprise conserved primary sequence, secondary structure, and/or three-dimensional conformation. Generally, domains are correlated with specific in vitro and/or in vivo activities. A domain can have a length of from 10 amino acids to 400 amino acids, e.g., 10 to 50 amino acids, or 25 to 100 amino acids, or 35 to 65 amino acids, or 35 to 55 amino acids, or 45 to 60 amino acids, or 200 to 300 amino acids, or 300 to 400 amino acids.

"Down-regulation" refers to regulation that decreases production of expression products (mRNA, polypeptide, or both) relative to basal or native states.

"Exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

"Expression" refers to the process of converting genetic information of a polynucleotide into RNA through transcription, which is catalyzed by an enzyme, RNA polymerase, and into protein, through translation of mRNA on ribosomes.

"Glucan," "Xylan" and "Arabinan" refer to the anhydro forms of glucose, xylose and arabinose that are found in cellulose and hemicellulose carbohydrate polymers. Thus, for example, "glucan" refers to a polysaccharide of D-glucose monomers linked by glycosidic bonds. The following are glucans: cellulose (β-1,4-glucan), dextran (α-1,6-glucan) and starch (α-1,4- and α-1,6-glucan).

"Hemicellulose" is a general term used to refer to cell wall polysaccharides that are not celluloses or pectins. Hemicelluloses contain repeating monomeric units of a five-carbon sugar (usually D-xylose or L-arabinose) and/or a six-carbon sugar (D-galactose, D-glucose, and D-mannose). See, U.S. Pat. No. 7,112,429. Hemicelluloses typically are shorter in length than cellulose and are highly branched. Xylan is often the structural backbone of hemicelluloses from hardwoods and grasses, and hydrolysis of these biomass types releases products high in the five-carbon sugar, xylose. Hemicelluloses from softwoods are most commonly gluco-galactomannans, which have a mannan backbone and yield mannose as the main product of hydrolysis. Hemicelluloses often contain side groups such as acetyl groups, uronic acids and ferulates.

"Heterologous polypeptide" as used herein refers to a polypeptide that is not a naturally occurring polypeptide in a plant cell, e.g., a transgenic *Panicum virgatum* plant transformed with and expressing the coding sequence for a nitrogen transporter polypeptide from a *Zea mays* plant.

"Higher heating value" (HHV) refers to the amount of heat released by a specified quantity of a fuel at an initial temperature of 25° C., following combustion, and return of the combustion products to a temperature of 25° C. The HHV is also known as the gross calorific value or gross energy.

"Isolated nucleic acid" as used herein includes a naturally-occurring nucleic acid, provided one or both of the sequences immediately flanking that nucleic acid in its naturally-occurring genome is removed or absent. Thus, an isolated nucleic acid includes, without limitation, a nucleic acid that exists as a purified molecule or a nucleic acid molecule that is incorporated into a vector or a virus. A nucleic acid existing among hundreds to millions of other nucleic acids within, for example, cDNA libraries, genomic libraries, or gel slices containing a genomic DNA restriction digest, is not to be considered an isolated nucleic acid.

"Lignin" refers to a polyphenolic polymeric substance of plant cells, with a complex, cross-linked, highly aromatic structure. Lignin is synthesized in plants principally from three monolignol monomers, which can be methoxylated to various degrees: sinapyl alcohol ($C_{11}H_{14}O_4$) that is incorporated into lignin as (S) syringyl units; coniferyl alcohol ($C_{10}H_{12}O_3$) that is incorporated into lignin as (G) guaiacyl units; and p-coumaryl alcohol ($C_9H_{10}O_2$) that is incorporated into lignin as (H) p-hydroxyphenyl units. These monomers can be synthesized into lignin by extensive condensation polymerization. The lignin present in different plant varieties can have different syringyl:guaiacyl:p-hydroxyphenyl weight percents (S:G:H weight percents). For example, certain grass varieties can have lignin composed almost entirely of guaiacyl (G). Lignin is a major structural constituent of plant cells in woody species.

"Modulation" of the level of biomass refers to the change in the level of the biomass that is observed as a result of expression of, or transcription from, an exogenous nucleic acid in a plant cell and/or plant. The change in level is measured relative to the corresponding level in control plants.

"NIR Model" refers to a series of validated mathematical equations that predict the chemical composition of a sample, based on NIR spectral data from the sample. The term also refers to a series of validated mathematical equations that predict saccharification conversion efficiency of a sample, based on NIR spectral data from the sample. In the case of saccharification conversion efficiency, a different NIR model is developed for each combination of pretreatment conditions and enzyme(s). NIR spectral data typically is obtained from the sample at a plurality of different wavelengths, and the mathematical equations are applied to the spectral data to calculate the predicted value. The calibration equations can be derived by regression among spectroscopic data for feedstock samples of the same type, e.g., by multiple-linear regression, by partial least squares, or by neural network analysis.

"NOX emissions" refers to mono-nitrogen oxides (NOx), such as NO and NO2, released into the atmosphere. While oxygen and nitrogen gases do not typically react at ambient temperatures, oxygen and nitrogen gases can react at higher temperatures to create various oxides of nitrogen, including mono-nitrogen oxides. Mono-nitrogen oxides can also be produced by combusting materials including elemental nitrogen. Mono-nitrogen oxides (NOx) released into the atmosphere can react with volatile organic compounds to produce smog. Accordingly, NOX emissions may be regulated by various governmental agencies. Oxides of sulfur (SOx), specifically sulfur dioxide, are often generated in the same processes. SOx emissions are known to contribute to acid rain.

"Nucleic acid" and "polynucleotide" are used interchangeably herein, and refer to both RNA and DNA, including cDNA, genomic DNA, synthetic DNA, and DNA or RNA containing nucleic acid analogs. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, nucleic acid probes and nucleic acid primers. A polynucleotide may contain unconventional or modified nucleotides.

"Operably linked" refers to the positioning of a regulatory region and a sequence to be transcribed in a nucleic acid so that the regulatory region is effective for regulating transcription or translation of the sequence. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site.

"Polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition.

"Progeny" includes descendants of a particular plant or plant line. Progeny of an instant plant include seeds formed on $F_1$, $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant.

"Recalcitrant carbohydrate material" refers to mono- and oligo-saccharides that are not released into the aqueous phase after processing of a biomass feedstock. It is related to the pretreatment and enzymatic saccharification conditions chosen for the saccharification process.

"Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al., *The Plant Cell*, 1:977-984 (1989).

"Saccharification" refers to the hydrolysis of carbohydrate material to the mono- and disaccharides that constitute the polymer. For example, saccharification of xylan results in the production of xylose, the monosaccharide constituent of xylan. Saccharification occurs during the biochemical processing of biomass in biorefineries, ultimately leading to the production of biofuels such as ethanol.

"Saccharification efficiency" of a feedstock sample refers to the total amount of mono and disaccharides solubilized by pretreatment/enzymatic saccharification processes, divided by the theoretical maximum amount of mono and disaccharides in the biomass sample that could have been released based on compositional analysis, converted to a percentage by multiplying by 100.

"Sustainability indicators" refer to components of biomass processing byproducts, such as the expected ash composition and soil nutrients, which may be recycled.

"Up-regulation" refers to regulation that increases the level of an expression product (mRNA, polypeptide, or both) relative to basal or native states.

"Vector" refers to a replicon, such as a plasmid, phage, or cosmid, into which another DNA segment may be inserted so as to bring about the replication of the inserted segment. Generally, a vector is capable of replication when associated with the proper control elements. The term "vector" includes cloning and expression vectors, as well as viral vectors and integrating vectors. An "expression vector" is a vector that includes a regulatory region.

II. Polypeptides

Polypeptides described herein include biomass composition-modulating polypeptides. Biomass composition-modulating polypeptides can be effective to modulate biomass composition when expressed in a plant or plant cell. Such polypeptides typically contain at least one domain indicative of a biomass composition-modulating polypeptide, as described in more detail herein. Biomass composition-modulating polypeptides also typically have an HMM bit score that is greater than 65 as described in more detail herein. In some embodiments, biomass composition-modulating polypeptides have greater than 80% identity to SEQ ID NOs: 2, 4, 6, 7, 8, 10, 12, 14, 15, 17, 18, 19, 20, 21, 22, 24, 26, 28, 29, 30, 32, 34, 36, 37, 39, 41, 43, 45, 47, 49, 50, 52, 53, 55, 57, 59, 61, 63, 65, 66, 68, 70, 71, 72, 73, 75, 77, 78, 79, 81, 82, 84, 86, 88, 90, 92, 94, 96, 97, 99, 100, 101, 102, 104, 105, 107, 109, 111, 113, 115, 117, 118, 120, 122, 124, 126, 128, 130, 132, 133, 135, 136, 138, 139, 141, 143, 145, 147, 148, 149, 151, 152, 153, 155, 157, 158, 160, 161, 162, 163, 164, 165, 167, 168, 170, 171, 172, 173, 175, 177, 179, 181, 182, 184, 185, 187, 189, 190, 192, 194, 196, 197, 199, 201, 202, 204, 205, 207, 208, 210, 211, 213, 215, 216, 218, 220, 221, 222, 223, 225, 226, 228, 230, 232, 234, 236, 238, 240, 242, 244, 246, 248, 250, 251, 252, 254, 256, 258, 260, 261, 262, 264, 266, 268, 270, 272, 274, 275, 276, 278, 280, 282, 283, 284, 285, 286, 288, 289, 290, 292, 294, 295, 296, 297, 298, 299, 300, 302, 303, 305, 306, 308, 309, 310, 311, 312, 314, 316, 317, 318, 320, 321, 323, 325, 326, 327, 328, 329, 331, 333, 335, 336, 337, 338, 339, 340, 342, 344, 346, 348, 350, 351, 353, 355, 357, 359, 360, 361, 362, 363, 364, 365, 366, 368, 370, 372, 373, 374, 375, 376, 377, 379, 380, 381, 383, 384, 386, 388, 390, 392, 393, 394, 396, 398, 400, 402, 404, 406, 407, 408, 410, 412, 413, 414, 416, 418, 419, 420, 422, 423, 424, 426, 427, 429, 430, 431, 433, 434, 436, 437, 439, 441, 442, 444, 446, 448, 449, 450, 451, 452, 454, 456, 458, 459, 460, 462, 463, 465, 466, 468, 470, 472, 473, 474, 476, 478, 479, 480, 481, 483, 485, 486, 488, 490, 492, 493, 495, 497, 498, 500, 501, 503, 504, 506, 508, 509, 510, 512, 514, 515, 516, 517, 519, 521, 522, 523, 525, 527, 529, 531, 533, 534, 535, 537, 539, 541, 543, 545, 547, 549, 551, 552, 554, 556, 557, 559, 562, 564, 565, 567, 568, 570, 572, 573, 574, 575, 576, 578, 580, 582, 584, 586, 588, 589, 590, 592, 594, 596, 598, 599, 601, 602, 603, 605, 607, 608, 609, 611, 613, 615, 617, 619, 621, 622, 624, 625, 627, 629, 630, 632, 634, 636, 638, 641, 643, 645, 646, 647, 648, 649, 650, 651, 652, 653, 654, 656, 658, 660, 662, 664, 666, 668, 670, 672, 674, 676, 677, 679, 680, 682, 684, 686, 687, 688, 689, 690, 691, 692, 694, 695, 697, 699, 701, 702, 704, 706, 708, 710, 712, 713, 715, 716, 718, 720, 721, 723, 724, 726, 727, 729, 730, 732, 733, 735, 736, 737, 739, 740, 742, 744, 746, 747, 748, 749, 750, 751, 753, 755, 757, 758, 760, 761, 763, 764, 765, 766, 767, 768, 769, 771, 772, 774, 775, 776, 777, 778, 780, 781, 782, 783, 785, 786, 788, 789, 791, 793, 795, 796, 798, 799, 800, 801, 802, 803, 805, 807, 808, 810, 811, 812, 813, 814, 815, 816, 817, 818, 819, 820, 821, and 823 as described in more detail herein.

A. Domains Indicative of Biomass Composition-Modulating Polypeptides

A biomass composition-modulating polypeptide can contain a methyltransferase_2 domain and a dimerization domain, which are predicted to be characteristic of a biomass composition-modulating polypeptide. SEQ ID NO: 562 sets forth the amino acid sequence of a *Panicum virgatum* clone, identified herein as CeresClone:1871180 (SEQ ID NO:561), that is predicted to encode a polypeptide containing a heavy-metal-associated domain. For example, a biomass composition-modulating polypeptide can comprise a heavy-metal-associated domain having 60 percent or greater (e.g., 65, 70, 75, 80, 85, 90, 95, 97, 98, 99, or 100 percent) sequence identity to residues 6 to 73 of SEQ ID NO: 562. In some embodiments, a biomass composition-modulating polypeptide can comprise a heavy-metal-associated domain having 60 percent or greater (e.g., 65, 70, 75, 80, 85, 90, 95, 97, 98, 99, or 100 percent) sequence identity to the heavy-metal-associated domain of one or more of the polypeptides set forth in SEQ ID NOs: 564, 565, 567, 568, 570, 572, 573, 574, 575, 576, 578, 580, 582, 584, 586, 588, 589, 590, 592, 594, 596, 598, 599, 601, 602, 603, 605, 607, 608, 609, 611, 613, 615, 617, 619, 621, 622, 624, 625, 627, 629, 630, 632, 634, 636, and 638. The heavy-metal-associated domains of such sequences are set forth in the Sequence Listing. The heavy-metal-associated domain is characteristic of proteins that transport heavy metals, and typically contains two conserved cysteines that may be involved in metal binding. See, e.g., Rosenzweig et al., *Structure Fold Des.,* 7:605-617 (1999).

A biomass composition-modulating polypeptide can contain a Myb-like DNA-binding domain, which is predicted to be characteristic of a biomass composition-modulating polypeptide. A polypeptide containing such a Myb-like DNA-binding domain can be useful, for example, for modulating sucrose content or conversion efficiency. SEQ ID NO: 246 sets forth the amino acid sequence of a *Zea mays* clone, identified herein as CeresClone:240112 (SEQ ID NO: 245) that is predicted to encode a polypeptide containing a Myb-like DNA-binding domain. For example, a biomass composition-modulating polypeptide can comprise a Myb-like DNA-binding domain having 60 percent or greater (e.g., 65, 70, 75, 80, 85, 90, 95, 97, 98, 99, or 100 percent) sequence identity to residues 212 to 263 of SEQ ID NO: 246. In some embodiments, a biomass composition-modulating polypeptide can comprise a Myb-like DNA-binding domain having 60 percent or greater (e.g., 65, 70, 75, 80, 85, 90, 95, 97, 98, 99, or 100 percent) sequence identity to the Myb-like DNA-binding domain of one or more of the polypeptides set forth in SEQ ID NOs: 248, 250, 251, 252, 254, 256, 258, 260, 261, 262, 264, 266, 268, 270, 272, 274, 275, 276, and 278. The Myb-like DNA-binding domains of such sequences are set forth in the Sequence Listing. The Myb_DNA-binding domain is found in the family of Myb proteins, as well as the SANT domain family. See, Aasland et al., *Trends Biochem Sci* 121:87-88 (1996). The SANT domain family specifically recognizes the sequence YAAC (G/T)G.

A biomass composition-modulating polypeptide can contain a DUF1070 domain, which is predicted to be characteristic of a biomass composition-modulating polypeptide. A polypeptide containing such a DUF1070 domain can be useful, for example, for modulating sucrose content. SEQ ID NO: 111 sets forth the amino acid sequence of a *Panicum virgatum* clone, identified herein as CeresClone:1764605 (SEQ ID NO:110) that is predicted to encode a polypeptide containing a DUF1070 domain. For example, a biomass composition-modulating polypeptide can comprise a DUF1070 domain having 60 percent or greater (e.g., 65, 70, 75, 80, 85, 90, 95, 97, 98, 99, or 100 percent) sequence identity to residues 4-52 of SEQ ID NO: 111. In some embodiments, a biomass composition-modulating polypeptide can comprise a DUF1070 domain having 60 percent or greater (e.g., 65, 70, 75, 80, 85, 90, 95, 97, 98, 99, or 100 percent) sequence identity to the DUF1070 domain of one or more of the polypeptides set forth in SEQ ID NOs: 113, 115, 117, 118, 120, 122, 124, 126, 128, 130, 132, 133, 135, 136, 138, 139, 141, 143, 145, 147, 148, 149, 151, 152, 153, 155. The DUF1070 domain is a conserved domain found in several short plant proteins, including the arabinogalactan peptide family. See, e.g., Schultz et al., *Plant Cell* 12:1751-68 (2000).

A biomass composition-modulating polypeptide can contain a glycosyl hydrolases family 16 domain and a xyloglucan endo-transglycosylase (XET) domain, which are predicted to be characteristic of a biomass composition-modulating polypeptide. A polypeptide containing such a glycosyl hydrolases family 16 domain and XET domain can be useful, for example, for modulating sucrose content or conversion efficiency. SEQ ID NO: 348 sets forth the amino acid sequence of a *Panicum virgatum* clone, identified herein as CeresClone:1776501 (SEQ ID NO: 347), that is predicted to encode a polypeptide containing a glycosyl hydrolases family 16 domain and a XET domain. For example, a biomass composition-modulating polypeptide can comprise a glycosyl hydrolases family 16 domain and a XET domain having 60 percent or greater (e.g., 65, 70, 75, 80, 85, 90, 95, 97, 98, 99, or 100 percent) sequence identity to residues 39 to 224 and 246 to 292 of SEQ ID NO: 348, respectively. In some embodiments, a biomass composition-modulating polypeptide can comprise a glycosyl hydrolases family 16 domain and a XET domain having 60 percent or greater (e.g., 65, 70, 75, 80, 85, 90, 95, 97, 98, 99, or 100 percent) sequence identity to the glycosyl hydrolases family 16 domain and XET domain of one or more of the polypeptides set forth in SEQ ID NOs: 350, 351, 353, 355, 357, 359, 360, 361, 362, 363, 364, 365, 366, 368, 370, 372, 373, 374, 375, 376, 377, 379, 380, 381, 383, 384, 386, 388, 390, 392, 393, 394, 396, 398, 400, 402, 404, 406, 407, 408, 410, 412, 413, and 414. The glycosyl hydrolases family 16 domain and XET domain of such sequences are set forth in the Sequence Listing. Proteins within the glycosyl hydrolase family 16 are O-glycosyl hydrolases that hydrolyze the glycosidic bond between two or more carbohydrates, or between a carbohydrate and a non-carbohydrate moiety. Members of the glycosyl hydrolase 16 family include lichenase, xyloglucan xyloglucosyltransferase, agarase, kappa-carrageenase, endo-beta-1,3-glucanase, endo-beta-1, 3-1,4-glucanase, and endo-beta-galactosidase. The XET domain is found in the C-terminus (approximately 60 residues) of plant xyloglucan endo-transglycosylases. Xyloglucan is the predominant hemicellulose in the cell walls of most dicotyledons. With cellulose, it forms a network that strengthens the cell wall. XET catalyzes the splitting of xyloglucan chains and the linking of the newly generated reducing end to the non-reducing end of another xyloglucan chain, thereby loosening the cell wall. See, for example, Schroder et al., *Planta,* 204:242-251 (1998).

A biomass composition-modulating polypeptide can contain an Alpha-L-AF_C domain and a CBM_4_9 domain, which are predicted to be characteristic of a biomass composition-modulating polypeptide. A polypeptide containing such an Alpha-L-AF_C domain and a CBM_4_9 domain can be useful, for example, for modulating sucrose content or conversion efficiency. SEQ ID NO: 774 sets forth the amino acid sequence of a *Panicum virgatum* clone, identified herein as CeresClone:1789981 (SEQ ID NO: 773), that is predicted to encode a polypeptide containing Alpha-L-AF_C and CBM_4_9 domains. For example, a biomass composition-modulating polypeptide can comprise an Alpha-L-AF_C domain having 60 percent or greater (e.g., 65, 70, 75, 80, 85, 90, 95, 97, 98, 99, or 100 percent) sequence identity to residues 454 to 643 of SEQ ID NO: 774 and a CBM_4_9 domain having 60 percent or greater (e.g., 65, 70, 75, 80, 85, 90, 95, 97, 98, 99, or 100 percent) sequence identity to residues 71 to 229 of SEQ ID NO: 774. In some embodiments, a biomass composition-modulating polypeptide can comprise Alpha-L-AF_C and CBM_4_9 domains having 60 percent or greater (e.g., 65, 70, 75, 80, 85, 90, 95, 97, 98, 99, or 100 percent) sequence identity to the Alpha-L-AF_C and CBM_4_9 domains of one or more of the polypeptides set forth in SEQ ID NOs: 775, 776, 777, 778, 780, 781, 782, 783, 785, 786, 788, 789, 791, 793, 795, 796, 798, 799, 800, 801, 802, 803, 805, 807, 808, 810, 811, 812, 813, 814, 815, 816, 817, 818, 819, 820, and 821. The Alpha-L-AF_C and CBM_4_9 domains of such sequences are set forth in the Sequence Listing. The Alpha-L-AF_C domain represents the approximately 200 C-terminal residues of bacterial and eukaryotic alpha-L-arabinofuranosidase (EC:3.2.1.55), which catalyzes the hydrolysis of nonreducing terminal alpha-L-arabinofuranosidic linkages in L-arabinose-containing polysaccharides. The CBM_4_9 domain is a carbohydrate binding domain. A biomass composition-modulating polypeptide can contain a COBRA domain, which is predicted to be characteristic of a biomass composition-modulating polypeptide. A polypeptide containing such a COBRA domain can be useful, for example, for modulating sucrose content or conversion efficiency. SEQ ID NO: 416 sets forth the amino acid sequence of a *Panicum virgatum* clone, identified herein as CeresClone: 1804732 (SEQ ID NO: 415), that is predicted to encode a polypeptide containing a COBRA domain. For example, a biomass composition-modulating polypeptide can comprise a COBRA domain having 60 percent or greater (e.g., 65, 70, 75, 80, 85, 90, 95, 97, 98, 99, or 100 percent) sequence identity to residues 45 to 209 of SEQ ID NO: 416. In some embodiments, a biomass composition-modulating polypeptide can comprise a COBRA domain having 60 percent or greater (e.g., 65, 70, 75, 80, 85, 90, 95, 97, 98, 99, or 100 percent) sequence identity to the COBRA domain of one or more of the polypeptides set forth in SEQ ID NOs: 418, 419, 420, 422, 423, 424, 426, 427, 429, 430, 431, 433, 434, 436, 437, 439, 441, 442, 444, 446, 448, 449, 450, 451, 452, 454, 456, 458, 459, 460, 462, 463, 465, 466, 468, 470, 472, 473, 474, 476, 478, 479, 480, and 481. COBRA domains are found within a family of plant proteins designated COBRA-like (COBL) proteins. Members of the family are extracellular glycosyl-phosphatidyl inositol-anchored proteins (GPI-linked). COBRA is involved in determining the orientation of cell expansion, probably by playing an important role in cellulose deposition. It may act by recruiting cellulose synthesizing complexes to discrete positions on the cell surface. See Roudier et al., *Plant Cell.* 17(6):1749-63 (2005), Epub 2005 April 22.

A biomass composition-modulating polypeptide can contain a glycosyl transferase family 8 domain, which is predicted to be characteristic of a biomass composition-modulating polypeptide. A polypeptide containing such a glycosyl transferase family 8 domain can be useful, for example, for modulating sucrose content. SEQ ID NO: 2 sets forth the amino acid sequence of a *Panicum virgatum* clone, identified herein as CeresClone:1807011 (SEQ ID NO: 1), that is predicted to encode a polypeptide containing a glycosyl transferase family 8 domain. For example, a biomass composition-modulating polypeptide can comprise a glycosyl transferase family 8 domain having 60 percent or greater (e.g., 65, 70, 75, 80, 85, 90, 95, 97, 98, 99, or 100 percent) sequence identity to residues 30 to 253 of SEQ ID NO: 2. In some embodiments, a biomass composition-modulating polypeptide can comprise a glycosyl transferase family 8 domain having 60 percent or greater (e.g., 65, 70, 75, 80, 85, 90, 95, 97, 98, 99, or 100 percent) sequence identity to the glycosyl transferase family 8 domain of one or more of the polypeptides set forth in SEQ ID NOs: 4, 6, 7, 8, 10, 12, 14, 15, 17, 18, 19, 20, 21, 22, and 24. The glycosyl transferase family 8 domains of such sequences are set forth in the Sequence Listing. The glycosyl transferase family 8 domain is found in a family of enzymes that transfer sugar residues to donor molecules. Members of this family include lipopolysaccharide galactosyltransferase, lipopolysaccharide glucosyltransferase 1, glycogenin glucosyltransferase, and inositol 1-alpha-galactosyltransferase. In some embodiments, a nucleic acid sequence encoding the amino acid sequence set forth in SEQ ID NO:2 or a homolog thereof can include a mutation (e.g., a deletion of a nucleotide) such that a truncated polypeptide is produced. For example, the nucleic acid sequence can include a mutation such that the amino acid sequence set forth in SEQ ID NO:2 is truncated at about position 142.

A biomass composition-modulating polypeptide can contain a DUF563 domain, which is predicted to be characteristic of a biomass composition-modulating polypeptide. A polypeptide containing such a DUF563 domain can be useful, for example, for modulating sucrose content. SEQ ID NO: 157 sets forth the amino acid sequence of a *Panicum virgatum* clone, identified herein as CeresClone:1888614 (SEQ ID NO: 156), that is predicted to encode a polypeptide containing a DUF563 domain. For example, a biomass composition-modulating polypeptide can comprise a DUF563 domain having 60 percent or greater (e.g., 65, 70, 75, 80, 85, 90, 95, 97, 98, 99, or 100 percent) sequence identity to residues 196 to 439 of SEQ ID NO: 157. In some embodiments, a biomass composition-modulating polypeptide can comprise a DUF563 domain having 60 percent or greater (e.g., 65, 70, 75, 80, 85, 90, 95, 97, 98, 99, or 100 percent) sequence identity to the DUF563 domain of one or more of the polypeptides set forth in SEQ ID NOs: 158, 160, 161, 162, 163, 164, 165, 167, 168, 170, 171, 172, 173, 175, 177, 179, 181, 182, 184, 185, 187, 189, 190, 192, 194, 196, 197, 199, 201, 202, 204, 205, 207, 208, 210, 211, 213, 215, 216, 218, 220, 221, 222, 223, 225, 226, 228, 230, 232, 234, 236, 238, 240, 242, and 244. The DUF563 domains of such sequences are set forth in the Sequence Listing. Proteins having a DUF563 domain are in glycosyltransferase family 61.

A biomass composition-modulating polypeptide can contain a xyloglucan fucosyltransferase (XG_FTase) domain, which is predicted to be characteristic of a biomass composition-modulating polypeptide. A polypeptide containing such an XG_FTase domain can be useful, for example, for modulating sucrose content. SEQ ID NO: 280 sets forth the amino acid sequence of a *Panicum virgatum* clone, identified herein as CeresClone:1900192 (SEQ ID NO: 279), that is predicted to encode a polypeptide containing an XG_FTase domain. For example, a biomass composition-modulating polypeptide can comprise an XG_FTase domain having 60 percent or greater (e.g., 65, 70, 75, 80, 85, 90, 95, 97, 98, 99, or 100 percent) sequence identity to residues 72 to 574 of SEQ ID NO: 280. In some embodiments, a biomass composition-modulating polypeptide can comprise an XG_FTase domain having 60 percent or greater (e.g., 65, 70, 75, 80, 85, 90, 95, 97, 98, 99, or 100 percent) sequence identity to the XG_FTase domain of one or more of the polypeptides set forth in SEQ ID NOs: 280, 282, 283, 284, 285, 286, 288, 289, 290, 292, 294, 295, 296, 297, 298, 299, 300, 302, 303, 305, 306, 308, 309, 310, 311, 312, 314, 316, 317, 318, 320, 321, 323, 325, 326, 327, 328, 329, 331, 333, 335, 336, 337, 338, 339, 340, 342, 344, and 346. The XG_FTase domains of such sequences are set forth in the Sequence Listing. The XG_FTase domain is found in a fucosyltransferase transfers the terminal fucosyl residue to xyloglucan (XG), the principal load-bearing hemicellulose of dicotyledonous plants. See, e.g., Perrin et al., *Science,* 284:1976-1979 (1999).

A biomass composition-modulating polypeptide can contain a glycosyl hydrolase family 16 domain and a xyloglucan endo-transglycosylase (XET) domain, which are predicted to be characteristic of a biomass composition-modulating polypeptide. A polypeptide containing such a glycosyl hydrolase family 16 domain and XET domain can be useful, for example, for modulating sucrose content or conversion efficiency. SEQ ID NO: 641 sets forth the amino acid sequence of a *Panicum virgatum* clone, identified herein as CeresClone:1955550 (SEQ ID NO: 640), that is predicted to encode a polypeptide containing a glycosyl hydrolase family 16 domain and a XET domain. For example, a biomass composition-modulating polypeptide can comprise a glycosyl hydrolases family 16 domain having 60 percent or greater (e.g., 65, 70, 75, 80, 85, 90, 95, 97, 98, 99, or 100 percent) sequence identity to residues 23 to 204 of SEQ ID NO: 641 and a XET domain having 60 percent or greater (e.g., 65, 70, 75, 80, 85, 90, 95, 97, 98, 99, or 100 percent) sequence identity to residues 228 to 280 of SEQ ID NO: 641. In some embodiments, a biomass composition-modulating polypeptide can comprise glycosyl hydrolases family 16 and XET domains having 60 percent or greater (e.g., 65, 70, 75, 80, 85, 90, 95, 97, 98, 99, or 100 percent) sequence identity to the glycosyl hydrolase family 16 and XET domains of one or more of the polypeptides set forth in SEQ ID NOs: 643, 645, 646, 647, 648, 649, 650, 651, 652, 653, 654, 656, 658, 660, 662, 664, 666, 668, 670, 672, 674, 676, 677, 679, 680, 682, 684, 686, 687, 688, 689, 690, 691, 692, 694, 695, 697, 699, 701, 702, 704, 706, 708, 710, 712, 713, 715, 716, 718, 720, 721, 723, 724, 726, 727, 729, 730, 732, 733, 735, 736, 737, 739, 740, 742, 744, 746, 747, 748, 749, 750, 751, 753, 755, 757, 758, 760, 761, 763, 764, 765, 766, 767, 768, 769, 771, 772, or 823. The glycosyl hydrolases family 16 and XET domains of such sequences are set forth in the Sequence Listing. The glycosyl hydrolases family 16 domain and XET domain are described above with reference to SEQ ID NO:348.

A biomass composition-modulating polypeptide can contain a potato inhibitor I family domain, which is predicted to be characteristic of a biomass composition-modulating polypeptide. A polypeptide containing such a potato inhibitor I family domain can be useful, for example, for modulating sucrose content. SEQ ID NO: 26 sets forth the amino acid sequence of a *Panicum virgatum* clone, identified herein as CeresClone:1955766 (SEQ ID NO: 25), that is predicted to encode a polypeptide containing a potato inhibitor I family domain. For example, a biomass composition-modulating polypeptide can comprise a potato inhibitor I family domain having 60 percent or greater (e.g., 65, 70, 75, 80, 85, 90, 95, 97, 98, 99, or 100 percent) sequence identity to residues 17 to 76 of SEQ ID NO: 26. In some embodiments, a biomass composition-modulating polypeptide can comprise a potato inhibitor I family domain having 60 percent or greater (e.g., 65, 70, 75, 80, 85, 90, 95, 97, 98, 99, or 100 percent) sequence identity to the potato inhibitor I family domain of one or more of the polypeptides set forth in SEQ ID NOs: 28, 29, 30, 32, 34, 36, 37, 39, 41, 43, 45, 47, 49, 50, 52, 53, 55, 57, 59, 61, 63, 65, 66, 68, 70, 71, 72, 73, 75, 77, 78, 79, 81, 82, 84, 86, 88, 90, 92, 94, 96, 97, 99, 100, 101, 102, 104, 105, 107, and 109. The potato inhibitor I family domains of such sequences are set forth in the Sequence Listing. Members of the potato inhibitor I family are proteinase inhibitors that inhibit peptidases of the S1 and S8 families. See, for example, Rawlings et al., *Biochem J.* 15, 378(Pt 3):705-16 (2004) Inhibitors in this family are small (60 to 90 residues) and lack disulfide bonds. Typically, the inhibitor is a wedge-shaped molecule, its pointed edge formed by the protease-binding loop, which contains the scissile bond. The loop binds tightly to the protease active site, with subsequent cleavage of the scissile bond causing inhibition of the enzyme. See, Bode et al., *EMBO J.*, 5(4):813-8 (1986).

In some embodiments, a biomass composition-modulating polypeptide is truncated at the amino- or carboxy-terminal end of a naturally occurring polypeptide. A truncated polypeptide may retain certain domains of the naturally occurring polypeptide while lacking others. Thus, length variants that are up to 5 amino acids shorter or longer typically exhibit the biomass composition-modulating activity of a truncated polypeptide. In some embodiments, a truncated polypeptide is a dominant negative polypeptide. Expression in a plant of such a truncated polypeptide confers a difference in biomass composition of a plant as compared to the corresponding level of a control plant that does not comprise the truncation.

B. Functional Homologs Identified by Reciprocal BLAST

In some embodiments, one or more functional homologs of a reference biomass composition-modulating polypeptide defined by one or more of the Pfam descriptions indicated above are suitable for use as biomass composition-modulating polypeptides. A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for a biomass composition-modulating polypeptide, or by combining domains from the coding sequences for different naturally-occurring biomass composition-modulating polypeptides ("domain swapping"). The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of biomass composition-modulating polypeptides. Sequence analysis can involve BLAST, Reciprocal BLAST, or PSI-BLAST analysis of nonredundant databases using a biomass composition-modulating polypeptide amino acid sequence as the reference sequence. Amino acid sequence is, in some instances, deduced from the nucleotide sequence. Those polypeptides in the database that have greater than 40% sequence identity are candidates for further evaluation for suitability as a biomass composition-modulating polypeptide Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in biomass composition-modulating polypeptides, e.g., conserved functional domains.

Conserved regions can be identified by locating a region within the primary amino acid sequence of a biomass composition-modulating polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/ and pfam.janelia.org/. A description of the information included at the Pfam database is described in Sonnhammer et al., *Nucl. Acids Res.,* 26:320-322 (1998); Sonnhammer et al., *Proteins,* 28:405-420 (1997); and Bateman et al., *Nucl. Acids Res.,* 27:260-262 (1999). Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

Examples of amino acid sequences of functional homologs of the polypeptide set forth in SEQ ID NO: 483 are provided in FIG. 1 and in the Sequence Listing. Such functional homologs include, for example, CeresAnnot: 8701398 (SEQ ID NO: 485), GI:21741986 (SEQ ID NO: 486), CeresClone:488555 (SEQ ID NO: 488), CeresAnnot: 1472210 (SEQ ID NO: 490), CeresClone:1839543 (SEQ ID NO: 492), GI:124360895 (SEQ ID NO: 493), CeresClone: 1778664 (SEQ ID NO: 495), CeresClone:2030878 (SEQ ID NO: 497), GI:115458882 (SEQ ID NO: 498), CeresAnnot: 8701404 (SEQ ID NO: 500), GI:115458830 (SEQ ID NO: 501), CeresAnnot:8701387 (SEQ ID NO: 503), GI:116310418 (SEQ ID NO: 504), CeresAnnot:8679943 (SEQ ID NO: 506), CeresAnnot:8701391 (SEQ ID NO: 508), GI:46806257 (SEQ ID NO: 509), GI:125540058 (SEQ ID NO: 510), CeresClone:1018979 (SEQ ID NO: 512), CeresClone:1725423 (SEQ ID NO: 514), GI:115446965 (SEQ ID NO: 515), GI:125540059 (SEQ ID NO: 516), GI:38606531 (SEQ ID NO: 517), CeresClone:1955791 (SEQ ID NO: 519), CeresClone:2032166 (SEQ ID NO: 521), GI:125540060 (SEQ ID NO: 522), GI:46806261 (SEQ ID NO: 523), CeresClone:100178733 (SEQ ID NO: 525), CeresClone:351547 (SEQ ID NO: 527), CeresClone: 1906874 (SEQ ID NO: 529), CeresClone:273420 (SEQ ID NO: 531), CeresAnnot:8701399 (SEQ ID NO: 533), GI:125540061 (SEQ ID NO: 534), GI:115446971 (SEQ ID NO: 535), CeresClone:1802499 (SEQ ID NO: 537), CeresClone:1850157 (SEQ ID NO: 539), CeresClone:1471240 (SEQ ID NO: 541), CeresAnnot:8679942 (SEQ ID NO: 543), CeresClone:1024049 (SEQ ID NO: 545), CeresAnnot: 885518 (SEQ ID NO: 547), CeresAnnot:871243 (SEQ ID NO: 549), CeresAnnot:1461629 (SEQ ID NO: 551), GI:27754556 (SEQ ID NO: 552), CeresAnnot:8679941 (SEQ ID NO: 554), CeresClone:1846767 (SEQ ID NO: 556), GI:118489467 (SEQ ID NO: 557), and CeresAnnot: 1480319 (SEQ ID NO: 559). In some cases, a functional homolog of SEQ ID NO: 483 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 483. In some cases, a functional homolog of SEQ ID NO: 483 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 483 described above or set forth in the Sequence Listing.

Figure 2B:
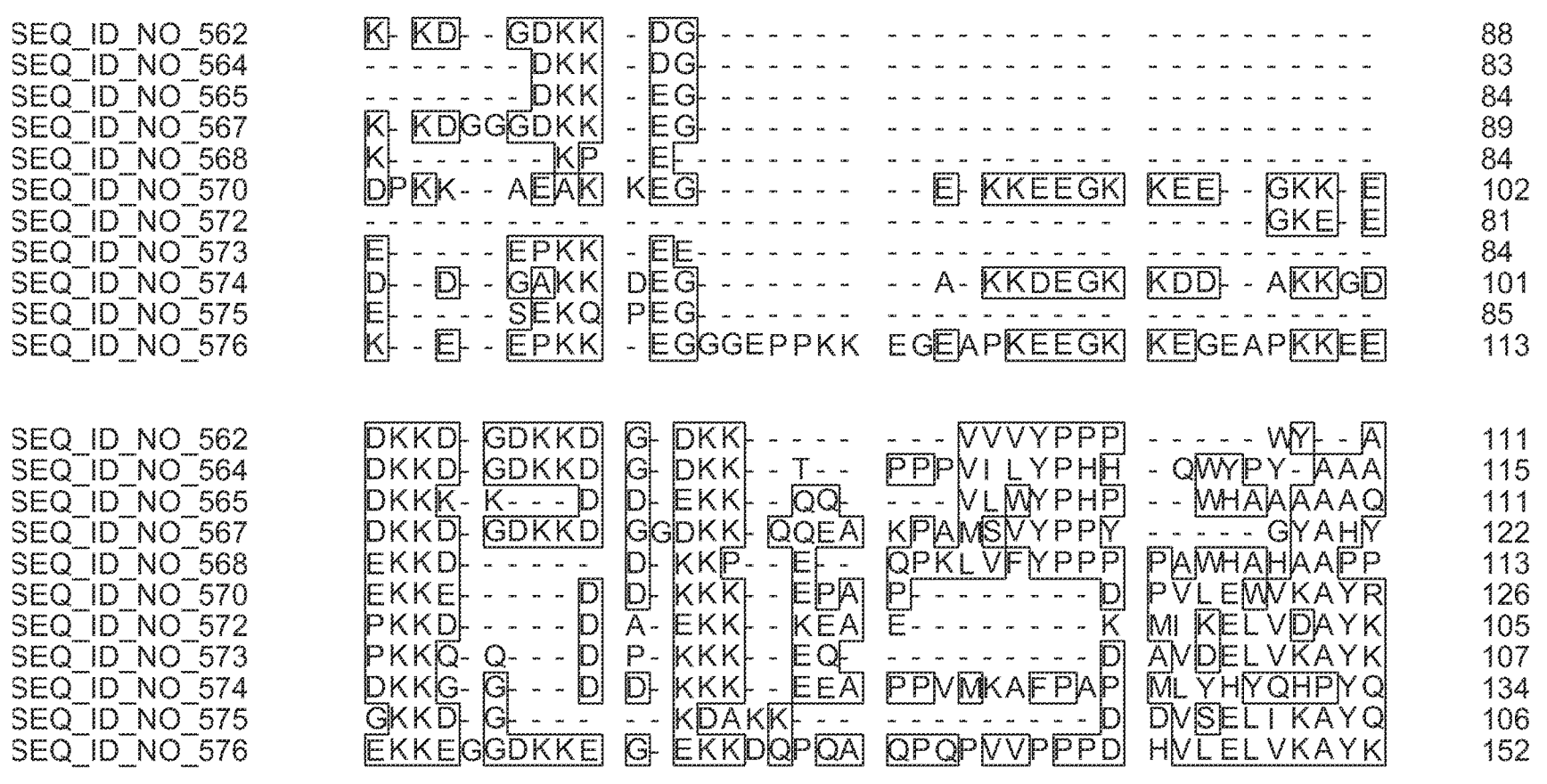

Examples of amino acid sequences of functional homologs of the polypeptide set forth in SEQ ID NO: 562 are provided in FIG. 2 and in the Sequence Listing. Such functional homologs include, for example, CeresAnnot: 8703443 (SEQ ID NO: 564), GI:194702514 (SEQ ID NO: 565), CeresClone:699934 (SEQ ID NO: 567), GI:32488374 (SEQ ID NO: 568), CeresClone:1642517 (SEQ ID NO: 570), CeresClone:1799746 (SEQ ID NO: 572), GI:224077486 (SEQ ID NO: 573), GI:83283997 (SEQ ID NO: 574), GI:171451994 (SEQ ID NO: 575), GI:15223416 (SEQ ID NO: 576), CeresClone:1999925 (SEQ ID NO: 578), CeresClone:100177220 (SEQ ID NO: 580), CeresClone:1822001 (SEQ ID NO: 582), CeresClone:570418 (SEQ ID NO: 584), CeresClone:1998324 (SEQ ID NO: 586), CeresClone:706252 (SEQ ID NO: 588), GI:77554837 (SEQ ID NO: 589), GI:125536425 (SEQ ID NO: 590), CeresAnnot:1447508 (SEQ ID NO: 592), CeresClone: 1965618 (SEQ ID NO: 594), CeresClone:1626139 (SEQ ID NO: 596), CeresAnnot:8640237 (SEQ ID NO: 598), GI:115450453 (SEQ ID NO: 599), CeresAnnot:1438634 (SEQ ID NO: 601), GI:147787209 (SEQ ID NO: 602), GI:115483110 (SEQ ID NO: 603), CeresClone:263964 (SEQ ID NO: 605), CeresAnnot:1449592 (SEQ ID NO: 607), GI:115461178 (SEQ ID NO: 608), GI:29124977 (SEQ ID NO: 609), CeresClone:476087 (SEQ ID NO: 611), CeresClone:1587840 (SEQ ID NO: 613), CeresClone: 1808797 (SEQ ID NO: 615), CeresClone:538771 (SEQ ID NO: 617), CeresClone:1851138 (SEQ ID NO: 619), CeresClone:1049645 (SEQ ID NO: 621), GI:92897781 (SEQ ID NO: 622), CeresAnnot:1487378 (SEQ ID NO: 624), GI:92897782 (SEQ ID NO: 625), CeresClone:648917 (SEQ ID NO: 627), CeresClone:100011205 (SEQ ID NO: 629), GI:116783342 (SEQ ID NO: 630), CeresAnnot:1449591 (SEQ ID NO: 632), CeresClone:521942 (SEQ ID NO: 634), CeresClone:1653508 (SEQ ID NO: 636), and CeresAnnot: 1487377 (SEQ ID NO: 638). In some cases, a functional homolog of SEQ ID NO: 562 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 562. In some cases, a functional homolog of SEQ ID NO: 562 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 562 described above or set forth in the Sequence Listing.

Examples of amino acid sequences of functional homologs of the polypeptide set forth in SEQ ID NO: 246 are provided in FIG. 3 and in the Sequence Listing. Such functional homologs include, for example, CeresClone: 1791988 (SEQ ID NO: 248), CeresAnnot:8632546 (SEQ ID NO: 250), GI:115455537 (SEQ ID NO: 251), GI:118486821 (SEQ ID NO: 252), CeresClone:537690 (SEQ ID NO: 254), CeresAnnot:880540 (SEQ ID NO: 256), CeresClone: 797459 (SEQ ID NO: 258), CeresClone:630408 (SEQ ID NO: 260), GI:125557053 (SEQ ID NO: 261), GI:125588020 (SEQ ID NO: 262), CeresAnnot:1733246 (SEQ ID NO: 264), CeresAnnot:1451294 (SEQ ID NO: 266), CeresAnnot: 1457031 (SEQ ID NO: 268), CeresClone:100063507 (SEQ ID NO: 270), CeresClone:560820 (SEQ ID NO: 272), CeresClone:1104471 (SEQ ID NO: 274), GI:30690890 (SEQ ID NO: 275), GI:18402692 (SEQ ID NO: 276), and CeresClone:2686 (SEQ ID NO: 278). In some cases, a functional homolog of SEQ ID NO: 246 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 246. In some cases, a functional homolog of SEQ ID NO: 246 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 246 described above or set forth in the Sequence Listing.

Examples of amino acid sequences of functional homologs of the polypeptide set forth in SEQ ID NO: 111 are provided in FIG. 4 and in the Sequence Listing. Such functional homologs include, for example, CeresAnnot: 8726250 (SEQ ID NO: 113), CeresClone:899059 (SEQ ID NO:115), CeresClone:945132 (SEQ ID NO:117), GI:115462673 (SEQ ID NO:118), CeresClone:16400 (SEQ ID NO:120), CeresClone:1712201 (SEQ ID NO:122), CeresAnnot:1524669 (SEQ ID NO:124), CeresAnnot:8672987 (SEQ ID NO:126), CeresClone:1434951 (SEQ ID NO:128), CeresClone:299745 (SEQ ID NO:130), CeresClone:323696 (SEQ ID NO:132), GI:194695666 (SEQ ID NO:133), CeresClone:1771257 (SEQ ID NO:135), GI:115445433 (SEQ ID NO:136), CeresAnnot:8667876 (SEQ ID NO:138), GI:115438957 (SEQ ID NO:139), CeresClone:1100814 (SEQ ID NO:141), CeresClone:1029710 (SEQ ID NO:143), CeresClone:969326 (SEQ ID NO:145), CeresClone: 100955392 (SEQ ID NO:147), GI:225454450 (SEQ ID NO:148), GI:116779724 (SEQ ID NO:149), CeresAnnot: 1447561 (SEQ ID NO:151), GI:20149060 (SEQ ID NO:152), GI:225462683 (SEQ ID NO:153), and CeresClone:595099 (SEQ ID NO:155). In some cases, a functional homolog of SEQ ID NO: 111 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 111. In some cases, a functional homolog of SEQ ID NO: 111 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 111 described above or set forth in the Sequence Listing.

Figure 5B:
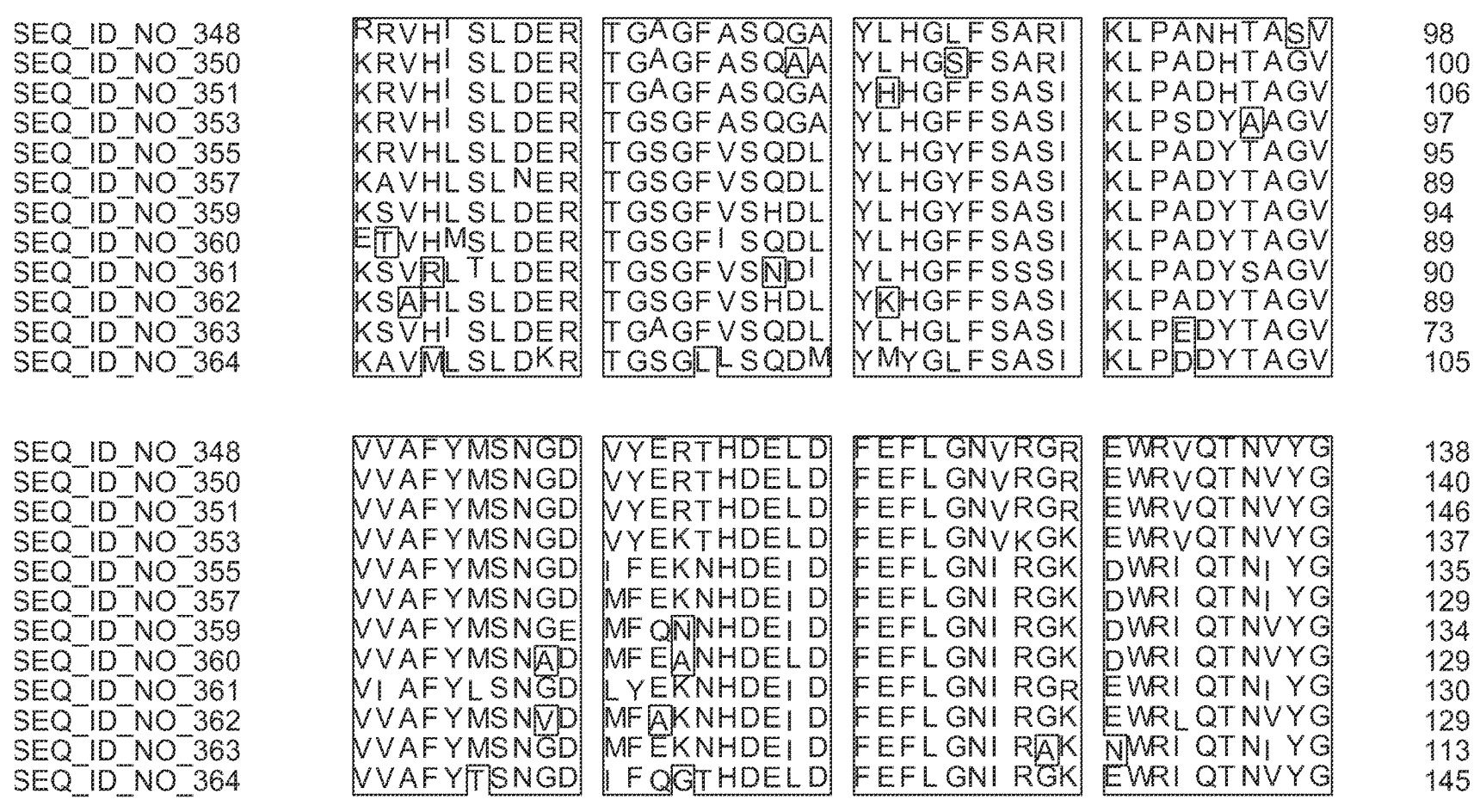
Figure 5C:
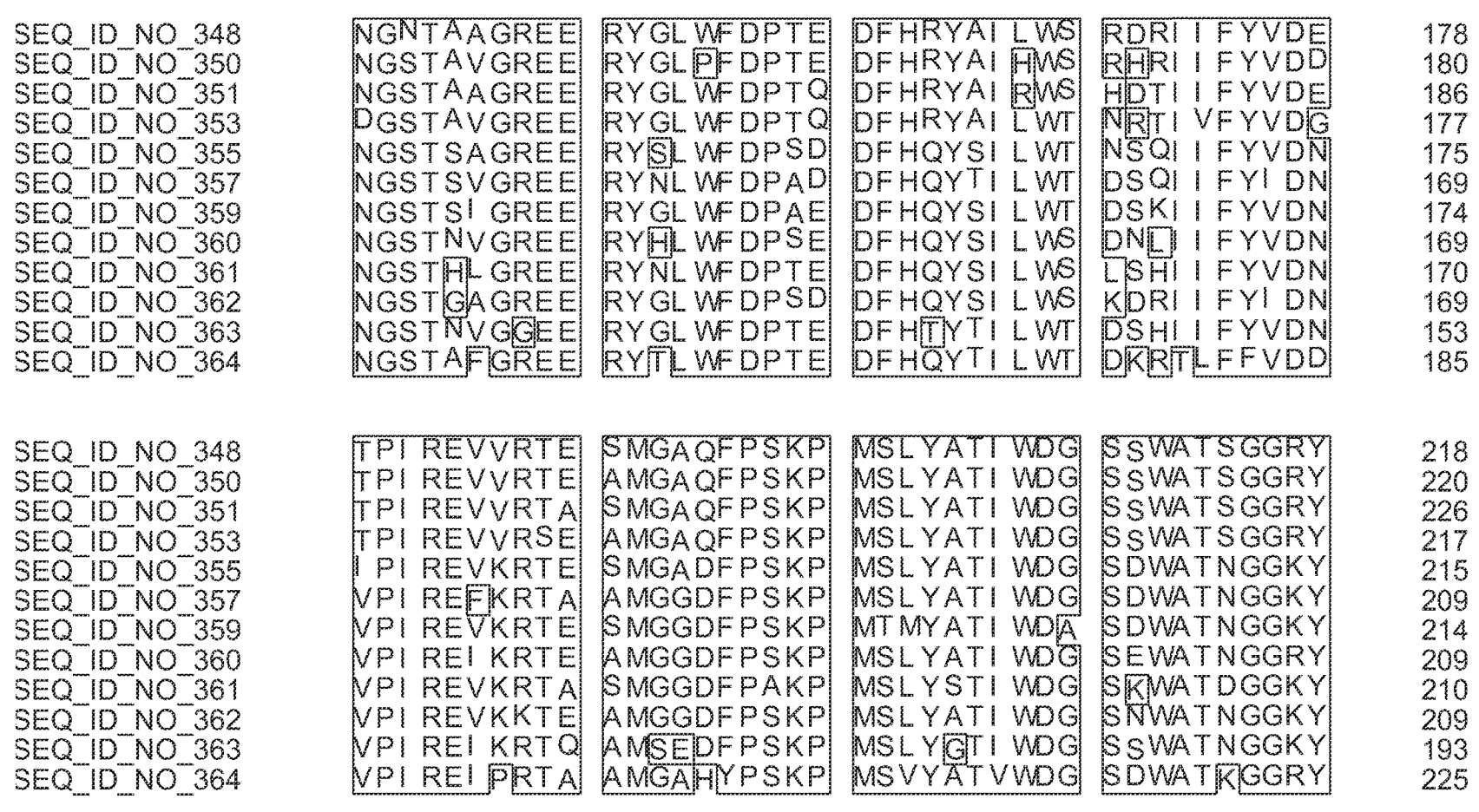

Examples of amino acid sequences of functional homologs of the polypeptide set forth in SEQ ID NO: 348 are provided in FIG. 5 and in the Sequence Listing. Such functional homologs include, for example, CeresAnnot: 8642214 (SEQ ID NO: 350), GI:115451805 (SEQ ID NO: 351), CeresClone:890595 (SEQ ID NO: 353), CeresAnnot: 1463701 (SEQ ID NO: 355), CeresClone:1840970 (SEQ ID NO: 357), CeresClone:672495 (SEQ ID NO: 359), GI:225424452 (SEQ ID NO: 360), GI:15223878 (SEQ ID NO: 361), GI:13560781 (SEQ ID NO: 362), GI:6681351 (SEQ ID NO: 363), GI:116786783 (SEQ ID NO: 364), GI:125543052 (SEQ ID NO: 365), GI:124109193 (SEQ ID NO: 366), CeresAnnot:8653921 (SEQ ID NO: 368), CeresClone:1995976 (SEQ ID NO: 370), CeresClone:369312 (SEQ ID NO: 372), GI:17047034 (SEQ ID NO: 373), GI:118482018 (SEQ ID NO: 374), GI:125530964 (SEQ ID NO: 375), GI:125563629 (SEQ ID NO: 376), GI:147797772 (SEQ ID NO: 377), CeresClone:18876 (SEQ ID NO: 379), GI:125540767 (SEQ ID NO: 380), GI:115448069 (SEQ ID NO: 381), CeresClone:683310 (SEQ ID NO: 383), GI:125605601 (SEQ ID NO: 384), CeresClone:1922671 (SEQ ID NO: 386), CeresClone:100961902 (SEQ ID NO: 388), CeresAnnot:1447077 (SEQ ID NO: 390), CeresClone: 1643790 (SEQ ID NO: 392), GI:125580663 (SEQ ID NO: 393), GI:116785331 (SEQ ID NO: 394), CeresAnnot: 1485570 (SEQ ID NO: 396), CeresAnnot:8681188 (SEQ ID NO: 398), CeresClone:1818189 (SEQ ID NO: 400), CeresClone:100861631 (SEQ ID NO: 402), CeresAnnot:8671232 (SEQ ID NO: 404), CeresClone:1813525 (SEQ ID NO: 406), GI:15222593 (SEQ ID NO: 407), GI:42795460 (SEQ ID NO: 408), CeresClone:1828819 (SEQ ID NO: 410), CeresAnnot:1460297 (SEQ ID NO: 412), GI:225424689 (SEQ ID NO: 413), and GI:76786474 (SEQ ID NO: 414). In some cases, a functional homolog of SEQ ID NO: 348 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 348. In some cases, a functional homolog of SEQ ID NO: 348 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 348 described above or set forth in the Sequence Listing.

Figure 6A:
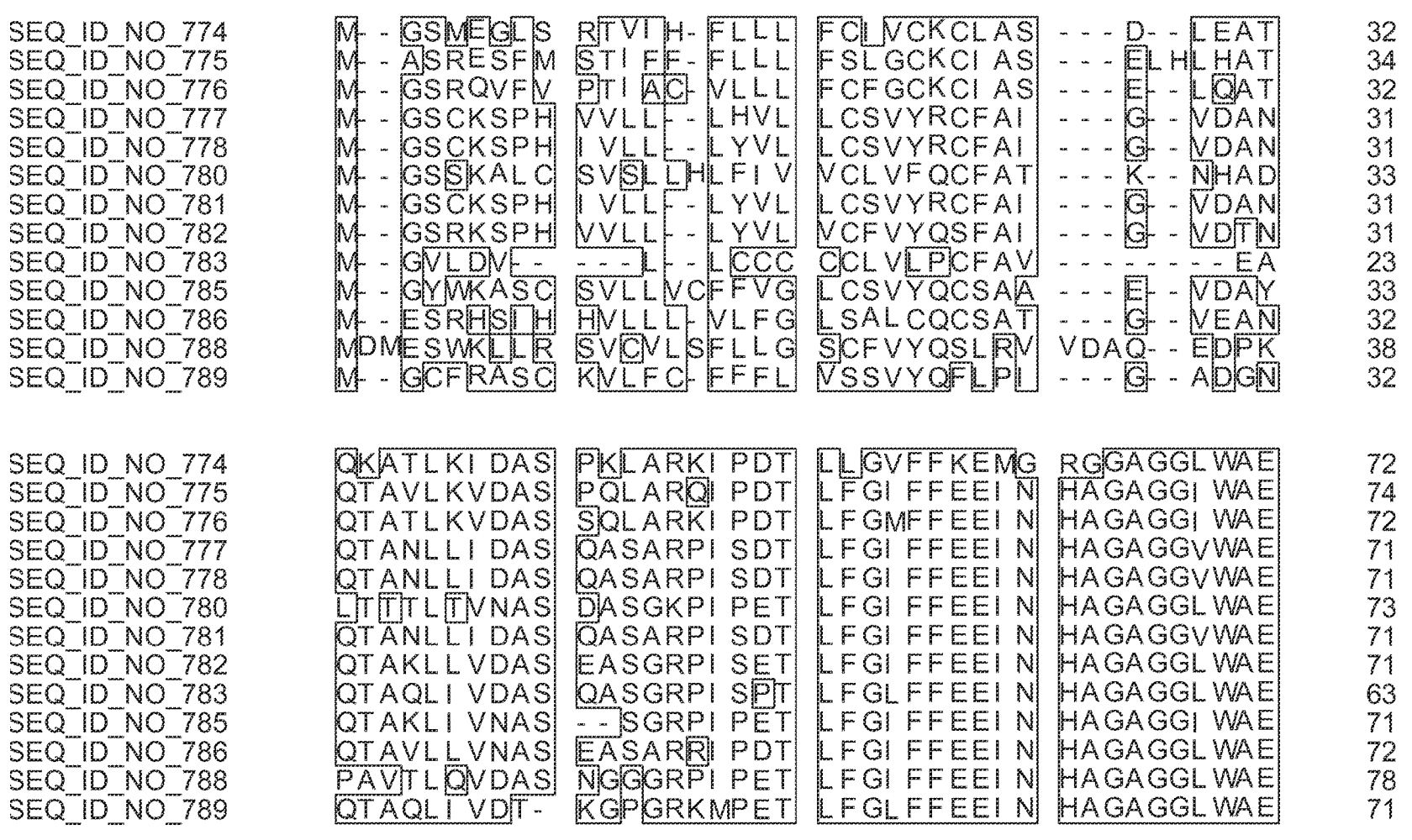
Figure 6D:
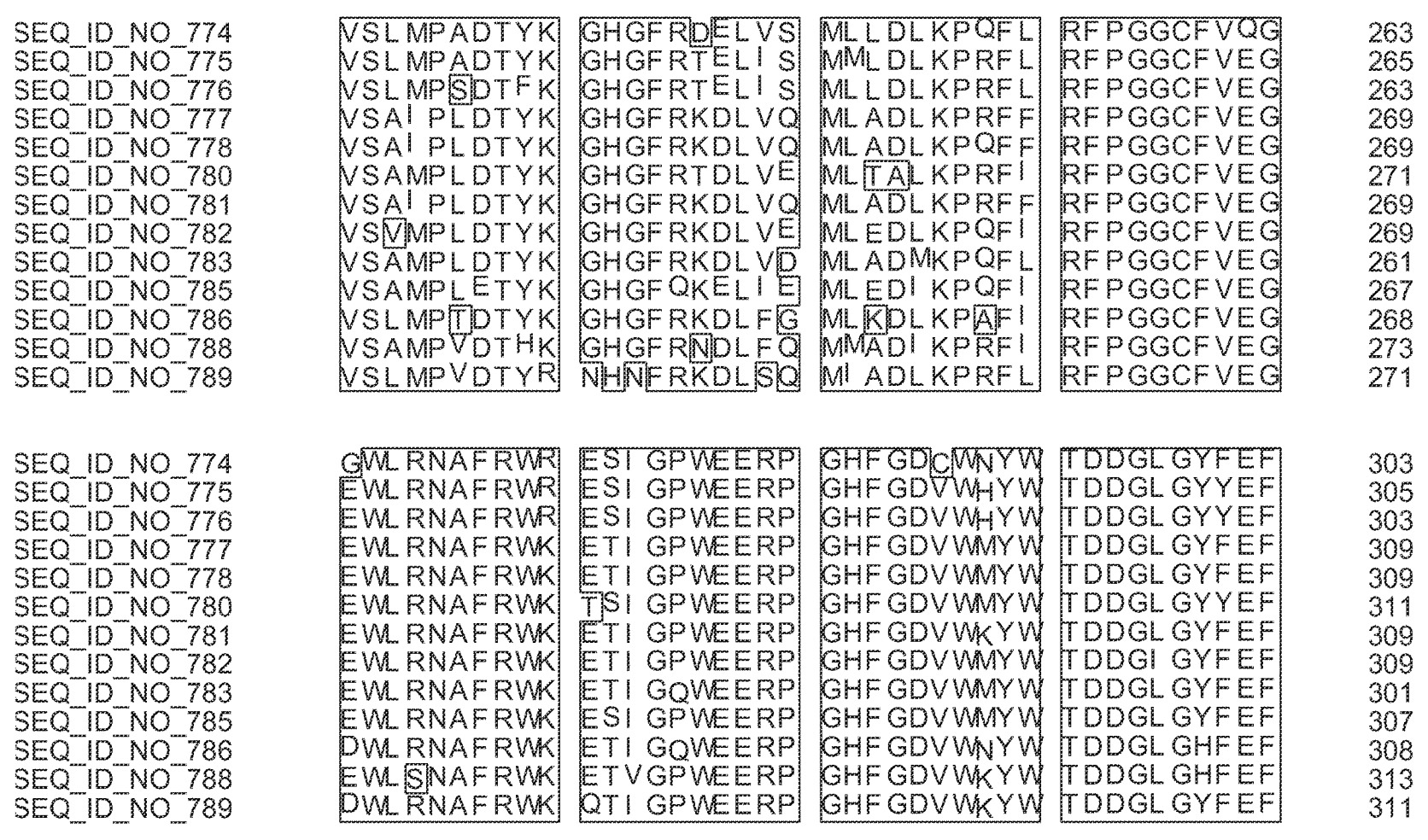

Examples of amino acid sequences of functional homologs of the polypeptide set forth in SEQ ID NO: 774 are provided in FIG. 6 and in the Sequence Listing. Such functional homologs include, for example, GI:115483997 (SEQ ID NO: 775), GI:13398414 (SEQ ID NO: 776), GI:33151175 (SEQ ID NO: 777), GI:119507455 (SEQ ID NO: 778), CeresClone:549408 (SEQ ID NO: 780), GI:37777015 (SEQ ID NO: 781), GI:157313302 (SEQ ID NO: 782), GI:157072586 (SEQ ID NO: 783), CeresAnnot: 1506572 (SEQ ID NO: 785), GI:16417958 (SEQ ID NO: 786), CeresAnnot:556941 (SEQ ID NO: 788), GI:225440254 (SEQ ID NO: 789), CeresClone:1753603 (SEQ ID NO: 791), CeresClone:236733 (SEQ ID NO: 793), CeresClone:1786359 (SEQ ID NO: 795), GI:115487150 (SEQ ID NO: 796), CeresAnnot:8682811 (SEQ ID NO: 798), GI:13398412 (SEQ ID NO: 799), GI:116310992 (SEQ ID NO: 800), GI:38347003 (SEQ ID NO: 801), GI:116739148 (SEQ ID NO: 802), GI:22324432 (SEQ ID NO: 803), CeresAnnot:1453426 (SEQ ID NO: 805), CeresAnnot:8657414 (SEQ ID NO: 807), GI:108707861 (SEQ ID NO: 808), CeresAnnot:1528070 (SEQ ID NO: 810), GI:22327075 (SEQ ID NO: 811), GI:50507838 (SEQ ID NO: 812), GI:168060089 (SEQ ID NO: 813), GI:160890886 (SEQ ID NO: 814), GI:189464007 (SEQ ID NO: 815), GI:154492683 (SEQ ID NO: 816), GI:146300858 (SEQ ID NO: 817), GI:150008552 (SEQ ID NO: 818), GI:86142284 (SEQ ID NO: 819), GI:148269769 (SEQ ID NO: 820), and GI:170288456 (SEQ ID NO: 821). In some cases, a functional homolog of SEQ ID NO: 774 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 774. In some cases, a functional homolog of SEQ ID NO: 774 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 774 described above or set forth in the Sequence Listing.

Examples of amino acid sequences of functional homologs of the polypeptide set forth in SEQ ID NO: 416 are provided in FIG. 7 and in the Sequence Listing. Such functional homologs include, for example, CeresAnnot: 8656625 (SEQ ID NO: 418), GI:162462515 (SEQ ID NO: 419), GI:75133694 (SEQ ID NO: 420), CeresClone:829440 (SEQ ID NO: 422), GI:118488472 (SEQ ID NO: 423), GI:90657534 (SEQ ID NO: 424), CeresClone:1237946 (SEQ ID NO: 426), GI:225456557 (SEQ ID NO: 427), CeresAnnot:1355066 (SEQ ID NO: 429), GI:38194917 (SEQ ID NO: 430), GI:116788824 (SEQ ID NO: 431), CeresClone:1848658 (SEQ ID NO: 433), GI:116790012 (SEQ ID NO: 434), CeresClone:570485 (SEQ ID NO: 436), GI:125559102 (SEQ ID NO: 437), CeresClone:1957107 (SEQ ID NO: 439), CeresClone:1781794 (SEQ ID NO: 441), GI:115453531 (SEQ ID NO: 442), CeresClone: 285169 (SEQ ID NO: 444), CeresAnnot:1450186 (SEQ ID NO: 446), CeresClone:1806851 (SEQ ID NO: 448), GI:38194916 (SEQ ID NO: 449), GI:225451792 (SEQ ID NO: 450), GI:225456559 (SEQ ID NO: 451), GI:224124236 (SEQ ID NO: 452), CeresClone:17250 (SEQ ID NO: 454), CeresAnnot:1363625 (SEQ ID NO: 456), CeresAnnot: 1450185 (SEQ ID NO: 458), GI:125552171 (SEQ ID NO: 459), GI:115463639 (SEQ ID NO: 460), CeresAnnot: 1809854 (SEQ ID NO: 462), GI:162462330 (SEQ ID NO: 463), CeresAnnot:1326475 (SEQ ID NO: 465), GI:125559101 (SEQ ID NO: 466), CeresAnnot:8632643 (SEQ ID NO: 468), CeresClone:1546455 (SEQ ID NO: 470), CeresClone:1788775 (SEQ ID NO: 472), GI:162462156 (SEQ ID NO: 473), GI:125545759 (SEQ ID NO: 474), CeresClone:236876 (SEQ ID NO: 476), CeresAnnot:8640602 (SEQ ID NO: 478), GI:30090032 (SEQ ID NO: 479), GI:38230578 (SEQ ID NO: 480), and GI:115453533 (SEQ ID NO: 481). In some cases, a functional homolog of SEQ ID NO: 416 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 416. In some cases, a functional homolog of SEQ ID NO: 416 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 416 described above or set forth in the Sequence Listing.

Examples of amino acid sequences of functional homologs of the polypeptide set forth in SEQ ID NO: 2 are provided in FIG. 8 and in the Sequence Listing. Such functional homologs include, for example, CeresAnnot: 8701928 (SEQ ID NO: 4), CeresClone:630287 (SEQ ID NO: 6), GI:115447391 (SEQ ID NO: 7), GI:225453032 (SEQ ID NO: 8), CeresClone:1919301 (SEQ ID NO: 10), CeresAnnot:883070 (SEQ ID NO: 12), CeresAnnot: 1469624 (SEQ ID NO: 14), GI:168065791 (SEQ ID NO: 15), CeresClone:1887777 (SEQ ID NO: 17), GI:57834149 (SEQ ID NO: 18), GI:116310214 (SEQ ID NO: 19), GI:18087513 (SEQ ID NO: 20), GI:147841543 (SEQ ID NO: 21), GI:168014382 (SEQ ID NO: 22), and CeresAnnot: 8462062 (SEQ ID NO: 24). In some cases, a functional homolog of SEQ ID NO: 2 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 2. In some cases, a functional homolog of SEQ ID NO: 2 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 2 described above or set forth in the Sequence Listing.

Examples of amino acid sequences of functional homologs of the polypeptide set forth in SEQ ID NO: 157 are provided in FIG. 9 and in the Sequence Listing. Such functional homologs include, for example, GI:56409850 (SEQ ID NO: 158), CeresAnnot:8740887 (SEQ ID NO: 160), GI:162460428 (SEQ ID NO: 161), GI:115453815 (SEQ ID NO: 162), GI:56409844 (SEQ ID NO: 163), GI:31339690 (SEQ ID NO: 164), GI:9294073 (SEQ ID NO: 165), CeresAnnot:1473325 (SEQ ID NO: 167), GI:31296713 (SEQ ID NO: 168), CeresClone:1925376 (SEQ ID NO: 170), GI:56409848 (SEQ ID NO: 171), GI:125544555 (SEQ ID NO: 172), GI:115445881 (SEQ ID NO: 173), CeresAnnot:8674833 (SEQ ID NO: 175), CeresClone:914572 (SEQ ID NO: 177), CeresAnnot:8659084 (SEQ ID NO: 179), CeresClone:1781320 (SEQ ID NO: 181), GI:53791307 (SEQ ID NO: 182), CeresAnnot: 8659080 (SEQ ID NO: 184), GI:212275650 (SEQ ID NO: 185), CeresClone:1818693 (SEQ ID NO: 187), CeresClone: 508386 (SEQ ID NO: 189), GI:53791309 (SEQ ID NO: 190), CeresAnnot:8659051 (SEQ ID NO: 192), CeresClone: 1862153 (SEQ ID NO: 194), CeresClone:1902844 (SEQ ID NO: 196), GI:212275101 (SEQ ID NO: 197), CeresClone: 1844210 (SEQ ID NO: 199), CeresAnnot:8658929 (SEQ ID NO: 201), GI:125555301 (SEQ ID NO: 202), CeresClone: 825530 (SEQ ID NO: 204), GI:115444075 (SEQ ID NO: 205), CeresClone:1748522 (SEQ ID NO: 207), GI:115445889 (SEQ ID NO: 208), CeresAnnot:8671335 (SEQ ID NO: 210), GI:53791308 (SEQ ID NO: 211), CeresClone:1899806 (SEQ ID NO: 213), CeresClone: 1726616 (SEQ ID NO: 215), GI:162460449 (SEQ ID NO: 216), CeresClone:1770027 (SEQ ID NO: 218), CeresAnnot: 1467806 (SEQ ID NO: 220), GI:55792425 (SEQ ID NO: 221), GI:56409862 (SEQ ID NO: 222), GI:115482674 (SEQ ID NO: 223), CeresClone:815962 (SEQ ID NO: 225), GI:56409860 (SEQ ID NO: 226), CeresAnnot:8670072 (SEQ ID NO: 228), CeresAnnot:1473327 (SEQ ID NO: 230), CeresClone:1726182 (SEQ ID NO: 232), CeresAnnot: 8734902 (SEQ ID NO: 234), CeresAnnot:8741882 (SEQ ID NO: 236), CeresClone:761431 (SEQ ID NO: 238), CeresAnnot:8678791 (SEQ ID NO: 240), CeresClone:845464 (SEQ ID NO: 242), and CeresClone:1726076 (SEQ ID NO: 244). In some cases, a functional homolog of SEQ ID NO: 157 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 157. In some cases, a functional homolog of SEQ ID NO: 157 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 157 described above or set forth in the Sequence Listing.

Examples of amino acid sequences of functional homologs of the polypeptide set forth in SEQ ID NO: 280 are provided in FIG. 10 and in the Sequence Listing. Such functional homologs include, for example, CeresAnnot: 8681689 (SEQ ID NO: 282), GI:226529851 (SEQ ID NO: 283), GI:115448865 (SEQ ID NO: 284), GI:154163107 (SEQ ID NO: 285), GI:147817757 (SEQ ID NO: 286), CeresClone:1925709 (SEQ ID NO: 288), GI:15227566 (SEQ ID NO: 289), GI:20138107 (SEQ ID NO: 290), CeresClone:934069 (SEQ ID NO: 292), CeresAnnot: 8681691 (SEQ ID NO: 294), GI:46805726 (SEQ ID NO: 295), GI:125541250 (SEQ ID NO: 296), GI:115448869 (SEQ ID NO: 297), GI:115467048 (SEQ ID NO: 298), GI:51090521 (SEQ ID NO:299), GI:125554524 (SEQ ID NO:300), CeresAnnot:8735787 (SEQ ID NO:302), GI:15227563 (SEQ ID NO:303), CeresAnnot:8681690 (SEQ ID NO:305), GI:15223062 (SEQ ID NO:306), CeresAnnot:8735782 (SEQ ID NO:308), GI:115467046 (SEQ ID NO:309), GI:125554519 (SEQ ID NO:310), GI:125596466 (SEQ ID NO:311), GI:20138442 (SEQ ID NO:312), CeresAnnot:1448326 (SEQ ID NO:314), CeresAnnot:8735776 (SEQ ID NO:316), GI:125554515 (SEQ ID NO:317), GI:154163097 (SEQ ID NO:318), CeresAnnot:8673445 (SEQ ID NO:320), GI:115445521 (SEQ ID NO:321), CeresAnnot:1448328 (SEQ ID NO:323), CeresAnnot:1437779 (SEQ ID NO:325), GI:15226507 (SEQ ID NO:326), GI:154163099 (SEQ ID NO:327), GI:93139696 (SEQ ID NO:328), GI:154163101 (SEQ ID NO:329), CeresAnnot:1448327 (SEQ ID NO:331), CeresAnnot:8681687 (SEQ ID NO:333), CeresAnnot:1437782 (SEQ ID NO:335), GI:20138443 (SEQ ID NO:336), GI:15226501 (SEQ ID NO:337), GI:125541240 (SEQ ID NO:338), GI:115458656 (SEQ ID NO:339), GI:125548499 (SEQ ID NO:340), (CeresAnnot:8654550 SEQ ID NO:342), CeresAnnot:8701112 (SEQ ID NO:344), and CeresClone:1530993 (SEQ ID NO:346). In some cases, a functional homolog of SEQ ID NO: 280 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 280. In some cases, a functional homolog of SEQ ID NO: 280 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 280 described above or set forth in the Sequence Listing.

Figure 11C:
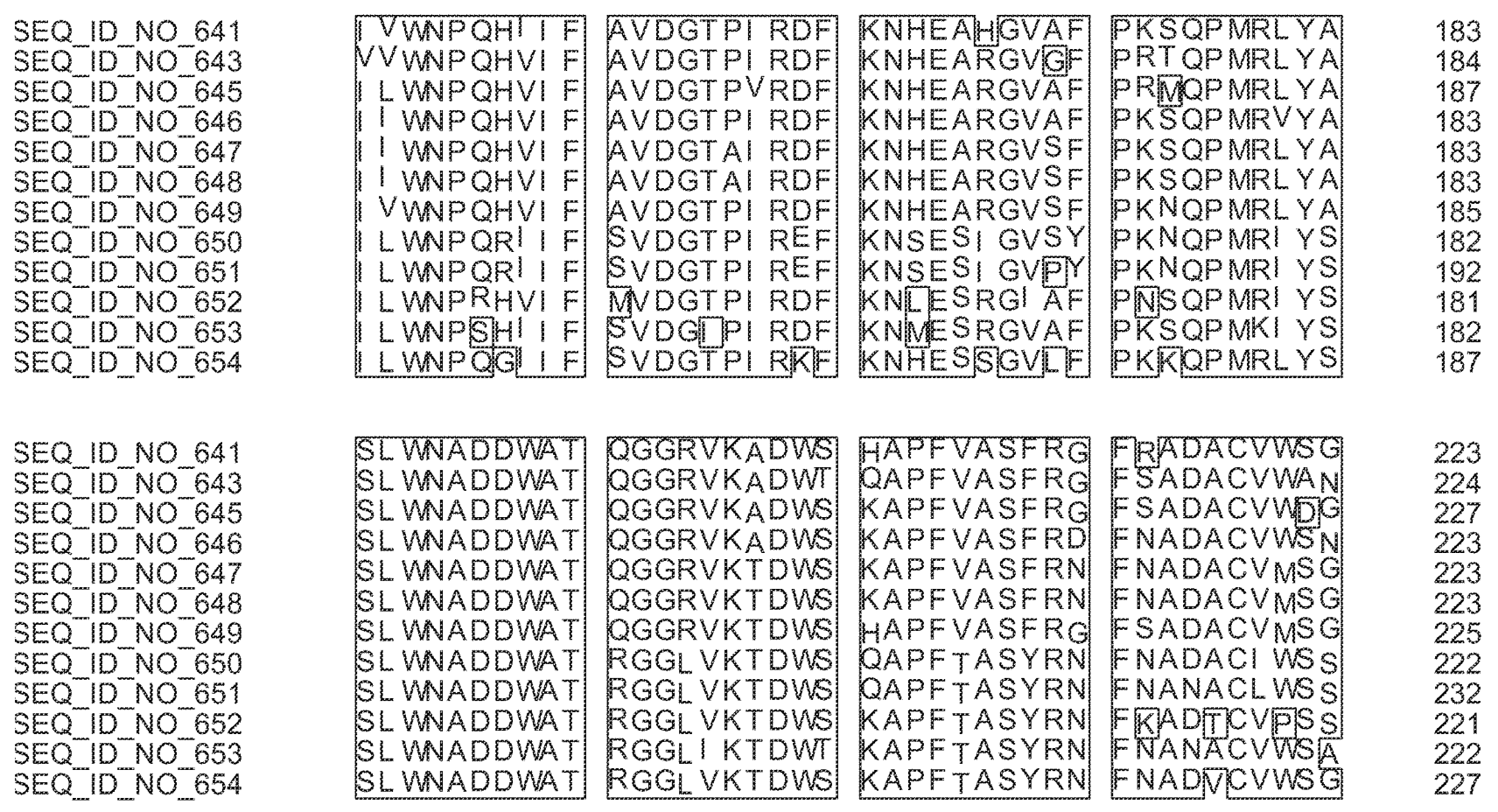

Examples of amino acid sequences of functional homologs of the polypeptide set forth in SEQ ID NO: 641 are provided in FIG. 11 and in the Sequence Listing. Such functional homologs include, for example, CeresAnnot:8744420 (SEQ ID NO: 643), CeresClone:331385 (SEQ ID NO: 645), GI:115469712 (SEQ ID NO:646), GI:1890577 (SEQ ID NO:647), GI:51039064 (SEQ ID NO:648), GI:14330332 (SEQ ID NO:649), GI:147854712 (SEQ ID NO:650), GI:157352236 (SEQ ID NO:651), GI:118722746 (SEQ ID NO:652), GI:8886867 (SEQ ID NO:653), GI:115334952 (SEQ ID NO:654), CeresClone:1789502 (SEQ ID NO:656), CeresClone:1805428 (SEQ ID NO:658), CeresClone:1724099 (SEQ ID NO:660), CeresClone:1724817 (SEQ ID NO:662), CeresClone:1804995 (SEQ ID NO:664), CeresClone:1446366 (SEQ ID NO:666), CeresClone:1054422 (SEQ ID NO:668), CeresClone:263803 (SEQ ID NO:670), CeresClone:1821034 (SEQ ID NO:672), CeresClone:1806021 (SEQ ID NO:674), CeresClone:1727689 (SEQ ID NO:676), GI:115469720 (SEQ ID NO:677), CeresAnnot:8744425 (SEQ ID NO:679), GI:212275237 (SEQ ID NO:680), CeresClone:1724271 (SEQ ID NO:682), CeresClone:247073 (SEQ ID NO:684), CeresClone:1020658 (SEQ ID NO:686), GI:1890575 (SEQ ID NO:687), GI:225446111 (SEQ ID NO:688), GI:225446115 (SEQ ID NO:689), GI:147854714 (SEQ ID NO:690), GI:68532877 (SEQ ID NO:691), GI:147779866 (SEQ ID NO:692), CeresClone:100062911 (SEQ ID NO:694), GI:225446117 (SEQ ID NO:695), CeresClone:1832719 (SEQ ID NO:697), CeresClone:1793297 (SEQ ID NO:699), CeresClone:1848637 (SEQ ID NO:701), GI:225446103 (SEQ ID NO:702), CeresAnnot:1362908 (SEQ ID NO:704), CeresClone:100064069 (SEQ ID NO:706), CeresAnnot:1469128 (SEQ ID NO:708), CeresClone:656868 (SEQ ID NO:710), CeresClone:1793334 (SEQ ID NO:712), GI:29500891 (SEQ ID NO:713), CeresClone:1895226 (SEQ ID NO:715), GI:8886865 (SEQ ID NO:716), CeresAnnot:878947 (SEQ ID NO:718), CeresClone:1045431 (SEQ ID NO:720), GI:22947852 (SEQ ID NO:721), CeresClone:1855067 (SEQ ID NO:723), GI:17064792 (SEQ ID NO:724), CeresClone:662227 (SEQ ID NO:726), GI:225446109 (SEQ ID NO:727), CeresClone:522574 (SEQ ID NO:729), GI:115334954 (SEQ ID NO:730), CeresClone:581426 (SEQ ID NO:732), GI:124109191 (SEQ ID NO:733), CeresAnnot:1471882 (SEQ ID NO:735), GI:34809190 (SEQ ID NO:736), GI:29500893 (SEQ ID NO:737), CeresAnnot:1452398 (SEQ ID NO:739), GI:124109199 (SEQ ID NO:740), CeresAnnot:1478206 (SEQ ID NO:742), CeresAnnot:1445599 (SEQ ID NO:744), CeresAnnot:1452397 (SEQ ID NO:746), GI:19911573 (SEQ ID NO:747), GI:124109181 (SEQ ID NO:748), GI:22327914 (SEQ ID NO:749), GI:42795468 (SEQ ID NO:750), GI:42795462 (SEQ ID NO:751), CeresAnnot:1466060 (SEQ ID NO:753), CeresAnnot:8461207 (SEQ ID NO:755), CeresAnnot:1506985 (SEQ ID NO:757), GI:3901012 (SEQ ID NO:758), CeresAnnot:1443040 (SEQ ID NO:760), GI:90811697 (SEQ ID NO:761), CeresAnnot:1443041 (SEQ ID NO:763), GI:157358970 (SEQ ID NO:764), GI:90656516 (SEQ ID NO:765), GI:577066 (SEQ ID NO:766), GI:90656520 (SEQ ID NO:767), GI:88683124 (SEQ ID NO:768), GI:90656518 (SEQ ID NO:769), CeresAnnot:1482565 (SEQ ID NO:771), GI:15238891 (SEQ ID NO:772), and CeresClone ID No. 933491 (SEQ ID NO: 823). In some cases, a functional homolog of SEQ ID NO: 641 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 641. In some cases, a functional homolog of SEQ ID NO: 641 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 641 described above or set forth in the Sequence Listing.

Figure 12:
FIG. 12 is an alignment of the amino acid sequence of CeresClone:1955766 (SEQ ID NO: 26) with homologous and/or orthologous amino acid sequences.

Examples of amino acid sequences of functional homologs of the polypeptide set forth in SEQ ID NO: 26 are provided in FIG. 12 and in the Sequence Listing. Such functional homologs include, for example, CeresClone:570179 (SEQ ID NO: 28), GI:54290293 (SEQ ID NO:29), GI:1617121 (SEQ ID NO:30), CeresAnnot:8724383 (SEQ ID NO:32), CeresClone:896724 (SEQ ID NO:34), CeresClone:607452 (SEQ ID NO:36), GI:37904392 (SEQ ID NO:37), CeresClone:1870473 (SEQ ID NO:39), CeresClone:2026564 (SEQ ID NO:41), CeresClone:2004365 (SEQ ID NO:43), CeresClone:2020677 (SEQ ID NO:45), CeresClone:2039538 (SEQ ID NO:47), CeresClone:844611 (SEQ ID NO:49), GI:125526847 (SEQ ID NO:50), CeresClone:597887 (SEQ ID NO:52), GI:58396949 (SEQ ID NO:53), CeresClone:684778 (SEQ ID NO:55), CeresClone:699511 (SEQ ID NO:57), CeresClone:1803377 (SEQ ID NO:59), CeresClone:1888961 (SEQ ID NO:61), CeresClone:897331 (SEQ ID NO:63), CeresClone:617775 (SEQ ID NO:65), GI:20513866 (SEQ ID NO:66), CeresAnnot:8724387 (SEQ ID NO:68), CeresClone:1804405 (SEQ ID NO:70), GI:48093396 (SEQ ID NO:71), GI:108862602 (SEQ ID NO:72), GI:115488400 (SEQ ID NO:73), CeresClone:759663 (SEQ ID NO:75), CeresClone:1801827 (SEQ ID NO:77), GI:48093418 (SEQ ID NO:78), GI:48093360 (SEQ ID NO:79), CeresClone:1457620 (SEQ ID NO:81), GI:48093370 (SEQ ID NO:82), CeresClone:639183 (SEQ ID NO:84), CeresClone:1453564 (SEQ ID NO:86), CeresClone:1531954 (SEQ ID NO:88), CeresClone:1460371 (SEQ ID NO:90), CeresClone:1627479 (SEQ ID NO:92), CeresClone:992630 (SEQ ID NO:94), CeresClone:685480 (SEQ ID NO:96), GI:75994159 (SEQ ID NO:97), CeresAnnot:8724380 (SEQ ID NO:99), GI:48093378 (SEQ ID NO:100), GI:75994143 (SEQ ID NO:101), GI:75994153

(SEQ ID NO:102), CeresAnnot:8724381 (SEQ ID NO:104), GI:75994157 (SEQ ID NO:105), CeresClone:730301 (SEQ ID NO:107), and CeresAnnot:8724388 (SEQ ID NO:109). In some cases, a functional homolog of SEQ ID NO: 26 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 26. In some cases, a functional homolog of SEQ ID NO: 26 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 26 described above or set forth in the Sequence Listing.

The identification of conserved regions in a biomass composition-modulating polypeptide facilitates production of variants of biomass composition-modulating polypeptides. Variants of biomass composition-modulating polypeptides typically have 10 or fewer conservative amino acid substitutions within the primary amino acid sequence, e.g., 7 or fewer conservative amino acid substitutions, 5 or fewer conservative amino acid substitutions, or between 1 and 5 conservative substitutions. A useful variant polypeptide can be constructed based on one of the alignments set forth in FIG. 1, FIG. 2, FIG. 3, FIG. 4, FIG. 5, FIG. 6, FIG. 7, FIG. 8, FIG. 9, FIG. 10, FIG. 11, or FIG. 12, and/or homologs identified in the Sequence Listing. Such a polypeptide includes the conserved regions, arranged in the order depicted in the Figure from amino-terminal end to carboxy-terminal end. Such a polypeptide may also include zero, one, or more than one amino acid in positions marked by dashes. When no amino acids are present at positions marked by dashes, the length of such a polypeptide is the sum of the amino acid residues in all conserved regions. When amino acids are present at a position marked by dashes, such a polypeptide has a length that is the sum of the amino acid residues in all conserved regions and all dashes.

C. Functional Homologs Identified by HMMER

In some embodiments, useful biomass composition-modulating polypeptides include those that fit a Hidden Markov Model based on the polypeptides set forth in any one of FIGS. 1-12. A Hidden Markov Model (HMM) is a statistical model of a consensus sequence for a group of functional homologs. See, Durbin et al., *Biological Sequence Analysis: Probabilistic Models of Proteins and Nucleic Acids*, Cambridge University Press, Cambridge, UK (1998). An HMM is generated by the program HMMER 2.3.2 with default program parameters, using the sequences of the group of functional homologs as input. The multiple sequence alignment is generated by ProbCons (Do et al., *Genome Res.*, 15(2):330-40 (2005)) version 1.11 using a set of default parameters: -c, —consistency REPS of 2; -ir, —iterative-refinement REPS of 100; -pre, —pre-training REPS of 0. ProbCons is a public domain software program provided by Stanford University.

The default parameters for building an HMM (hmmbuild) are as follows: the default "architecture prior" (archpri) used by MAP architecture construction is 0.85, and the default cutoff threshold (idlevel) used to determine the effective sequence number is 0.62. HMMER 2.3.2 was released Oct. 3, 2003 under a GNU general public license, and is available from various sources on the World Wide Web such as hmmer.janelia.org; hmmer wustl.edu; and fr.com/hmmer232/. Hmmbuild outputs the model as a text file.

The HMM for a group of functional homologs can be used to determine the likelihood that a candidate biomass composition-modulating polypeptide sequence is a better fit to that particular HMM than to a null HMM generated using a group of sequences that are not structurally or functionally related. The likelihood that a candidate polypeptide sequence is a better fit to an HMM than to a null HMM is indicated by the HMM bit score, a number generated when the candidate sequence is fitted to the HMM profile using the HMMER hmmsearch program. The following default parameters are used when running hmmsearch: the default E-value cutoff (E) is 10.0, the default bit score cutoff (T) is negative infinity, the default number of sequences in a database (Z) is the real number of sequences in the database, the default E-value cutoff for the per-domain ranked hit list (domE) is infinity, and the default bit score cutoff for the per-domain ranked hit list (domT) is negative infinity. A high HMM bit score indicates a greater likelihood that the candidate sequence carries out one or more of the biochemical or physiological function(s) of the polypeptides used to generate the HMM. A high HMM bit score is at least 20, and often is higher. Slight variations in the HMM bit score of a particular sequence can occur due to factors such as the order in which sequences are processed for alignment by multiple sequence alignment algorithms such as the ProbCons program. Nevertheless, such HMM bit score variation is minor.

The biomass composition-modulating polypeptides discussed below fit the indicated HMM with an HMM bit score greater than to 65. (e.g., greater than 70, 80, 90, 100, 120, 140, 200, 300, 500, 1000, 1500, or 2000). In some embodiments, the HMM bit score of a biomass composition-modulating polypeptide discussed below is about 50%, 60%, 70%, 80%, 90%, or 95% of the HMM bit score of a functional homolog provided in the Sequence Listing of this application. In some embodiments, a biomass composition-modulating polypeptide discussed below fits the indicated HMM with an HMM bit score greater than 210, and has a domain indicative of a biomass composition-modulating polypeptide. In some embodiments, a biomass composition-modulating polypeptide discussed below fits the indicated HMM with an HMM bit score greater than 210, and has 65% or greater sequence identity (e.g., 75%, 80%, 85%, 90%, 95%, or 100% sequence identity) to an amino acid sequence shown in any one of FIGS. 1-12.

Examples of polypeptides are shown in the sequence listing that have HMM bit scores greater than 84 (e.g., greater than 100, 120, 140, 160, 180, 200, 220, 240, 250, 260, 270, 280, or 290) when fitted to an HMM generated from the amino acid sequences set forth in FIG. 1 are identified in the Sequence Listing of this application. Such polypeptides include, for example, SEQ ID NOs: 483, 485, 486, 488, 490, 492, 493, 495, 497, 498, 500, 501, 503, 504, 506, 508, 509, 510, 512, 514, 515, 516, 517, 519, 521, 522, 523, 525, 527, 529, 531, 533, 534, 535, 537, 539, 541, 543, 545, 547, 549, 551, 552, 554, 556, 557, and 559.

Examples of polypeptides are shown in the sequence listing that have HMM bit scores greater than 120 (e.g., greater than 125, 130, 140, 150, 160, 170, 180, 200, 220, 240, 260, 280, 300, or 315) when fitted to an HMM generated from the amino acid sequences set forth in FIG. 2 are identified in the Sequence Listing of this application. Such polypeptides include, for example, SEQ ID NOs: 562, 564, 565, 567, 568, 570, 572, 573, 574, 575, 576, 578, 580, 582, 584, 586, 588, 589, 590, 592, 594, 596, 598, 599, 601, 602, 603, 605, 607, 608, 609, 611, 613, 615, 617, 619, 621, 622, 624, 625, 627, 629, 630, 632, 634, 636, and 638.

Examples of polypeptides are shown in the sequence listing that have HMM bit scores greater than 200 (e.g., greater than 250, 300, 350, 400, 450, 500, 550, 600, 650, 700, 750, 800, 850, 900, 950, 975, or 1000) when fitted to an HMM generated from the amino acid sequences set forth in FIG. 3 are identified in the Sequence Listing of this application. Such polypeptides include, for example, SEQ ID NOs: 246, 248, 250, 251, 252, 254, 256, 258, 260, 261, 262, 264, 266, 268, 270, 272, 274, 275, 276, and 278.

Examples of polypeptides are shown in the sequence listing that have HMM bit scores greater than 93 (e.g., greater than 95, 100, 105, 110, 115, 120, 125, 130, 135, 140, or 145) when fitted to an HMM generated from the amino acid sequences set forth in FIG. 4 are identified in the Sequence Listing of this application. Such polypeptides include, for example, SEQ ID NOs: 111, 113, 115, 117, 118, 120, 122, 124, 126, 128, 130, 132, 133, 135, 136, 138, 139, 141, 143, 145, 147, 148, 149, 151, 152, 153, and 155.

Examples of polypeptides are shown in the sequence listing that have HMM bit scores greater than 387 (e.g., greater than 400, 450, 500, 550, 600, 650, 700, 750, 800, 850, 900, or 920) when fitted to an HMM generated from the amino acid sequences set forth in FIG. 5 are identified in the Sequence Listing of this application. Such polypeptides include, for example, SEQ ID NOs: 348, 350, 351, 353, 355, 357, 359, 360, 361, 362, 363, 364, 365, 366, 368, 370, 372, 373, 374, 375, 376, 377, 379, 380, 381, 383, 384, 386, 388, 390, 392, 393, 394, 396, 398, 400, 402, 404, 406, 407, 408, 410, 412, 413, and 414.

Examples of polypeptides are shown in the sequence listing that have HMM bit scores greater than 315 (e.g., greater than 350, 400, 450, 500, 550, 600, 650, 700, 750, 800, 850, 900, 950, 1000, 1050, 1100, 1150, 1200, 1250, 1300, 1350, 1400, 1450, 1500, 1500, 1550, 1600, 1620, 1630, or 1640) when fitted to an HMM generated from the amino acid sequences set forth in FIG. 6 are identified in the Sequence Listing of this application. Such polypeptides include, for example, SEQ ID NOs: 774, 775, 776, 777, 778, 780, 781, 782, 783, 785, 786, 788, 789, 791, 793, 795, 796, 798, 799, 800, 801, 802, 803, 805, 807, 808, 810, 811, 812, 813, 814, 815, 816, 817, 818, 819, 820, and 821.

Examples of polypeptides are shown in the sequence listing that have HMM bit scores greater than 914 (e.g., greater than 920, 940, 960, 980, 1000, 1020, 1040, 1060, 1080, 1090, or 1100) when fitted to an HMM generated from the amino acid sequences set forth in FIG. 7 are identified in the Sequence Listing of this application. Such polypeptides include, for example, SEQ ID NOs: 416, 418, 419, 420, 422, 423, 424, 426, 427, 429, 430, 431, 433, 434, 436, 437, 439, 441, 442, 444, 446, 448, 449, 450, 451, 452, 454, 456, 458, 459, 460, 462, 463, 465, 466, 468, 470, 472, 473, 474, 476, 478, 479, 480, and 481.

Examples of polypeptides are shown in the sequence listing that have HMM bit scores greater than 659 (e.g., greater than 675, 700, 800, 900, 1000, 1050, 1100, 1150, 1200, 1250, 1300, 1350, 1400, 1425, or 1440) when fitted to an HMM generated from the amino acid sequences set forth in FIG. 8 are identified in the Sequence Listing of this application. Such polypeptides include, for example, SEQ ID NOs: 2, 4, 6, 7, 8, 10, 12, 14, 15, 17, 18, 19, 20, 21, 22, and 24. In some embodiments, an HMM can be generated based on the amino acid sequences set forth in FIG. 8 that are truncated at about residue 142.

Examples of polypeptides are shown in the sequence listing that have HMM bit scores greater than 406 (e.g., greater than 420, 450, 500, 550, 600, 650, 700, 750, 800, 850, 900, 950, 1000, 1050, 1100, 1150, 1200, 1250, 1300, 1350, 1400, 1420, or 1440) when fitted to an HMM generated from the amino acid sequences set forth in FIG. 9 are identified in the Sequence Listing of this application. Such polypeptides include, for example, SEQ ID NOs: 157, 158, 160, 161, 162, 163, 164, 165, 167, 168, 170, 171, 172, 173, 175, 177, 179, 181, 182, 184, 185, 187, 189, 190, 192, 194, 196, 197, 199, 201, 202, 204, 205, 207, 208, 210, 211, 213, 215, 216, 218, 220, 221, 222, 223, 225, 226, 228, 230, 232, 234, 236, 238, 240, 242, and 244.

Examples of polypeptides are shown in the sequence listing that have HMM bit scores greater than 640 (e.g., greater than 650, 700, 750, 800, 850, 900, 950, 1000, 1050, 1100, 1150, 1200, 1250, 1300, 1350, 1400, 1450, 1500, or 1510), when fitted to an HMM generated from the amino acid sequences set forth in FIG. 10 are identified in the Sequence Listing of this application. Such polypeptides include, for example, SEQ ID NOs: 280, 282, 283, 284, 285, 286, 288, 289, 290, 292, 294, 295, 296, 297, 298, 299, 300, 302, 303, 305, 306, 308, 309, 310, 311, 312, 314, 316, 317, 318, 320, 321, 323, 325, 326, 327, 328, 329, 331, 333, 335, 336, 337, 338, 339, 340, 342, 344, and 346.

Examples of polypeptides are shown in the sequence listing that have HMM bit scores greater than 234 (e.g., greater than 250, 275, 300, 325, 350, 375, 400, 424, 450, 475, 500, 525, 550, 575, 600, 626, 650, 675, 700, or 720) when fitted to an HMM generated from the amino acid sequences set forth in FIG. 11 are identified in the Sequence Listing of this application. Such polypeptides include, for example, SEQ ID NOs: 641, 643, 645, 646, 647, 648, 649, 650, 651, 652, 653, 654, 656, 658, 660, 662, 664, 666, 668, 670, 672, 674, 676, 677, 679, 680, 682, 684, 686, 687, 688, 689, 690, 691, 692, 694, 695, 697, 699, 701, 702, 704, 706, 708, 710, 712, 713, 715, 716, 718, 720, 721, 723, 724, 726, 727, 729, 730, 732, 733, 735, 736, 737, 739, 740, 742, 744, 746, 747, 748, 749, 750, 751, 753, 755, 757, 758, 760, 761, 763, 764, 765, 766, 767, 768, 769, 771, 772, and 823.

Examples of polypeptides are shown in the sequence listing that have HMM bit scores greater than 131 (e.g., greater than 135, 140, 145, 150, 151, 152, 153, or 154) when fitted to an HMM generated from the amino acid sequences set forth in FIG. 12 are identified in the Sequence Listing of this application. Such polypeptides include, for example, SEQ ID NOs: 26, 28, 29, 30, 32, 34, 36, 37, 39, 41, 43, 45, 47, 49, 50, 52, 53, 55, 57, 59, 61, 63, 65, 66, 68, 70, 71, 72, 73, 75, 77, 78, 79, 81, 82, 84, 86, 88, 90, 92, 94, 96, 97, 99, 100, 101, 102, 104, 105, 107, and 109.

D. Percent Identity

In some embodiments, a biomass composition-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one of the amino acid sequences set forth in SEQ ID NOs: 2, 4, 6, 7, 8, 10, 12, 14, 15, 17, 18, 19, 20, 21, 22, 24, 26, 28, 29, 30, 32, 34, 36, 37, 39, 41, 43, 45, 47, 49, 50, 52, 53, 55, 57, 59, 61, 63, 65, 66, 68, 70, 71, 72, 73, 75, 77, 78, 79, 81, 82, 84, 86, 88, 90, 92, 94, 96, 97, 99, 100, 101, 102, 104, 105, 107, 109, 111, 113, 115, 117, 118, 120, 122, 124, 126, 128, 130, 132, 133, 135, 136, 138, 139, 141, 143, 145, 147, 148, 149, 151, 152, 153, 155, 157, 158, 160, 161, 162, 163, 164, 165, 167, 168, 170, 171, 172, 173, 175, 177, 179, 181, 182, 184, 185, 187, 189, 190, 192, 194, 196, 197, 199, 201, 202, 204, 205, 207, 208, 210, 211, 213, 215, 216, 218, 220, 221, 222, 223, 225, 226, 228, 230, 232, 234, 236, 238, 240, 242, 244, 246, 248, 250, 251, 252, 254, 256, 258, 260, 261, 262, 264, 266, 268, 270, 272, 274, 275, 276, 278, 280, 282, 283, 284, 285, 286, 288, 289, 290, 292, 294, 295, 296, 297, 298, 299, 300, 302, 303, 305, 306, 308, 309, 310, 311, 312, 314, 316, 317, 318, 320, 321, 323, 325, 326, 327, 328, 329, 331, 333, 335, 336, 337, 338, 339, 340, 342, 344, 346, 348, 350, 351, 353, 355, 357, 359, 360, 361, 362, 363, 364, 365, 366, 368, 370, 372, 373, 374, 375, 376, 377, 379, 380, 381, 383, 384, 386, 388, 390, 392, 393, 394, 396, 398, 400, 402, 404, 406, 407, 408, 410, 412, 413, 414, 416, 418, 419, 420, 422, 423, 424, 426, 427, 429, 430, 431, 433, 434, 436, 437, 439, 441, 442, 444, 446, 448, 449, 450, 451, 452, 454, 456, 458, 459, 460, 462, 463, 465, 466, 468, 470, 472, 473, 474, 476, 478, 479, 480, 481, 483, 485, 486, 488, 490, 492, 493, 495, 497, 498, 500, 501, 503, 504, 506, 508, 509, 510, 512, 514, 515, 516, 517, 519, 521, 522, 523, 525, 527, 529, 531, 533, 534, 535, 537, 539, 541, 543, 545, 547, 549, 551, 552, 554, 556, 557, 559, 562, 564, 565, 567, 568, 570, 572, 573, 574, 575, 576, 578, 580, 582, 584, 586, 588, 589, 590, 592, 594, 596, 598, 599, 601, 602, 603, 605, 607, 608, 609, 611, 613, 615, 617, 619, 621, 622, 624, 625, 627, 629, 630, 632, 634, 636, 638, 641, 643, 645, 646, 647, 648, 649, 650, 651, 652, 653, 654, 656, 658, 660, 662, 664, 666, 668, 670, 672, 674, 676, 677, 679, 680, 682, 684, 686, 687, 688, 689, 690, 691, 692, 694, 695, 697, 699, 701, 702, 704, 706, 708, 710, 712, 713, 715, 716, 718, 720, 721, 723, 724, 726, 727, 729, 730, 732, 733, 735, 736, 737, 739, 740, 742, 744, 746, 747, 748, 749, 750, 751, 753, 755, 757, 758, 760, 761, 763, 764, 765, 766, 767, 768, 769, 771, 772, 774, 775, 776, 777, 778, 780, 781, 782, 783, 785, 786, 788, 789, 791, 793, 795, 796, 798, 799, 800, 801, 802, 803, 805, 807, 808, 810, 811, 812, 813, 814, 815, 816, 817, 818, 819, 820, 821, and 823. Polypeptides having such a percent sequence identity often have a domain indicative of a biomass composition-modulating polypeptide and/or have an HMM bit score that is greater than 65, as discussed above. Amino acid sequences of biomass composition-modulating polypeptides having at least 80% sequence identity to one of the amino acid sequences set forth in SEQ ID NOs: 2, 4, 6, 7, 8, 10, 12, 14, 15, 17, 18, 19, 20, 21, 22, 24, 26, 28, 29, 30, 32, 34, 36, 37, 39, 41, 43, 45, 47, 49, 50, 52, 53, 55, 57, 59, 61, 63, 65, 66, 68, 70, 71, 72, 73, 75, 77, 78, 79, 81, 82, 84, 86, 88, 90, 92, 94, 96, 97, 99, 100, 101, 102, 104, 105, 107, 109, 111, 113, 115, 117, 118, 120, 122, 124, 126, 128, 130, 132, 133, 135, 136, 138, 139, 141, 143, 145, 147, 148, 149, 151, 152, 153, 155, 157, 158, 160, 161, 162, 163, 164, 165, 167, 168, 170, 171, 172, 173, 175, 177, 179, 181, 182, 184, 185, 187, 189, 190, 192, 194, 196, 197, 199, 201, 202, 204, 205, 207, 208, 210, 211, 213, 215, 216, 218, 220, 221, 222, 223, 225, 226, 228, 230, 232, 234, 236, 238, 240, 242, 244, 246, 248, 250, 251, 252, 254, 256, 258, 260, 261, 262, 264, 266, 268, 270, 272, 274, 275, 276, 278, 280, 282, 283, 284, 285, 286, 288, 289, 290, 292, 294, 295, 296, 297, 298, 299, 300, 302, 303, 305, 306, 308, 309, 310, 311, 312, 314, 316, 317, 318, 320, 321, 323, 325, 326, 327, 328, 329, 331, 333, 335, 336, 337, 338, 339, 340, 342, 344, 346, 348, 350, 351, 353, 355, 357, 359, 360, 361, 362, 363, 364, 365, 366, 368, 370, 372, 373, 374, 375, 376, 377, 379, 380, 381, 383, 384, 386, 388, 390, 392, 393, 394, 396, 398, 400, 402, 404, 406, 407, 408, 410, 412, 413, 414, 416, 418, 419, 420, 422, 423, 424, 426, 427, 429, 430, 431, 433, 434, 436, 437, 439, 441, 442, 444, 446, 448, 449, 450, 451, 452, 454, 456, 458, 459, 460, 462, 463, 465, 466, 468, 470, 472, 473, 474, 476, 478, 479, 480, 481, 483, 485, 486, 488, 490, 492, 493, 495, 497, 498, 500, 501, 503, 504, 506, 508, 509, 510, 512, 514, 515, 516, 517, 519, 521, 522, 523, 525, 527, 529, 531, 533, 534, 535, 537, 539, 541, 543, 545, 547, 549, 551, 552, 554, 556, 557, 559, 562, 564, 565, 567, 568, 570, 572, 573, 574, 575, 576, 578, 580, 582, 584, 586, 588, 589, 590, 592, 594, 596, 598, 599, 601, 602, 603, 605, 607, 608, 609, 611, 613, 615, 617, 619, 621, 622, 624, 625, 627, 629, 630, 632, 634, 636, 638, 641, 643, 645, 646, 647, 648, 649, 650, 651, 652, 653, 654, 656, 658, 660, 662, 664, 666, 668, 670, 672, 674, 676, 677, 679, 680, 682, 684, 686, 687, 688, 689, 690, 691, 692, 694, 695, 697, 699, 701, 702, 704, 706, 708, 710, 712, 713, 715, 716, 718, 720, 721, 723, 724, 726, 727, 729, 730, 732, 733, 735, 736, 737, 739, 740, 742, 744, 746, 747, 748, 749, 750, 751, 753, 755, 757, 758, 760, 761, 763, 764, 765, 766, 767, 768, 769, 771, 772, 774, 775, 776, 777, 778, 780, 781, 782, 783, 785, 786, 788, 789, 791, 793, 795, 796, 798, 799, 800, 801, 802, 803, 805, 807, 808, 810, 811, 812, 813, 814, 815, 816, 817, 818, 819, 820, 821, and 823 are provided in FIGS. 1-12 and in the Sequence Listing.

"Percent sequence identity" refers to the degree of sequence identity between any given reference sequence, e.g., SEQ ID NO: 1, and a candidate biomass composition-modulating sequence. A candidate sequence typically has a length that is from 80 percent to 200 percent of the length of the reference sequence, e.g., 82, 85, 87, 89, 90, 93, 95, 97, 99, 100, 105, 110, 115, 120, 130, 140, 150, 160, 170, 180, 190, or 200 percent of the length of the reference sequence. A percent identity for any candidate nucleic acid or polypeptide relative to a reference nucleic acid or polypeptide can be determined as follows. A reference sequence (e.g., a nucleic acid sequence or an amino acid sequence) is aligned to one or more candidate sequences using the computer program ClustalW (version 1.83, default parameters), which allows alignments of nucleic acid or polypeptide sequences to be carried out across their entire length (global alignment). Chenna et al., *Nucleic Acids Res.*, 31(13):3497-500 (2003).

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site on the World Wide Web (searchlauncher.bcm.tmc.edu/multi-align/multi-align.html) and at the European Bioinformatics Institute site on the World Wide Web (ebi.ac.uk/clustalw).

To determine percent identity of a candidate nucleic acid or amino acid sequence to a reference sequence, the sequences are aligned using ClustalW, the number of identical matches in the alignment is divided by the length of the reference sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

In some cases, a biomass composition-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 483 Amino acid sequences of polypeptides having greater than 45% sequence identity to the polypeptide set forth in SEQ ID NO: 483 are provided in FIG. 1 and in the Sequence Listing.

In some cases, a biomass composition-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 562 Amino acid sequences of polypeptides having greater than 45% sequence identity to the polypeptide set forth in SEQ ID NO: 562 are provided in FIG. 2 and in the Sequence Listing.

In some cases, a biomass composition-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 246 Amino acid sequences of polypeptides having greater than 45% sequence identity to the polypeptide set forth in SEQ ID NO: 246 are provided in FIG. 3 and in the Sequence Listing.

In some cases, a biomass composition-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 111. Amino acid sequences of polypeptides having greater than 45% sequence identity to the polypeptide set forth in SEQ ID NO: 111 are provided in FIG. 4 and in the Sequence Listing.

In some cases, a biomass composition-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 348 Amino acid sequences of polypeptides having greater than 45% sequence identity to the polypeptide set forth in SEQ ID NO: 348 are provided in FIG. 5 and in the Sequence Listing.

In some cases, a biomass composition-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 774 Amino acid sequences of polypeptides having greater than 45% sequence identity to the polypeptide set forth in SEQ ID NO: 774 are provided in FIG. 6 and in the Sequence Listing.

In some cases, a biomass composition-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 416 Amino acid sequences of polypeptides having greater than 45% sequence identity to the polypeptide set forth in SEQ ID NO: 416 are provided in FIG. 7 and in the Sequence Listing.

In some cases, a biomass composition-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 2 Amino acid sequences of polypeptides having greater than 45% sequence identity to the polypeptide set forth in SEQ ID NO: 2 are provided in FIG. 8 and in the Sequence Listing.

In some cases, a biomass composition-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 157 Amino acid sequences of polypeptides having greater than 45% sequence identity to the polypeptide set forth in SEQ ID NO: 157 are provided in FIG. 9 and in the Sequence Listing.

In some cases, a biomass composition-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 280. Amino acid sequences of polypeptides having greater than 45% sequence identity to the polypeptide set forth in SEQ ID NO: 280 are provided in FIG. 10 and in the Sequence Listing.

In some cases, a biomass composition-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 641. Amino acid sequences of polypeptides having greater than 45% sequence identity to the polypeptide set forth in SEQ ID NO: 641 are provided in FIG. 11 and in the Sequence Listing.

In some cases, a biomass composition-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 26. Amino acid sequences of polypeptides having greater than 45% sequence identity to the polypeptide set forth in SEQ ID NO: 26 are provided in FIG. 12 and in the Sequence Listing.

E. Other Sequences

It should be appreciated that a biomass composition-modulating polypeptide can include additional amino acids that are not involved in biomass modulation, and thus such a polypeptide can be longer than would otherwise be the case. For example, a biomass composition-modulating polypeptide can include a purification tag, a chloroplast transit peptide, a mitochondrial transit peptide, an amyloplast peptide, or a leader sequence added to the amino or carboxy terminus. In some embodiments, a biomass composition-modulating polypeptide includes an amino acid sequence that functions as a reporter, e.g., a green fluorescent protein or yellow fluorescent protein.

III. Nucleic Acids

Nucleic acids described herein include nucleic acids that are effective to modulate biomass composition when transcribed in a plant or plant cell. Such nucleic acids include, without limitation, those that encode a biomass composition-modulating polypeptide and those that can be used to inhibit expression of a biomass composition-modulating polypeptide via a nucleic acid based method.

A. Nucleic Acids Encoding Biomass Composition-Modulating Polypeptides

Nucleic acids encoding biomass composition-modulating polypeptides are described herein. Examples of such nucleic acids include SEQ ID NOs: 1, 3, 5, 9, 11, 13, 16, 23, 25, 27, 31, 33, 35, 38, 40, 42, 44, 46, 48, 51, 54, 56, 58, 60, 62, 64, 67, 69, 74, 76, 80, 83, 85, 87, 89, 91, 93, 95, 98, 103, 106, 108, 110, 112, 114, 116, 119, 121, 123, 125, 127, 129, 131, 134, 137, 140, 142, 144, 146, 150, 154, 156, 159, 166, 169, 174, 176, 178, 180, 183, 186, 188, 191, 193, 195, 198, 200, 203, 206, 209, 212, 214, 217, 219, 224, 227, 229, 231, 233, 235, 237, 239, 241, 243, 245, 247, 249, 253, 255, 257, 259, 263, 265, 267, 269, 271, 273, 277, 279, 281, 287, 291, 293, 301, 304, 307, 313, 315, 319, 322, 324, 330, 332, 334, 341, 343, 345, 347, 349, 352, 354, 356, 358, 367, 369, 371, 378, 382, 385, 387, 389, 391, 395, 397, 399, 401, 403, 405, 409, 411, 415, 417, 421, 425, 428, 432, 435, 438, 440, 443, 445, 447, 453, 455, 457, 461, 464, 467, 469, 471, 475, 477, 482, 484, 487, 489, 491, 494, 496, 499, 502, 505, 507, 511, 513, 518, 520, 524, 526, 528, 530, 532, 536, 538, 540, 542, 544, 546, 548, 550, 553, 555, 558, 560, 561, 563, 566, 569, 571, 577, 579, 581, 583, 585, 587, 591, 593, 595, 597, 600, 604, 606, 610, 612, 614, 616, 618, 620, 623, 626, 628, 631, 633, 635, 637, 639, 640, 642, 644, 655, 657, 659, 661, 663, 665, 667, 669, 671, 673, 675, 678, 681, 683, 685, 693, 696, 698, 700, 703, 705, 707, 709, 711, 714, 717, 719, 722, 725, 728, 731, 734, 738, 741, 743, 745, 752, 754, 756, 759, 762, 770, 773, 779, 784, 787, 790, 792, 794, 797, 804, 806, 809, and 822, as described in more detail below. A nucleic acid also can be a fragment that is at least 40% (e.g., at least 45, 50, 55, 60, 65, 70, 75, 80, 85, 90, 95, or 99%) of the length of the full-length nucleic acid set forth in SEQ ID NOs: 1, 3, 5, 9, 11, 13, 16, 23, 25, 27, 31, 33, 35, 38, 40, 42, 44, 46, 48, 51, 54, 56, 58, 60, 62, 64, 67, 69, 74, 76, 80, 83, 85, 87, 89, 91, 93, 95, 98, 103, 106, 108, 110, 112, 114, 116, 119, 121, 123, 125, 127, 129, 131, 134, 137, 140, 142, 144, 146, 150, 154, 156, 159, 166, 169, 174, 176, 178, 180, 183, 186, 188, 191, 193, 195, 198, 200, 203, 206, 209, 212, 214, 217, 219, 224, 227, 229, 231, 233, 235, 237, 239, 241, 243, 245, 247, 249, 253, 255, 257, 259, 263, 265, 267, 269, 271, 273, 277, 279, 281, 287, 291, 293, 301, 304, 307, 313, 315, 319, 322, 324, 330, 332, 334, 341, 343, 345, 347, 349, 352, 354, 356, 358, 367, 369, 371, 378, 382, 385, 387, 389, 391, 395, 397, 399, 401, 403, 405, 409, 411, 415, 417, 421, 425, 428, 432, 435, 438, 440, 443, 445, 447, 453, 455, 457, 461, 464, 467, 469, 471, 475, 477, 482, 484, 487, 489, 491, 494, 496, 499, 502, 505, 507, 511, 513, 518, 520, 524, 526, 528, 530, 532, 536, 538, 540, 542, 544, 546, 548, 550, 553, 555, 558, 560, 561, 563, 566, 569, 571, 577, 579, 581, 583, 585, 587, 591, 593, 595, 597, 600, 604, 606, 610, 612, 614, 616, 618, 620, 623, 626, 628, 631, 633, 635, 637, 639, 640, 642, 644, 655, 657, 659, 661, 663, 665, 667, 669, 671, 673, 675, 678, 681, 683, 685, 693, 696, 698, 700, 703, 705, 707, 709, 711, 714, 717, 719, 722, 725, 728, 731, 734, 738, 741, 743, 745, 752, 754, 756, 759, 762, 770, 773, 779, 784, 787, 790, 792, 794, 797, 804, 806, 809, and 822.

A biomass composition-modulating nucleic acid can comprise the nucleotide sequence set forth in SEQ ID NO: 482. Alternatively, a biomass composition-modulating nucleic acid can be a variant of the nucleic acid having the nucleotide sequence set forth in SEQ ID NO: 482. For example, a biomass composition-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 482.

A biomass composition-modulating nucleic acid can comprise the nucleotide sequence set forth in SEQ ID NO: 561. Alternatively, a biomass composition-modulating nucleic acid can be a variant of the nucleic acid having the nucleotide sequence set forth in SEQ ID NO: 561. For example, a biomass composition-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 561.

A biomass composition-modulating nucleic acid can comprise the nucleotide sequence set forth in SEQ ID NO: 245. Alternatively, a biomass composition-modulating nucleic acid can be a variant of the nucleic acid having the nucleotide sequence set forth in SEQ ID NO: 245. For example, a biomass composition-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 245.

A biomass composition-modulating nucleic acid can comprise the nucleotide sequence set forth in SEQ ID NO: 110. Alternatively, a biomass composition-modulating nucleic acid can be a variant of the nucleic acid having the nucleotide sequence set forth in SEQ ID NO: 110. For example, a biomass composition-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 110.

A biomass composition-modulating nucleic acid can comprise the nucleotide sequence set forth in SEQ ID NO: 347. Alternatively, a biomass composition-modulating nucleic acid can be a variant of the nucleic acid having the nucleotide sequence set forth in SEQ ID NO: 347. For example, a biomass composition-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 347.

A biomass composition-modulating nucleic acid can comprise the nucleotide sequence set forth in SEQ ID NO: 773. Alternatively, a biomass composition-modulating nucleic acid can be a variant of the nucleic acid having the nucleotide sequence set forth in SEQ ID NO: 773. For example, a biomass composition-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 773.

A biomass composition-modulating nucleic acid can comprise the nucleotide sequence set forth in SEQ ID NO: 415. Alternatively, a biomass composition-modulating nucleic acid can be a variant of the nucleic acid having the nucleotide sequence set forth in SEQ ID NO: 415. For example, a biomass composition-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 415.

A biomass composition-modulating nucleic acid can comprise the nucleotide sequence set forth in SEQ ID NO: 1 or a fragment of the nucleotide sequence set forth in SEQ ID NO: 1. For example, a deletion can be made at nucleotide position 657 of SEQ ID NO: 1 such that a truncated protein is encoded (e.g., a truncated protein having about 142 residues). Alternatively, a biomass composition-modulating nucleic acid can be a variant of the nucleic acid having the nucleotide sequence set forth in SEQ ID NO: 1. For example, a biomass composition-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 1. Such variant biomass composition-modulating nucleotide sequences can have a deletion at the nucleotide position corresponding to position 657 of SEQ ID NO: 1 such that a truncated protein is encoded.

A biomass composition-modulating nucleic acid can comprise the nucleotide sequence set forth in SEQ ID NO: 156. Alternatively, a biomass composition-modulating nucleic acid can be a variant of the nucleic acid having the nucleotide sequence set forth in SEQ ID NO: 156. For example, a biomass composition-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 156.

A biomass composition-modulating nucleic acid can comprise the nucleotide sequence set forth in SEQ ID NO: 279. Alternatively, a biomass composition-modulating nucleic acid can be a variant of the nucleic acid having the nucleotide sequence set forth in SEQ ID NO: 279. For example, a biomass composition-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 279.

A biomass composition-modulating nucleic acid can comprise the nucleotide sequence set forth in SEQ ID NO: 640. Alternatively, a biomass composition-modulating nucleic acid can be a variant of the nucleic acid having the nucleotide sequence set forth in SEQ ID NO: 640. For example, a biomass composition-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 640.

A biomass composition-modulating nucleic acid can comprise the nucleotide sequence set forth in SEQ ID NO: 25. Alternatively, a biomass composition-modulating nucleic acid can be a variant of the nucleic acid having the nucleotide sequence set forth in SEQ ID NO: 25. For example, a biomass composition-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 25.

Isolated nucleic acid molecules can be produced by standard techniques. For example, polymerase chain reaction (PCR) techniques can be used to obtain an isolated nucleic acid containing a nucleotide sequence described herein. PCR can be used to amplify specific sequences from DNA as well as RNA, including sequences from total genomic DNA or total cellular RNA. Various PCR methods are described, for example, in *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid. Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring DNA.

B. Use of Nucleic Acids to Modulate Expression of Polypeptides i. Expression of a Biomass Composition-Modulating Polypeptide A nucleic acid encoding one of the biomass composition-modulating polypeptides described herein can be used to express the polypeptide in a plant species of interest, typically by transforming a plant cell with a nucleic acid having the coding sequence for the polypeptide operably linked in sense orientation to one or more regulatory regions. It will be appreciated that because of the degeneracy of the genetic code, a number of nucleic acids can encode a particular biomass composition-modulating polypeptide; i.e., for many amino acids, there is more than one nucleotide triplet that serves as the codon for the amino acid. Thus, codons in the coding sequence for a given biomass composition-modulating polypeptide can be modified such that optimal expression in a particular plant species is obtained, using appropriate codon bias tables for that species.

In some cases, expression of a biomass composition-modulating polypeptide inhibits one or more functions of an endogenous polypeptide. For example, a nucleic acid that encodes a dominant negative polypeptide can be used to inhibit protein function. A dominant negative polypeptide typically is mutated or truncated relative to an endogenous wild type polypeptide, and its presence in a cell inhibits one or more functions of the wild type polypeptide in that cell, i.e., the dominant negative polypeptide is genetically dominant and confers a loss of function. The mechanism by which a dominant negative polypeptide confers such a phenotype can vary but often involves a protein-protein interaction or a protein-DNA interaction. For example, a dominant negative polypeptide can be an enzyme that is truncated relative to a native wild type enzyme, such that the truncated polypeptide retains domains involved in binding a first protein but lacks domains involved in binding a second protein. The truncated polypeptide is thus unable to properly modulate the activity of the second protein. See, e.g., US 2007/0056058. As another example, a point mutation that results in a non-conservative amino acid substitution in a catalytic domain can result in a dominant negative polypeptide. See, e.g., US 2005/032221. As another example, a dominant negative polypeptide can be a transcription factor that is truncated relative to a native wild type transcription factor, such that the truncated polypeptide retains the DNA binding domain(s) but lacks the activation domain(s). Such a truncated polypeptide can inhibit the wild type transcription factor from binding DNA, thereby inhibiting transcription activation.

ii. Inhibition of Expression of a Biomass Composition-Modulating Polypeptide

Polynucleotides and recombinant constructs described herein can be used to inhibit expression of a biomass composition-modulating polypeptide in a plant species of interest. See, e.g., Matzke and Birchler, *Nature Reviews Genetics* 6:24-35 (2005); Akashi et al., *Nature Reviews Mol. Cell Biology* 6:413-422 (2005); Mittal, *Nature Reviews Genetics* 5:355-365 (2004); and *Nature Reviews RNA interference collection*, October 2005 on the World Wide Web at nature.com/reviews/focus/mai. A number of nucleic acid based methods, including antisense RNA, ribozyme directed RNA cleavage, post-transcriptional gene silencing (PTGS), e.g., RNA interference (RNAi), and transcriptional gene silencing (TGS) are known to inhibit gene expression in plants. Suitable polynucleotides include full-length nucleic acids encoding biomass composition-modulating polypeptides or fragments of such full-length nucleic acids. In some embodiments, a complement of the full-length nucleic acid or a fragment thereof can be used. Typically, a fragment is at least 10 nucleotides, e.g., at least 12, 13, 14, 15, 16, 17, 18, 19, 20, 21, 22, 23, 24, 25, 26, 27, 30, 35, 40, 50, 80, 100, 200, 500 nucleotides or more. Generally, higher homology can be used to compensate for the use of a shorter sequence.

Antisense technology is one well-known method. In this method, a nucleic acid of a gene to be repressed is cloned and operably linked to a regulatory region and a transcription termination sequence so that the antisense strand of RNA is transcribed. The recombinant construct is then transformed into plants, as described herein, and the antisense strand of RNA is produced. The nucleic acid need not be the entire sequence of the gene to be repressed, but typically will be substantially complementary to at least a portion of the sense strand of the gene to be repressed.

In another method, a nucleic acid can be transcribed into a ribozyme, or catalytic RNA, that affects expression of an mRNA. See, U.S. Pat. No. 6,423,885. Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman et al., *Proc. Natl. Acad. Sci. USA*, 92(13):6175-6179 (1995); de Feyter and Gaudron, Methods in Molecular Biology, Vol. 74, Chapter 43, "Expressing Ribozymes in Plants", Edited by Turner, P. C., Humana Press Inc., Totowa, N.J. RNA endoribonucleases which have been described, such as the one that occurs naturally in *Tetrahymena thermophila*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence or a fragment thereof of a biomass composition-modulating polypeptide, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises a sequence that is similar or identical to the antisense strand or a fragment thereof of the coding sequence of the biomass composition-modulating polypeptide, and can have a length that is shorter, the same as, or longer than the corresponding length of the sense sequence. In some cases, one strand of the stem portion of a double stranded RNA comprises a sequence that is similar or identical to the 3' or 5' untranslated region, or a fragment thereof, of an mRNA encoding a biomass composition-modulating polypeptide, and the other strand of the stem portion of the double stranded RNA comprises a sequence that is similar or identical to the sequence that is complementary to the 3' or 5' untranslated region, respectively, or a fragment thereof, of the mRNA encoding the biomass composition-modulating polypeptide. In other embodiments, one strand of the stem portion of a double stranded RNA comprises a sequence that is similar or identical to the sequence of an intron, or a fragment thereof, in the pre-mRNA encoding a biomass composition-modulating polypeptide, and the other strand of the stem portion comprises a sequence that is similar or identical to the sequence that is complementary to the sequence of the intron, or a fragment thereof, in the pre-mRNA.

The loop portion of a double stranded RNA can be from 3 nucleotides to 5,000 nucleotides, e.g., from 3 nucleotides to 25 nucleotides, from 15 nucleotides to 1,000 nucleotides, from 20 nucleotides to 500 nucleotides, or from 25 nucleotides to 200 nucleotides. The loop portion of the RNA can include an intron or a fragment thereof. A double stranded RNA can have zero, one, two, three, four, five, six, seven, eight, nine, ten, or more stem-loop structures.

A construct including a sequence that is operably linked to a regulatory region and a transcription termination sequence, and that is transcribed into an RNA that can form a double stranded RNA, is transformed into plants as described herein. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330, and 20030180945.

Constructs containing regulatory regions operably linked to nucleic acid molecules in sense orientation can also be used to inhibit the expression of a gene. The transcription product can be similar or identical to the sense coding sequence, or a fragment thereof, of a biomass composition-modulating polypeptide. The transcription product also can be unpolyadenylated, lack a 5' cap structure, or contain an unspliceable intron. Methods of inhibiting gene expression using a full-length cDNA as well as a partial cDNA sequence are known in the art. See, e.g., U.S. Pat. No. 5,231,020.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA, or an intron in a pre-mRNA encoding a biomass composition-modulating polypeptide, or a fragment of such sequences. In some embodiments, the sense or antisense sequence is identical or complementary to a sequence of the regulatory region that drives transcription of the gene encoding a biomass composition-modulating polypeptide. In each case, the sense sequence is the sequence that is complementary to the antisense sequence.

The sense and antisense sequences can be a length greater than about 10 nucleotides (e.g., 12, 13, 14, 15, 16, 17, 18, 19, 20, 21, 22, 23, 24, 25, 26, 27, 28, 29, 30, or more nucleotides). For example, an antisense sequence can be 21 or 22 nucleotides in length. Typically, the sense and antisense sequences range in length from about 15 nucleotides to about 30 nucleotides, e.g., from about 18 nucleotides to about 28 nucleotides, or from about 21 nucleotides to about 25 nucleotides.

In some embodiments, an antisense sequence is a sequence complementary to an mRNA sequence, or a fragment thereof, encoding a biomass composition-modulating polypeptide described herein. The sense sequence complementary to the antisense sequence can be a sequence present within the mRNA of the biomass composition-modulating polypeptide. Typically, sense and antisense sequences are designed to correspond to a 15-30 nucleotide sequence of a target mRNA such that the level of that target mRNA is reduced.

In some embodiments, a construct containing a nucleic acid having at least one strand that is a template for more than one sense sequence (e.g., 2, 3, 4, 5, 6, 7, 8, 9, 10 or more sense sequences) can be used to inhibit the expression of a gene. Likewise, a construct containing a nucleic acid having at least one strand that is a template for more than one antisense sequence (e.g., 2, 3, 4, 5, 6, 7, 8, 9, 10 or more antisense sequences) can be used to inhibit the expression of a gene. For example, a construct can contain a nucleic acid having at least one strand that is a template for two sense sequences and two antisense sequences. The multiple sense sequences can be identical or different, and the multiple antisense sequences can be identical or different. For example, a construct can have a nucleic acid having one strand that is a template for two identical sense sequences and two identical antisense sequences that are complementary to the two identical sense sequences. Alternatively, an isolated nucleic acid can have one strand that is a template for (1) two identical sense sequences 20 nucleotides in length, (2) one antisense sequence that is complementary to the two identical sense sequences 20 nucleotides in length, (3) a sense sequence 30 nucleotides in length, and (4) three identical antisense sequences that are complementary to the sense sequence 30 nucleotides in length. The constructs provided herein can be designed to have a suitable arrangement of sense and antisense sequences. For example, two identical sense sequences can be followed by two identical antisense sequences or can be positioned between two identical antisense sequences.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand, and one from the bottom strand. See, for example, Yan et al., *Plant Physiol.*, 141: 1508-1518 (2006). The two regulatory regions can be the same or different. The two transcripts can form double-stranded RNA molecules that induce degradation of the target RNA. In some cases, a nucleic acid can be positioned within a T-DNA or plant-derived transfer DNA (P-DNA) such that the left and right T-DNA border sequences or the left and right border-like sequences of the P-DNA flank, or are on either side of, the nucleic acid. See, US 2006/ 0265788. The nucleic acid sequence between the two regulatory regions can be from about 15 to about 300 nucleotides in length. In some embodiments, the nucleic acid sequence between the two regulatory regions is from about 15 to about 200 nucleotides in length, from about 15 to about 100 nucleotides in length, from about 15 to about 50 nucleotides in length, from about 18 to about 50 nucleotides in length, from about 18 to about 40 nucleotides in length, from about 18 to about 30 nucleotides in length, or from about 18 to about 25 nucleotides in length.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller, *Antisense Nucleic Acid Drug Dev.*, 7:187-195 (1997); Hyrup et al., *Bioorgan. Med. Chem.*, 4:5-23 (1996). In addition, the deoxyphosphate backbone can be replaced with, for example, a phosphorothioate or phosphorodithioate backbone, a phosphoroamidite, or an alkyl phosphotriester backbone.

C. Constructs/Vectors

Recombinant constructs provided herein can be used to transform plants or plant cells in order to modulate biomass levels. A recombinant nucleic acid construct can comprise a nucleic acid encoding a biomass composition-modulating polypeptide as described herein, operably linked to a regulatory region suitable for expressing the biomass composition-modulating polypeptide in the plant or cell. Thus, a nucleic acid can comprise a coding sequence that encodes a biomass composition-modulating polypeptides as set forth in SEQ ID NOs: 2, 4, 6, 7, 8, 10, 12, 14, 15, 17, 18, 19, 20, 21, 22, 24, 26, 28, 29, 30, 32, 34, 36, 37, 39, 41, 43, 45, 47, 49, 50, 52, 53, 55, 57, 59, 61, 63, 65, 66, 68, 70, 71, 72, 73, 75, 77, 78, 79, 81, 82, 84, 86, 88, 90, 92, 94, 96, 97, 99, 100, 101, 102, 104, 105, 107, 109, 111, 113, 115, 117, 118, 120, 122, 124, 126, 128, 130, 132, 133, 135, 136, 138, 139, 141, 143, 145, 147, 148, 149, 151, 152, 153, 155, 157, 158, 160, 161, 162, 163, 164, 165, 167, 168, 170, 171, 172, 173, 175, 177, 179, 181, 182, 184, 185, 187, 189, 190, 192, 194, 196, 197, 199, 201, 202, 204, 205, 207, 208, 210, 211, 213, 215, 216, 218, 220, 221, 222, 223, 225, 226, 228, 230, 232, 234, 236, 238, 240, 242, 244, 246, 248, 250, 251, 252, 254, 256, 258, 260, 261, 262, 264, 266, 268, 270, 272, 274, 275, 276, 278, 280, 282, 283, 284, 285, 286, 288, 289, 290, 292, 294, 295, 296, 297, 298, 299, 300, 302, 303, 305, 306, 308, 309, 310, 311, 312, 314, 316, 317, 318, 320, 321, 323, 325, 326, 327, 328, 329, 331, 333, 335, 336, 337, 338, 339, 340, 342, 344, 346, 348, 350, 351, 353, 355, 357, 359, 360, 361, 362, 363, 364, 365, 366, 368, 370, 372, 373, 374, 375, 376, 377, 379, 380, 381, 383, 384, 386, 388, 390, 392, 393, 394, 396, 398, 400, 402, 404, 406, 407, 408, 410, 412, 413, 414, 416, 418, 419, 420, 422, 423, 424, 426, 427, 429, 430, 431, 433, 434, 436, 437, 439, 441, 442, 444, 446, 448, 449, 450, 451, 452, 454, 456, 458, 459, 460, 462, 463, 465, 466, 468, 470, 472, 473, 474, 476, 478, 479, 480, 481, 483, 485, 486, 488, 490, 492, 493, 495, 497, 498, 500, 501, 503, 504, 506, 508, 509, 510, 512, 514, 515, 516, 517, 519, 521, 522, 523, 525, 527, 529, 531, 533, 534, 535, 537, 539, 541, 543, 545, 547, 549, 551, 552, 554, 556, 557, 559, 562, 564, 565, 567, 568, 570, 572, 573, 574, 575, 576, 578, 580, 582, 584, 586, 588, 589, 590, 592, 594, 596, 598, 599, 601, 602, 603, 605, 607, 608, 609, 611, 613, 615, 617, 619, 621, 622, 624, 625, 627, 629, 630, 632, 634, 636, 638, 641, 643, 645, 646, 647, 648, 649, 650, 651, 652, 653, 654, 656, 658, 660, 662, 664, 666, 668, 670, 672, 674, 676, 677, 679, 680, 682, 684, 686, 687, 688, 689, 690, 691, 692, 694, 695, 697, 699, 701, 702, 704, 706, 708, 710, 712, 713, 715, 716, 718, 720, 721, 723, 724, 726, 727, 729, 730, 732, 733, 735, 736, 737, 739, 740, 742, 744, 746, 747, 748, 749, 750, 751, 753, 755, 757, 758, 760, 761, 763, 764, 765, 766, 767, 768, 769, 771, 772, 774, 775, 776, 777, 778, 780, 781, 782, 783, 785, 786, 788, 789, 791, 793, 795, 796, 798, 799, 800, 801, 802, 803, 805, 807, 808, 810, 811, 812, 813, 814, 815, 816, 817, 818, 819, 820, 821, and 823. Examples of nucleic acids encoding biomass composition-modulating polypeptides are set forth in SEQ ID NOs: 1, 3, 5, 9, 11, 13, 16, 23, 25, 27, 31, 33, 35, 38, 40, 42, 44, 46, 48, 51, 54, 56, 58, 60, 62, 64, 67, 69, 74, 76, 80, 83, 85, 87, 89, 91, 93, 95, 98, 103, 106, 108, 110, 112, 114, 116, 119, 121, 123, 125, 127, 129, 131, 134, 137, 140, 142, 144, 146, 150, 154, 156, 159, 166, 169, 174, 176, 178, 180, 183, 186, 188, 191, 193, 195, 198, 200, 203, 206, 209, 212, 214, 217, 219, 224, 227, 229, 231, 233, 235, 237, 239, 241, 243, 245, 247, 249, 253, 255, 257, 259, 263, 265, 267, 269, 271, 273, 277, 279, 281, 287, 291, 293, 301, 304, 307, 313, 315, 319, 322, 324, 330, 332, 334, 341, 343, 345, 347, 349, 352, 354, 356, 358, 367, 369, 371, 378, 382, 385, 387, 389, 391, 395, 397, 399, 401, 403, 405, 409, 411, 415, 417, 421, 425, 428, 432, 435, 438, 440, 443, 445, 447, 453, 455, 457, 461, 464, 467, 469, 471, 475, 477, 482, 484, 487, 489, 491, 494, 496, 499, 502, 505, 507, 511, 513, 518, 520, 524, 526, 528, 530, 532, 536, 538, 540, 542, 544, 546, 548, 550, 553, 555, 558, 560, 561, 563, 566, 569, 571, 577, 579, 581, 583, 585, 587, 591, 593, 595, 597, 600, 604, 606, 610, 612, 614, 616, 618, 620, 623, 626, 628, 631, 633, 635, 637, 639, 640, 642, 644, 655, 657, 659, 661, 663, 665, 667, 669, 671, 673, 675, 678, 681, 683, 685, 693, 696, 698, 700, 703, 705, 707, 709, 711, 714, 717, 719, 722, 725, 728, 731, 734, 738, 741, 743, 745, 752, 754, 756, 759, 762, 770, 773, 779, 784, 787, 790, 792, 794, 797, 804, 806, 809, and 822, or in the Sequence Listing. The biomass composition-modulating polypeptide encoded by a recombinant nucleic acid can be a native biomass composition-modulating polypeptide, or can be heterologous to the cell. In some cases, the recombinant construct contains a nucleic acid that inhibits expression of a biomass composition-modulating polypeptide, operably linked to a regulatory region. Examples of suitable regulatory regions are described in the section entitled "Regulatory Regions."

Vectors containing recombinant nucleic acid constructs such as those described herein also are provided. Suitable vector backbones include, for example, those routinely used in the art such as plasmids, viruses, artificial chromosomes, BACs, YACs, or PACs. Suitable expression vectors include, without limitation, plasmids and viral vectors derived from, for example, bacteriophage, baculoviruses, and retroviruses. Numerous vectors and expression systems are commercially available from such corporations as Novagen® (Madison, Wis.), Clontech® (Palo Alto, Calif.), Stratagene® (La Jolla, Calif.), and Invitrogen/Life Technologies® (Carlsbad, Calif.).

The vectors provided herein also can include, for example, origins of replication, scaffold attachment regions (SARs), and/or markers. A marker gene can confer a selectable phenotype on a plant cell. For example, a marker can confer biocide resistance, such as resistance to an antibiotic (e.g., kanamycin, G418, bleomycin, or hygromycin), or an herbicide (e.g., glyphosate, chlorsulfuron or phosphinothricin). In addition, an expression vector can include a tag sequence designed to facilitate manipulation or detection (e.g., purification or localization) of the expressed polypeptide. Tag sequences, such as luciferase, β-glucuronidase (GUS), green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

D. Regulatory Regions

The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a nucleic acid can be modulated in a similar manner.

Some suitable regulatory regions initiate transcription only, or predominantly, in certain cell types. Methods for identifying and characterizing regulatory regions in plant genomic DNA are known, including, for example, those described in the following references: Jordano et al., *Plant Cell*, 1:855-866 (1989); Bustos et al., *Plant Cell*, 1:839-854 (1989); Green et al., *EMBO J.*, 7:4035-4044 (1988); Meier et al., *Plant Cell*, 3:309-316 (1991); and Zhang et al., *Plant Physiology*, 110:1069-1079 (1996).

Examples of various classes of regulatory regions are described below. Some of the regulatory regions indicated below as well as additional regulatory regions are described in more detail in U.S. patent application Ser. Nos. 60/505,689; 60/518,075; 60/544,771; 60/558,869; 60/583,691; 60/619,181; 60/637,140; 60/757,544; 60/776,307; 10/957,569; 11/058,689; 11/172,703; 11/208,308; 11/274,890; 60/583,609; 60/612,891; 11/097,589; 11/233,726; 11/408,791; 11/414,142; 10/950,321; 11/360,017; PCT/US05/011105; PCT/US05/23639; PCT/US05/034308; PCT/US05/034343; and PCT/US06/038236; PCT/US06/040572; PCT/US07/62762; PCT/US2009/032485; and PCT/US2009/038792.

For example, the sequences of regulatory regions p326, YP0144, YP0190, p13879, YP0050, p32449, 21876, YP0158, YP0214, YP0380, PT0848, PT0633, YP0128, YP0275, PT0660, PT0683, PT0758, PT0613, PT0672, PT0688, PT0837, YP0092, PT0676, PT0708, YP0396, YP0007, YP0111, YP0103, YP0028, YP0121, YP0008, YP0039, YP0115, YP0119, YP0120, YP0374, YP0101, YP0102, YP0110, YP0117, YP0137, YP0285, YP0212, YP0097, YP0107, YP0088, YP0143, YP0156, PT0650, PT0695, PT0723, PT0838, PT0879, PT0740, PT0535, PT0668, PT0886, PT0585, YP0381, YP0337, PT0710, YP0356, YP0385, YP0384, YP0286, YP0377, PD1367, PT0863, PT0829, PT0665, PT0678, YP0086, YP0188, YP0263, PT0743 and YP0096 are set forth in the sequence listing of PCT/US06/040572; the sequence of regulatory region PT0625 is set forth in the sequence listing of PCT/US05/034343; the sequences of regulatory regions PT0623, YP0388, YP0087, YP0093, YP0108, YP0022 and YP0080 are set forth in the sequence listing of U.S. patent application Ser. No. 11/172,703; the sequence of regulatory region PRO924 is set forth in the sequence listing of PCT/US07/62762; and the sequences of regulatory regions p530c10, pOsFIE2-2, pOsMEA, pOsYp102, and pOsYp285 are set forth in the sequence listing of PCT/US06/038236.

It will be appreciated that a regulatory region may meet criteria for one classification based on its activity in one plant species, and yet meet criteria for a different classification based on its activity in another plant species.

i. Broadly Expressing Promoters

A promoter can be said to be "broadly expressing" when it promotes transcription in many, but not necessarily all, plant tissues. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in the nucleic acid constructs provided herein include the p326, YP0144, YP0190, p13879, YP0050, p32449, 21876, YP0158, YP0214, YP0380, PT0848, and PT0633 promoters. Additional examples include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter, and ubiquitin promoters such as the maize ubiquitin-1 promoter. In some cases, the CaMV 35S promoter is excluded from the category of broadly expressing promoters.

ii. Root Promoters

Root-active promoters confer transcription in root tissue, e.g., root endodermis, root epidermis, or root vascular tissues. In some embodiments, root-active promoters are root-preferential promoters, i.e., confer transcription only or predominantly in root tissue. Root-preferential promoters include the YP0128, YP0275, PT0625, PT0660, PT0683, and PT0758 promoters. Other root-preferential promoters include the PT0613, PT0672, PT0688, and PT0837 promoters, which drive transcription primarily in root tissue and to a lesser extent in ovules and/or seeds. Other examples of root-preferential promoters include the root-specific subdomains of the CaMV 35S promoter (Lam et al., *Proc. Natl. Acad. Sci. USA*, 86:7890-7894 (1989)), root cell specific promoters reported by Conkling et al., *Plant Physiol.*, 93:1203-1211 (1990), and the tobacco RD2 promoter.

iii. Maturing Endosperm Promoters

In some embodiments, promoters that drive transcription in maturing endosperm can be useful. Transcription from a maturing endosperm promoter typically begins after fertilization and occurs primarily in endosperm tissue during seed development and is typically highest during the cellularization phase. Most suitable are promoters that are active predominantly in maturing endosperm, although promoters that are also active in other tissues can sometimes be used. Non-limiting examples of maturing endosperm promoters that can be included in the nucleic acid constructs provided herein include the napin promoter, the Arcelin-5 promoter, the phaseolin promoter (Bustos et al., *Plant Cell*, 1(9):839-853 (1989)), the soybean trypsin inhibitor promoter (Riggs et al., *Plant Cell*, 1(6):609-621 (1989)), the ACP promoter (Baerson et al., *Plant Mol. Biol.*, 22(2):255-267 (1993)), the stearoyl-ACP desaturase promoter (Slocombe et al., *Plant Physiol.*, 104(4):167-176 (1994)), the soybean a' subunit of β-conglycinin promoter (Chen et al., *Proc. Natl. Acad. Sci. USA*, 83:8560-8564 (1986)), the oleosin promoter (Hong et al., *Plant Mol. Biol.*, 34(3):549-555 (1997)), and zein promoters, such as the 15 kD zein promoter, the 16 kD zein promoter, 19 kD zein promoter, 22 kD zein promoter and 27 kD zein promoter. Also suitable are the Osgt-1 promoter from the rice glutelin-1 gene (Zheng et al., *Mol. Cell Biol.*, 13:5829-5842 (1993)), the beta-amylase promoter, and the barley hordein promoter. Other maturing endosperm promoters include the YP0092, PT0676, and PT0708 promoters.

iv. Ovary Tissue Promoters

Promoters that are active in ovary tissues such as the ovule wall and mesocarp can also be useful, e.g., a polygalacturonidase promoter, the banana TRX promoter, the melon actin promoter, YP0396, and PT0623. Examples of promoters that are active primarily in ovules include YP0007, YP0111, YP0092, YP0103, YP0028, YP0121, YP0008, YP0039, YP0115, YP0119, YP0120, and YP0374.

v. Embryo Sac/Early Endosperm Promoters

To achieve expression in embryo sac/early endosperm, regulatory regions can be used that are active in polar nuclei and/or the central cell, or in precursors to polar nuclei, but not in egg cells or precursors to egg cells. Most suitable are promoters that drive expression only or predominantly in polar nuclei or precursors thereto and/or the central cell. A pattern of transcription that extends from polar nuclei into early endosperm development can also be found with embryo sac/early endosperm-preferential promoters, although transcription typically decreases significantly in later endosperm development during and after the cellularization phase. Expression in the zygote or developing embryo typically is not present with embryo sac/early endosperm promoters.

Promoters that may be suitable include those derived from the following genes: *Arabidopsis* viviparous-1 (see, GenBank No. U93215); *Arabidopsis* atmycl (see, Urao, *Plant Mol. Biol.*, 32:571-57 (1996); Conceicao, *Plant*, 5:493-505 (1994)); *Arabidopsis* FIE (GenBank No. AF129516); *Arabidopsis* MEA; *Arabidopsis* FIS2 (GenBank No. AF096096); and FIE 1.1 (U.S. Pat. No. 6,906,244). Other promoters that may be suitable include those derived from the following genes: maize MAC1 (see, Sheridan, *Genetics*, 142:1009-1020 (1996)); maize Cat3 (see, GenBank No. L05934; Abler, *Plant Mol. Biol.*, 22:10131-1038 (1993)). Other promoters include the following *Arabidopsis* promoters: YP0039, YP0101, YP0102, YP0110, YP0117, YP0119, YP0137, DME, YP0285, and YP0212. Other promoters that may be useful include the following rice promoters: p530c10, pOsFIE2-2, pOsMEA, pOsYp102, and pOsYp285.

vi. Embryo Promoters

Regulatory regions that preferentially drive transcription in zygotic cells following fertilization can provide embryo-preferential expression. Most suitable are promoters that preferentially drive transcription in early stage embryos prior to the heart stage, but expression in late stage and maturing embryos is also suitable. Embryo-preferential promoters include the barley lipid transfer protein (Ltpl) promoter (*Plant Cell Rep* 20:647-654 (2001)), YP0097, YP0107, YP0088, YP0143, YP0156, PT0650, PT0695, PT0723, PT0838, PT0879, and PT0740.

vii. Photosynthetic Tissue Promoters

Promoters active in photosynthetic tissue confer transcription in green tissues such as leaves and stems. Most suitable are promoters that drive expression only or predominantly in such tissues. Examples of such promoters include the ribulose-1,5-bisphosphate carboxylase (RbcS) promoters such as the RbcS promoter from eastern larch (*Larix laricina*), the pine cab6 promoter (Yamamoto et al., *Plant Cell Physiol.*, 35:773-778 (1994)), the Cab-1 promoter from wheat (Fejes et al., *Plant Mol. Biol.*, 15:921-932 (1990)), the CAB-1 promoter from spinach (Lubberstedt et al., *Plant Physiol.*, 104:997-1006 (1994)), the cab1R promoter from rice (Luan et al., *Plant Cell*, 4:971-981 (1992)), the pyruvate orthophosphate dikinase (PPDK) promoter from corn (Matsuoka et al., *Proc. Natl. Acad. Sci. USA*, 90:9586-9590 (1993)), the tobacco Lhcb1*2 promoter (Cerdan et al., *Plant Mol. Biol.*, 33:245-255 (1997)), the *Arabidopsis thaliana* SUC2 sucrose-H+ symporter promoter (Truernit et al., *Planta*, 196:564-570 (1995)), and thylakoid membrane protein promoters from spinach (psaD, psaF, psaE, PC, FNR, atpC, atpD, cab, rbcS). Other photosynthetic tissue promoters include PT0535, PT0668, PT0886, YP0144, YP0380 and PT0585.

viii. Vascular Tissue Promoters

Examples of promoters that have high or preferential activity in vascular bundles include YP0087, YP0093, YP0108, YP0022, and YP0080. Other vascular tissue-preferential promoters include the glycine-rich cell wall protein GRP 1.8 promoter (Keller and Baumgartner, *Plant Cell*, 3(10):1051-1061 (1991)), the Commelina yellow mottle virus (CoYMV) promoter (Medberry et al., *Plant Cell*, 4(2):185-192 (1992)), and the rice tungro bacilliform virus (RTBV) promoter (Dai et al., *Proc. Natl. Acad. Sci. USA*, 101(2):687-692 (2004)).

ix. Inducible Promoters

Inducible promoters confer transcription in response to external stimuli such as chemical agents or environmental stimuli. For example, inducible promoters can confer transcription in response to hormones such as giberellic acid or ethylene, or in response to light or drought. Examples of drought-inducible promoters include YP0380, PT0848, YP0381, YP0337, PT0633, YP0374, PT0710, YP0356, YP0385, YP0396, YP0388, YP0384, PT0688, YP0286, YP0377, PD1367, and PD0901. Examples of nitrogen-inducible promoters include PT0863, PT0829, PT0665, and PT0886. Examples of shade-inducible promoters include PRO924 and PT0678. An example of a promoter induced by salt is rd29A (Kasuga et al. (1999) Nature Biotech 17: 287-291).

x. Basal Promoters

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

xi. Stem Promoters

A stem promoter may be specific to one or more stem tissues or specific to stem and other plant parts. Stem promoters may have high or preferential activity in, for example, epidermis and cortex, vascular cambium, procambium, or xylem. Examples of stem promoters include YP0018 which is disclosed in US20060015970 and CryIA (b) and CryIA(c) (Braga et al. 2003, Journal of New Seeds 5:209-221).

xii. Other Promoters

Other classes of promoters include, but are not limited to, shoot-preferential, callus-preferential, trichome cell-preferential, guard cell-preferential such as PT0678, tuber-preferential, parenchyma cell-preferential, and senescence-preferential promoters. In some embodiments, a promoter may preferentially drive expression in reproductive tissues (e.g., PO2916 promoter, SEQ ID NO:31 in 61/364,903). Promoters designated YP0086, YP0188, YP0263, PT0758, PT0743, PT0829, YP0119, and YP0096, as described in the above-referenced patent applications, may also be useful.

xiii. Other Regulatory Regions

A 5' untranslated region (UTR) can be included in nucleic acid constructs described herein. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a recombinant polynucleotide, e.g., introns, enhancers, upstream activation regions, transcription terminators, and inducible elements. Thus, for example, more than one regulatory region can be operably linked to the sequence of a polynucleotide encoding a biomass composition-modulating polypeptide.

Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

IV. Transgenic Plants and Plant Cells

A. Transformation

The invention also features transgenic plant cells and plants comprising at least one recombinant nucleic acid construct described herein. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Transgenic plant cells used in methods described herein can constitute part or all of a whole plant. Such plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques. As used herein, a transgenic plant also refers to progeny of an initial transgenic plant provided the progeny inherits the transgene. Seeds produced by a transgenic plant can be grown and then selfed (or outcrossed and selfed) to obtain seeds homozygous for the nucleic acid construct.

Transgenic plants can be grown in suspension culture, or tissue or organ culture. For the purposes of this invention, solid and/or liquid tissue culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium. A solid medium can be, for example, Murashige and Skoog (MS) medium containing agar and a suitable concentration of an auxin, e.g., 2,4-dichlorophenoxyacetic acid (2,4-D), and a suitable concentration of a cytokinin, e.g., kinetin.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous biomass composition-modulating polypeptide whose expression has not previously been confirmed in particular recipient cells.

Techniques for introducing nucleic acids into monocotyledonous and dicotyledonous plants are known in the art, and include, without limitation, *Agrobacterium*-mediated transformation, viral vector-mediated transformation, electroporation and particle gun transformation, e.g., U.S. Pat. Nos. 5,538,880; 5,204,253; 6,329,571 and 6,013,863. If a cell or cultured tissue is used as the recipient tissue for transformation, plants can be regenerated from transformed cultures if desired, by techniques known to those skilled in the art.

B. Screening/Selection

A population of transgenic plants can be screened and/or selected for those members of the population that have a trait or phenotype conferred by expression of the transgene. For example, a population of progeny of a single transformation event can be screened for those plants having a desired level of expression of a biomass composition-modulating polypeptide or nucleic acid. Physical and biochemical methods can be used to identify expression levels. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known. As an alternative, a population of plants comprising independent transformation events can be screened for those plants having a desired trait, such as a modulated level of biomass. Selection and/or screening can be carried out over one or more generations, and/or in more than one geographic location. In some cases, transgenic plants can be grown and selected under conditions which induce a desired phenotype or are otherwise necessary to produce a desired phenotype in a transgenic plant. In addition, selection and/or screening can be applied during a particular developmental stage in which the phenotype is expected to be exhibited by the plant. Selection and/or screening can be carried out to choose those transgenic plants having a statistically significant difference in a biomass level relative to a control plant that lacks the transgene. Selected or screened transgenic plants have an altered phenotype as compared to a corresponding control plant, as described in the "Transgenic Plant Phenotypes" section herein.

C. Plant Species

The polynucleotides and vectors described herein can be used to transform a number of monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Suitable species may include members of the genus *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis,* and *Zea.*

Suitable species include *Panicum* spp., *Sorghum* spp., *Miscanthus* spp., *Saccharum* spp., *Erianthus* spp., *Populus* spp., *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cordgrass), *Medicago sativa* (alfalfa), *Arundo donax* (giant reed), *Secale cereale* (rye), *Salix* spp. (willow), *Eucalyptus* spp. (eucalyptus), Triticosecale (triticum—wheat×rye) and bamboo.

Suitable species also include *Helianthus annuus* (sunflower), *Carthamus tinctorius* (safflower), *Jatropha curcas* (jatropha), *Ricinus communis* (castor), *Elaeis guineensis* (palm), *Linum usitatissimum* (flax), and *Brassica juncea.*

Suitable species also include *Beta vulgaris* (sugarbeet), and *Manihot esculenta* (cassava)

Suitable species also include *Lycopersicon esculentum* (tomato), *Lactuca sativa* (lettuce), *Musa paradisiaca* (banana), *Solanum tuberosum* (potato), *Brassica oleracea* (broccoli, cauliflower, Brussels sprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum annum* (hot & sweet pepper), *Allium cepa* (onion), *Cucumis melo* (melon),

*Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), and *Solanum melongena* (eggplant).

Suitable species also include *Papaver somniferum* (opium poppy), *Papaver orientale*, *Taxus baccata*, *Taxus brevifolia*, *Artemisia annua*, *Cannabis sativa*, *Camptotheca acuminate*, *Catharanthus roseus*, *Vinca rosea*, *Cinchona officinalis*, *Colchicum autumnale*, *Veratrum californica*, *Digitalis lanata*, *Digitalis purpurea*, *Dioscorea* spp., *Andrographis paniculata*, *Atropa belladonna*, *Datura stomonium*, *Berberis* spp., *Cephalotaxus* spp., *Ephedra sinica*, *Ephedra* spp., *Erythroxylum coca*, *Galanthus wornorii*, *Scopolia* spp., *Lycopodium serratum* (*Huperzia serrata*), *Lycopodium* spp., *Rauwolfia serpentina*, *Rauwolfia* spp., *Sanguinaria canadensis*, *Hyoscyamus* spp., *Calendula officinalis*, *Chrysanthemum parthenium*, *Coleus forskohlii*, and *Tanacetum parthenium*.

Suitable species also include *Parthenium argentatum* (guayule), *Hevea* spp. (rubber), *Mentha spicata* (mint), *Mentha piperita* (mint), *Bixa orellana*, and *Alstroemeria* spp.

Suitable species also include *Rosa* spp. (rose), *Dianthus caryophyllus* (carnation), *Petunia* spp. (petunia) and *Poinsettia pulcherrima* (poinsettia).

Suitable species also include *Nicotiana tabacum* (tobacco), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple), *Hordeum vulgare* (barley), *Poa pratensis* (bluegrass), *Lolium* spp. (ryegrass) and *Phleum pratense* (timothy).

In some embodiments, a suitable species can be a wild, weedy, or cultivated *Pennisetum* species such as, but not limited to, *Pennisetum alopecuroides*, *Pennisetum arnhemicum*, *Pennisetum caffrum*, *Pennisetum clandestinum*, *Pennisetum divisum*, *Pennisetum glaucum*, *Pennisetum latifolium*, *Pennisetum macrostachyum*, *Pennisetum macrourum*, *Pennisetum orientale*, *Pennisetum pedicellatum*, *Pennisetum polystachion*, *Pennisetum polystachion* ssp. *Setosum*, *Pennisetum purpureum*, *Pennisetum setaceum*, *Pennisetum subangustum*, *Pennisetum typhoides*, *Pennisetum villosum*, or hybrids thereof (e.g., *Pennisetum purpureum*×*Pennisetum typhoidum*).

In some embodiments, a suitable species can be a wild, weedy, or cultivated *Miscanthus* species and/or variety such as, but not limited to, *Miscanthus*×*giganteus*, *Miscanthus sinensis*, *Miscanthus*×*ogiformis*, *Miscanthus floridulus*, *Miscanthus transmorrisonensis*, *Miscanthus oligostachyus*, *Miscanthus nepalensis*, *Miscanthus sacchariflorus*, *Miscanthus*×*giganteus* 'Amuri', *Miscanthus*×*giganteus* 'Nagara', *Miscanthus*×*giganteus* 'Illinois', *Miscanthus sinensis* var. 'Goliath', *Miscanthus sinensis* var. 'Roland', *Miscanthus sinensis* var. 'Africa', *Miscanthus sinensis* var. 'Fern Osten', *Miscanthus sinensis* var. *gracillimus*, *Miscanthus sinensis* var. *variegates*, *Miscanthus sinensis* var. *purpurascens*, *Miscanthus sinensis* var. 'Malepartus', *Miscanthus sacchariflorus* var. 'Robusta', *Miscanthus sinensis* var. 'Silberfedher' (aka. Silver Feather), *Miscanthus transmorrisonensis*, *Miscanthus condensatus*, *Miscanthus yakushimanum*, *Miscanthus* var. 'Alexander', *Miscanthus* var. 'Adagio', *Miscanthus* var. 'Autumn Light', *Miscanthus* var. 'Cabaret', *Miscanthus* var. 'Condensatus', *Miscanthus* var. 'Cosmopolitan', *Miscanthus* var. 'Dixieland', *Miscanthus* var. 'Gilded Tower' (U.S. Pat. No. PP14,743), *Miscanthus* var. 'Gold Bar' (U.S. Pat. No. PP15,193), *Miscanthus* var. 'Gracillimus', *Miscanthus* var. 'Graziella', *Miscanthus* var. 'Grosse Fontaine', *Miscanthus* var. 'Hinjo aka Little Nicky'™, *Miscanthus* var. 'Juli', *Miscanthus* var. 'Kaskade', *Miscanthus* var. 'Kirk Alexander', *Miscanthus* var. 'Kleine Fontaine', *Miscanthus* var. 'Kleine Silberspinne' (aka. 'Little Silver Spider'), *Miscanthus* var. 'Little Kitten', *Miscanthus* var. 'Little Zebra' (U.S. Pat. No. PP 13,008), *Miscanthus* var. 'Lottum', *Miscanthus* var. 'Malepartus', *Miscanthus* var. 'Morning Light', *Miscanthus* var. 'Mysterious Maiden' (U.S. Pat. No. PP 16,176), *Miscanthus* var. 'Nippon', *Miscanthus* var. 'November Sunset', *Miscanthus* var. 'Parachute', *Miscanthus* var. 'Positano', *Miscanthus* var. 'Puenktchen'(aka 'Little Dot'), *Miscanthus* var. 'Rigoletto', *Miscanthus* var. 'Sarabande', *Miscanthus* var. 'Silberpfeil' (aka. Silver Arrow), *Miscanthus* var. 'Silverstripe', *Miscanthus* var. 'Super Stripe' (U.S. Pat. No. PP18,161), *Miscanthus* var. 'Strictus', or *Miscanthus* var. 'Zebrinus'.

In some embodiments, a suitable species can be a wild, weedy, or cultivated sorghum species and/or variety such as, but not limited to, *Sorghum almum*, *Sorghum amplum*, *Sorghum angustum*, *Sorghum arundinaceum*, *Sorghum bicolor* (such as bicolor, guinea, caudatum, kafir, and durra), *Sorghum brachypodum*, *Sorghum bulbosum*, *Sorghum burmahicum*, *Sorghum controversum*, *Sorghum drummondii*, *Sorghum ecarinatum*, *Sorghum exstans*, *Sorghum grande*, *Sorghum halepense*, *Sorghum interjectum*, *Sorghum intrans*, *Sorghum laxiflorum*, *Sorghum leiocladum*, *Sorghum macrospermum*, *Sorghum matarankense*, *Sorghum miliaceum*, *Sorghum nigrum*, *Sorghum nitidum*, *Sorghum plumosum*, *Sorghum propinquum*, *Sorghum purpureosericeum*, *Sorghum stipoideum*, *Sorghum sudanensese*, *Sorghum timorense*, *Sorghum trichocladum*, *Sorghum versicolor*, *Sorghum virgatum*, *Sorghum vulgare*, or hybrids such as *Sorghum*× *almum*, *Sorghum*×*sudangrass* or *Sorghum*×*drummondii*.

Thus, the methods and compositions can be used over a broad range of plant species, including species from the dicot genera *Brassica*, *Carthamus*, *Glycine*, *Gossypium*, *Helianthus*, *Jatropha*, *Parthenium*, *Populus*, and *Ricinus*; and the monocot genera *Elaeis*, *Festuca*, *Hordeum*, *Lolium*, *Oryza*, *Panicum*, *Pennisetum*, *Phleum*, *Poa*, *Saccharum*, *Secale*, *Sorghum*, *Triticosecale*, *Triticum*, and *Zea*. In some embodiments, a plant is a member of the species *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

In certain embodiments, the polynucleotides and vectors described herein can be used to transform a number of monocotyledonous and dicotyledonous plants and plant cell systems, wherein such plants are hybrids of different species or varieties of a specific species (e.g., *Saccharum* sp.× *Miscanthus* sp., *Sorghum* sp.×*Miscanthus* sp., e.g., *Panicum virgatum*×*Panicum amarum*, *Panicum virgatum*×*Panicum amarulum*, and *Pennisetum purpureum*×*Pennisetum typhoidum*).

D. Transgenic Plant Phenotypes

In some embodiments, a plant in which expression of a biomass composition-modulating polypeptide is modulated has increased or decreased levels of sucrose, ash, or cell wall content. A plant in which expression of a biomass composition-modulating polypeptide is modulated also can have increased or decreased conversion efficiency. A component of biomass composition can be increased by at least 2 percent, e.g., 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the level of the biomass component in a corresponding control plant that does not express the transgene. In some embodiments, a plant in which expression of a biomass composition-modulating polypeptide is modulated can have decreased levels of a biomass component. The level can be decreased by at least 2 percent, e.g., 2, 3, 4, 5, 10, 15, 20, 25, 30, 35, or more than 35 percent, as compared to the level in a corresponding control plant that does not express the transgene.

Increases in a component of biomass composition (e.g., sucrose) in such plants can provide improved nutritional availability in geographic locales where intake of plant foods is often insufficient, or for energy production (e.g., conversion efficiency). In some embodiments, decreases in a component of biomass composition in such plants can be useful in energy production.

In some embodiments, a plant in which expression of a biomass composition-modulating polypeptide is modulated can have increased or decreased levels of a biomass component (e.g., sucrose content) in one or more plant tissues, e.g., vegetative tissues, reproductive tissues, or root tissues. For example, the level of a biomass component can be increased by at least 2 percent, e.g., 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the level in a corresponding control plant that does not express the transgene. In some embodiments, a plant in which expression of a biomass composition-modulating polypeptide is modulated can have decreased levels of a biomass component in one or more plant tissues. The level can be decreased by at least 2 percent, e.g., 2, 3, 4, 5, 10, 15, 20, 25, 30, 35, or more than 35 percent, as compared to the level in a corresponding control plant that does not express the transgene.

Typically, a difference in the amount of a biomass component in a transgenic plant or cell relative to a control plant or cell is considered statistically significant at $p \leq 0.05$ with an appropriate parametric or non-parametric statistic, e.g., Chi-square test, Student's t-test, Mann-Whitney test, or F-test. In some embodiments, a difference in the amount of a biomass component is statistically significant at $p<0.01$, $p<0.005$, or $p<0.001$. A statistically significant difference in, for example, the amount of a biomass component in a transgenic plant compared to the amount of a control plant indicates that the recombinant nucleic acid present in the transgenic plant results in altered biomass composition.

The phenotype of a transgenic plant is evaluated relative to a control plant. A plant is said "not to express" a polypeptide when the plant exhibits less than 10%, e.g., less than 9%, 8%, 7%, 6%, 5%, 4%, 3%, 2%, 1%, 0.5%, 0.1%, 0.01%, or 0.001%, of the amount of polypeptide or mRNA encoding the polypeptide exhibited by the plant of interest. Expression can be evaluated using methods including, for example, RT-PCR, Northern blots, S1 RNase protection, primer extensions, Western blots, protein gel electrophoresis, immunoprecipitation, enzyme-linked immunoassays, chip assays, and mass spectrometry. It should be noted that if a polypeptide is expressed under the control of a tissue-preferential or broadly expressing promoter, expression can be evaluated in the entire plant or in a selected tissue. Similarly, if a polypeptide is expressed at a particular time, e.g., at a particular time in development or upon induction, expression can be evaluated selectively at a desired time period.

Biomass can include harvestable plant tissues such as leaves, stems, and reproductive structures, or all plant tissues such as leaves, stems, roots, and reproductive structures. In some embodiments, biomass encompasses only above ground plant parts. In some embodiments, biomass encompasses only stem plant parts. In some embodiments, biomass encompasses only above ground plant parts except inflorescence and seed parts of a plant. Biomass can be measured as described in the examples section. Biomass can be quantified as dry matter yield, which is the mass of biomass produced (usually reported in T/acre) if the contribution of water is subtracted from the fresh mater weight. Dry matter yield (DMY) yield is calculated using the fresh matter weight (FMW) and a measurement of weight percent moisture (M) in the following equation. $DMY=((100-M)/100)*FMW$. Biomass can be quantified as fresh matter yield, which is the mass of biomass produced (usually reported in T/acre) on an as-received basis, which includes the weight of moisture.

V. Modifying Endogenous Nucleic Acids Encoding Biomass Composition-Modulating Polypeptides This document also features plant cells and plants in which an endogenous biomass composition-modulating nucleic acid described herein has been modified (e.g., a regulatory region, intron, or coding region of the biomass composition-modulating nucleic acid has been modified). The biomass composition of such plants is altered relative to the corresponding composition of a control plant in which the endogenous nucleic acid is not modified. Such plants are referred to herein as modified plants and may be used to produce, for example, increased amounts of a biomass component (e.g., sucrose).

Endogenous nucleic acid can be modified by homologous recombination techniques. For example, sequence specific endonucleases (e.g., zinc finger nucleases (ZFNs)) and meganucleases can be used to stimulate homologous recombination at endogenous plant genes. See, e.g., Townsend et al., *Nature* 459:442-445 (2009); Tovkach et al., *Plant J.,* 57:747-757 (2009); and Lloyd et al., *Proc. Natl. Acad. Sci. USA,* 102:2232-2237 (2005). In particular, ZFNs engineered to create DNA double strand breaks at specific loci can be used to make targeted sequence changes in endogenous plant genes. For example, an endogenous plant gene can be replaced with a variant containing one or more mutations (e.g., produced using site-directed mutagenesis or directed evolution). In some embodiments, site directed mutagenesis is achieved via non-homologous end joining such that after breaking DNA, endogenous DNA repair mechanisms ligate the break, often introducing slight deletions or additions that can be screened at the cell or plant level for desired phenotypes. Moore and Haber, *Mol Cell Biol.,* 16(5):2164-73 (1996).

In some embodiments, endogenous nucleic acids can be modified by methylation or demethylation such that the expression of the modified endogenous nucleic acid is altered. For example, a double stranded RNA can be used to activate gene expression by targeting noncoding regulatory regions in gene promoters. See Shibuya et al., *Proc Natl Acad Sci USA,* 106(5): 1660-1665 (2009); and Li et al., *Proc Natl Acad Sci USA,* 103(46):17337-42 (2006). In some embodiments, ZFNs engineered to create DNA double strand breaks at specific loci can be used to insert a DNA fragment having at least one region that overlaps with the endogenous DNA to facilitate homologous recombination, such that the non-overlapping portion of the DNA fragment is integrated at the break site. For example, a fragment can be inserted into an endogenous promoter and/or regulatory region at a specific site where a ZFN created a double stranded break to alter the expression of an endogenous gene. For example, a fragment that is inserted into an endogenous gene coding region at a specific site where a ZFN created a double stranded break can result in expression of a chimeric gene. For example, a fragment that functions as a regulatory region or promoter that is inserted into an endogenous DNA region immediately upstream of a gene coding sequence at a specific site where a ZFN creates a double strand break can result in altered expression of the endogenous gene.

In some embodiments, endogenous nucleic acids can be modified using activation tagging. For example, a vector containing multiple copies of an enhancer element from the constitutively active promoter of the cauliflower mosaic virus (CaMV) 35S gene can be used to activate an endogenous gene. See, Weigel et al., *Plant Physiology,* 122:1003-1013 (2000).

In some embodiments, endogenous nucleic acids can be modified by introducing an engineered transcription activation/repression factor (e.g., zinc finger protein transcription factor, or ZFP TF. See, for example, the world wide web at sangamo.com/tech/tech_plat_over.html#whatarezfp). For example, a synthetic transcription facto sequence of a zinc finger DNA binding domain and a VP16 activation domain can be designed to bind to a specific endogenous DNA site and alter expression of an endogenous gene. An engineered transcription activation/repression factor (such as ZFP TF) can activate, repress, or switch the target endogenous biomass, sucrose, and/or conversion-gene expression by binding specifically to the promoter region or coding region of the endogenous gene. Engineered nucleases that cleave specific DNA sequences in vivo can also be valuable reagents for targeted mutagenesis. One such class of sequence-specific nucleases can be created by fusing transcription activator-like effectors (TALEs) to the catalytic domain of the FoId endonuclease. Both native and custom TALE-nuclease fusions direct DNA double-strand breaks to specific, targeted sites. Christian, et al., *Genetics* 186: 757-761 (2010).

In some embodiments, endogenous nucleic acids can be modified by mutagenesis. Genetic mutations can be introduced within regenerable plant tissue using one or more mutagenic agents. Suitable mutagenic agents include, for example, ethyl methane sulfonate (EMS), N-nitroso-N-ethylurea (ENU), methyl N-nitrosoguanidine (MNNG), ethidium bromide, diepoxybutane, ionizing radiation, x-rays, UV rays and other mutagens known in the art. Suitable types of mutations include, for example, insertions or deletions of nucleotides, and transitions or transversions in the endogenous nucleic acid sequence. In one embodiment, TILLING (Targeted Induced Local Lesions In Genomes) can be used to produce plants having a modified endogenous nucleic acid. TILLING combines high-density mutagenesis with high-throughput screening methods. See, for example, McCallum et al., *Nat Biotechnol* 18: 455-457 (2000); reviewed by Stemple, *Nat Rev Genet.* 5(2):145-50 (2004).

In some embodiments, an endogenous nucleic acid can be modified via a gene silencing technique. See, for example, the section herein regarding "Inhibition of Expression of a Biomass composition-modulating Polypeptide."

A population of plants can be screened and/or selected for those members of the population that have a modified nucleic acid. A population of plants also can be screened and/or selected for those members of the population that have a trait or phenotype conferred by expression of the modified nucleic acid. As an alternative, a population of plants can be screened for those plants having a desired trait, such as a modulated level of biomass. For example, a population of progeny can be screened for those plants having a desired level of expression of a biomass composition-modulating polypeptide or nucleic acid. Physical and biochemical methods can be used to identify modified nucleic acids and/or expression levels as described with transgenic plants. Selection and/or screening can be carried out over one or more generations, and/or in more than one geographic location. In some cases, plants can be grown and selected under conditions which induce a desired phenotype or are otherwise necessary to produce a desired phenotype in a modified plant. In addition, selection and/or screening can be applied during a particular developmental stage in which the phenotype is expected to be exhibited by the plant. Selection and/or screening can be carried out to choose those modified plants having a statistically significant difference in biomass composition relative to a control plant in which the nucleic acid has not been modified. Selected or screened modified plants have an altered phenotype as compared to a corresponding control plant, as described in the "Transgenic Plant Phenotypes" section herein.

Although a plant or plant cell in which an endogenous biomass composition-modulating nucleic acid has been modified is not transgenic for that particular nucleic acid, it will be appreciated that such a plant or cell may contain transgenes. For example, a modified plant can contain a transgene for other traits, such as herbicide tolerance or insect resistance. As another example, a modified plant can contain one or more transgenes that, in conjunction with modifications of one or more endogenous nucleic acids, exhibits an increase in a component of biomass.

As with transgenic plant cells, modified plant cells can constitute part or all of a whole plant. Such plants can be grown in the same manner as described for transgenic plants and can be bred or propagated in the same manner as described for transgenic plants.

VI. Plant Breeding

Genetic polymorphisms that are useful in such methods include simple sequence repeats (SSRs, or microsatellites), rapid amplification of polymorphic DNA (RAPDs), single nucleotide polymorphisms (SNPs), amplified fragment length polymorphisms (AFLPs) and restriction fragment length polymorphisms (RFLPs). SSR polymorphisms can be identified, for example, by making sequence specific probes and amplifying template DNA from individuals in the population of interest by PCR. For example, PCR techniques can be used to enzymatically amplify a genetic marker associated with a nucleotide sequence conferring a specific trait (e.g., nucleotide sequences described herein). PCR can be used to amplify specific sequences from DNA as well as RNA, including sequences from total genomic DNA or total cellular RNA. When using RNA as a source of template, reverse transcriptase can be used to synthesize complementary DNA (cDNA) strands. Various PCR methods are described, for example, in *PCR Primer: A Laboratory Manual,* Dieffenbach and Dveksler, eds., Cold Spring Harbor Laboratory Press, 1995.

Generally, sequence information from polynucleotides flanking the region of interest or beyond is employed to design oligonucleotide primers that are identical or similar in sequence to opposite strands of the template to be amplified. Primers are typically 14 to 40 nucleotides in length, but can range from 10 nucleotides to hundreds of nucleotides in length. Template and amplified DNA is repeatedly denatured at a high temperature to separate the double strand, then cooled to allow annealing of primers and the extension of nucleotide sequences through the microsatellite, resulting in sufficient DNA for detection of PCR products. If the probes flank an SSR in the population, PCR products of different sizes will be produced. See, e.g., U.S. Pat. No. 5,766,847.

PCR products can be qualitative or quantitatively analyzed using several techniques. For example, PCR products can be stained with a fluorescent molecule (e.g., PicoGreen® or OliGreen®) and detected in solution using spectrophotometry or capillary electrophoresis. In some cases, PCR products can be separated in a gel matrix (e.g., agarose or polyacrylamide) by electrophoresis, and size-fractionated bands comprising PCR products can be visualized using nucleic acid stains. Suitable stains can fluoresce under UV light (e.g., Ethidium bromide, GR Safe, SYBR® Green, or SYBR® Gold). The results can be visualized via transillumination or epi-illumination, and an image of the fluorescent pattern can be acquired using a camera or scanner, for example. The image can be processed and analyzed using specialized software (e.g., ImageJ) to measure and compare the intensity of a band of interest against a standard loaded on the same gel.

Alternatively, SSR polymorphisms can be identified by using PCR product(s) as a probe against Southern blots from different individuals in the population. See, Refseth et al., (1997) *Electrophoresis* 18: 1519. Briefly, PCR products are separated by length through gel electrophoresis and transferred to a membrane. SSR-specific DNA probes, such as oligonucleotides labeled with radioactive, fluorescent, or chromogenic molecules, are applied to the membrane and hybridize to bound PCR products with a complementary nucleotide sequence. The pattern of hybridization can be visualized by autoradiography or by development of color on the membrane, for example.

In some cases, PCR products can be quantified using a real-time thermocycler detection system. For example, Quantitative real-time PCR can use a fluorescent dye that forms a DNA-dye-complex (e.g., SYBR® Green), or a fluorophore-containing DNA probe, such as single-stranded oligonucleotides covalently bound to a fluorescent reporter or fluorophore (e.g. 6-carboxyfluorescein or tetrachlorofluorescin) and quencher (e.g., tetramethylrhodamine or dihydrocyclopyrroloindole tripeptide minor groove binder). The fluorescent signal allows detection of the amplified product in real time, thereby indicating the presence of a sequence of interest, and allowing quantification of the copy number of a sequence of interest in cellular DNA or expression level of a sequence of interest from cellular mRNA.

The identification of RFLPs is discussed, for example, in Alonso-Blanco et al. (*Methods in Molecular Biology*, vol. 82, "*Arabidopsis* Protocols", pp. 137-146, J. M. Martinez-Zapater and J. Salinas, eds., c. 1998 by Humana Press, Totowa, N.J.); Burr ("Mapping Genes with Recombinant Inbreds", pp. 249-254, in Freeling, M. and V. Walbot (Ed.), *The Maize Handbook*, c. 1994 by Springer-Verlag New York, Inc.: New York, N.Y., USA; Berlin Germany; Burr et al. *Genetics* (1998) 118: 519; and Gardiner, J. et al., (1993) Genetics 134: 917). For example, to produce a RFLP library enriched with single- or low-copy expressed sequences, total DNA can be digested with a methylation-sensitive enzyme (e.g., PstI). The digested DNA can be separated by size on a preparative gel. Polynucleotide fragments (500 to 2000 bp) can be excised, eluted and cloned into a plasmid vector (e.g., pUC18). Southern blots of plasmid digests can be probed with total sheared DNA to select clones that hybridize to single- and low-copy sequences. Additional restriction endonucleases can be tested to increase the number of polymorphisms detected.

The identification of AFLPs is discussed, for example, in EP 0 534 858 and U.S. Pat. No. 5,878,215. In general, total cellular DNA is digested with one or more restriction enzymes. Restriction halfsite-specific adapters are ligated to all restriction fragments and the fragments are selectively amplified with two PCR primers that have corresponding adaptor and restriction site specific sequences. The PCR products can be visualized after size-fractionation, as described above.

In some embodiments, the methods are directed to breeding a plant line. Such methods use genetic polymorphisms identified as described above in a marker assisted breeding program to facilitate the development of lines that have a desired alteration in biomass composition. Once a suitable genetic polymorphism is identified as being associated with variation for the trait, one or more individual plants are identified that possess the polymorphic allele correlated with the desired variation. Those plants are then used in a breeding program to combine the polymorphic allele with a plurality of other alleles at other loci that are correlated with the desired variation. Techniques suitable for use in a plant breeding program are known in the art and include, without limitation, backcrossing, mass selection, pedigree breeding, bulk selection, crossing to another population and recurrent selection. These techniques can be used alone or in combination with one or more other techniques in a breeding program. Thus, each identified plants is selfed or crossed a different plant to produce seed which is then germinated to form progeny plants. At least one such progeny plant is then selfed or crossed with a different plant to form a subsequent progeny generation. The breeding program can repeat the steps of selfing or outcrossing for an additional 0 to 5 generations as appropriate in order to achieve the desired uniformity and stability in the resulting plant line, which retains the polymorphic allele. In most breeding programs, analysis for the particular polymorphic allele will be carried out in each generation, although analysis can be carried out in alternate generations if desired.

In some cases, selection for other useful traits is also carried out, e.g., selection for fungal resistance or bacterial resistance. Selection for such other traits can be carried out before, during or after identification of individual plants that possess the desired polymorphic allele.

VII. Articles of Manufacture

Transgenic plants provided herein have various uses in the agricultural and energy production industries. For example, transgenic plants described herein can be used to make animal feed and food products. Such plants, however, are often particularly useful as a feedstock for energy production.

Transgenic plants described herein often produce higher yields of grain and/or biomass per hectare, relative to control plants that lack the exogenous nucleic acid. In some embodiments, such transgenic plants provide equivalent or even increased yields of grain and/or biomass per hectare relative to control plants when grown under conditions of reduced inputs such as fertilizer and/or water. Thus, such transgenic plants can be used to provide yield stability at a lower input cost and/or under environmentally stressful conditions such as drought. In some embodiments, plants described herein have a composition that permits more efficient processing into free sugars, and subsequently ethanol, for energy production. In some embodiments, such plants provide higher yields of ethanol, butanol, dimethyl ether, other biofuel molecules, and/or sugar-derived co-products per kilogram of plant material, relative to control plants. Such processing efficiencies are believed to be derived from the composition of the plant material, including, but not limited to, content of glucan, cellulose, hemicellulose, and lignin. By providing higher biomass yields at an equivalent or even decreased cost of production, the transgenic plants described herein improve profitability for farmers and processors as well as decrease costs to consumers.

Seeds from transgenic plants described herein can be conditioned and bagged in packaging material by means known in the art to form an article of manufacture. Packaging material such as paper and cloth are well known in the art. A package of seed can have a label, e.g., a tag or label secured to the packaging material, a label printed on the packaging material, or a label inserted within the package, that describes the nature of the seeds therein.

VIII. Uses and Advantages

*Sorghum* plants described herein can be grown in large fields (e.g., 50 to 10,000 acre fields) to obtain harvestable biomass. For example, the sorghum plants provided herein can be grown in fields of 100 acres or more at locations suitable for sorghum growth such as southern United States, Brazil, and Mexico.

In one embodiment, the stalks of sorghum plants described herein are harvested and processed, e.g., extracted using pressing and/or milling techniques, to obtain sorghum stem juice. For example, the stalks can be harvested by hand or mechanical harvesters, and then crushed and pressed with a horizontal or vertical mill to extract the juice. One objective of the pressing and/or milling processes is to extract the largest possible amount of juice from the sorghum biomass. Another objective is to produce bagasse with a low moisture content to be burned as a boiler fuel for electricity generation, thereby allowing a production plant to be self-sufficient in energy.

Sucrose, i.e., table sugar, can be produced from the juice using techniques including filtering, clarifying, decolorizing, and repeated concentration and crystallization. In some embodiments, table sugar is produced by blending sweet sorghum juice with sugarcane juice prior to crystallization, thereby increasing the total yield of table sugar.

In other embodiments, the sugars in the juice can be fermented to produce a biofuel. For example, the juice can be filtered and used in a fermentation reaction to produce a biofuel. Examples of biofuels include, without limitation, biodiesel, methanol, ethanol, butanol, linear alkanes (C5-C20), branched-chain alkanes (C5-C26), mixed alkanes, linear alcohols (C1-C20), branched-chain alcohols (C1-C26), linear carboxylic acids (C2-C20), and branched-chain carboxylic acids (C2-C26). In some cases, the methods and materials provided herein can be used to make other chemical compounds such as ethers, esters, and amides of the aforementioned acids and alcohols, as well as other conjugates of these chemicals. In some cases, one or more of these compounds can be chemically converted into other high value and/or high volume chemicals.

Any appropriate microorganism can be used to produce biofuel in a fermentation reaction. For example, one or more microorganisms designed to produce ethanol can be used in fermentation reactions with sorghum juice to produce ethanol-containing reaction products. In some cases, a microorganism useful for producing one or more biofuels as described herein is from a genus such as *Clostridium, Zymomonas, Escherichia, Salmonella, Rhodococcus, Pseudomonas, Bacillus, Lactobacillus, Enterococcus, Alcaligenes, Klebsiella, Paenibacillus, Arthrobacter, Corynebacterium, Brevibacterium, Pichia, Candida, Hansenula,* and *Saccharomyces*. For example, ethanologenic yeast can be used in a fermentation reaction containing sorghum juice to produce ethanol.

Any appropriate fermentation process can be used to produce biofuel using sorghum juice. For example, batch, fed-batch, or continuous fermentation processes can be used to produce a biofuel using sorghum juice. A batch fermentation process can include adding sorghum juice substrate, fermentation organism(s) and culture medium at the beginning of the fermentation and not replenishing once fermentation has begun. In some cases, one or more culture parameters, e.g., pH and oxygen concentration, are monitored and adjusted during the fermentation process.

In some cases, a fed-batch fermentation process can be used to produce biofuel using sorghum juice obtained from sorghum plants provided herein. A fed-batch fermentation process is similar to a batch fermentation process except that substrate is added, and optionally culture medium nutrients, at intervals as fermentation progresses. In some cases, one or more culture parameters, e.g., pH, dissolved oxygen concentration, and/or carbon dioxide to oxygen ratio, are monitored and adjusted during the fermentation process. Fed-batch fermentation processes can allow users to control the amount of substrate within the fermentation reaction.

Continuous fermentation processes also can be used to produce biofuel using sorghum juice obtained from sorghum plants provided herein. A continuous fermentation process can be an open system in which a defined fermentation medium containing sorghum juice material is continuously added to a bioreactor and an amount (e.g., an equal amount) of conditioned media is continuously removed for subsequent processing. Continuous fermentation can often be performed such that the fermentation organism is maintained at a high cell density and in a prolonged exponential growth phase, resulting in higher productivity than batch fermentation.

Examples of batch, fed-batch, and continuous fermentation processes that can be used to produce biofuel using sorghum juice obtained from plants provided herein are described elsewhere (Thomas D. Brock in Biotechnology: A Textbook of Industrial Microbiology, Second Edition (1989) Sinauer Associates, Inc., Sunderland, Mass.; and Deshpande, Mukund V., *Appl. Biochem. Biotechnol.*, 36:227 (1992)).

Any appropriate fermentation media containing sorghum juice can be used in a fermentation reaction to produce biofuel. In some cases, fermentation media used to produce biofuel as described herein can contain sorghum juice as the primary carbon source (e.g., primary source of glucose, fructose, sucrose, mannose, or other sugars). In some cases, one or more other carbon sources can be used in combination with sorghum juice provided herein to form fermentation media for producing biofuel. For example, sorghum juice obtained from sorghum plants provided herein can be combined with sugarcane juice (garapa) to form fermentation media for producing biofuel. In some cases, one or more other components such as minerals, salts, cofactors, and buffers can be included within fermentation media to promote culture growth and/or biofuel production. Examples of commercially available broths that can be used in combination with sorghum juice material to create fermentation media include, without limitation, Luria Bertani (LB) broth, Sabouraud Dextrose (SD) broth, and Yeast medium (YM) broth.

Any appropriate culture conditions can be used to perform fermentation reactions designed to produce biofuel using sorghum juice. For example, fermentation cultures can be grown or maintained at a temperature in the range of about 25° C. to about 40° C. and at a pH in the range of pH 5.0 to pH 9.0 (e.g., a pH in the range of 6.0 and 8.0, of 6.5 and 7.5, or 6.5 and 7.0). A fermentation reaction can be performed under aerobic, microaerobic, or anaerobic conditions.

In some cases, biofuel production can be monitored during a fermentation reaction or can be assessed when the fermentation reaction is completed. Any appropriate method can be used to assess biofuel production. For example, high performance liquid chromatography (HPLC) or gas chromatography (GC) can be used to measure biofuel production.

Once produced, biofuel can be isolated from the fermentation product. For example, techniques such as centrifugation, filtration, decantation, or combinations thereof can be performed to remove solids from the fermentation product. Once most or all of the solid material is removed, biofuel present within the remaining material can be isolated by, for example, techniques such as distillation, liquid-liquid extraction, dehydration, membrane-based separation, or combinations thereof. In some cases, molecular sieves, distillation techniques, azeotropic distillation techniques, centrifugation, vacuum distillation, or combinations thereof can be used to separate biofuel (e.g., ethanol) from water and/or fermentation byproducts. For example, water can be removed from an azeotropic ethanol/water mixture obtained from a fermentation reaction by azeotropic distillation to result in hydrous ethanol having about 95 to about 96.5 percent ethanol and about 3.5 to about 5 percent water. Azeotropic distillation can include adding benzene or cyclohexane to an ethanol/water mixture. When these components are added to the mixture, they can form a heterogeneous azeotropic mixture in vapor-liquid-liquid equilibrium. This can be distilled to produce anhydrous ethanol at the bottom of a column and a vapor mixture of water and cyclohexane/benzene. When condensed, the material can become a two-phase liquid mixture. In some cases, an extractive distillation process that involves adding a ternary component that increases the volatility of ethanol can be performed. Distillation of the ternary mixture can result in anhydrous ethanol on the top stream of a column.

In some cases, dehydration methods such as those involving molecular sieve techniques can be used to remove water from a biofuel. For example, ethanol vapor under pressure can be passed through a bed of molecular sieve beads. The pore size of the beads can be designed to allow absorption of water while excluding ethanol. After a period of time, the bed can be regenerated under vacuum or through the flow of inert gas (e.g., N2) to remove absorbed water. In some cases, two or more beds of beads can be used. In such cases, one can be used to absorb water, while the other one is undergoing regeneration. In some cases, the use of molecular sieve techniques can be performed in a manner that does not involve the use of distillation techniques.

In some cases, production of ethanol for biofuel involves denaturation of the ethanol. Ethanol can be denatured by, for example, combining it with natural gasoline, unleaded gasoline, or gasoline blend stocks. Corrosion inhibitors such as Ashland Amergy ECI-6 or Petrolite Tolad 3222 can be added to fuel ethanol if desired. Ethanol for fuel use can meet the specifications of ASTM D4806 (e.g., ASTM D4806-09). In some cases, the ethanol meets the specifications of ASTM D5453-93 for sulfur content, the specifications of ASTM D5580-95 for benzene or aromatic content, and/or the specifications of ASTM D6550-00 for olefin content. In some cases, ethanol for fuel use, produced as described herein, can meet Brazilian specification ANP#36 for hydrous ethanol or anhydrous ethanol.

In some cases, biomass remaining after extraction of juice (e.g., bagasse such as low moisture bagasse) or biomass not used for juice extraction can be used as a source of cellulosic material. Such cellulosic material can be used in fermentation reactions designed to metabolize cellulose and/or other sorghum biomolecules in order to produce biofuel or can be used in combustion reactions designed to produce heat for use in energy production.

The invention will be further described in the following examples, which do not limit the scope of the invention described in the claims.

IX. Examples

Example 1

Procedures for Conversion Analysis

The conversion efficiency of control and transgenic switchgrass lines was determined indirectly using NIR composition and conversion models for switchgrass. See, WO2009/059176. Samples were prepared for analysis by drying the tissue samples for at least 3 days in an incubator set at 45° C. Dried tissues were milled using a Wiley Mill fitted with 20-mesh filter. Milled samples contained in a vial were scanned three times. The average scan was run through the NIR model and the predicted pretreatment liquid (PL) and saccharification (SAC) values were determined accordingly.

The yield of conversion was directly calculated as follows: [PLN value+SAC value]/amount of biomass weight, wherein "PLN" refers to pretreatment liquor neutralization, and "SAC" refers to the sugar value from the saccrification analysis. The following procedures were used to obtain the PLN and SAC values.

Microwave Pretreatment: Milled tissues were weighed to obtain approximately 0.025 g. The moisture content of the weighed tissues was determined using the Denver Moisture Content analyzer. Tissues were transferred into separate Biotage microwave vials that were previously tared. Appropriate volume of sulfuric acid was then added into the samples to give a final concentration of 1.3%. Samples were pretreated in the microwave using the following settings: 165° C., 5 minutes, very high absorbance, 2.0-5.0 vial, 600 rpm stir speed (SWAVE default). The vials with the microwaved samples were centrifuged at 4000 rpm for 5 min with a deceleration rate set at ≤5. A minimum of 4 ml of PL from each vial was transferred into pre-labeled 15 ml Corning conical tubes. The pH of the PL fraction was measured. The PL was kept frozen until ready to analyze. The residue in each vial was washed several times by adding 5 ml water followed by centrifugation step at 4000 rpm for 5 min. The pH of the wash was monitored until it reached between 5 and 6 using appropriate pH indicator strips. The solid fraction was stored for saccharification analysis.

Pretreatment Liquor Analysis: To determine PLN (neutralized pretreatment liquor), calcium carbonate was added to an appropriate aliquot of each PL fraction until its pH reached between 5 and 6. The neutralized mixture was centrifuged at 4000 rpm for 2 min; after which 2 ml of the neutralized liquor was transferred to storage tubes.

To determine the sugar content, the neutralized fraction (PLN) was analyzed using a YSI Sugar Analyzer and/or by HPLC.

Saccharification Analysis: Water was added to the solid fraction obtained from the microwave pretreatment. Appropriate volume of enzyme mixture (containing appropriate weight of proprietary enzymes, tetracycline and cyclohexamide in citrate buffer) was added to the mixture followed by incubation at 50° C. in a rotating incubator. At the appropriate time period, an aliquot from the reaction was transferred to a microcentrifuge tube. The reaction was stopped by boiling the mixture for 5 min. The mixture was centrifuged for 2 min at 14,000 rpm. The supernatant was taken for sugar analysis using a YSI Sugar Analyzer and/or by HPLC. This sugar value represents the SAC value.

Example 2

Protocol for Sucrose Analysis

The sucrose content of control and transgenic switchgrass lines was determined indirectly using the NIR composition model for switchgrass. See WO2009/059176. Samples were prepared for analysis by drying the tissue samples for at least 3 days in an incubator set at 45° C. Dried tissues were milled using a Wiley Mill fitted with 20-mesh filter. Milled samples contained in a vial were scanned three times. The average scan was run through the NIR model and the predicted PL and SAC values were determined accordingly.

The sucrose content of selected samples was directly analyzed as follows. An appropriate amount of milled biomass (3-4 g) was placed into cell vial for extraction using the ASE200 extractor. Extraction was performed using water as solvent with the extractor set at following parameters: 1500 psi pressure, 100° C. temperature, no preheating, 5 min ramping, 7 min static step, and purging for 2 min. The volume of the collected extract was measured. Appropriate dilutions of the extracts were run through HPLC analysis to quantify the amount of sucrose using reference standards. The % sucrose content was calculated as follows: the amount of sucrose divided by the amount of biomass used in the extraction.

Example 3

Transgenic Switchgrass Lines

The following symbols are used in with respect to transformations: $T_0$: plant regenerated from transformed tissue culture; $T_1$: first generation progeny of self-pollinated $T_0$ plants; $T_2$: second generation progeny of self-pollinated $T_1$ plants; $T_3$: third generation progeny of self-pollinated $T_2$ plants.

The following nucleic acids were isolated from *Panicum virgatum* plants: CeresClone: 1807011 (SEQ ID NO:1); CeresClone 1955550 (SEQ ID NO:64); CeresClone: 240112 (SEQ ID NO:245); CeresClone: 1900192 (SEQ ID NO:279); CeresClone: 1776501 (SEQ ID NO:347); CeresClone: 1804732 (SEQ ID NO:415); CeresClone: 1955550 (SEQ ID NO:640); and CeresClone: 1789981 (SEQ ID NO:773).

Each isolated nucleic acid described above was cloned into T-DNA binary vectors, which were introduced into switchgrass (A26 or A10 clonally propagated lines) by *Agrobacterium*-mediated transformation essentially as described in Richards et al., *Plant Cell. Rep.* 20:48-54 (2001) and Somleva et al., *Crop Sci.* 42:2080-2087 (2002). At least two independent events from each transformation were selected for further study; these events were referred to as switchgrass screening lines. T0 plants were grown in a greenhouse. The presence of each construct was confirmed by PCR.

Example 4

NIR Conversion Prediction for Transgenic Line PV00467

$T_0$ tissues from 22 events of PV00467 containing Ceres-Clone 1955550 (SEQ ID NO:64) were analyzed as described in Example 1. Several non-transgenic wild-type plants that were regenerated at the same time as the transgenic plants were used as controls (also called batch wild-type control). The amount of glucose released after acid pretreatment (mg/g) of PV00467 lines is presented in Table 1. The average of the batch wild-type control plants (i.e., wt batch average) and the overall average of different wild-type controls from different batches (i.e., wt running average) are also presented in Table 1. The predicted glucose released in the pretreated liquor of some of the PV00467 transgenic events was higher as compared to the wild-type controls (either using the wt batch average value or the wt running average value).

TABLE 1

| Plant Line | PLN Glu Rel |
| --- | --- |
| PV00467-04 | 65.3 |
| PV00467-05 | 58.9 |
| PV00467-06 | 82 |
| PV00467-10 | 59.4 |
| PV00467-11 | 62.3 |
| PV00467-12 | 77.7 |
| PV00467-13 | 65.4 |
| PV00467-14 | 67.7 |
| PV00467-15 | 62.9 |
| PV00467-19 | 49.4 |
| PV00467-20 | 69.2 |
| PV00467-21 | 67.7 |
| PV00467-22 | 65.2 |
| PV00467-24 | 53.7 |
| PV00467-26 | 49.8 |
| PV00467-27 | 52.5 |
| PV00467-28 | 53.5 |
| PV00467-29 | 52.6 |
| PV00467-30 | 74.7 |
| PV00467-31 | 51.3 |
| PV00467-32 | 60.1 |
| PV00467-36 | 58.3 |
| WT (Batch) Ave | 55.18 |
| WT (Batch) SD | 4.90 |
| WT Running Ave | 58.33 |
| WT Running SD | 9.08 |

Example 5

NIR Conversion Prediction for Transgenic Line PV00508

$T_0$ tissues from 25 events of PV00508 containing Ceres-Clone 1776501 (SEQ ID NO:347) were analyzed as described in Example 1. Several non-transgenic wild-type plants that were regenerated at the same time as the transgenic plants were used as controls (also called as batch wild-type control). The amount of glucose released after acid pretreatment (mg/g) of PV00508 lines is presented in Table 2. The average of the batch wild-type control plants (i.e., wt batch average) and the average of different wild-type controls from different batches (i.e., wt running average) are also presented in Table 2. The predicted glucose released in the pretreated liquor of some of the PV00508 transgenic events was higher as compared to the wild-type controls (either using the wt batch average value or the wt running average value).

TABLE 2

| Plant Line | PLN Glu Rel |
| --- | --- |
| PV00508-02 | 103.7 |
| PV00508-03 | 98.9 |
| PV00508-04 | 114.7 |
| PV00508-05 | 97.7 |
| PV00508-08 | 109.7 |
| PV00508-09 | 103.3 |
| PV00508-10 | 98.5 |
| PV00508-12 | 93.4 |
| PV00508-13 | 89 |
| PV00508-15 | 78.2 |
| PV00508-18 | 80.5 |
| PV00508-19 | 70.6 |
| PV00508-20 | 84.7 |
| PV00508-21 | 76 |
| PV00508-22 | 90.4 |
| PV00508-23 | 92.1 |
| PV00508-24 | 91.3 |
| PV00508-26 | 102.1 |
| PV00508-27 | 84.1 |
| PV00508-29 | 74.4 |
| PV00508-30 | 86.2 |
| PV00508-31 | 97.4 |
| PV00508-33 | 96.8 |
| PV00508-34 | 97.3 |
| PV00508-35 | 81.3 |
| WT (Batch) Ave | 77.05 |
| WT (Batch) SD | 12.77 |
| WT Running Ave | 58.33 |
| WT Running SD | 9.08 |

Example 6

Sucrose Content of Transgenic Lines UAC-20, UAC-22, and UAC-15

$T_0$ tissues from 5 events of UAC-20 containing Ceres Clone 1900192 (SEQ ID NO:279), 7 events of UAC-22 containing Ceres Clone 1807011 (SEQ ID NO:1), and 3 events of UAC-15 containing Ceres Clone 1804732 (SEQ ID NO:415) were analyzed as described in Example 2. Further analysis of the events of UAC-22 indicated that Ceres Clone 1807011 contains a deletion of a nucleotide at position 657 of SEQ ID NO:1, resulting in the production of a truncated protein. UAC-FA4 and UAC-NK4K were used as controls. UAC-FA4 is a wild-type plant regenerated from callus that was not transformed. UAC-NB4K corresponds to plants that were regenerated from callus transformed with an empty vector (i.e., with no insert). The average total sucrose content is presented in Table 3. All seven of the events of UAC-22 had an increased total sucrose content while three of the UAC-20 events and two of the UAC-15 events had an increased total sucrose content.

TABLE 3

|  | Avg total % SUC | StdDev |
| --- | --- | --- |
| UAC-20-14 | 9.62 | 0.15 |
| UAC-20-15 | 2.55 | 0.12 |
| UAC-20-21 | 7.85 | 0.03 |
| UAC-20-5 | 11.56 | 0.10 |
| UAC-20-9 | 9.98 | 0.01 |
| UAC-22-10 | 10.67 | 0.41 |
| UAC-22-11 | 10.11 | 1.00 |
| UAC-22-14 | 7.91 | 0.30 |
| UAC-22-15 | 5.29 | 0.19 |
| UAC-22-17 | 11.73 | 0.63 |
| UAC-22-21 | 8.41 | 0.18 |
| UAC-22-26 | 9.98 | 0.26 |
| UAC-15-1 | 4.35 | 0.08 |
| UAC-15-3 | 9.66 | 1.00 |
| UAC-15-5 | 6.94 | 0.08 |
| UAC-FA4-12 | 1.13 | 0.04 |
| UAC-FA4-12 | 3.04 | 0.22 |
| UAC-NB4K-1 | 4.37 | 0.06 |
| UAC-NB4K-9 | 1.46 | 0.05 |

Example 7

NIR Conversion Prediction for Transgenic Lines UAC-15, UAC-19, and UAC-22

$T_0$ tissues from one event of UAC-15 containing Ceres Clone 1804732 (SEQ ID NO:415), one event of UAC-19 containing Ceres Clone 1789981 (SEQ ID NO:773), and one event of UAC-22 containing Ceres Clone 1807011 (SEQ ID NO:1) were each analyzed as described in Example 1. Further analysis of the events of UAC-22 indicated that Ceres Clone 1807011 contains a deletion of a nucleotide at position 657 of SEQ ID NO:1, resulting in the production of a truncated protein. UAC-FA4 and UAC-NK4K were used as controls and NREL SWG was used as a standard reference. UAC-FA4 is a wild-type plant regenerated from callus. UAC-NB4K corresponds to plants that were regenerated from callus transformed with an empty vector (i.e., with no insert). NREL SWG is a composite switchgrass biomass obtained from National Renewable Energy Laboratory (NREL) and was used as a method control to determine consistency of analytical techniques. The amount of total glucose released per gram dry weight, PLN, and SAC values are presented in Table 4 for four experiments in which different amount of enzymes were used in the saccharification analysis. Increased total glucose released per gram of dry weight was observed for each of the transgenic lines regardless of the enzyme amount. At standard level amount of enzymes (i.e., 20 mgP/g), the total glucose released by the transgenic lines UAC-15-6 and UAC-19-2 was higher than that of the controls and the reference standard. This increase was primarily due to the increase of glucose released during the pretreatment. When the amount of enzymes was reduced by 8-fold (i.e., 2.5 mgP/g), the total glucose released by the transgenic lines UAC-15-6 and UAC-19-2 was similar to the control treated at the standard enzyme level.

Example 8

NIR Conversion Prediction for Transgenic Line PV00460

$T_0$ tissues from three events of PV00460 containing CeresClone 240112 (SEQ ID NO:245) were analyzed as described in Example 1. Pv-WT(A26)-72 was the wild-type control used, which corresponds to a regenerated but untransformed plant. The amount of total glucose released per g dry weight, PLN, and SAC values are presented in Table 5 for four experiments in which different amount of enzymes were used in the saccharification analysis. Increased total glucose released per gram of dry weight was observed for each of the transgenic lines regardless of the enzyme amount. At standard level amount of enzymes (i.e., 20 mgP/g), the total glucose released by the transgenic lines PV00460 (especially event #18) was higher than that of the control. This increase was primarily due to the increase of glucose released during the pretreatment. When the amount of enzymes was reduced by 8-fold (i.e., 2.5 mgP/g), the total glucose released by the PV00460 transgenic line (for example event #18) was similar to the control treated at the standard enzyme level.

TABLE 4

| Type | Lines | Enzymes Amount | Total Glucose Released Per g dry weight | StdDev | PLN | StdDev | SAC | stdev |
|---|---|---|---|---|---|---|---|---|
| Control | NREL SWG | 20 mgP/g | 272.81 | 18.21 | 45.47 | 1.86 | 227.34 | 16.34 |
| Control | UAC-NB4K-1 | 20 mgP/g | 280.54 | 6.20 | 59.78 | 0.85 | 220.77 | 5.35 |
| Control | UAC-FA4-1 | 20 mgP/g | 328.69 | 23.57 | 118.38 | 3.69 | 210.30 | 19.88 |
| Transgenic Line | UAC-15-6 | 20 mgP/g | 332.16 | 11.11 | 158.01 | 4.79 | 174.15 | 6.32 |
| Transgenic Line | UAC-19-2 | 20 mgP/g | 322.05 | 7.47 | 124.06 | 3.36 | 198.00 | 10.82 |
| Transgenic Line | UAC-22-11 | 20 mgP/g | 336.61 | 12.68 | 113.24 | 1.67 | 223.37 | 14.34 |
| Control | NREL SWG | 5.0 mgP/g | 208.86 | 13.36 | 43.82 | 1.43 | 165.04 | 11.93 |
| Control | UAC-NB4K-1 | 5.0 mgP/g | 234.31 | 16.46 | 57.90 | 3.30 | 176.41 | 13.16 |
| Control | UAC-FA4-1 | 5.0 mgP/g | 263.34 | 4.04 | 111.18 | 1.07 | 152.16 | 5.11 |
| Transgenic Line | UAC-15-6 | 5.0 mgP/g | 293.04 | 12.46 | 154.26 | 6.15 | 138.78 | 6.32 |
| Transgenic Line | UAC-19-2 | 5.0 mgP/g | 276.58 | 15.36 | 117.96 | 4.86 | 158.61 | 10.51 |
| Transgenic Line | UAC-22-11 | 5.0 mgP/g | 287.47 | 13.08 | 115.32 | 0.17 | 172.16 | 12.91 |
| Control | NREL SWG | 2.5 mgP/g | 184.61 | 15.02 | 44.98 | 3.59 | 139.63 | 11.42 |
| Control | UAC-NB4K-1 | 2.5 mgP/g | 200.15 | 11.21 | 61.69 | 1.82 | 138.45 | 9.40 |
| Control | UAC-FA4-1 | 2.5 mgP/g | 222.18 | 6.37 | 114.04 | 0.67 | 108.14 | 7.03 |
| Transgenic Line | UAC-15-6 | 2.5 mgP/g | 268.36 | 8.95 | 155.02 | 3.25 | 113.33 | 5.70 |
| Transgenic Line | UAC-19-2 | 2.5 mgP/g | 239.20 | 22.92 | 121.76 | 4.39 | 117.44 | 18.53 |
| Transgenic Line | UAC-22-11 | 2.5 mgP/g | 247.62 | 21.78 | 115.54 | 3.83 | 132.09 | 17.95 |
| Control | NREL SWG | 1.0 mgP/g | 125.35 | 13.67 | 41.55 | 2.81 | 83.80 | 10.86 |
| Control | UAC-NB4K-1 | 1.0 mgP/g | 153.46 | 5.10 | 61.19 | 1.88 | 92.27 | 3.22 |
| Control | UAC-FA4-1 | 1.0 mgP/g | 184.70 | 2.55 | 119.55 | 2.57 | 65.15 | 0.02 |
| Transgenic Line | UAC-15-6 | 1.0 mgP/g | 243.99 | 1.27 | 164.69 | 2.24 | 79.30 | 0.97 |
| Transgenic Line | UAC-19-2 | 1.0 mgP/g | 203.52 | 0.86 | 120.25 | 4.05 | 83.27 | 4.90 |
| Transgenic Line | UAC-22-11 | 1.0 mgP/g | 202.32 | 2.31 | 115.67 | 4.54 | 86.65 | 6.85 |

TABLE 5

| Type | Lines | Enzymes Amount | Total Glucose Released Per g dry weight | StdDev | PLN | StdDev | SAC | StdDev |
|---|---|---|---|---|---|---|---|---|
| Control | NREL SWG | 20 mgP/g | 273.37 | 18.08 | 42.60 | 2.69 | 230.77 | 15.38 |
| Transgenic Line | PV00460-15 | 20 mgP/g | 333.23 | 11.09 | 99.60 | 2.55 | 233.62 | 8.54 |
| Transgenic Line | PV00460-18 | 20 mgP/g | 344.73 | 10.71 | 115.11 | 1.73 | 229.61 | 8.98 |
| Transgenic Line | PV00460-22 | 20 mgP/g | 323.11 | 13.52 | 88.89 | 0.05 | 234.22 | 13.57 |
| Control | Pv-WT (A26)-72 | 20 mgP/g | 282.99 | 10.83 | 53.96 | 0.99 | 229.03 | 9.84 |
| Control | NREL SWG | 5.0 mgP/g | 227.04 | 30.85 | 44.53 | 4.33 | 182.51 | 26.52 |
| Transgenic Line | PV00460-15 | 5.0 mgP/g | 310.22 | 10.57 | 103.72 | 0.89 | 206.50 | 11.46 |
| Transgenic Line | PV00460-18 | 5.0 mgP/g | 312.94 | 14.85 | 116.72 | 1.37 | 196.22 | 13.48 |
| Transgenic Line | PV00460-22 | 5.0 mgP/g | 287.63 | 11.73 | 89.26 | 0.04 | 198.38 | 11.69 |
| Control | Pv-WT (A26)-72 | 5.0 mgP/g | 243.22 | 4.08 | 52.16 | 1.54 | 191.06 | 2.54 |
| Control | NREL SWG | 2.5 mgP/g | 177.44 | 11.91 | 44.51 | 2.24 | 132.93 | 9.67 |
| Transgenic Line | PV00460-15 | 2.5 mgP/g | 268.84 | 6.50 | 104.91 | 0.10 | 163.94 | 6.41 |
| Transgenic Line | PV00460-18 | 2.5 mgP/g | 275.39 | 3.64 | 119.88 | 6.48 | 155.51 | 10.12 |
| Transgenic Line | PV00460-22 | 2.5 mgP/g | 250.62 | 8.11 | 89.65 | 1.49 | 160.97 | 6.62 |
| Control | Pv-WT (A26)-72 | 2.5 mgP/g | 220.13 | 1.31 | 52.16 | 1.41 | 167.97 | 2.71 |
| Control | NREL SWG | 1.0 mgP/g | 122.39 | 6.33 | 41.22 | 2.45 | 81.17 | 3.88 |
| Transgenic Line | PV00460-15 | 1.0 mgP/g | 207.42 | 9.99 | 106.12 | 2.86 | 101.30 | 7.13 |
| Transgenic Line | PV00460-18 | 1.0 mgP/g | 218.39 | 3.17 | 119.80 | 4.70 | 98.59 | 7.87 |
| Transgenic Line | PV00460-22 | 1.0 mgP/g | 196.32 | 1.90 | 93.97 | 1.09 | 102.35 | 2.99 |
| Control | Pv-WT (A26)-72 | 1.0 mgP/g | 141.59 | 5.82 | 51.56 | 0.52 | 90.03 | 6.34 |
| Control | NREL SWG | 0 mgP/g | 47.39 | 0.91 | 42.67 | 0.49 | 4.72 | 0.42 |
| Transgenic Line | PV00460-15 | 0 mgP/g | 107.20 | 0.32 | 104.09 | 0.70 | 3.11 | 0.39 |
| Transgenic Line | PV00460-18 | 0 mgP/g | 119.00 | 2.87 | 116.43 | 2.45 | 2.57 | 0.42 |
| Transgenic Line | PV00460-22 | 0 mgP/g | 94.54 | 1.21 | 91.87 | 1.64 | 2.67 | 0.43 |
| Control | Pv-WT (A26)-72 | 0 mgP/g | 57.74 | 0.11 | 54.62 | 0.07 | 3.12 | 0.18 |

Example 9

Transgenic sorghum plants were made using the same construct containing Ceres Clone 1807011 (SEQ ID NO:1) as was used to make the transgenic switchgrass of Examples 3, 6, and 7. As described above, this results in the production of a truncated protein (e.g., about 142 residues in length). Sorghum stalk juice samples were harvested from four events containing CeresClone 1807011 and a control plant at approximately soft to hard dough stages. After harvesting, the Brix value of each juice sample was measured using a refractometer.

HPLC was carried out with the sorghum juice stalk extracts. Samples were run on HPLC (Agilent 1100 series) to determine the sugar profile. A HPLC carbohydrate analysis column (Aminex® HPX-87P column) was used for the sugar analysis. The column was heated at 80° C. and the flow rate was set at 1 ml/min for analyzing extracts, respectively. Corona® CAD® detector (Thermo Scientific) was used to analyze the sugar samples. The data was analyzed using Agilent Chemstation software.

Table 6 presents the Brix and HPLC-determined sugar profiles from juice samples of transgenic and control plants. The data for each event were based on one juice sample for single plants. Each sample was divided to run in duplicate so the data represent an average of the duplicates for each sample. As shown in Table 6, all four transgenic events had an increased sucrose content, an increased total sugar content, and an increased Brix value compared to the control event. The sucrose content ranged from 48.18 to 75.85 mg/ml, with two of the events having a sucrose content of 62.23 to 75.85 mg/ml. The total sugar content ranged from 54.04 to 80.57 mg/ml, with three of the events having a total sugar content of 63.13 to 80.57 mg/ml. The Brix value ranged from 10.5 to 13.1%, with two of the events having a Brix value that ranged from 11.8 to 13.1%. Two of the transgenic events also had an increased glucose content compared to the control event.

TABLE 6

| Sample name | Suc (mg/ml) | Glc (mg/ml) | Frc (mg/ml) | Total sugars | Brix value (%) |
|---|---|---|---|---|---|
| Transgenic 204-02 | 54.54 | 5.19 | 3.4 | 63.13 | 10.5 |
| Transgenic 204-11 | 62.23 | 5.93 | 4.09 | 72.25 | 11.8 |
| Transgenic 204-25 | 48.18 | 3.66 | 2.2 | 54.04 | 11 |
| Transgenic 204-26 | 75.85 | 3.06 | 1.66 | 80.57 | 13.1 |
| 204-07 (pcr negative) | 13.78 | 3.26 | 2.22 | 19.26 | 6.6 |

Example 10

Determination of Functional Homologs by Reciprocal BLAST

A candidate sequence was considered a functional homolog of a reference sequence if the candidate and reference sequences encoded proteins having a similar function and/or activity. A process known as Reciprocal BLAST (Rivera et al., Proc. Natl. Acad. Sci. USA, 95:6239-6244 (1998)) was used to identify potential functional homolog sequences from databases consisting of all available public and proprietary peptide sequences, including NR from NCBI and peptide translations from Ceres clones.

Before starting a Reciprocal BLAST process, a specific reference polypeptide was searched against all peptides from its source species using BLAST in order to identify polypeptides having BLAST sequence identity of 80% or greater to the reference polypeptide and an alignment length of 85% or greater along the shorter sequence in the alignment. The reference polypeptide and any of the aforementioned identified polypeptides were designated as a cluster.

The BLASTP version 2.0 program from Washington University at Saint Louis, Mo., USA was used to determine BLAST sequence identity and E-value. The BLASTP version 2.0 program includes the following parameters: 1) an E-value cutoff of 1.0e-5; 2) a word size of 5; and 3) the -postsw option. The BLAST sequence identity was calculated based on the alignment of the first BLAST HSP (High-scoring Segment Pairs) of the identified potential functional homolog sequence with a specific reference polypeptide. The number of identically matched residues in the BLAST HSP alignment was divided by the HSP length, and then multiplied by 100 to get the BLAST sequence identity. The HSP length typically included gaps in the alignment, but in some cases gaps were excluded.

The main Reciprocal BLAST process consists of two rounds of BLAST searches; forward search and reverse search. In the forward search step, a reference polypeptide sequence, "polypeptide A," from source species SA was BLASTed against all protein sequences from a species of interest. Top hits were determined using an E-value cutoff of $10^{-5}$ and a sequence identity cutoff of 35%. Among the top hits, the sequence having the lowest E-value was designated as the best hit, and considered a potential functional homolog or ortholog. Any other top hit that had a sequence identity of 80% or greater to the best hit or to the original reference polypeptide was considered a potential functional homolog or ortholog as well. This process was repeated for all species of interest.

In the reverse search round, the top hits identified in the forward search from all species were BLASTed against all protein sequences from the source species SA. A top hit from the forward search that returned a polypeptide from the aforementioned cluster as its best hit was also considered as a potential functional homolog.

Functional homologs were identified by manual inspection of potential functional homolog sequences. Representative functional homologs for SEQ ID NOs: 483, 562, 246, 111, 348, 774, 416, 2, 157, 280, 641, and 26 are shown in FIGS. 1-12, respectively. Additional exemplary homologs are correlated to certain Figures in the Sequence Listing.

Example 11

Determination of Functional Homologs by Hidden Markov Models

Hidden Markov Models (HMMs) were generated by the program HMMER 2.3.2. To generate each HMM, the default HMMER 2.3.2 program parameters, configured for global alignments, were used.

An HMM was generated using the sequences shown in FIG. 1 as input. These sequences were fitted to the model and a representative HMM bit score for each sequence is shown in the Sequence Listing. Additional sequences were fitted to the model, and representative HMM bit scores for any such additional sequences are shown in the Sequence Listing. The results indicate that these additional sequences are functional homologs of SEQ ID NO: 483.

The procedure above was repeated and an HMM was generated for each group of sequences shown in FIGS. 2-12, using the sequences shown in each Figure as input for that HMM. A representative bit score for each sequence is shown in the Sequence Listing. Additional sequences were fitted to certain HMMs, and representative HMM bit scores for such additional sequences are shown in the Sequence Listing. The results indicate that these additional sequences are functional homologs of the sequences used to generate that HMM.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09828608B2). An electronic copy of the "Sequence Listing" will also be available from the USPTO upon request and payment of the fee set forth in 37 CFR 1.19(b)(3).

What is claimed is:

1. A method of producing a plant, said method comprising growing a plant cell comprising an exogenous nucleic acid, said exogenous nucleic acid comprising a regulatory region operably linked to a nucleotide sequence encoding a polypeptide having 95 percent or greater sequence identity to residues 1 to 142 of SEQ ID NO: 2, wherein a plant produced from said plant cell has an increase in sucrose content or increase in conversion efficiency as compared to a control plant that does not comprise said nucleic acid.

2. The method of claim 1, wherein the polypeptide comprises residues 1 to 142 of SEQ ID NO: 2.

3. The method of claim 1, wherein said exogenous nucleic acid comprises a nucleotide sequence having 95 percent or greater sequence identity to residues 1 to 657 of SEQ ID NO: 1.

4. The method of claim 1, wherein the increase in sucrose content or increase in conversion efficiency in said plant is an increase in the sucrose content.

5. The method of claim 1, wherein the increase in sucrose content or increase in conversion efficiency in said plant is an increase in the conversion efficiency.

6. A method of increasing sucrose content or conversion efficiency in a plant, said method comprising introducing into a plant cell an exogenous nucleic acid, said exogenous nucleic acid comprising a regulatory region operably linked to a nucleotide sequence encoding a polypeptide having 95 percent or greater sequence identity to residues 1 to 142 of SEQ ID NO: 2, wherein a plant produced from said plant cell has an increase difference in sucrose content or increase in conversion efficiency as compared to a control plant that does not comprise said nucleic acid.

7. The method of claim 6, wherein the increase in sucrose content or increase in conversion efficiency in said plant is an increase in the sucrose content.

8. The method of claim 6, wherein the increase in sucrose content or increase in conversion efficiency in said plant is an increase in the conversion efficiency.

9. The method of claim 6, wherein said polypeptide comprises residues 1 to142 of SEQ ID NO:2.

10. The method of claim 6, wherein said exogenous nucleic acid comprises a nucleotide sequence having 95 percent or greater sequence identity to residues 1 to657 of SEQ ID NO: 1.

11. A plant cell comprising an exogenous nucleic acid, said exogenous nucleic acid comprising:
 a) a regulatory region operably linked to a nucleotide sequence encoding a polypeptide having 95 percent or greater sequence identity to residues 1 to 142 of SEQ ID NO: 2, or
 b) a regulatory region operably linked to a nucleotide sequence having 95 percent or greater sequence identity to residues 1 to 657 of SEQ ID NO: 1, wherein a plant produced from said plant cell has an increase difference in sucrose content or increase in conversion efficiency as compared to a control plant that does not comprise said nucleic acid.

12. A transgenic plant comprising the plant cell of claim 11.

13. The transgenic plant of claim 12, wherein said plant is a member of a species selected from the group consisting of *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

14. A transgenic plant comprising the plant cell of claim 11, wherein said polypeptide comprises residues 1 to 142 of SEQ ID NO:2.

15. A seed product comprising embryonic tissue from the transgenic plant according to claim 12, wherein the seed product comprises the exogenous nucleic acid.

16. The method of claim 3, wherein said nucleotide sequence comprises residues 1 to 657 of SEQ ID NO: 1.

17. The method of claim 10, wherein said nucleotide sequence comprises residues 1to 657 of SEQ ID NO: 1.

18. The plant cell of claim 11, wherein said exogenous nucleic acid comprises a nucleotide sequence comprising residues 1 to 657 of SEQ ID NO: 1.

* * * * *